(12) United States Patent
Zhu et al.

(10) Patent No.: US 8,129,512 B2
(45) Date of Patent: Mar. 6, 2012

(54) METHODS OF IDENTIFYING AND CREATING RUBISCO LARGE SUBUNIT VARIANTS WITH IMPROVED RUBISCO ACTIVITY, COMPOSITIONS AND METHODS OF USE THEREOF

(75) Inventors: Genhai Zhu, San Jose, CA (US); Itzhak Kurek, San Francisco, CA (US); Lu Liu, Palo Alto, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 672 days.

(21) Appl. No.: 12/102,639

(22) Filed: Apr. 14, 2008

(65) Prior Publication Data
US 2008/0256666 A1    Oct. 16, 2008

Related U.S. Application Data

(60) Provisional application No. 60/911,433, filed on Apr. 12, 2007.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .............. 536/23.6; 435/257.2; 435/320.1; 435/419; 800/284

(58) Field of Classification Search .............. 800/298; 435/419; 536/23.6
See application file for complete search history.

(56) References Cited

U.S. PATENT DOCUMENTS

| 2002/0132308 | A1 | 9/2002 | Liu et al. | |
|---|---|---|---|---|
| 2002/0151017 | A1* | 10/2002 | Stemmer et al. | .............. 435/189 |
| 2006/0272044 | A1 | 11/2006 | Zhu | |

* cited by examiner

*Primary Examiner* — Russell Kallis
(74) *Attorney, Agent, or Firm* — Alston & Bird LLP

(57) ABSTRACT

Methods for identifying one or more amino acid substitutions in a Rubisco large subunit polypeptide (variant) that confer increased Rubisco activity in a unicellular photosynthetic organism and transferring those substitutions to a Rubisco large subunit polypeptide of a higher plant cell are described herein. Methods and compositions for modulating plant productivity using the modified Rubisco large subunit polypeptide variants are provided. The Rubisco large subunit sequences are used in a variety of methods including increasing plant productivity in a plant. Transformed plants, plant cell, tissues, seed, and expression vectors are also provided.

45 Claims, 17 Drawing Sheets

Figure 2A

```
                         10         20         30         40         50         60         70
 1. C. reinhardtii:      MVPQTETKAG AGFKAGVKDY RLTYYTPDYV VRDTDILAAF RMTPQPGVPP EECGAAVAAE SSTGTWTTVW
 2. Oryza sativa: MSCREGR MSPQTETKAS VGFKAGVKDY KLTYYTPEYE TKDTDILAAF RVTPQPGVPP EEAGAAVAAE SSTGTWTTVW
 3. Triticum aestivum:   MSPQTETKAS VGFKAGVKDY KLTYYTPEYE TKDTDILAAF RVSPQPGVPP EEAGAAVAAE SSTGTWTTVW
 4. Saccharum hybrid:    MSPQTETKAS VGFKAGVKDY KLTYYTPEYE TKDTDILAAF RVTPQLGVPP EEAGAAVAAE SSTGTWTTVW
 5. Sorghum bicolor:     MSPQTETKAS VGFKAGVKDY KLTYYTPEYE TKDTDILAAF RVTPQLGVPP EEAGAAVAAE SSTGTWTTVW
 6. Zea mays:            MSPQTETKAS VGFKAGVKDY KLTYYTPEYE TKDTDILAAF RVTPQLGVPP EEAGAAVAAE SSTGTWTTVW
 7. Gossypium hirsutum:  MSPQTETKAS VGFKAGVKEY KLTYYTPEYE VKDTDILAAF RVTPQPGVPP EEAGAAVAAE SSTGTWTTVW
 8. Glycine max:         MSPQTETKAS VGFKAGVKDY KLTYYTPDYE TKDTDILAAF RVTPQPGVPP EEAGAAVAAE SSTGTWTTVW
 9. Medicago sativa:     MSPQTETKAT VGFKAGVKDY RLTYYTPEYE TKDTDILAAF RVSPQPGVPA EEAGAAVAAE SSTGTWTTVW
10. Spinacia oleracea:   MSPQTETKAS VGFKAGVKDY KLTYYTPEYE TLDTDILAAF RVSPQPGVPP EEAGAAVAAE SSTGTWTTVW
11. Nicotiana tabacum:   MSPQTETKAS VGFKAGVKEY KLTYYTPEYQ TKDTDILAAF RVTPQPGVPP EEAGAAVAAE SSTGTWTTVW
12. Solanum lycopersium: MSPQTETKAS VGFKAGVKDY KLTYYTPEYQ TKDTDILAAF RVTPQPGVPP EEAGAAVAAE SSTGTWTTVW
13. Solanum tuberosum:   MSPQTETKAS VGFKAGVKEY KLTYYTPEYQ TKDTDILAAF RVTPQPGVPP EEAGAAVAAE SSTGTWTTVW
14. Hordeum vulgare:     MSPQTETKAG VGFQAGVKDY KLTYYTPEYE TKDTDILAAF RVSPQPGVPP EEAGAAVAAE SSTGTWTTVW
15. Substitution:                  S VA                    V         G          GV        S
                                                                                 C 80         90        100        110        120        130        140        150        160
 1. TDGLTSLDRY KGRCYDIEPV PGEDNQYIAY VAYPLDLFEE GSVTNMFTSI VGNVFGFKAL RALRLEDLRI PPAYVKTFVG PPHGIQVERD
 2. TDGLTSLDRY KGRCYHTEPV VGEDNQYIAY VAYPLDLFEE GSVTNMFTSI VGNVFGFKAL RALRLEDLRI PPTYSKTFQG PPHGIQVERD
 3. TDGLTSLDRY KGRCYHIEPV AGEDSQWICY VAYPLDLFEE GSVTNMFTSI VGNVFGFKAL RALRLEDLRI PPTYSKTFQG PPHGIQVERD
 4. TDGLTSLDRY KGRCYHIEPV PGDPDQYICY VAYPLDLFEE GSVTNMFTSI VGNVFGFKAL RALRLEDLRI PPAYVKTFQG PPHGIQVERD
 5. TDGLTSLDRY KGRCYHIEPV PGDPDQYICY VAYPLDLFEE GSVTNMFTSI VGNVFGFKAL RALRLEDLRI PPAYVKTFQG PPHGIQVERD
 6. TDGLTSLDRY KGRCYHIEPV PGDPDQYICY VAYPLDLFEE GSVTNMFTSI VGNVFGFKAL RALRLEDLRI PPAYSKTFQG PPHGIQVERD
 7. TDGLTSLDRY KGRCYDIEPV PGEEDQYICY VAYPLDLFEE GSVTNMFTSI VGNVFGFKAL RALRLEDLRI PTAYIKTFQG PPHGIQVERD
 8. TDGLTSLDRY KGRCYGLEPV AGEENQYIAY VAYPLDLFEE GSVTNMFTSI VGNVFGFKAL RALRLEDLRV PTAYIKTFQG PPHGIQVERD
 9. TDGLTSLDRY KGRCYHIEPV AGEETQFIAY VAYPLDLFEE GSVNYMFTSI VGNVFGFKAL RALRLEDLRI PAAYVKTFQG PPQGIQVERD
10. TDGLTNLDRY KGRCYHIEPV AGEENQYICY VAYPLDLFEE GSVTNMFTSI VGNVFGFKAL RALRLEDLRI PVAYVKTFQG PPHGIQVERD
11. TDGLTSLDRY KGRCYRIERV VGEKDQYIAY VAYPLDLFEE GSVTNMFTSI VGNVFGFKAL RALRLEDLRI PPAYVKTFQG PPHGIQVERD
12. TDGLTSLDRY KGRCYRIERV VGEKDQYIAY VAYPLDLFEE GSVTNMFTSI VGNVFGFKAL RALRLEDLRI PPAYSKTFQG PPHGIQVERD
13. TDGLTSLDRY KGRCYRIERV VGEKDQYIAY VAYPLDLFEE GSVTNMLTSI VGNVFGFKAL RALRLEDLRI PVAYVKTFQG PPHGIQVERD
14. TDGLTSLDRY KGRCYHIEPV AGEDSQWICY VAYPLDLFEE GSVTNMFTSI VGNVFGFKAL RALRLEDLRI PPTYSKTFQG PPHGIQVERD
    S   CG      RC   GG  ED    T AV  L           I    L                           S   H  ALA
    A   G
```

Figure 2B

```
        170        180        190        200        210        220        230        240        250
 1. KLNKYGRGLL GCTIKPKLGL SAKNYGRAVY ECLRGGLDFT KDDENVNSQP FMRWRDRFLF VAEAIYKAQA ETGEVKGHYL NATAGTCEEM
 2. KLNKYGRPLL GCTIKPKLGL SAKNYGRACY ECLRGGLDFT KDDENVNSQP FMRWRDRFVF CAEAIYKSQA ETGEIKGHYL NATAGTCEEM
 3. KLNKYGRPLL GCTIKPKLGL SAKNYGRACY ECLRGGLDFT KDDENVNSQP FMRWRDRFVP CAEAIYKAQA ETGEIKGHYL NATAGTCEEM
 4. KLNKYGRPLL GCTIKPKLGL SAKNYGRACY ECLRGGLDFT KDDENVNSQP FMRWRDRFVF CAEAIYKAQA ETGEIKGHYL NATAGTCEEM
 5. KLNKYGRPLL GCTIKPKLGL SAKNYGRACY ECLRGGLDFT KDDENVNSQP FMRWRDRFVF CAEAIYKAQA ETGEIKGHYL NATAGTCEEM
 6. KLNKYGRPLL GCTIKPKLGL SAKNYGRACY ECLRGGLDFT KDDENVNSQP FMRWRDRFVF CAEAIYKSQA ETGEIKGHYL NATAGTCEEM
 7. KLNKYGRPLL GCTIKPKLGL SAKNYGRAVY ECLRGGLDFT KDDENVNSQP FMRWRDRFVF CAEAIFKSQA ETGEIKGHYL NATAGTCEEM
 8. KLNKYGRPLL GCTIKPKLGL SAKNYGRAVY ECLRGGLDFT KDDENVNSQP FMRWRDRFLF CAEAIFKSQA ETGEIKGHYL NATAGTCEEM
 9. KLNKYGRPLL GCTIKPKLGL SAKNYGRAVY ECLRGGLDFT KDDENVNSQP FMRWRDRFLF CAEAIYKAQA ETGEIKGHYL NATAGTCEEM
10. KLNKYGRPLL GCTIKPKLGL SAKNYGRAVY ECLRGGLDFT KDDENVNSQP FMRWRDRFLF CAEAIYKAQA ETGEIKGHYL NATAGTCEDM
11. KLNKYGRPLL GCTIKPKLGL SAKNYGRAVY ECLRGGLDFT KDDENVNSQP FMRWRDRFLF CAEAIYKAQA ETGEIKGHYL NATAGTCEEM
12. KLNKYGRPLL GCTIKPKLGL SAKNYGRAVY ECLRGGLDFT KDDENVNSQP FMRWRDRFLF CAEALFKAQT ETGEIKGHYL NATAGTCEEM
13. KLNKYGRPLL GCTIKPKLGL SAKNYGRAVY ECLRGGLDFT KDDENVNSQP FMRWRDRFLF CAEALFKAQA ETGEIKGHYL NATAGTCEEM
14. KLNKYGRPLL GCTIKPKLGL SAKNYGRACY ECLRGGLDFT KDDENVNSQP FMRWRDRFVF CAEAIYKSQA ETGEIKGHYL NATAGTCEEM
                              S          V                          A    T                    I  G
                              V 260        270        280        290        300        310        320        330        340
 1. MKRAVCAKEL GVPIVMHDYL TGGFTANTSL AIYCRDNGLL LHIHRAMHAV IDRQRNHGIH FRVLAKALRM SGGDHLHSGT VVGKLEGERE
 2. IKRAVFAREL GVPIVMHDYL TGGFTANTSL AHYCRDNGLL LHIHRAMHAV IDRQKNHGMH FRVLAKALRM SGGDHIHSGT VVGKLEGERE
 3. IKRAVFAREL GVPIVMHDYL TGGFTANTTL AHYCRDNGLL LHIHRAMHAV IDRQKNHGMH FRVLAKALRM SGGDHIHSGT VVGKLEGERE
 4. IKRAVFAREL GVPIVMHDYL TGGFTANTTL AHYCRDNGLL LHIHRAMHAV IDRQKNHGMH FRVLAKALRM SGGDHIHSGT VVGKLEGERE
 5. IKRAVFAKEL GVPIVMHDYL TGGFTANTTL SHYCRDNGLL LHIHRAMHAV IDRQKNHGMH FRVLAKALRM SGGDHIHSGT VVGKLEGERE
 6. IKRAVFAREL GVPIVMHDYL TGGFTANTTL SHYCRDNGLL LHIHRAMHAV IDRQKNHGMH FRVLAKALRM SGGDHIHSGT VVGKLEGERE
 7. IKRAMCAREL GVPIVMHDYL TGGFTANTTL AHYCRDNGLL LHIHRAMHAV IDRQKNHGMH FRVLAKALRM SGGDHIHAGT VVGKLEGERD
 8. MKRAVFAREL GVPIVMHDYL TGGFTANTSL AHYCRDNGLL LHIHRAMHAV IDRQKNHGMH FRVLAKALRL SGGDVHAGT VVGKLEGERD
 9. MKRAVFAREL GVPIVMHDYL TVGFTANTTL AHYCRDNGLL LHIHRAMHAV IDRQKNHGMH FRVLAKALRL SGGDHIHSGT VVGKLEGERD
10. MKRAVFAREL GVPIVMHDYL TGGFTANTTL AHYCRDNGLL LHIHRAMHAV IDRQKNHGIH FRVLAKALRM SGGDHIHSGT VVGKLEGERD
11. IKRAVFAREL GVPIVMHDYL TGGFTANTTL AHYCRDNGLL LHIHRAMHAV IDRQKNHGMH FRVLAKALRM SGGDHIHSGT VVGKLEGERD
12. IKRAVFAREL GVPIVMHDYL TGGFTANTTL AHYCRDNGLL LHIHRAMHAV IDRQKNHGIH FRVLAXALRM SGGDHIHSGT VVGKLEGERD
13. MKRAVFAREL GTPIVMHDYL TGGFTANTTL AHYCRDNGLL LHIHRAMHAV IDRQKNHGMH FRVLAKALRM SGGDHIHSGT VVGKLEGERD
14. IKRAVFAREL GVPIVMHDYL TGGFTANTTL AHYCRDNGLL LHIHRAMHAV IDRQKNHGMH FRVLAKALRM SGGDHIHSGT VVGKLEGERD
    V I       A   V                  S S                  I
```

Figure 2C

```
             350        360        370         380          390        400        410        420        430
 1. VTLGFVDLMR DDYVEKDRSR GIYFTQDMCS MPGVMPVASG GIHVWNHMPAL VEIFGDDACL QFGGGTLGHP WGNAPGAAAN RVALEACTQA
 2. MTLGFVDLLR DDFIEKDRAR GIFFTQDMVS MPGVIPVASG GIHVWNHMPAL TEIFGDDSVL QFGGGTLGHP WGNAPGAAAN RVALEACVQA
 3. MTLGFVDLLR DDFIEKDRSR GIFFTQDMVS MPGVIPVASG GIHVWNHMPAL TEIFGDDSVL QFGGGTLGHP WGNAPGAAAN RVALEACVQA
 4. ITLGFVDLLR DDFIEKDRSR GIFFTQDMVS MPGVIPVASG GIHVWNHMPAL TEIFGDDSVL QFGGGTLGHP WGNAPGAAAN RVALEACVQA
 5. ITLGFVDLLR DDFIEKDRSR GIFFTQDMVS MPGVIPVASG GIHVWNHMPAL TEIFGDDSVL QFGGGTLGHP WGNAPGAAAN RVALEACVQA
 6. ITLGFVDLLR DDFIEKDRSR GIFFTQDMVS MPGVIPVASG GIHVWNHMPAL TEIFGDDSVL QFGGGTLGHP WGNAPGAAAN RVALEACVQA
 7. ITLGFVDLLR DDFIEKDRSR GIFFTQDMVS MPGVLPVASG GIHVWNHMPAL TEIFGDDSVL QFGGGTLGHP WGNAPGAAAN RVALEACVQA
 8. ITLGFVDLLR DDFVEKDRSR GIYFTQDMVS LPGVLPVASG GIHVWNHMPAL TEIFGDDSVL QFGGGTLGHP WGNAPGAVAN RVALEACVQA
 9. ITLGFVDLLR DDFIEKDRSR GIFFTQDMVS LPGVLPVASG GIHVWNHMPAL TEIFGDDSVL QFGGGTLGHP WGNAPGAVAN RVALEACVQA
10. ITLGFVDLLR DDYIEKDRSR GIYFTQSWVS TPGVLPVASG GIHVWNHMPAL TEIFGDDSVL QFGGGTLGHP WGNAPGAVAN RVALEACVQA
11. ITLGFVDLLR DDFVEQDRSR GIYFTQDMVS LPGVLPVASG GIHVWNHMPAL TEIFGDDSVL QFGGGTLGHP WGNAPGAVAN RVALEACVKA
12. ITLGFVDLLR DDFVEQDRSR GIYFTQDMVS LPGVLPVASG GIHVWNHMPAL TEIFGDDSVL QFGGGTLGHP WGNAPGAVAN RVALEACVKA
13. ITLGFVDLLR DDFIEQDRSR GIYFTQDMVS LPGVLPVASG GIHVWNHMPAL TEIFGDDSVL QFGGGTLGHP WGNAPGAVAN RVALEACVKA
14. MTLGFVDLLR DDFIEKDRAR GIFFTQDMVS MPGVIPVASG GIHVWNHMPAL TEIFGDDSVL QFGGGTLGHP WGNAPGAAAN RVALEACVQA
    ES        HGCA       DR         A            IS        TG                                          A
                H        G                                   T
                R 440        450        460        470
 1. RNEGRDLARE GGDVIRSACK WSPELAAACE VWKKEIKFE-F DTIDKL      (SEQ ID NO: 2)
 2. RNEGRDLARE GNEIIRSACK WSPELAAACE IWKAIKFE-F  EPVDKLDS    (SEQ ID NO: 7)
 3. RNEGRDLARE GNEIIRAACK WSPELAAACE VWKAIKFE-F  EPVDTIDK    (SEQ ID NO: 8)
 4. RNEGRDLARE GNEIIKAACK WSAELAAACE IWKEIKFDTP  KAMDTL      (SEQ ID NO: 9)
 5. RNEGRDLARE GNEIIKAACK WSAELAAACE IWKEIKFDTF  KAMDTL      (SEQ ID NO: 10)
 6. RNEGRDLARE GNEIIKAACK WSAELAAACE IWKEIKFDGF  KAMDTI      (SEQ ID NO: 11)
 7. RNEGRDLARE GNEIIREASK WSPELAAACE VWKAIKFE-F  DAVDKLDKVE K (SEQ ID NO: 12)
 8. RNEGRDLARE GNEIIREASK WSPELAAACE VWKEIKFE-F  EAMDTL      (SEQ ID NO: 13)
 9. RNEGRDLARE GNEIIREATK WSPELAAACE VWKEIKFE-F  PAMDN       (SEQ ID NO: 14)
10. RNEGRDLARE GNTIIREATK WSPELAAACE VWKEIKFE-F  PAMDTV      (SEQ ID NO: 15)
11. RNEGRDLAQE GNEIIREACK WSPELAAACE VWKEIVFN-F  AAVDVLDK    (SEQ ID NO: 6)
12. RNEGRDLARE GNEIIREACK WSPELAAACE VWKEIVEN-F  AAVDVLDK    (SEQ ID NO: 16)
13. RNEGRDLARE GNEIIREAAK WSPELAAACE VWKEIVEN-F  AAMDVLDK    (SEQ ID NO: 17)
14. RNEGRDLARE GNEIIRAACK WSPELAAACE VWKAIKFE-F  EPVDTIDKKV  (SEQ ID NO: 18)
                I               TP       C  VT  L
                L                                           (SEQ ID NO: 4)
                G
```

Figure 3A

```
         1                                        10                                        20
Wild type: atg gtt cca caa aca gaa act aaa gca ggt gct gga ttc aaa gcc ggt gta aaa gac tac cgt tta aca tac
Mutation:                                         a        t  c 30                                        40                                       50
tac aca cct gat tac gta gta aga gat act gat att tta gct gca ttc cgt atg act cca caa cca ggt gtt cca cct gaa
                        a  g                            g        g g                             t 60                                        70
gaa tgt ggt gct gta gct gct gaa tct tca aca ggt aca gta tgg act gac ggt tta aca agt ctt gac
     a                      t                           gt   gg                    t     g
                                                                                   g
         80                                        90                                       100
cgt tac aaa ggt cgt tgt tac gat atc gaa cca gtt ccg ggt gaa gac aac caa tac att gct gta gct tac cca atc
         g                  t                   g                           a         t  c 110                                       120                                       130
gac tta ttc gaa ggt tca gta act gta act aac atg ttc act tct att gta ggt aac gta ttc ggt ttc aaa gct tta cgt gct
          a                    a                        t                                   g
        140                                       150
cta cgt ctt gaa gac ctt cgt att cca cct gct tac gtt aaa aca ttc gta ggt cct cca cac ggt att cag gta gaa cgt
                                                          c              g    a c 160                                       170                                       180
gac aaa tta aac aaa tat ggt cgt ttc ctt gac ggt ctt tgt aca atc aaa cct aaa tta ggt ctt tca gct aaa aac tac ggt
                                                        t                                          at 190                                       200                                       210
cgt gca gtt tat gaa tgt tta cgt ggt gtt gct gaa gct gta tac aaa gct act aaa gac gaa aac gta aac tca caa ttc atg cgt
                                                        t                                         g 220                                       230                                       240
tgg cgt gac cgt ttc ctt ttc gtt gct gaa ttc act tac aaa gct caa gca gaa aca ggt gaa gtt aaa ggt cac tac tta
                                                            c                                c 250                                       260
aac gct act gct ggt act gaa atg aaa gaa gaa tta ggt gta cgt gca gta tgt gct aaa gaa tta ggt gta cct att atg cac
                                                   g                    a                        c
                t
```

Figure 3B

```
                              280                    290                              320
         270                       tta gct atc tac tgt cgt gac aac ggt ctt ctt cta cac atc cac
gac tac tta aca ggt ggt ttc aca gct aac act tca                                        atg tct
                                        c t a 300                    310                          340
cgt gct atg cac gcg gtt att gac cgt caa aac cac ttc cgt gtt ctt gct aaa gct ctt cgt atg tct
                            c                               a                           a 330                                        370
ggt ggt gac cac ctt cac tct ggt act gtt gta ggt aaa cta gaa ggt gaa gtt act cta ggt tca gac tta
                                            ga                              c                 a 350                              360                                400
atg cgt gat gac tac gtt gaa aaa gac cgt agc cgt ggt att cac gta tgg cac atg cca tca atg cca ggt gtt atg
        c         g cg                  ga                                    at          g c 380                    390
cca gtt gct tca gct ggt att cac gta tgg cac atg cca gct tta gtt gaa atc ttc ggt gat gac gca tgt ctt cag ttc
                                                              at   ac                                    a 410                              420
ggt ggt act cta ggt cac cct tgg ggt aac gct gca gct gta gct ctt gaa gct tgt tgt act caa
                                                        c                         g 430                              440                    450
gct cgt aac gaa ggt cgt gac ctt gct gaa ggt ggc gac gta att cgt tca gct tgt aaa tgg tct cca gaa ctt gct
                                            t                                       g                 a 460                              470
gct gca tgt gaa gtt tgg aaa gaa att aaa ttc gaa gat act att gac aaa ttc taa (SEQ ID NO: 1)
    c                       t       gc         c
                                                                            (SEQ ID NO: 3)
```

Figure 4A

```
tgaatcagaa tctttgagaaa gtctttcatt tgtctatcat tatagacaat cccatccata ttatctattc tatggaattc
gaacctgaac tttattttct attcttatta cgattcatta tttgtatcta tttgctcct attgctcct ctcttattt attttgatt
tcaatttcag catatcgatt tatgcctagc ctattcttt cttgtgttt ttctttcttt tttataccctt tcatagattc
atagaggaat tccgtatatt ttcacatcta cgatttacat atacaacata taccactgtc aagggggaag ttcttattat
ttaggttagt cagttatttc catttcaaaa aaaaaaaaag taaaaaagaa aaattgggtt gcgctatata tatgaaagag
tatacaataa tgatgtattt gcaaatcaa ataccatgt ctaataatca aacattctga ttagttgata atattagtat
tagttggaaa ttttgtgaaa gattcctatg aaaagttca ttaacacgga attcgtgtcg agtagaccctt gttgttgtga
gaattcttaa ttcatgagtt gtaggaggg attatgtca ccacaaacag agactaaagc aagtgttgga ttcaaagctg
gtgttaaaga gtacaaattg acttattata ctcctgagta ccaaaccaag gatactgata tattggcagc attccgagta
actcctcaaa ctggagttcc acctgagtca gcaggggccg cggtagctgc cgaatcttct actggtacat ggacaactgt
atggaccgat ggacttacca gcctttatcg ttacaaaggg catgctacc gcatcgagcg tgttgttgga geaaaagatc
aatatattgc ttatgtagct tacctttga acctttttga agaaggttct gttaccaaca tgtttacttc cattgtaggt
aacgtattg gttcaaagc ctgcgcgct ctagtctgg aagatctgcg aatccctcct gcttatgtta aaactttcca
agtccgcct catgggatcc aagttgaaag agataaattg aacaagtatg gtgtccctt gttgggatgt actattaaac
ctaaattggg gttatctgct aaaaactacg gtagagcgt ttatgaatgt cttcgcggtg gacttgattt tactaaagat
gatgaaacg tgaactcaca accattatg cgttggagag atcgttcttt attttgtgcc gaagcacttt ataaagcaca
ggctgaaatca ggtgaaatca aaggcatta cttgaatgct actgcaggta catgcgaaga aatgatcaaa agagctgtat
ttgctagaga attgggcgtt ccgatcgtaa tgcatgacta cttaacgggg ggattcaccg caaatactag cttggctcat
tattgccgag ataatggtct acttcttcac atccacgtg caatgcatgc ggttattgat agacagaaga atcatgtat
ccacttccgg gtattagcaa aagcgttacg tatgtctgt ggagatcata ttcactctgg taccgtagta ggtaaacttg
aagtgaaag agacataact ttgggctttg ttgattact gcgtgttcact tttgttgaac aagatcgaag tgcggtatt
tatttcactc aagattgggt ctcttaca ggtgttctac ccgtggcttc agaaggtatt cacgttttgc atatgcctgc
tctgaccgag atcttgggg atgatccgt actacagttc ggtgaggaa cttaggaca tccttgggt aatgcgccag
gtgcgtagc taatcgagta gctctagaag catgtgtaaa agctcgtaat gaaggacgtg atcttgctca ggaaggtaat
gaaattattc gcgaggcttg caaatggagc ccggaactag ctgctgcttg tgaagtatgg aaagagatcg tatttaattt
tgcagcagtg gacgttttgg ataagtaaaa acagtagaca ttagcagata aattagcagg aataaaagaa ggataagagg
aaagaactca agtaattatc cttcgttctc ttaattgaat tgcaattaaa ctcggcccaa tcttttacta aaaggattga
gccgaataca acaaagattc tattgcatat atttgacta agtatatact tacctagata tacaagatt gaaatacaaa
atctagaaaa ctaaatcaaa atctaagact caaatctttc tattgttgtc ttgatccac attaatcct acggatcctt
aggattggta tattcttttc tatcctgtag tttgtagttc cctgaatca agccaagtat cacaccctctt tctacccatc
ctgtatattg tcccctttgt tccgtgtttga aatagaacct taatttatta cttattttt tattaaattt tagattgttt
agtgattaga tattagatt agacgagatt ttacgaaaca attattttt tattctttta taggagagga caaatctctt
```

Figure 4B

```
tttcgatgc gaatttgaca cgacatagga gaagccgccc tttattaaaa attatattat tttaaataat ataaaggggg
ttccaacata ttaatatata gtgaagtgtt cccccagatt cagaactttt tttcaatact cacaatcctt attagttaat
aatcctagtg attggatttc tatgcttagt ctgataggaa ataagatatt caaataaata attttatagc gaatgactat
tcatctattg tatttcatg caaatagggg gcaagaaaac tctatggaaa gatggtggtt taattcgatg ttgtttaaga
aggagttcga acgcaggtgt gggctaaata aatcaatggg cagtcttggt cctattgaaa ataccaatga agatccaaat
cgaaaagtga aaaacattca tagttggagg aatcgtgaca attctagttg cagtaatgtt gattattat tcggcgttaa
agacattcgg aatttcatct ctgatgacac ttttttactt agtgatagga atggagacag ttattccatc tatttgata (SEQ ID
NO: 19)
```

Figure 5

MVPQTETKAGAGFKAGVKDYRLTYYTPDYVVRDTDILAAFRMTPQPGVPPEECGAAVAAESSTGT
WTTVWTDGLTSLDRYKGRCYDIEPVPGEDNQYIAYVAYPIDLFEEGSVTNMFTSIVGNVFGFKAL
RALRLEDLRIPPAYVKTFVGPPHGIQVERDKLNKYGRGLLGCTIKPKLGLSAKNYGRAVYECLRG
GLDFTKDDENVNSQPFMRWRDRFLFVAEAIYKAQAETGEVKGHYLNATAGTCEEMMKRAVCAKEL
GVPIIMHDYLTGGFTANTSLAIYCRDNGLLLHIHRAMHAVIDRQRNHGIHFRVLAKALRMSGGDH
LHSGTVVGKLEGEREVTLGFVDLMRDDYVEKDRSRGIYFTQDWCSMPGVMPVASGGIHVWHMPAL
VEIFGDDACLQFGGGTLGHPWGNAPGAAANRVALEACTQARNEGRDLAREGGDVIRSACKWSPEL
AAACEVWKEIKFEFDTIDKL (SEQ ID NO: 2)

Figure 6

MVPQTETKAGAGFKAGVKDYRLTYYTPDYVVRDTDILAAFRMTPQPGVPPEECGAAVAAESSTGT
WTTVWTDGLTSLDRYKGRCYDIEPVPGEDNQYITYVAYPIDLFEEGSVTNMFTSIVGNVFGFKAL
RALRLEDLRIPPAYVKTFVGPPHGIQVERDKLNKYGRGLLGCTIKPKLGLSAKNYGRAVYECLRG
GLDFTKDDENVNSQPFMRWRDRFLFVAEAIYKAQAETGEVKGHYLNATAGTCEEMMKRAVCAKEL
GVPIIMHDYLTGGFTANTSLSIYCRDNGLLLHIHRAMHAVIDRQRNHGIHFRVLAKALRMSGGDH
LHSGTVVGKLEGEREVTLGFVDLMRDGYVEKDRSRGIYFTQDWCSMPGVMPVASGGIHVWHMPAL
VEIFGDDACLQFGGGTLGHPWGNAPGAAANRVALEACTQARNEGRDLAREGGDVIRSACKWSPEL
AAACEVWKEIKFEFDTIDKL (SEQ ID NO:21)

Figure 7

MVPQTETKAGAGFKAGVKDYRLTYYTPDYVVRDTDILAAFRMTPQPGVPPEECGAAVAAESSTGT
WTTVWTDGLTSLDRYKGRCYDIEPVPGEDNQYIAYVVYPIDLFEEGSVTNMFTSIVGNVFGFKAL
RALRLEDLRIPPAYVKTFVGPPHGIQVERDKLNKYGRGLLGCTIKPKLGLSAKNYGRAVYECLRG
GLDFTKDDENVNSQPFMRWRDRFLFVAEAIYKAQAETGEVKGHYLNATAGTCEEMMKRAVCAKEL
GVPIVMHDYLTGGFTANTSLAIYCRDNGLLLHIHRAMHAVIDRQRNHGIHFRVLAKALRMSGGDH
LHSGTVVGKLEGEREVTLGFVDLMRDDHVEKDRSRGIYFTQDWCAMPGVMPVASGGIHVWHMPAL
VEIFGDDACLQFGGGTLGHPWGNAPGAAANRVALEACTQARNEGRDLAREGGDVIRSACKWSPEL
AAACEVWKEIKFEFDTIDKL (SEQ ID NO: 23)

Figure 8

MVPQTETKAGAGFKAGVKDYRLTYYTPDYVVRDTDILAAFRVTPQPGVPPEECGAAVAAESSTGT
WTTVWTDGLTSLDRYKGRCYDIEPVPGEDNQYIAYVAYPIDLFEEGSVTNMFTSIVGNVFGFKAL
RALRLEDLRIPPAYVKTFVGPPHGIQVERDKLNKYGRGLLGCTIKPKLGLSAKNYGRAVYECLRG
GLDFTKDDENVNSQPFMRWRDRFLFVAEAIYKAQAETGEVKGHYLNATAGTCEEMMKRAVCAKEL
GVPIVMHDYLTGGFTANTSLAIYCRDNGLLLHIHRAMHAVIDRQRNHGIHFRVLAKALRMSGGDH
LHSGTVVGKLEGEREVTLGFVDLMRDDYVEKDRSRGIYFTQDWCAMPGVMPVASGGIHVWHMPAL
VEIFGDDACLQFGGGTLGHPWGNAPGAAANRVALEACTQARNEGRDLAREGGDVIRSACKWSPEL
AAACEVWKEVKFEFDTIDKL (SEQ ID NO: 25)

Figure 9

ATGGTTCCACAAACAGAAACTAAAGCAGGTGCTGGATTCAAAGCCGGTGTAAAAGACTACCGTTT
AACATACTACACACCTGATTACGTAGTAAGAGATACTGATATTTTAGCTGCATTCCGTATGACTC
CACAACCAGGTGTTCCACCTGAAGAATGTGGTGCTGCTGTAGCTGCTGAATCTTCAACAGGTACA
TGGACTACAGTATGGACTGACGGTTTAACAAGTCTTGACCGTTACAAAGGTCGTTGTTACGATAT
CGAACCAGTTCCGGGTGAAGACAACCAATACATTGCTTACGTAGCTTACCCAATCGACTTATTCG
AAGAAGGTTCAGTAACTAACATGTTCACTTCTATTGTAGGTAACGTATTCGGTTTCAAAGCTTTA
CGTGCTCTACGTCTTGAAGACCTTCGTATTCCACCTGCTTACGTTAAAACATTCGTAGGTCCTCC
ACACGGTATTCAGGTAGAACGTGACAAATTAAACAAATATGGTCGTGGTCTTTTAGGTTGTACAA
TCAAACCTAAATTAGGTCTTTCAGCTAAAAACTACGGTCGTGCAGTTTATGAATGTTTACGTGGT
GGTCTTGACTTTACTAAAGACGACGAAAACGTAAACTCACAACCATTCATGCGTTGGCGTGACCG
TTTCCTTTTCGTTGCTGAAGCTATTTACAAAGCTCAAGCAGAAACAGGTGAAGTTAAAGGTCACT
ACTTAAACGCTACTGCTGGTACTTGTGAAGAAATGATGAAACGTGCAGTATGTGCTAAAGAATTA
GGTGTACCTATTATTATGCACGACTACTTAACAGGTGGTTTCACAGCTAACACTTCATTAGCTAT
CTACTGTCGTGACAACGGTCTTCTTCTACACATCCACCGTGCTATGCACGCGGTTATTGACCGTC
AACGTAACCACGGTATTCACTTCCGTGTTCTTGCTAAAGCTCTTCGTATGTCTGGTGGTGACCAC
CTTCACTCTGGTACTGTTGTAGGTAAACTAGAAGGTGAACGTGAAGTTACTCTAGGTTTCGTAGA
CTTAATGCGTGATGACTACGTTGAAAAAGACCGTAGCCGTGGTATTTACTTCACTCAAGACTGGT
GTTCAATGCCAGGTGTTATGCCAGTTGCTTCAGGTGGTATTCACGTATGGCACATGCCAGCTTTA
GTTGAAATCTTCGGTGATGACGCATGTCTTCAGTTCGGTGGTGGTACTCTAGGTCACCCTTGGGG
TAACGCTCCAGGTGCTGCAGCTAACCGTGTAGCTCTTGAAGCTTGTACTCAAGCTCGTAACGAAG
GTCGTGACCTTGCTCGTGAAGGTGGCGACGTAATTCGTTCAGCTTGTAAATGGTCTCCAGAACTT
GCTGCTGCATGTGAAGTTTGGAAAGAAATTAAATTCGAATTTGATACTATTGACAAACTTTAA
(SEQ ID NO: 1)

Figure 10

ATGGTTCCACAAACAGAAACTAAAGCAGGTGCTGGATTCAAAGCCGGTGTAAAAGACTACCGTTT
AACATACTACACACCTGATTACGTAGTAAGAGATACTGATATTTTAGCTGCATTCCGTATGACTC
CACAACCAGGTGTTCCACCTGAAGAATGTGGTGCTGCTGTAGCTGCTGAATCTTCAACAGGTACA
TGGACTACAGTATGGACTGACGGTTTAACAAGTCTTGACCGTTACAAAGGTCGTTGTTACGATAT
CGAACCAGTTCCGGGTGAAGACAACCAATACATTACTTACGTAGCTTACCCAATCGACTTATTCG
AAGAAGGTTCAGTAACTAACATGTTCACTTCTATTGTAGGTAACGTATTCGGTTTCAAAGCTTTA
CGTGCTCTACGTCTTGAAGACCTTCGTATTCCACCTGCTTACGTTAAAACATTCGTAGGTCCTCC
ACACGGTATTCAGGTAGAACGTGACAAATTAAACAAATATGGTCGTGGTCTTTTAGGTTGTACAA
TCAAACCTAAATTAGGTCTTTCAGCTAAAAACTACGGTCGTGCAGTTTATGAATGTTTACGTGGT
GGTCTTGACTTTACTAAAGACGACGAAAACGTAAACTCACAACCATTCATGCGTTGGCGTGACCG
TTTCCTTTTCGTTGCTGAAGCTATTTACAAAGCTCAAGCAGAAACAGGTGAAGTTAAAGGTCACT
ACTTAAACGCTACTGCTGGTACTTGTGAAGAAATGATGAAACGTGCAGTATGTGCTAAAGAATTA
GGTGTACCTATTATTATGCACGACTACTTAACAGGTGGTTTCACAGCTAACACTTCATTATCAAT
CTACTGTCGTGACAACGGTCTTCTTCTACACATCCACCGTGCTATGCACGCGGTTATTGACCGTC
AACGTAACCACGGTATTCACTTCCGTGTTCTTGCTAAAGCTCTTCGTATGTCTGGTGGTGACCAC
CTTCACTCTGGTACTGTTGTAGGTAAACTAGAAGGTGAACGTGAAGTTACTCTAGGTTTCGTAGA
CTTAATGCGTGATGGCTACGTTGAAAAAGACCGTAGCCGTGGTATTTACTTCACTCAAGACTGGT
GTTCAATGCCAGGTGTTATGCCAGTTGCTTCAGGTGGTATTCACGTATGGCACATGCCAGCTTTA
GTTGAAATCTTCGGTGATGACGCATGTCTTCAGTTCGGTGGTGGTACTCTAGGTCACCCTTGGGG
TAACGCTCCAGGTGCTGCAGCTAACCGTGTAGCTCTTGAAGCTTGTACTCAAGCTCGTAACGAAG
GTCGTGACCTTGCTCGTGAAGGTGGCGACGTAATTCGTTCAGCTTGTAAATGGTCTCCAGAACTT
GCTGCTGCATGTGAAGTTTGGAAAGAAATTAAATTCGAATTTGATACTATTGACAAACTTTAA
(SEQ ID NO: 20)

Figure 11

ATGGTTCCACAAACAGAAACTAAAGCAGGTGCTGGATTCAAAGCCGGTGTAAAAGACTACCGTTT
AACATACTACACACCTGATTACGTAGTAAGAGATACTGATATTTTAGCTGCATTCCGTATGACTC
CACAACCAGGTGTTCCACCTGAAGAATGTGGTGCTGCTGTAGCTGCTGAATCTTCAACAGGTACA
TGGACTACAGTATGGACTGACGGTTTAACAAGTCTTGACCGTTACAAAGGTCGTTGTTACGATAT
CGAACCAGTTCCGGGTGAAGACAACCAATACATTGCTTACGTAGTTTACCCAATCGACTTATTCG
AAGAAGGTTCAGTAACTAACATGTTCACTTCTATTGTAGGTAACGTATTCGGTTTCAAAGCTTTA
CGTGCTCTACGTCTTGAAGACCTTCGTATTCCACCTGCTTACGTTAAAACATTCGTAGGTCCTCC
ACACGGTATTCAGGTAGAACGTGACAAATTAAACAAATATGGTCGTGGTCTTTTAGGTTGTACAA
TCAAACCTAAATTAGGTCTTTCAGCTAAAAACTACGGTCGTGCAGTTTATGAATGTTTACGTGGT
GGTCTTGACTTTACTAAAGACGACGAAAACGTAAACTCACAACCATTCATGCGTTGGCGTGACCG
TTTCCTTTTCGTTGCTGAAGCTATTTACAAAGCTCAAGCAGAAACAGGTGAAGTTAAAGGTCACT
ACTTAAACGCTACTGCTGGTACTTGTGAAGAAATGATGAAACGTGCAGTATGTGCTAAAGAATTA
GGTGTACCTATTGTAATGCACGACTACTTAACAGGTGGTTTCACAGCTAACACTTCATTAGCTAT
CTACTGTCGTGACAACGGTCTTCTTCTACACATCCACCGTGCTATGCACGCGGTTATTGACCGTC
AACGTAACCACGGTATTCACTTCCGTGTTCTTGCTAAAGCTCTTCGTATGTCTGGTGGTGACCAC
CTTCACTCTGGTACTGTTGTAGGTAAACTAGAAGGTGAACGTGAAGTTACTCTAGGTTTCGTAGA
CTTAATGCGTGATGACCACGTTGAAAAAGACCGTAGCCGTGGTATTTACTTCACTCAAGACTGGT
GTGCAATGCCAGGTGTTATGCCAGTTGCTTCAGGTGGTATTCACGTATGGCACATGCCAGCTTTA
GTTGAAATCTTCGGTGATGACGCATGTCTTCAGTTCGGTGGTGGTACTCTAGGTCACCCTTGGGG
TAACGCTCCAGGTGCTGCAGCTAACCGTGTAGCTCTTGAAGCTTGTACTCAAGCTCGTAACGAAG
GTCGTGACCTTGCTCGTGAAGGTGGCGACGTAATTCGTTCAGCTTGTAAATGGTCTCCAGAACTT
GCTGCTGCATGTGAAGTTTGGAAAGAAATTAAATTCGAATTTGATACTATTGACAAACTTTAA
(SEQ ID NO: 22)

Figure 12

ATGGTTCCACAAACAGAAACTAAAGCAGGTGCTGGATTCAAAGCCGGTGTAAAAGACTACCGTTT
AACATACTACACACCTGATTACGTAGTAAGAGATACTGATATTTTAGCTGCATTCCGTGTGACTC
CACAACCAGGTGTTCCACCTGAAGAATGTGGTGCTGCTGTAGCTGCTGAATCTTCAACAGGTACA
TGGACTACAGTATGGACTGACGGTTTAACAAGTCTTGACCGTTACAAAGGTCGTTGTTACGATAT
CGAACCAGTTCCGGGTGAAGACAACCAATACATTGCTTACGTAGCTTACCCAATCGACTTATTCG
AAGAAGGTTCAGTAACTAACATGTTCACTTCTATTGTAGGTAACGTATTCGGTTTCAAAGCTTTA
CGTGCTCTACGTCTTGAAGACCTTCGTATTCCACCTGCTTACGTTAAAACATTCGTAGGTCCTCC
ACACGGTATTCAGGTAGAACGTGACAAATTAAACAAATATGGTCGTGGTCTTTTAGGTTGTACAA
TCAAACCTAAATTAGGTCTTTCAGCTAAAAACTACGGTCGTGCAGTTTATGAATGTTTACGTGGT
GGTCTTGACTTTACTAAAGACGACGAAAACGTAAACTCACAACCATTCATGCGTTGGCGTGACCG
TTTCCTTTTCGTTGCTGAAGCTATTTACAAAGCTCAAGCAGAAACAGGTGAAGTTAAAGGTCACT
ACTTAAACGCTACTGCTGGTACTTGTGAAGAAATGATGAAACGTGCAGTATGTGCTAAAGAATTA
GGTGTACCTATTGTAATGCACGACTACTTAACAGGTGGTTTCACAGCTAACACTTCATTAGCTAT
CTACTGTCGTGACAACGGTCTTCTTCTACACATCCACCGTGCTATGCACGCGGTTATTGACCGTC
AACGTAACCACGGTATTCACTTCCGTGTTCTTGCTAAAGCTCTTCGTATGTCTGGTGGTGACCAC
CTTCACTCTGGTACTGTTGTAGGTAAACTAGAAGGTGAACGTGAAGTTACTCTAGGTTTCGTAGA
CTTAATGCGTGATGACTACGTTGAAAAAGACCGTAGCCGTGGTATTTACTTCACTCAAGACTGGT
GTGCAATGCCAGGTGTTATGCCAGTTGCTTCAGGTGGTATTCACGTATGGCACATGCCAGCTTTA
GTTGAAATCTTCGGTGATGACGCATGTCTTCAGTTCGGTGGTGGTACTCTAGGTCACCCTTGGGG
TAACGCTCCAGGTGCTGCAGCTAACCGTGTAGCTCTTGAAGCTTGTACTCAAGCTCGTAACGAAG
GTCGTGACCTTGCTCGTGAAGGTGGCGACGTAATTCGTTCAGCTTGTAAATGGTCTCCAGAACTT
GCTGCTGCATGTGAAGTTTGGAAAGAAGTTAAATTCGAATTTGATACTATTGACAAACTTTAA
(SEQ ID NO: 24)

Figure 13

MSPQTETKASVGFKAGVKEYKLTYYTPEYQTKDTDILAAFRVTPQPGVPPEEAGAAVAAESSTG
TWTTVWTDGLTSLDRYKGRCYRIERVVGEKDQYIAYVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSLAHYCRDNGLLLHIHRAMHAVIDRQKNHGIHFRVLAKALRM
SGGDHIHSGTVVGKLEGERDITLGFVDLLRDDFVEQDRSRGIYFTQDWVSLPGVLPVASGGIHV
WHMPALTEIFGDDSVLQFGGGTLGHPWGNAPGAVANRVALEACVKARNEGRDLAQEGNEIIREA
CKWSPELAAACEVWKEIVFNFAAVDVLDK (SEQ ID NO: 6)

Figure 14

MSPQTETKASVGFKAGVKEYKLTYYTPEYQTKDTDILAAFRVTPQPGVPPEEAGAAVAAESSTGT
WTTVWTDGLTSLDRYKGRCYRIERVVGEKDQYI_TY_VAYPLDLFEEGSVTNMFTSIVGNVFGFKAL
RALRLEDLRIPPAYVKTFQGPPHGIQVERDKLNKYGRPLLGCTIKPKLGLSAKNYGRAVYECLRG
GLDFTKDDENVNSQPFMRWRDRFLFCAEALYKAQAETGEIKGHYLNATAGTCEEMIKRAVFAREL
GVPIVMHDYLTGGFTANTSL_S_HYCRDNGLLLHIHRAMHAVIDRQKNHGIHFRVLAKALRMSGGDH
IHSGTVVGKLEGERDITLGFVDLLRD_G_FVEQDRSRGIYFTQDWVSLPGVLPVASGGIHVWHMPAL
TEIFGDDSVLQFGGGTLGHPWGNAPGAVANRVALEACVKARNEGRDLAQEGNEIIREACKWSPEL
AAACEVWKEIVFNFAAVDVLDK (SEQ ID NO: 27)

Figure 15

MSPQTETKASVGFKAGVKEYKLTYYTPEYQTKDTDILAAFRVTPQPGVPPEEAGAAVAAESSTG
TWTTVWTDGLTSLDRYKGRCYRIERVVGEKDQYIAYVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSLAHYCRDNGLLLHIHRAMHAVIDRQKNHGIHFRVLAKALRM
SGGDHIHSGTVVGKLEGERDITLGFVDLLRDDFVEQDRSRGIYFTQDWV_A_LPGVLPVASGGIHV
WHMPALTEIFGDDSVLQFGGGTLGHPWGNAPGAVANRVALEACVKARNEGRDLAQEGNEIIREA
CKWSPELAAACEVWKE_V_VFNFAAVDVLDK (SEQ ID NO: 29)

Figure 16

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTGCTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCAAGAAATGATCAAAAGAGCTGTATTTGCTAGAGAATTG
GGCGTTCCGATCGTAATGCATGACTACTTAACGGGGGGATTCACCGCAAATACTAGCTTGGCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGATTTTGTTGAACAAGATCGAAGTCGCGGTATTTATTTCACTCAAGATTGGG
TCTCTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGATCGTATTTAATTTTGCAGCAGTGGACGTTTTGGATAA
GTAA (SEQ ID NO: 5)

Figure 17

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTACTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCAAGAAATGATCAAAAGAGCTGTATTTGCTAGAGAATTG
GGCGTTCCGATCGTAATGCATGACTACTTAACGGGGGGATTCACCGCAAATACTAGCTTGTCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGGTTTTGTTGAACAAGATCGAAGTCGCGGTATTTATTTCACTCAAGATTGGG
TCTCTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGATCGTATTTAATTTTGCAGCAGTGGACGTTTTGGATAA
GTAA (SEQ ID NO: 26)

Figure 18

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTGCTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCGAAGAAATGATCAAAAGAGCTGTATTTGCTAGAGAATTG
GGCGTTCCGATCGTAATGCATGACTACTTAACGGGGGGATTCACCGCAAATACTAGCTTGGCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGATTTTGTTGAACAAGATCGAAGTCGCGGTATTTATTTCACTCAAGATTGGG
TCGCTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGGTAGTATTTAATTTTGCAGCAGTGGACGTTTTGGATAA
GTAA (SEQ ID NO: 28)

Figure 19

MSPQTETKASVGFKAGVKEYKLTYYTPEYQTKDTDILAAFRVTPQPGVPPEEAGAAVAAESSTG
TWTTVWTDGLTSLDRYKGRCYRIERVVGEKDQYIAYVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSLSHYCRDNGLLLHIHRAMHAVIDRQKNHGIHFRVLAKALRM
SGGDHIHSGTVVGKLEGERDITLGFVDLLRDDFVEQDRSRGIYFTQDWVALPGVLPVASGGIHV
WHMPALTEIFGDDSVLQFGGGTLGHPWGNAPGAVANRVALEACVKARNEGRDLAQEGNEIIREA
CKWSPELAAPCEVWKEIVFNFAAVDVLDK (SEQ ID NO: 31)

Figure 20

MSPQTETKASVGFKAGVKEYKLTYYTPEYQTKDTDILAAFRVTPQPGVPPEEAGAAVAAESSTG
TWTTVWTDGLTSLDRYKGRCYGIERVVGEKDQYIAYVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSLAHYCRDNGLLLHIHRAMHAVIDRQKNHGIHFRVLAKALRM
SGGDHIHSGTVVGKLEGERDITLGFVDLLRDGFVEQDRSRGIYFTQDWVALPGVLPVASGGIHV
WHTPALTEIFGDDSVLQFGGGTLGHPWGNAPGAVANRVALEACVKARNEGRDLAQEGNEIIREA
CKWSPELAAACEVWKEIVFNFAAVDVLDK (SEQ ID NO: 33)

Figure 21

MSPQTETKASVGFKAGVKEYKLTYYTPEYQTKDTDILAAFRVTPQPGVPPEEAGAAVAAESSTG
TWTTVWTDGLTSLDRYKGRCYRIERVVGEKDQYI_T_YVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSLAHYCRDNGLLLHIHRAMHAVIDRQKNHGIHFRVLAKALRM
SGGDHIHSGTVVGKLEGERDITLGFVDLLRDD_H_VEQDRSRGIYFTQDWV_A_LPGVLPVASGGIHV
WHMPALTEIFGDDSVLQFGGGTLGHPWGNAPGAVANRVALEACVKARNEGRDLAQEGNEIIREA
CKWSPELAAACEVWKEIVFNFAAVDVLDK (SEQ ID NO: 35)

Figure 22

MSPQTETKASVGFKAGVKEYKLTYYTPEYQTKDTDILAAFRVTPQPGVPPEEAGAAVAAESSTG
TWTTVWTDGLTSLDRYKGRCYRIERVVGEKDQYIAYVAYPLDLFEEGSVTNMFTSIVGNVFGFK
ALRALRLEDLRIPPAYVKTFQGPPHGIQVERDKLNKYGRPLLGCTIKPKLGLSAKNYGRAVYEC
LRGGLDFTKDDENVNSQPFMRWRDRFLFCAEALYKAQAETGEIKGHYLNATAGTCEEMIKRAVF
ARELGVPIVMHDYLTGGFTANTSL_S_HYCRDNGLLLHIHRAMHAVIDRQKNHGIHFRVLAKALRM
SGGDHIHSGTVVGKLEGERDITLGFVDLLRD_G_FVEQDRSRGIYFTQDWVSLPGVLPVASGGIHV
WHMPALTEIFGDDSVLQFGGGTLGHPWGNAPGAVANRVALEACVKARNEGRDLAQEGNEIIREA
CKWSPELAAACEVWKE_V_VFNFAAVDVLDK (SEQ ID NO: 37)

Figure 23

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTGCTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCCTGTTGGGATGTACTA
TTAAACCTAAATTGGGGTTATCTGCTAAAAACTACGGTAGAGCTGTTTATGAATGCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCGAAGAAATGATCAAAAGAGCTGTATTTGCTAGAGAATTG
GGCGTTCCGATCGTAATGCATGACTACTTAACGGGGGGATTCACCGCAAATACTAGCTTG_T_CTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGATTTTGTTGAACAAGATCGAAGTCGCGGTATTTATTTCACTCAAGATTGGG
TC_G_CTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCT_C_CTTGTGAAGTATGGAAAGAGATCGTATTTAATTTTGCAGCAGTGGACGTTTTGGATAA
GTAA(SEQ ID NO: 30)

Figure 24

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACGGAAT
CGAGCGTGTTGTTGGAGAAAAAGATCAATATATTGCTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCAAGAAATGATCAAAAGAGCTGTATTTGCTAGAGAATTG
GGCGTTCCGATCGTAATGCATGACTACTTAACGGGGGATTCACCGCAAATACTAGCTTGGCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGGTTTTGTTGAACAAGATCGAAGTCGCGGTATTTATTTCACTCAAGATTGGG
TCGCTTTACCAGGTGTTCTACCCGTGGCTTCAGGAGGTATTCACGTTTGGCATACTCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGATCGTATTTAATTTTGCAGCAGTGGACGTTTTGGATAA
GTAA (SEQ ID NO: 32)

Figure 25

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTACTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCAAGAAATGATCAAAAGAGCTGTATTTGCTAGAGAATTG
GGCGTTCCGATCGTAATGCATGACTACTTAACGGGGGATTCACCGCAAATACTAGCTTGGCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGATCATGTTGAACAAGATCGAAGTCGCGGTATTTATTTCACTCAAGATTGGG
TCGCTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGATCGTATTTAATTTTGCAGCAGTGGACGTTTTGGATAA
GTAA (SEQ ID NO: 34)

Figure 26

ATGTCACCACAAACAGAGACTAAAGCAAGTGTTGGATTCAAAGCTGGTGTTAAAGAGTACAAATT
GACTTATTATACTCCTGAGTACCAAACCAAGGATACTGATATATTGGCAGCATTCCGAGTAACTC
CTCAACCTGGAGTTCCACCTGAAGAAGCAGGGGCCGCGGTAGCTGCCGAATCTTCTACTGGTACA
TGGACAACTGTATGGACCGATGGACTTACCAGCCTTGATCGTTACAAAGGGCGATGCTACCGCAT
CGAGCGTGTTGTTGGAGAAAAAGATCAATATATTGCTTATGTAGCTTACCCTTTAGACCTTTTTG
AAGAAGGTTCTGTTACCAACATGTTTACTTCCATTGTAGGTAACGTATTTGGGTTCAAAGCCCTG
CGCGCTCTACGTCTGGAAGATCTGCGAATCCCTCCTGCTTATGTTAAAACTTTCCAAGGTCCGCC
TCATGGGATCCAAGTTGAAAGAGATAAATTGAACAAGTATGGTCGTCCCTGTTGGGATGTACTA
TTAAACCTAAATTGGGGTTATCTGCTAAAAACTACGGTAGAGCTGTTTATGAATGTCTTCGCGGT
GGACTTGATTTTACCAAAGATGATGAGAACGTGAACTCACAACCATTTATGCGTTGGAGAGATCG
TTTCTTATTTTGTGCCGAAGCACTTTATAAAGCACAGGCTGAAACAGGTGAAATCAAAGGGCATT
ACTTGAATGCTACTGCAGGTACATGCGAAGAAATGATCAAAAGAGCTGTATTTGCTAGAGAATTG
GGCGTTCCGATCGTAATGCATGACTACTTAACGGGGGGATTCACCGCAAATACTAGCTTGTCTCA
TTATTGCCGAGATAATGGTCTACTTCTTCACATCCACCGTGCAATGCATGCGGTTATTGATAGAC
AGAAGAATCATGGTATCCACTTCCGGGTATTAGCAAAAGCGTTACGTATGTCTGGTGGAGATCAT
ATTCACTCTGGTACCGTAGTAGGTAAACTTGAAGGTGAAAGAGACATAACTTTGGGCTTTGTTGA
TTTACTGCGTGATGGTTTTGTTGAACAAGATCGAAGTCGCGGTATTTATTTCACTCAAGATTGGG
TCTCTTTACCAGGTGTTCTACCCGTGGCTTCAGGAGGTATTCACGTTTGGCATATGCCTGCTCTG
ACCGAGATCTTTGGGGATGATTCCGTACTACAGTTCGGTGGAGGAACTTTAGGACATCCTTGGGG
TAATGCGCCAGGTGCCGTAGCTAATCGAGTAGCTCTAGAAGCATGTGTAAAAGCTCGTAATGAAG
GACGTGATCTTGCTCAGGAAGGTAATGAAATTATTCGCGAGGCTTGCAAATGGAGCCCGGAACTA
GCTGCTGCTTGTGAAGTATGGAAAGAGGTAGTATTTAATTTTGCAGCAGTGGACGTTTTGGATAA
GTAA(SEQ ID NO: 36)

United States Patent

METHODS OF IDENTIFYING AND CREATING RUBISCO LARGE SUBUNIT VARIANTS WITH IMPROVED RUBISCO ACTIVITY, COMPOSITIONS AND METHODS OF USE THEREOF

CROSS-REFERENCE TO RELATED APPLICATIONS

This application claims priority under 35 U.S.C. §119 of a provisional application Ser. No. 60/911,433 filed Apr. 12, 2007, which application is hereby incorporated by reference in its entirety.

GRANT REFERENCE

Work for this invention was funded in part by a grant from the United States National Institute of Standards and Technology, Grant No. 70NANBIH3060. The Government has certain rights in this invention.

FIELD OF THE INVENTION

The invention relates to the field of the genetic manipulation of plants, particularly the modulation of gene activity and development in plants.

BACKGROUND OF THE INVENTION

Ribulose-1,5-bisphosphate carboxylase/oxygenase (Rubisco, E. C. 4.1.1.39) is the most abundant and perhaps most important enzyme on earth. It catalyzes the first and rate-limiting step in photosynthetic carbon fixation, the transfer of atmospheric $CO_2$ to ribulose-1,5-bisphosphate. As such, it is the only known enzyme able to remove $CO_2$ from the atmosphere. Because of its keystone position in biomass production, the importance of Rubisco to agriculture is hard to overstate. Cash receipts for American agricultural products in 1997 were $209 billion, of which $112 billion were earned directly from crops (Economic Research Service, USDA). Thus, any incremental increase in crop productivity will be leveraged through a huge sector of the US agricultural economy. For several reasons, it is widely supposed that increasing Rubisco's catalytic efficiency will result in a significant increase in plant productivity. First, the reaction catalyzed by Rubisco is rate limiting to plant growth under optimum growing conditions (high temperature and light intensity, abundant nitrogen). Second, compared to many other enzymes, Rubisco seems to be an inefficient catalyst that leaves a great deal of room to be optimized.

As a catalyst, Rubisco appears to be sub-optimal in three respects. First, its catalytic cycling rate ($k_{cat}$) at about 3 reactions per second, for the enzymes from higher plants, is relatively slow. To compensate for its low activity, plants deposit large amounts of Rubisco enzyme in their green tissues. Indeed, Rubisco accounts for more than 35% of leaf total soluble proteins. Increasing Rubisco's catalytic efficiency would proportionally increase the rate of photosynthesis and, in turn, increase plant productivity. Second, Rubisco cannot effectively distinguish $CO_2$ from $O_2$ and, consequently, it catalyzes an oxygenation reaction that leads to the loss of approximately 25% to 40% of fixed carbon. Theoretically, it is possible to increase plant productivity up to 50% by reducing or eliminating Rubisco's oxygenase activity.

Rubisco has become one of the most intensively investigated plant enzymes. Evolution and adaptation of Rubisco in its various native hosts have resulted in a naturally occurring diversity of enzymatic properties (Jordan and Ogren, 1981). Compared to plant Rubisco, the enzyme from prokaryotic photosynthetic bacteria generally possesses higher catalytic activity ($k_{cat} \approx 8\text{-}16$ s$^{-1}$), but low $CO_2/O_2$ selectivity ($\tau \approx 13\text{-}40$). $\tau$ is the ratio of $k_{cat}$ (carboxylation)/$K_m$($CO_2$) over $k_{cat}$ (oxygenation)/$K_m$ ($O_2$) (Laing, et al., 1974). Rubisco from higher plants including crop species exhibits low $k_{cat}$ ($\approx 3$ s$^{-1}$), and an intermediate $CO_2/O_2$ selectivity ($\tau \approx 80$). The recently-assayed Rubisco from red algae shows the highest $CO_2/O_2$ selectivity yet measured ($\tau \approx 140\text{-}300$, Ezaki, et al., 1999; Read and Tabita, 1994; Uemura, et al., 1997), but the $k_{cat}$ assayed at 25° C. is lower than that of higher plant Rubisco. This diversity among Rubisco enzymes stimulated research aimed at understanding the structure/function relationships that account for the variation of the catalytic parameters $k_{cat}$ and $\tau$. Engineering a better Rubisco through knowledge of the structural determinants of $k_{cat}$ and $\tau$ constitutes the so called "rational approach."

Rubisco from different organisms displays different physical and chemical features. Its holoenzyme is a multi-subunit complex. The primitive form is a large/large subunit dimer ($L_2$). The $L_2$ enzyme is mainly present in anaerobic proteobacteria, but the $L_2$ enzyme is also formed in some eukaryotic algae under anaerobic conditions. In all higher plants and cyanobacteria, Rubisco is composed of eight large (L) and eight small (S) subunits ($L_8S_8$). The L subunit is encoded by a chloroplast gene (rbcL), and the S subunit is encoded by a nuclear gene family (rbcS). So far, only $L_2$, the cyanobacterial $L_8S_8$ enzyme, and an $L_8$ enzyme from a hyperthermophilic alga have been expressed and assembled in *E. coli*. Expression of higher plant Rubisco L and S simultaneously in *E. coli* resulted in no holoenzyme being formed. Consequently, most Rubisco engineering research has been limited to prokaryotic enzymes and the enzyme from the eukaryotic algae *Chlamydomonas reinhardtii*.

For more than 30 years a number of researchers have attempted to improve Rubisco, using a variety of approaches. See, e.g., Mann, C. C., (1999) Science, 283:314-316, and references cited therein. Indeed, the quest for a better Rubisco has been called a "Holy Grail" of plant biology. To date, there has been little success in the creation of an improved Rubisco. Recombination based methods for producing a modified Rubisco enzyme having increased catalytic efficiency and selectivity for $CO_2$ are described in U.S. patent application Ser. No. 09/437,726.

An obstacle hindering the improvement of Rubisco is the deficiencies in currently available host systems for the expression and assembly of functional higher plant Rubisco. In screening a large number of variants for enhanced activity, preferred host systems have included *E. coli*, yeast, cyanobacteria and green algae. In the case of prokaryotic Rubisco, the large subunit (i.e., the $L_8$ core) of prokaryotic Rubisco is soluble, and catalytically competent holoenzyme can be formed in *E. coli* with the help of a chaperone protein (GroEL) present in *E. coli*. In contrast, the large subunit from higher plant Rubisco is insoluble; this is thought to be caused by a hydrophobic surface that is protected by the small subunit in the holoenzyme. In chloroplasts, assembly of the large subunits with mature small subunits is mediated by a chaperone protein, Rubisco binding protein (cpn60). The chaperone protein is believed to prevent improper aggregation of large subunits by protecting exposed hydrophobic surfaces during the last stages of the folding or assembly process. Co-expression of large and small subunits in *E. coli* results in no active holoenzyme being formed, suggesting that inappropriate folding of the large subunit may have occurred before the small subunit was able to bind. The difficulty in expressing higher plant Rubisco in a suitable host has made it difficult to engineer improved variants of the enzyme.

For these and other reasons, there exists a need for improved methods for producing plants and agricultural photosynthetic microbes with improved variants of enzymes involved in carbon fixation, for example, Rubisco.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference, whether specifically noted as such or not.

BRIEF SUMMARY OF THE INVENTION

Generally, it is an object of the invention to provide a method of identifying Rubisco large subunits that have increased Rubisco activity in a higher plant cell. It is an object of the present invention to provide polynucleotides and polypeptides of Rubisco large subunits. It is an object of the present invention to provide transgenic plants comprising the polynucleotides and polypeptides of the present invention or identified by methods of the invention. Additionally, it is an object of the present invention to provide methods of modulating, in a plant cell or in a transgenic plant, the expression of the polynucleotides and polypeptides of the present invention. Yet another object of the present invention is to provide methods of increasing plant productivity in a plant.

Therefore, in one aspect, the present invention relates to a method of identifying Rubisco large subunits that have increased Rubisco activity when expressed with a Rubisco small subunit in a higher plant cell. In one aspect, the method comprises identifying one or more amino acid substitutions in a Rubisco large subunit polypeptide (variant) that confer increased Rubisco activity in a unicellular photosynthetic organism. In one aspect, the Rubisco activity is increased when compared to Rubisco activity of a Rubisco large subunit that does not contain the amino acid substitutions. In another aspect, the method provides for making the identified amino acid substitutions in a Rubisco large subunit that is endogenous to a higher plant cell. In another aspect, the method includes introducing into the higher plant cell the endogenous Rubisco large subunit polynucleotide that encodes a polypeptide containing the amino acid substitutions identified in the unicellular photosynthetic organism. The Rubisco activity may be determined in the higher plant cell. The present invention also provides for an expression cassette comprising at least one Rubisco large subunit polynucleotide encoding a Rubisco large subunit identified by a method of the present invention. In another aspect, the present invention is directed to a host cell transfected with the recombinant expression cassette comprising a promoter functional in a plant operably linked to any of the isolated polynucleotides encoding polypeptides of the present invention.

In another aspect, the present invention relates to an isolated Rubisco polynucleotide that encodes any of the polypeptides of SEQ ID NOS: 4, 21, 23, 25, 27, 29, 31, 33, 35, and 37; a polynucleotide having any of the sequences of SEQ ID NOS: 3, 20, 22, 24, 26, 28, 30, 32, 34, and 36; a polynucleotide having at least 30 nucleotides in length which hybridizes under stringent conditions to any of the former polynucleotides. In another aspect, the present invention includes a polynucleotide having at least 80% sequence identity to any of the sequences of SEQ ID NOS: 3, 20, 22, 24, 26, 28, 30, 32, 34, and 36. Also included are isolated polynucleotides amplified from a nucleic acid library using the primers of 5'-cctaaaggcccttctatgctcg-3' (SEQ ID NO: 38) and 5'-atgtttaggtatttaacctaaacacc-3'(SEQ ID NO: 39). In one aspect, the nucleic acid library is an algal Rubisco large subunit library. In another aspect, the nucleic acid library is a cDNA library. Provided herein in another aspect of the invention are isolated polynucleotides degenerate as a result of the genetic code for any of the Rubisco large subunits of the present invention. In another aspect, an isolated polynucleotide is complimentary to a polynucleotide of any one of the Rubisco large subunits of the present invention. In another aspect, the present invention relates to an isolated polynucleotide that encodes a Rubisco large subunit polypeptide that increases plant productivity.

In yet another aspect, the present invention relates to a transgenic plant including a recombinant expression cassette of a promoter functional in a plant or chloroplast operably linked to any of the isolated polynucleotides of the present invention. The present invention also provides for transgenic seed from the transgenic plant. In another aspect, the present invention is directed to a host cell transfected with the recombinant expression cassette of a promoter functional in a plant or chloroplast operably linked to any of the isolated polynucleotides of the present invention. In one aspect, the host cell is an algal, tobacco, soybean, rice, cotton, sugarcane, sorghum, soybean, alfalfa, spinach, tomato, potato, sunflower, canola, barley, millet, wheat or maize cell.

In a further aspect, the present invention relates to an isolated polypeptide having an amino acid sequence having at least 80% sequence identity to any of the amino acid sequences set forth in SEQ ID NOS: 4, 21, 23, 25, 27, 29, 31, 33, 35, and 37 and having Rubisco activity. In yet another aspect, the present invention relates to a transgenic plant of a recombinant expression cassette comprising a promoter functional in a plant or chloroplast operably linked to an isolated polynucleotide encoding a polypeptide that has an amino acid sequence that has at least 80% sequence identity to any of the amino acid sequences set forth in SEQ ID NOS: 4, 21, 23, 25, 27, 29, 31, 33, 35, and 37 and has Rubisco activity. The present invention also provides for transgenic seed from the transgenic plant. In another aspect, the present invention is directed to a host cell transfected with the recombinant expression cassette comprising a promoter functional in a plant operably linked to any of the isolated polynucleotides encoding polypeptides of the present invention.

In a further aspect, the present invention relates to a method of modulating the level of Rubisco large subunit proteins in a plant cell. In one aspect, the method includes transforming a plant cell with a Rubisco large subunit polynucleotide operably linked to a promoter. The polynucleotide may be in sense or antisense orientation. The method further includes expressing the polynucleotide for an amount of time sufficient to modulate the Rubisco large subunit protein in the plant cell.

In another aspect, the present invention provides a method of modulating the level of Rubisco large subunit protein in a plant. The method includes stably transforming a plant cell with a Rubisco large subunit polynucleotide, in sense or antisense orientation, operably linked to a promoter functional in a plant cell or chloroplast. The method includes regenerating the transformed plant cell into a transformed plant that expresses the Rubisco large subunit polynucleotide in an amount sufficient to modulate the level of Rubisco large subunit protein in the plant.

In another aspect, the present invention relates to a method of increasing plant productivity in a plant. In one aspect, the method includes introducing into plant cells or chloroplasts a construct comprising a polynucleotide encoding a Rubisco large subunit of the present invention. The polynucleotide may be operably linked to a promoter functional in plant cells or chloroplasts to yield transformed plant cells. The transformed plant cells are regenerated into a transgenic plant. The Rubisco large subunit is expressed in the cells of the transgenic plant at levels sufficient to increase Rubisco activity. In one aspect, the Rubisco large subunit is expressed in the cells of the transgenic plant at levels sufficient to increase plant productivity. In another aspect, the increased biomass, increased plant yield, increase plant growth rate, or increased plant size.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE FIGURES

FIG. 2. Substitutions (in bold) found in shuffled *Chlamydomonas reinhardtii* rbcL variants which are functional. (SEQ ID NOS: 2, 4, and 6-18).

FIG. 3. Mutations (in bold) found in shuffled *Chlamydomonas reinhardtii* rbcL variants which are functional. (SEQ ID NOS: 1 and 3).

FIG. 4. *Nicotiana tabacum* (Tobacco) rbcL and flanking sequence (highlighted in bold and underlined is rbcL coding sequence). (SEQ ID NO: 19).

FIG. 5: *Chlamydomonas reinhardtii* Rubisco large subunit protein sequence (wild type) (SEQ ID NO: 2).

FIG. 6: Shuffled variant CiL-12 Rubisco large subunit protein sequence (SEQ ID NO: 21). Substitutions in *Chlamydomonas reinhardtii* rbcL in bold and underlined.

FIG. 7: Shuffled variant CiL-10 Rubisco large subunit protein sequence (SEQ ID NO: 23). Substitutions in *Chlamydomonas reinhardtii* rbcL in bold and underlined.

FIG. 8: Shuffled variant OS4C-11 Rubisco large subunit protein sequence (SEQ ID NO: 25). Substitutions in *Chlamydomonas reinhardtii* rbcL in bold and underlined.

FIG. 9: *Chlamydomonas reinhardtii* rbcL coding (1 bp-1428 bp, direct) Wild type rbcL sequence (SEQ ID NO: 1).

FIG. 10: Shuffled variant from *Chlamydomonas reinhardtii* CiL-12 rbcL coding sequence (1 bp-1428 bp, direct) (SEQ ID NO: 20). Substitutions in *Chlamydomonas reinhardtii* rbcL in bold and underlined.

FIG. 11: Shuffled variant from *Chlamydomonas reinhardtii* CiL-10 rbcL coding sequence (1 bp-1428 bp, direct) (SEQ ID NO: 22). Substitutions in *Chlamydomonas reinhardtii* rbcL in bold and underlined.

FIG. 12: Shuffled variant from *Chlamydomonas reinhardtii* OS4C-11 rbcL coding sequence (1 bp-1428 bp, direct) (SEQ ID NO: 24). Substitutions in *Chlamydomonas reinhardtii* rbcL in bold and underlined.

FIG. 13: *Nicotiana tabacum* (tobacco) Rubisco large subunit protein sequence) (SEQ ID NO: 6).

FIG. 14: Transgenic tobacco line T798 Rubisco large subunit protein sequence (SEQ ID NO: 27). Substitutions in Tobacco petite hovana rbcL in bold and underlined.

FIG. 15: Transgenic tobacco line T796 Rubisco large subunit protein sequence (SEQ ID NO: 29). Substitutions in Tobacco petite hovana rbcL in bold and underlined.

FIG. 16: *Nicotiana tabacum* (tobacco) rbcL sequence) (SEQ ID NO: 5).

FIG. 17: Transgenic tobacco line T798 rbcL coding sequence, direct (SEQ ID NO: 26). Substitutions in Tobacco petite hovana rbcL in bold and underlined.

FIG. 18: Transgenic tobacco line T796 rbcL coding sequence, direct (SEQ ID NO: 28). Substitutions in Tobacco petite hovana rbcL in bold and underlined.

FIG. 19: Rubisco large subunit protein sequence of transgenic tobacco line T805-1-4 recovered from transformation of library variants (SEQ ID NO: 31). Substitutions in Tobacco petite hovana rbcL in bold and underlined. FIG. 20: Rubisco large subunit protein sequence of transgenic tobacco line T805-8-2 recovered from transformation of library variants (SEQ ID NO: 33). Substitutions in Tobacco petite hovana rbcL in bold and underlined.

FIG. 21: Rubisco large subunit protein sequence of transgenic tobacco line T834-7-1 recovered from transformation of library variants (SEQ ID NO: 35). Substitutions in Tobacco petite hovana rbcL in bold and underlined.

FIG. 22: Rubisco large subunit protein sequence of transgenic tobacco line T836-3-1 recovered from transformation of library variants (SEQ ID NO: 37). Substitutions in Tobacco petite hovana rbcL in bold and underlined.

FIG. 23: rbcL coding sequence of transgenic tobacco line T805-1-4 recovered from transformation of library variants (SEQ ID NO: 30). Substitutions in Tobacco petite hovana rbcL in bold and underlined.

FIG. 24: rbcL coding sequence of transgenic tobacco line T805-8-2 recovered from transformation of library variants (SEQ ID NO: 32). Substitutions in Tobacco petite hovana rbcL in bold and underlined.

FIG. 25: rbcL coding sequence of transgenic tobacco line T834-7-1 recovered from transformation of library variants (SEQ ID NO: 34). Substitutions in Tobacco petite hovana rbcL in bold and underlined.

FIG. 26: rbcL coding sequence of transgenic tobacco line T836-3-1 recovered from transformation of library variants (SEQ ID NO: 36). Substitutions in Tobacco petite hovana rbcL in bold and underlined.

BRIEF DESCRIPTION OF THE SEQUENCES

Figure 1:
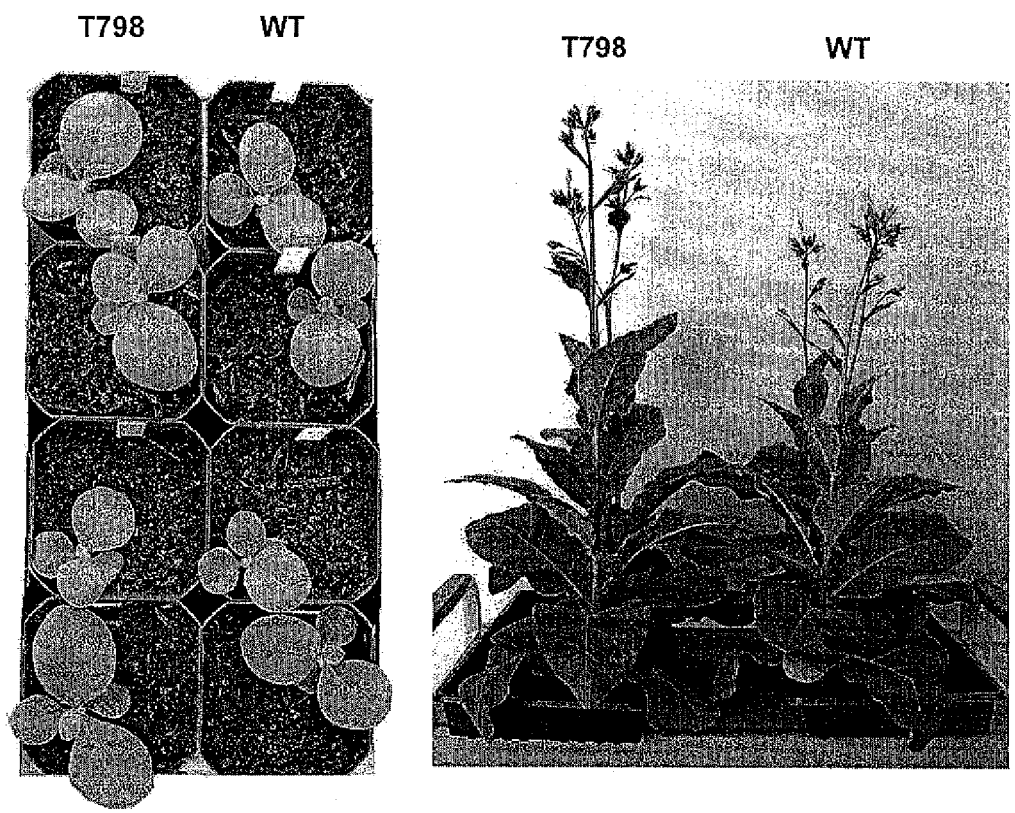
FIG. 1. Growth test of transgenic line T798 and wild type. Left panel: 12 day-old plants after transplanting; Right panel: 33 day-old plants after transplanting.

The application provides details of Rubisco sequences as shown in Table 1 below.

Table 1A and 1B

Table 1A shows amino acid substitutions in Rubisco large subunit that were found to be functional and may influence either Rubisco carboxylase activity or specificity or both.

| Sequence Listing | Polypeptide (ppt) | Length | Identification and position of amino acid substitution in wild type Rubisco large subunit of *Chlamydomonas reinhardtii* (SEQ ID NO: 2) |
|---|---|---|---|
| | | | 1 amino acid substitution |
| 4 | ppt | 475 | G54S |
| 4 | ppt | 475 | A99T |
| 4 | ppt | 475 | V221A |
| 4 | ppt | 475 | I265V |

Table 1A shows amino acid substitutions in Rubisco large subunit that were found to be functional and may influence either Rubisco carboxylase activity or specificity or both.

| Sequence Listing | Polypeptide (ppt) | Length | Identification and position of amino acid substitution in wild type Rubisco large subunit of *Chlamydomonas reinhardtii* (SEQ ID NO: 2) |
|---|---|---|---|
| 4 | ppt | 475 | A281S |
| 4 | ppt | 475 | D352G |
| 4 | ppt | 475 | Y353C |
| 4 | ppt | 475 | V391T |
| 4 | ppt | 475 | E392G |
| 4 | ppt | 475 | A398T |
| 4 | ppt | 475 | V444I |
| | | | 2 amino acids substitutions |
| 4 | ppt | 475 | A99T/I265V |
| 4 | ppt | 475 | A99T/A281S |
| 4 | ppt | 475 | A99T/D352G |
| 4 | ppt | 475 | A99T/S370A |
| 4 | ppt | 475 | A99T/E392G |
| 4 | ppt | 475 | A99T/V444L |
| 4 | ppt | 475 | A99T/V444I |
| 4 | ppt | 475 | A99T/A458P |
| 4 | ppt | 475 | A99T/I465V |
| 4 | ppt | 475 | A99T/K466T |
| 4 | ppt | 475 | A281S/Y353H |
| 4 | ppt | 475 | A281S/E392G |
| 4 | ppt | 475 | G54S/A398T |
| 4 | ppt | 475 | F108L/S359D |
| 4 | ppt | 475 | E231Q/A458P |
| 4 | ppt | 475 | Y353H/S370A |
| | | | 3 amino acids substitutions |
| 4 | ppt | 475 | A99T/G179S/E392G |
| 4 | ppt | 475 | A99T/V262A/I465V |
| 4 | ppt | 475 | A99T/I265V/D352G |
| 4 | ppt | 475 | A99T/I265V/E392G |
| 4 | ppt | 475 | A99T/A281S/D352G |
| 4 | ppt | 475 | A99T/D352G/I465V |
| 4 | ppt | 475 | A99T/S370A/E392G |
| 4 | ppt | 475 | A99T/S370A/I465V |
| 4 | ppt | 475 | A99T/V444I/A458P |
| 4 | ppt | 475 | A11V/G12A/G54S |
| 4 | ppt | 475 | A11V/G54S/A99T |
| 4 | ppt | 475 | A11V/I265V/E392G |
| 4 | ppt | 475 | A11V/I265V/V444I |
| 4 | ppt | 475 | A11V/A281S/I465V |
| 4 | ppt | 475 | A11V/V391T/I472L |
| 4 | ppt | 475 | G54S/A99T/A398T |
| 4 | ppt | 475 | G54S/P141S/V444I |
| 4 | ppt | 475 | G54S/E249G/E392G |
| 4 | ppt | 475 | G54S/S370A/I465V |
| 4 | ppt | 475 | G10S/A11V/V221A |
| 4 | ppt | 475 | G10S/A11V/A281S |
| 4 | ppt | 475 | G10S/A11V/V444I |
| 4 | ppt | 475 | G10S/D78G/S359G |
| 4 | ppt | 475 | D86G/A99T/I465V |
| 4 | ppt | 475 | D94E/A99T/I465V |
| 4 | ppt | 475 | N95D/A99T/I465V |
| 4 | ppt | 475 | V101A/S370A/E392G |
| 4 | ppt | 475 | Y144H/E392G/V444I |
| 4 | ppt | 475 | T147A/G179V/S370A |
| 4 | ppt | 475 | G179V/T246I/I465V |
| 4 | ppt | 475 | A182G/A281S/I465V |
| 4 | ppt | 475 | I265V/Y353H/S370A |
| 4 | ppt | 475 | D347E/E392G/V444I |
| 4 | ppt | 475 | G10S/A11V/V444I |
| | | | 4 amino acids substitutions |
| 4 | ppt | 475 | A99T/F148L/S370A/A458P |
| 4 | ppt | 475 | A99T/I265V/A281S/I465V |
| 4 | ppt | 475 | A99T/I265V/D347E/I465V |
| 4 | ppt | 475 | A99T/I265V/Y353H/S370A |
| 4 | ppt | 475 | A99T/I265V/S370A/E392G |
| 4 | ppt | 475 | A99T/A281S/D352G/S370A |
| 4 | ppt | 475 | A99T/A281S/S370A/E392G |
| 4 | ppt | 475 | A99T/A281S/S370A/V444I |
| 4 | ppt | 475 | A99T/D351H/D352G/R435L |
| 4 | ppt | 475 | M42V/I265V/S370A/I465V |
| 4 | ppt | 475 | G54S/A99T/V221A/A398T |
| 4 | ppt | 475 | G54S/A99T/V313I/V444I |
| 4 | ppt | 475 | G54S/A99T/S370A/E392G |
| 4 | ppt | 475 | G54S/A99T/E392G/V444I |
| 4 | ppt | 475 | G54S/V221A/M387I/E392G |
| 4 | ppt | 475 | G54S/I265V/D347E/I465V |
| 4 | ppt | 475 | G54S/A281S/S370A/E392G |
| 4 | ppt | 475 | G54S/A398T/V422A/V444I |
| 4 | ppt | 475 | F148E/I265V/Y353H/S370A |
| 4 | ppt | 475 | I265V/L280S/S370A/E392G |
| 4 | ppt | 475 | I265V/Y353H/V354A/I465V |
| 4 | ppt | 475 | I265V/Y353H/S370A/A448G |
| 4 | ppt | 475 | I265V/Y353R/S370A/I465V |
| 4 | ppt | 475 | A11V/A99T/I225T/S370A |
| 4 | ppt | 475 | L22V/A99T/D198V/E392G |
| 4 | ppt | 475 | V31I/A99T/D352G/I465V |
| 4 | ppt | 475 | R32G/A99T/G179V/S370A |
| 4 | ppt | 475 | R41G/R83C/A99T/V444L |
| 4 | ppt | 475 | P46S/D347E/S370A/V444I |
| 4 | ppt | 475 | S76C/V149A/A281S/V444I |
| 4 | ppt | 475 | S76G/I265V/L348S/V444I |
| 4 | ppt | 475 | K81R/A99T/A281S/I465V |
| 4 | ppt | 475 | A102V/I265V/Y353H/S370A |
| 4 | ppt | 475 | F148L/I265V/Y353H/S370A |
| | | | 5 amino acids substitutions |
| 4 | ppt | 475 | A99T/V113I/A281S/V444L/A458P |
| 4 | ppt | 475 | A99T/F117L/D352G/S370A/I465V |
| 4 | ppt | 475 | A99T/V221A/I265V/D352G/V444I |
| 4 | ppt | 475 | A99T/V221A/A281S/D352G/I465V |
| 4 | ppt | 475 | A99T/I265V/D352G/V444I/I465V |
| 4 | ppt | 475 | A11V/G54S/A281S/S370A/E392G |
| 4 | ppt | 475 | T71S/M251V/I265V/Y353H/S370A |
| 4 | ppt | 475 | S76C/V149A/A281S/A398T/V444I |
| 4 | ppt | 475 | E88G/I265V/Y353H/S370A/K466T |
| 4 | ppt | 475 | V221A/G361R/S370A/E392G/A456T |
| | | | 6 amino acids substitutions |
| 4 | ppt | 475 | G54S/A99T/V149A/I265V/S370A/E392G |
| 4 | ppt | 475 | G54S/A99T/I265V/M387I/E392G/I465T |
| 4 | ppt | 475 | A99T/V255I/I265V/D352G/S370A/V444I |
| | | | 7 amino acids substitutions |
| 4 | ppt | 475 | A11V/A99T/A281S/S370A/P388S/ E392G/I465V |
| | | | 8 amino acids substitutions |
| 4 | ppt | 475 | G10S/A11V/T71A/S76C/A99T/A281S/ M371T/E392G |
| | | | 10 amino acids substitutions |
| 4 | ppt | 475 | A38G/R41C/E88G/F148L/I265V/Y353H/ S370A/V444L/W462C/K466T |

TABLE 1B

Table 1B shows nucleotide substitutions in Rubisco large subunit that were found to encode polypeptides that are functional and may influence either Rub

| Sequence Listing | Polypeptide (pnt) | Length | Identification and position of nucleotide polymorphism in wild type Rubisco large subunit polynucleotide of *Chlamydomonas reinhardtii* (SEQ ID NO: 1) |
|---|---|---|---|
| *Nucleotide mutation(s) causes 1 amino acid substitution* | | | |
| 3 | pnt | 1428 | g160a |
| 3 | pnt | 1428 | g295a |
| 3 | pnt | 1428 | t662c |
| 3 | pnt | 1428 | a793g |
| 3 | pnt | 1428 | g841t, t843a |
| 3 | pnt | 1428 | a1055g |
| 3 | pnt | 1428 | a1058g |
| 3 | pnt | 1428 | g1171a, t1172c |
| 3 | pnt | 1428 | a1175g |
| 3 | pnt | 1428 | g1192a |
| 3 | pnt | 1428 | g1330a |
| *Nucleotide mutations cause 2 amino acids substitutions* | | | |
| 3 | pnt | 1428 | g295a, a793g |
| 3 | pnt | 1428 | g295a, g841t, t843a |
| 3 | pnt | 1428 | g295a, a1055g |
| 3 | pnt | 1428 | g295a, t1108g |
| 3 | pnt | 1428 | g295a, a1175g |
| 3 | pnt | 1428 | g295a, g1330c |
| 3 | pnt | 1428 | g295a, g1330a |
| 3 | pnt | 1428 | g295a, g1372c |
| 3 | pnt | 1428 | g295a, a1393g |
| 3 | pnt | 1428 | g295a, a1397c |
| 3 | pnt | 1428 | g841t, t843a, t1057c |
| 3 | pnt | 1428 | g841t, t843a, a1175g |
| 3 | pnt | 1428 | g160a, g1192a |
| 3 | pnt | 1428 | c324a, a1075g, g1076a |
| 3 | pnt | 1428 | g691c, g1372c |
| 3 | pnt | 1428 | 1057c, t1108g |
| *Nucleotide mutations cause 3 amino acids substitutions* | | | |
| 3 | pnt | 1428 | g295a, g535a, a1175g |
| 3 | pnt | 1428 | g295a, t785c, a1393g |
| 3 | pnt | 1428 | g295a, a793g, a1055g |
| 3 | pnt | 1428 | g295a, a793g, a1175g |
| 3 | pnt | 1428 | g295a, g841t, t843a, a1055g |
| 3 | pnt | 1428 | g295a, a1055g, a1393g |
| 3 | pnt | 1428 | g295a, t1108g, a1175g |
| 3 | pnt | 1428 | g295a, t1108g, a1393g |
| 3 | pnt | 1428 | g295a, g1330a, g1372c |
| 3 | pnt | 1428 | c32t, g35c, g160a |
| 3 | pnt | 1428 | c32t, g160a, g295a |
| 3 | pnt | 1428 | c32t, a793g, a1175g |
| 3 | pnt | 1428 | c32t, a793g, g1330a |
| 3 | pnt | 1428 | c32t, g841t, t843a, a1393g |
| 3 | pnt | 1428 | c32t, g1171a, t1172c, a1414c |
| 3 | pnt | 1428 | g160a, g295a, g1192a |
| 3 | pnt | 1428 | g160a, c421t, g1330a |
| 3 | pnt | 1428 | g160a, a746g, a1175g |
| 3 | pnt | 1428 | g160a, t1108g, a1393g |
| 3 | pnt | 1428 | g28a, c32t, t662c |
| 3 | pnt | 1428 | g28a, c32t, g841t, t843a |
| 3 | pnt | 1428 | g28a, c32t, g1330a |
| 2 | pnt | 1428 | g28a, a233g, a1075g |
| 3 | pnt | 1428 | a257g, g295a, a1393g |
| 3 | pnt | 1428 | c282a, g295a, a1393g |
| 3 | pnt | 1428 | a283g, g295a, a1393g |
| 3 | pnt | 1428 | t302c, t1108g, a1175g |
| 3 | pnt | 1428 | t430c, a1175g, g1330a |
| 3 | pnt | 1428 | a439g, g536t, t1108g |
| 3 | pnt | 1428 | g536t, c737t, a1393g |
| 2 | pnt | 1428 | c545g, g841t, t843a, a1393g |
| 3 | pnt | 1428 | a793g, t1057c, t1108g |
| 3 | pnt | 1428 | c1041a, a1175g, g1330a |
| 3 | pnt | 1428 | g28a, c32t, g1330a |
| *Nucleotide mutations cause 4 amino acids substitutions* | | | |
| 3 | pnt | 1428 | g295a, c444a, t1108g, g1372c |
| 3 | pnt | 1428 | g295a, a793g, g841t, t843a, a1393g |
| 3 | pnt | 1428 | g295a, a793g, c1041a, a1393g |
| 3 | pnt | 1428 | g295a, a793g, t1057c, t1108g |
| 3 | pnt | 1428 | g295a, a793g, t1108g, a1175g |
| 3 | pnt | 1428 | g295a, g841t, t843a, a1055g, t1108g |
| 3 | pnt | 1428 | g295a, g841t, t843a, t1108g, a1175g |
| 3 | pnt | 1428 | g295a, g841t, t843a, t1108g, g1330a |
| 3 | pnt | 1428 | g295a, g1051c, a1055g, c1304t |
| 3 | pnt | 1428 | a124g, a793g, t1108g, a1393g |
| 3 | pnt | 1428 | g160a, g295a, t662c, g1192a |
| 3 | pnt | 1428 | g160a, g295a, g937a, g1330a |
| 3 | pnt | 1428 | g160a, g295a, t1108g, a1175g |
| 3 | pnt | 1428 | g160a, g295a, a1175g, g1330a |
| 3 | pnt | 1428 | g160a, t662c, g1161a, a1175g |
| 3 | pnt | 1428 | g160a, a793g, c1041a, a1393g |
| 3 | pnt | 1428 | g160a, g841t, t843a, t1108g, a1175g |
| 3 | pnt | 1428 | g160a, g1192a, t1265c, g1330a |
| 3 | pnt | 1428 | c444a, a793g, t1057c, t1108g |
| 3 | pnt | 1428 | a793g, t839c, t1108g, a1175g |
| 3 | pnt | 1428 | a793g, t1057c, t1061c, a1393g |
| 3 | pnt | 1428 | a793g, t1057c, t1108g, c1343g |
| 3 | pnt | 1428 | a793g, t1057c, a1058g, t1108g, a1393g |
| 3 | pnt | 1428 | c32t, g295a, t674c, t1108g |
| 3 | pnt | 1428 | t64g, g295a, a593t, a1175g |
| 3 | pnt | 1428 | g91a, g295a, a1055g, a1393g |
| 3 | pnt | 1428 | a94g, g295a, g536t, t1108g |
| 3 | pnt | 1428 | c121g, c247t, g295a, g1330c |
| 3 | pnt | 1428 | c136t, c1041a, t1108g, g1330a |
| 3 | pnt | 1428 | a226t, t446c, g841t, t843a, g1330a |
| 3 | pnt | 1428 | a226g, a793g, t1043c, g1330a |
| 3 | pnt | 1428 | a242g, g295a, g841t, t843a, a1393g |
| 3 | pnt | 1428 | c305t, a793g, t1057c, t1108g |
| 3 | pnt | 1428 | c444a, a793g, t1057c, t1108g |
| *Nucleotide mutations cause 5 amino acids substitutions* | | | |
| 3 | pnt | 1428 | g295a, g337a, g841t, t843a, g1330c, g1372c |
| 3 | pnt | 1428 | g295a, c351a, a1055g, t1108g, a1393g |
| 3 | pnt | 1428 | g295a, t662c, a793g, a1055g, g1330a |
| 3 | pnt | 1428 | g295a, t662c, g841t, t843a, a1055g, a1393g |
| 3 | pnt | 1428 | g295a, a793g, a1055g, g1330a, a1393g |
| 3 | pnt | 1428 | c32t, g160a, g841t, t843a, t1108g, a1175g |
| 3 | pnt | 1428 | c212g, a751g, a793g, t1057c, t1108g |
| 3 | pnt | 1428 | a226t, t446c, g841t, t843a, g1192a, g1330a |
| 3 | pnt | 1428 | a263g, a793g, t1057c, t1108g, a1397c |
| 3 | pnt | 1428 | t662c, g1081c, t1108g, a1175g, g1366a |
| *Nucleotide mutations cause 6 amino acids substitutions* | | | |
| 3 | pnt | 1428 | g160a, g295a, t446c, a793g, t1108g, a1175g |
| 3 | pnt | 1428 | g160a, g295a, a793g, g1161a, a1175g, t1394c |
| 3 | pnt | 1428 | g295a, g763a, a793g, a1055g, t1108g, g1330a |
| *Nucleotide mutations cause 7 amino acids substitutions* | | | |
| 3 | pnt | 1428 | c32t, g295a, g841t, t843a, t1108g, c1162t, a1175g, a1393g |
| *Nucleotide mutations cause 8 amino acids substitutions* | | | |
| 3 | pnt | 1428 | g28a, c32t, a211g, a226t, g295a, g841t, t843a, t1112c, a1175g |
| *Nucleotide mutations cause 10 amino acids substitutions* | | | |
| 3 | pnt | 1428 | c113g, c121t, a263g, c444a, a793g, t1057c, t1108g, g1330c, g1386t, a1397c |

DETAILED DESCRIPTION OF THE INVENTION

The present invention now will be described more fully hereinafter with reference to the accompanying examples, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains, having the benefit of the teachings presented in the descriptions and the drawings herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The articles "a" and "an" are used herein to refer to one or more than one (i.e., to at least one) of the grammatical object of the article. By way of example, "an element" means one or more than one element.

As used herein, the term "Rubisco large subunit" includes but is not limited to the sequences or substitutions, mutations or polymorphisms disclosed herein, their conservatively modified variants, regardless of source and any other variants which retain or increase the biological properties of the Rubisco large subunit, for example, Rubisco activity when expressed with a small subunit of Rubisco to form a functional Rubisco enzyme as disclosed herein.

Although *Chlamydomonas* Rubisco large subunit (rbcL) shares high amino acid sequence identity (about 90%) to other higher plant Rubisco large subunits, the present inventors believe, without wishing to be bound by this theory, that over-expression of *Chlamydomonas* rbcL in a higher plant is not likely to result in an optimally functional Rubisco enzyme complex with an endogenous Rubisco small subunit due to Rubisco large and small subunit compatibility problems.

The present inventors have discovered a method of identifying Rubisco large subunits that, when expressed with a Rubisco small subunit, have increased Rubisco activity in a higher plant cell. In one aspect, the method involves identifying amino acid substitutions in Rubisco large subunits that confer a functional Rubisco enzyme or increased Rubisco activity in a unicellular photosynthetic eukaryotic organism or lower plant cell. The Rubisco large subunit variants may be generated using shuffling or site-directed mutagenesis or other methods known to one skilled in the art. The variants, including Rubisco large subunit polypeptides or polynucleotides, may be assayed for Rubisco activity in vitro or in vivo.

As used interchangeably herein, "Rubisco activity", "biological activity of Rubisco" or "functional activity of Rubisco", refers to an activity exerted by a Rubisco enzyme of a large and small subunit of Rubisco, or portion of each subunit thereof, as determined in vivo or in vitro, according to standard techniques.

In a preferred embodiment, Rubisco activity is at least one or more of the following activities either in vivo or in vitro: (i) modulation of photosynthetic rate; (ii) modulation of carboxylase activity; (iii) modulation of $CO_2/O_2$ specificity; (iv) modulation of ribulose biphosphate (RuBP) carboxylase rate; (v) modulation of RuBP oxygenase rate, (vi) modulation of $K_m$ for $O_2$; (vii) modulation of $K_m$ for $CO_2$; (viii) modulation of ratio of $K_m$ for $CO_2$ to $K_m$ for $O_2$; (ix) modulation of velocity for $O_2$; (x) modulation of velocity for $CO_2$ and; (xi) plant productivity.

In one aspect, an increase in Rubisco activity includes but is not limited to increasing photosynthetic rate, increasing carboxylase activity and/or specificity, for example, increased ribulose biphosphate (RuBP) carboxylase rate, decreased RuBP oxygenase rate, increased $K_m$ for $O_2$, decreased $K_m$ for $CO_2$, decreased ratio of $K_m$ for $CO_2$ to $K_m$ for $O_2$, velocity for $O_2$ or $CO_2$ and the like as compared to a wild type Rubisco enzyme. In another aspect, an increase in Rubisco activity includes but is not limited to increasing photosynthetic rate and/or plant productivity.

This activity may be determined using any number of methods, including photoautotrophic or competitive growth assays, or assays that determine increased carboxylase activity and specificity, for example, increased RuBP carboxylase rate, decreased RuBP oxygenase rate, increased $K_m$ for $O_2$, decreased $K_m$ for $CO_2$, or decreased ratio of $K_m$ for $CO_2$ to $K_m$ for $O_2$ or combinations thereof.

In one aspect, the method includes screening one or more Rubisco large subunit variants in a host cell, such as a unicellular photosynthetic eukaryotic organism. Any suitable host cell may be used so long as the host cell allows for the Rubisco large and small subunits to form a Rubisco enzyme so that Rubisco activity can occur. In one aspect, the host cell allows for proper folding and processing of the Form I large subunit of Rubisco. In another aspect, the host cell is deficient in the large subunit of Rubisco but expresses the Rubisco small subunit so that Rubisco activity can occur with an exogenous Rubisco large subunit. The Rubisco small subunit may be endogenous or exogenous to the host cell.

In one aspect, the host cell is a unicellular photosynthetic eukaryotic organism. In one aspect, the unicellular photosynthetic eukaryotic organism is alga. In one aspect, the algae belongs to the genus of *Chlamydomonas* (Weeks, 1992, The Plant Cell), such as *Chlamydomonas reinhardtii*. In another aspect, the host cell is a *Chlamydomonas* rbcL deletion mutant, for example, the deltarbcL mutant named MX3312 (See Zhu G, Kurek I, True T, Zhang X, Majumdar M, Liu L and Lassner M (2005) Enhancing Photosynthesis by Improving Rubisco Carboxylase Activity and Specificity, and Rubisco Activase Thermostability through DNA Shuffling. In Photosynthesis: fundamental aspects to global perspectives. Proceedings of 13$^{th}$ International Congress on Photosynthesis, pp 841-843, Lawrence, Kans., USA). In another aspect, the host is a prokaryotic algae, such as *Synechococcus* ($S^+L^-$; for selecting L gene shufflants, $S^-L^+$; for selecting S gene shufflants). In another aspect, the host is a lower plant cell. In another aspect, the host cell is a higher plant cell, for example, a Rubisco-deficient tobacco mutant (e.g., H7 and Sp25; (Foyer et al. (1995) J. Exp. Botany 266:1445). Other exemplary host cells include without limitation maize, wheat, rice, sorghum, rye, millet, barley, soybean, sunflower, safflower, tobacco, alfalfa, potato, *Brassica* spp., cotton, tomato, tobacco cell and the like.

Use of unicellular photosynthetic eukaryotic organisms are advantageous in that they are amenable for high throughput screening. The host cell including a Rubisco large subunit variant may be assayed to identify one or more substitutions (mutations), deletions or polymorphisms in the Rubisco large subunit, for example, so that the large subunit variant, when expressed with a small Rubisco subunit, confers Rubisco activity. In another aspect, the method includes identifying the position and nature of the substitution, deletions or polymorphism(s) compared to the sequence of a wild type Rubisco large subunit or template used to generate to the variant. The method also includes correlating the position and nature of the mutation or polymorphism identified in the variant to a corresponding position in a higher plant rbcL sequence. In one aspect, the method provides for making the amino acid substitutions identified in the variant in a Rubisco large subunit sequence of a higher plant cell. The Rubisco large subunit sequence of a higher plant cell may be derived from or endogenous to a maize, wheat, rice, sorghum, rye, millet, barley, soybean, sunflower, safflower, tobacco, alfalfa, potato, *Brassica* spp., cotton, tomato, or tobacco cell and the like.

In another aspect, the higher plant cell Rubisco large subunit sequence is introduced into a higher plant cell. Any polynucleotide encoding a Rubisco large subunit variant may be expressed in any suitable host cell so long as the Rubisco large subunit variant is compatible with the host cell's Rubisco small subunit to form a functional Rubisco enzyme with Rubisco activity. Accordingly, the host cell and the Rubisco large subunit variant may be from differing organisms, plants or species thereof. Without wishing to be bound by this theory, the present inventors believe that this method will allow for the identification of Rubisco large subunits that, when expressed in a higher plant cell or chloroplast thereof, have increased Rubisco activity or plant productivity in a higher plant cell or chloroplast by decreasing Rubisco large and small subunit incompatibility caused by overexpression of a native non-modified Rubisco large subunit endogenous to another organism, such as algae.

The present inventors have demonstrated that mutations identified in *Chlamydomonas reinhardtii* Rubisco large subunit as conferring photoautotrophic growth and/or competitive growth in *Chlamydomonas reinhardtii* when "transferred" to a Rubisco large subunit tobacco sequence and expressed as a transgenic in tobacco plants result in Rubisco enzymes with increased Rubisco activity and plants with improved properties, for example, increased plant productivity. This method of identifying amino acid substitutions in a Rubisco large subunit that have increased Rubisco activity in a higher plant cell by first identifying amino acid substitutions in a unicellular photosynthetic eukaryotic organism or lower plant cell and transferring the polymorphisms, mutations or substitutions to a Rubisco large subunit of a higher plant is believed to be applicable to increasing Rubisco activity in numerous higher plants, not just tobacco.

In addition, the present invention provides novel compositions and methods for modulating, for example, increasing or decreasing, the level of Rubisco large subunit protein in a plant cell or plant. In particular, the polynucleotides and polypeptides of the present invention can be used to generate transgenic plants expressing Rubisco large subunits of the present invention. The present inventors have discovered at least 111 novel Rubisco large subunit variants and at least 78 substitutions that alone or in combination may increase Rubisco activity or plant productivity, for example, in a higher plant. Modulation of the Rubisco large subunits of the present invention would provide a mechanism for increasing a plant's productivity, for example, increased biomass, increased plant yield, increased plant growth rate, increased plant size, such as increased plant leaf size, shoot growth, root growth, increased seed weight and viability, or enhanced plant development, such as earlier flowering. Thus, the present invention also provides methods for modulating, for example, increasing or decreasing, a plant's growth or productivity using Rubisco large subunit polynucleotides and polypeptides of the present invention or identified by methods of the present invention.

In one embodiment, the present invention includes a method of identifying Rubisco large subunits that, when expressed with a Rubisco small subunit in a higher plant cell, have increased Rubisco activity. One aspect of the method includes identifying one or more amino acid substitutions in a Rubisco large subunit polypeptide that confers Rubisco activity or increased Rubisco activity in a host cell of a unicellular photosynthetic eukaryotic organism or lower plant cell when compared to a control, e.g. Rubisco activity of a Rubisco large subunit that does not contain the one or more of the amino acid substitutions.

Polynucleotides of the present invention encoding Rubisco large subunit variants having amino acid substitutions and Rubisco activity, e.g. increased Rubisco activity, may be created by any number of methods, including but not limited to shuffling, site-directed mutagenesis, and the like. For example, routine molecular biology techniques may be used to substitute 1, 2, 3, 4, 5, 6, 7, 8, 9, 10 or more amino acid residues in a Rubisco large subunit polypeptide so that the substituted Rubisco polypeptide differs from the polypeptide encoded by the parental or template Rubisco large subunit polynucleotide. In one aspect, the parental or template Rubisco large subunit polynucleotide is endogenous to a unicellular photosynthetic eukaryotic organism, lower plant cell or higher plant cell. In one aspect, the parental or template Rubisco large subunit polynucleotide is wild type.

Rubisco large subunit polynucleotides may be generated by any suitable shuffling method, for example, from one or more parental Rubisco large subunit sequences. The shuffling may optionally include mutagenesis, in vitro manipulation, in vivo manipulation of one or more sequences or in silico manipulation of sequences. The resultant shuffled polynucleotides may be introduced into a suitable host cell, typically in the form of expression cassettes wherein the shuffled polynucleotide sequence encoding the Rubisco large subunit may be operably linked to a transcriptional regulatory sequence and any necessary sequences for ensuring transcription, translation, and processing of the encoded Rubisco large subunit protein. Each such expression cassette or its shuffled Rubisco large subunit encoding sequence can be referred to as a "library member" composing a library of shuffled Rubisco large subunit sequences. In one aspect, *Chlamydomonas* rbcL libraries may be constructed from single gene shuffling or semi-synthetic shuffling or combinations thereof in which the oligonucleotides are "spiked" to contain amino acid substitutions that differ from wild type Rubisco large subunits endogenous to the host cell. See Examples 2 as described herein. The library may be introduced into a population of host cells, such that individual host cells receive substantially one or a few species of library member(s), to form a population of shufflant host cells expressing a library of shuffled Rubisco large subunit species.

A variety of Rubisco large and small subunit genomic, cDNA, mRNA sources are known and can be used in the recombination processes herein. Coding sequences for Rubisco L and S subunits for various species are disclosed in the literature and Genbank, among other public sources, and may be obtained by cloning, PCR, or from deposited materials. For example, as noted, a variety of references herein describe such genes. For example, Croy, (ed.) (1993) Plant Molecular Biology Bios Scientific Publishers, Oxford, U.K. describes several Rubisco genes and sequence sources in public databases. Examples of public databases that include Rubisco sources include: Genbank: ncbi.nlm.nih.gov/genbank/: EMBL: ebi.ac.uk.embl/: as well as, e.g., the protein databank, Brookhaven Laboratories; the University of Wisconsin Biotechnology Center, the DNA databank of Japan, Laboratory of genetic Information Research, Misuina, Shizuda, Japan. As noted, over 1,000 different Rubisco homologues are available in Genbank alone. In addition, specific internet sites which provide information regarding Rubisco include, e.g., world wide web at ss.tnaes.affrc.go jp/pub/suzuki/rubisco.html; icdweb.cc.purdue.edu/.about.knollje/Rubisco.html; agron.missouri.edu/cgi-bin/sybgw_mdb/mdb3/Locus/114858; gdb.wehi.edu.au/scop/data/scop.

1.004.037.001.000.000.html; blc.arizona.edu/courses/181 gh/rick/photosynthesis/Calvin.html-; tarweed.com/pgr/ PGR98-207.html; and homepage.ruhr-uni-bochum.de/Marc-.Saric/rubisco3.html.

The following publications describe a variety of recursive recombination procedures and/or methods which can be incorporated into such procedures, e.g., for shuffling of Rubisco polynucleotides and/or fragments: Stemmer, et al., (1999) "Molecular breeding of viruses for targeting and other clinical properties. Tumor Targeting" 4:1-4; Nesset al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proceedings of the National Academy of Sciences, U.S.A. 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling", Nature Biotechnology 14:315-319; Gates et al. (1996) "Affinity selective isolation of ligands from peptide libraries through display on a lac repressor 'headpiece dimer'" Journal of Molecular Biology 255:3732 386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid form large numbers of oligodeoxyribonucleotides" Gene, 164:49-53; Stemmer (1995) "The Evolution of Molecular Computation" Science 270:1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: in vitro recombination for molecular evolution." Proceedings of the National Academy of Sciences. U.S.A. 91:10747-10751.

Additional details regarding DNA shuffling methods are found in numerous U.S. Patents, including: U.S. Pat. No. 5,605,793 to Stemmer (Feb. 25, 1997), "Methods For in vitro Recombination;" U.S. Pat. No. 5,811,238 to Stemmer et al. (Sep. 22, 1998) "Methods for Generating Polynucleotides Having Desired Characteristics by Iterative Selection and Recombination"; U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction," and U.S. Pat. No. 5,837,458 to Minshull, et al. (Nov. 17, 1998), "Methods and Compositions for Cellular and Metabolic Engineering."

In addition, details and formats for DNA shuffling are found in a variety of PCT and foreign patent application publications, including: Stemmer and Crameri, "DNA Mutagenesis by Random Fragmentation and Reassembly" WO95/22625; Stemmer and Lipshutz "End Complementary Polymerase Chain Reaction" WO96/33207; Stemmer and Crameri "Methods for Generating Polynucleotides Having Desired Characteristics by Iterative Selection and Recombination" WO97/0078; Minshul and Stemmer, "Methods and Compositions for Cellular and Metabolic Engineering" WO97/35966; Punnonen et al. "Targeting of Genetic Vaccine Vectors" WO99/41402; Punnonen et al. "Antigen Library Immunization" WO99/41383; Punnonen et al. "Genetic Vaccine Vector Engineering" WO99/41369; Punnonen et al. "Optimization of Immunomodulatory Properties of Genetic Vaccines" WO99/41368; Stemmer and Crameri, "DNA Mutagenesis by Random Fragmentation and Reassembly" EP 0934999; Stemmer "Evolving Cellular DNA Uptake by Recursive Sequence Recombination" EP 0932670; Stemmer et al., "Modification of Virus Tropism and Host Range by Viral Genome Shuffling" WO99/23107; Apt et al., "Human Papillomavirus Vectors" WO99/21979; Del Cardayre et al. "Evolution of Whole Cells and Organisms by Recursive Sequence Recombination" WO98/31837; Patten and Stemmer, "Methods and Compositions for Polypeptide Engineering" WO98/27230; Stemmer et al., and "Methods for Optimization of Gene Therapy by Recursive Sequence Shuffling and Selection" WO98/13487.

Certain U.S. Applications provide additional details regarding DNA shuffling and related techniques, including "Shuffling of Codon Altered Genes" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407, 800; "Evolution of Whole Cells and Organisms by Recursive Sequence Recombination", by del Cardyre et al. filed Jul. 15, 1998 (U.S. Ser. No. 09/166,188), and Jul. 15, 1999 (U.S. Ser. No. 09/354,922); "Oligonucleotide Mediated Polynucleotide Recombination" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408, 392; and "Use of Codon-Based Oligonucleotide Synthesis for Synthetic Shuffling" by Welch et al., filed Sep. 28, 1999 (U.S. Ser. No. 09/408,393); and "Methods for Making Character Strings, Polynucleotides & Polypeptides Having Desired Characteristics" by Selifonov and Stemmer, filed Feb. 5, 1999 (U.S. Ser. No. 60/118,854) and "Methods for Making Character Strings, Polynucleotides & Polypeptides Having Desired Characteristics" by Selifonov et al. filed Oct. 12, 1999 (U.S. Ser. No. 09/416,375).

As review of the foregoing publications, patents, published applications and U.S. patent applications reveals, recursive recombination and selection of polynucleotides to provide new Rubisco large subunit polynucleotides with increased Rubisco activity can be carried out by a number of established methods. Any of these methods can be adapted to the present invention to evolve Rubisco large subunit coding polynucleotides or homologues to produce new Rubisco large subunit polypeptides with increased Rubisco activity. Both the methods of making such enzymes and the enzymes or enzyme coding libraries produced by these methods are encompassed by the present invention.

A number of different general classes of recombination methods may be used to generate Rubisco large subunits of the present invention. First, polynucleotides can be recombined in vitro by any of a variety of techniques discussed in the references above, including e.g., DNAse digestion of polynucleotides to be recombined followed by ligation and/or PCR reassembly of the polynucleotides. Second, polynucleotides can be recursively recombined in vivo, e.g., by allowing recombination to occur between polynucleotides in cells.

Third, whole cell genome recombination methods can be used in which whole genomes of cells are recombined, optionally including spiking of the genomic or chloroplast recombination mixtures so that they encode the desired amino acid substitutions shown to produce functional Rubisco enzymes through complementation or confer a growth advantage to the host cells. See, for example, Example 10. Fourth, synthetic recombination methods can be used, in which oligonucleotides corresponding to different Rubisco homologues are synthesized and reassembled in PCR or ligation reactions which include oligonucleotides which correspond to more than one parental polynucleotide, thereby generating new recombined polynucleotides. Oligonucleotides can be made by standard nucleotide addition methods, or can be made, e.g., by tri-nucleotide synthetic approaches. Fifth, in silico methods of recombination can be effected in which genetic algorithms are used in a computer to recombine sequence strings which correspond to Rubisco large subunit homologues. The resulting recombined sequence strings are optionally converted into polynucleotides by synthesis of polynucleotides which correspond to the recombined sequences, e.g., in concert with oligonucleotide synthesis/gene reassembly techniques. Any of the preceding general recombination formats can be practiced in a reiterative fashion to generate a more diverse set of recombinant polynucleotides.

Combinations of in vitro and in vivo shuffling may be used to enhance combinatorial diversity. As mentioned previously, "in silico" shuffling may be used to generate Rubisco large subunit polynucleotides using computer algorithms to perform "virtual" shuffling using genetic operators in a computer. As applied to the present invention, Calvin or Krebs cycle enzymes such as Rubisco large subunit polynucleotide sequence strings may be recombined in a computer system and desirable products are made, e.g., by reassembly PCR or ligation of synthetic oligonucleotides, or other available techniques. In silico shuffling may be described in detail in Selifonov and Stemmer in "Methods for Making Character Strings, Polynucleotides & Polypeptides Having Desired Characteristics" filed Feb. 5, 1999, U.S. Ser. No. 60/118,854 and "Methods for Making Character Strings, Polynucleotides & Polypeptides Having Desired Characteristics" by Selifonov et al. filed Oct. 12, 1999 (U.S. Ser. No. 09/416,375). In brief, genetic operators (algorithms which represent given genetic events such as point mutations, recombination of two strands of homologous polynucleotides, etc.) are used to model recombinational or mutational events which can occur in one or more polynucleotide, e.g., by aligning polynucleotide sequence strings (using standard alignment software, or by manual inspection and alignment) and predicting recombinational outcomes based upon selected genetic algorithms (mutation, recombination, etc.). The predicted recombinational outcomes are used to produce corresponding molecules, e.g., by oligonucleotide synthesis and reassembly PCR. As applied to the present invention, Rubisco polynucleotides are aligned and recombined in silico, using any desired genetic operator, to produce character strings which are then generated synthetically for subsequent screening.

Another shuffling format may be referred to as "oligonucleotide mediated shuffling" where oligonucleotides corresponding to a family of related homologous polynucleotides (e.g., as applied to the present invention, families of homologous Rubisco variants of a polynucleotide) are recombined to produce selectable Rubisco large subunit polynucleotides. This format is be described in detail in Crameri et al. "Oligonucleotide Mediated Polynucleotide Recombination" filed Feb. 5, 1999, U.S. Ser. No. 60/118,813, Crameri et al. "Oligonucleotide Mediated Polynucleotide Recombination" filed Jun. 24, 1999, U.S. Ser. No. 60/141,049; Crameri et al. "Oligonucleotide Mediated Polynucleotide Recombination" filed Sep. 28, 1999 (U.S. Ser. No. 09/408,392); and "Use of Codon-Based Oligonucleotide Synthesis for Synthetic Shuffling" by Welch et al., filed Sep. 28, 1999 (U.S. Ser. No. 09/408,393). In brief, selected oligonucleotides corresponding to multiple homologous parental polynucleotides are synthesized, ligated and elongated (typically in a recursive format), typically either in a polymerase or ligase-mediated elongation reaction, to produce full-length Rubisco large subunit polynucleotides. The technique can be used to recombine homologous or even non-homologous Rubisco large subunit polynucleotide sequences.

One advantage of oligonucleotide-mediated recombination may be the ability to recombine homologous polynucleotides with low sequence similarity, or even non-homologous polynucleotides. In these low-homology oligonucleotide shuffling methods, one or more set of fragmented polynucleotides (e.g., oligonucleotides corresponding to multiple Rubisco large subunit polynucleotides) are recombined, e.g., with a set of crossover family diversity oligonucleotides. Each of these crossover oligonucleotides have a plurality of sequence diversity domains corresponding to a plurality of sequence diversity domains from homologous or non-homologous polynucleotides with low sequence similarity. The fragmented oligonucleotides, which are derived by comparison to one or more homologous or non-homologous polynucleotides, can hybridize to one or more region of the crossover oligonucleotides, facilitating recombination.

When recombining homologous polynucleotides, sets of overlapping family gene shuffling oligonucleotides (which are derived by comparison of homologous polynucleotides, by synthesis of corresponding oligonucleotides) are hybridized and elongated (e.g., by reassembly PCR or ligation), providing a population of recombined polynucleotides, which can be selected for a desired trait or property. The set of overlapping family shuffling gene oligonucleotides includes a plurality of oligonucleotide member types which have consensus region subsequences derived from a plurality of homologous target polynucleotides.

In one aspect, family gene shuffling oligonucleotides that include one or more Rubisco large subunit polynucleotide(s) are provided by aligning homologous polynucleotide sequences to select conserved regions of sequence identity and regions of sequence diversity. A plurality of family gene shuffling oligonucleotides may be synthesized (serially or in parallel) which correspond to at least one region of sequence diversity.

Sets of fragments, or subsets of fragments used in oligonucleotide shuffling approaches can be provided by cleaving one or more homologous polynucleotides (e.g., with a DNase), or, more commonly, by synthesizing a set of oligonucleotides corresponding to a plurality of regions of at least one polynucleotide (typically oligonucleotides corresponding to a full-length polynucleotide may be provided as members of a set of polynucleotide fragments). Cleavage fragments may be used in conjunction with family gene shuffling oligonucleotides, e.g., in one or more recombination reaction to produce recombinant Rubisco large subunit polynucleotide(s).

Another approach of shuffling may be found in "Shuffling of Codon Altered Genes" by Patten et al. filed Sep. 29, 1998, (U.S. Ser. No. 60/102,362), Jan. 29, 1999 (U.S. Ser. No. 60/117,729), and Sep. 28, 1999, PCT/US99/22588. One way of generating diversity in a set of polynucleotides to be shuffled (i.e., as applied to the present invention, Rubisco large subunit polynucleotides), may be to provide "spiked" polynucleotides containing mutations shown to functionally complement Rubisco small subunits and/or confer faster growth to a host cell by synthesizing polynucleotides in which the nucleotides which encode certain amino acid residues are altered, it may be possible to access a completely different mutational spectrum upon subsequent mutation of the polynucleotide. This increases the sequence diversity of the starting polynucleotides for shuffling protocols, which alters the rate and results of forced evolution procedures. Codon modification procedures can be used to modify any Rubisco large subunit polynucleotide or shuffled polynucleotide, e.g., prior to performing DNA shuffling.

The above references provide these and other basic recombination formats as well as many modifications of these formats. Regardless of the format which may be used, the polynucleotides of the invention can be recombined (with each other or with related (or even unrelated) polynucleotides to produce a diverse set of recombinant polynucleotides, including homologous polynucleotides.

Thus, in a general aspect, a sequence shuffling method provides for generating libraries or cells containing recombinant Rubisco large subunit polynucleotides that may be screened for Rubisco activity, for example, increased Rubisco activity. Libraries of recombinant polynucleotides are generated from a population of related-sequence polynucleotides which comprise sequence regions which have substantial sequence identity and can be homologously recombined in vitro or in vivo. In the method, at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide. Recombination systems suitable for generating sequence-recombined polynucleotides can be either: (1) in vitro systems for homologous recombination or sequence shuffling via amplification or other formats or (2) in vivo systems for homologous recombination or site-specific recombination.

The population of sequence-recombined Rubisco large subunit polynucleotides comprises a subpopulation of polynucleotides which are suspected of encoding polypeptides with Rubisco activity, preferably increased Rubisco activity. The selected sequence-recombined polynucleotides may be subjected to at least one recursive cycle wherein at least one selected sequence-recombined polynucleotide may be combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined Rubisco large subunit polynucleotides possessing increased Rubisco activity.

Polynucleotide sequence shuffling may be a method for recursive in vitro or in vivo homologous or non-homologous recombination of pools of Rubisco large subunit polynucleotide fragments or polynucleotides (e.g., genes from agricultural organisms or portions thereof). Mixtures of related Rubisco large subunit polynucleotide sequences or polynucleotides are randomly or pseudorandomly fragmented, and reassembled to yield a library or mixed population of recombinant Rubisco large subunit polynucleotides or polypeptides.

The present invention may be directed to a method for generating selected Rubisco large subunit polynucleotide sequences or a population of selected polynucleotide sequences, typically in the form of amplified and/or cloned polynucleotides, whereby the selected polynucleotide sequence(s) encode a Rubisco large subunit polypeptide variant that, when combined with a Rubisco small subunit or subunits thereof to form Rubisco enzymes, can be selected for, and whereby the selected polynucleotide sequences have Rubisco activity, for example, increased Rubisco activity.

In a general aspect, the invention provides a method for generating libraries of recombinant polynucleotides having a subpopulation of library members which encode a Rubisco large subunit protein variant having increased Rubisco activity when complemented with a Rubisco small subunit. Libraries of recombinant polynucleotides are generated from a population of related-sequence Rubisco large subunit polynucleotides which comprise sequence regions which have substantial sequence identity and can be homologously recombined in vitro or in vivo. In another aspect, the libraries may be "spiked" to contain mutations not found in wild type Rubisco large subunits and that are found to produce functional Rubisco enzymes and/or confer growth advantages to a host cell. See Examples 2 and 3 as described herein.

In one aspect, at least two Rubisco large subunit polynucleotides are combined in a recombination system suitable for generating sequence-recombined polynucleotides. In one aspect, the method includes a Rubisco large subunit endogenous to the host cell that may be used as a template, for example, a shuffling template. In one aspect, the template is a rbcL gene or cDNA or other nucleotide sequence from an alga, preferably from the genus of *Chlamydomonas* or a species of *Chlamydomonas*, preferably from *Chlamydomona reinhardtii*. In another aspect, the polynucleotides may be from a number of different organisms or species if desired, including but not limited to those of higher or lower plants, for example, maize, wheat, rice, sorghum, rye, millet, barley, soybean, sunflower, safflower, tobacco, alfalfa, potato, *Brassica* spp., cotton, tomato, or tobacco and the like.

Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein, or template-switching of a retroviral genome replication event. The population of sequence-recombined polynucleotides comprises a subpopulation of Rubisco large subunit polynucleotides which possess desired or advantageous enzymatic characteristics and which can be selected by a suitable selection or screening method. The selected sequence-recombined Rubisco large subunit polynucleotides, which may be related-sequence Rubisco large subunit polynucleotides, can then be subjected to at least one recursive cycle wherein at least one selected sequence-recombined Rubisco large subunit polynucleotide may be combined with another related-sequence Rubisco large subunit polynucleotide (which may itself be a selected sequence-recombined polynucleotide) in a recombination system suitable for generating sequence-recombined Rubisco large subunit polynucleotides, such that additional generations of sequence-recombined polynucleotide sequences are generated from the selected sequence-recombined polynucleotides obtained by the selection or screening method employed.

In this manner, recursive sequence recombination generates library members which are sequence-recombined polynucleotides possessing increased Rubisco activity when in the form of a complex with a Rubisco small subunit.

In one aspect, Rubisco large subunit polynucleotides, e.g. library members, may be fragmented and homologously recombined by PCR in vitro. Fragment generation may be by nuclease digestion, partial extension PCR amplification, PCR stuttering, or other suitable fragmenting means, such as described herein and in WO95/22625 published Aug. 24, 1995, and in commonly owned U.S. Ser. No. 08/621,859 filed Mar. 25, 1996, PCT/US96/05480 filed Apr. 18, 1996, which are incorporated herein by reference. Stuttering may be fragmentation by incomplete polymerase extension of templates. A recombination format based on very short PCR extension times can be employed to create partial PCR products, which continue to extend off a different template in the next (and subsequent) cycle(s), and effect de facto fragmentation. Template-switching and other formats which accomplish sequence shuffling between a plurality of Rubisco large subunit sequence-related polynucleotides can be used. Such alternative formats will be apparent to those skilled in the art.

In one aspect, Rubisco large subunit polynucleotides, e.g. library members, may be fragmented in vitro, the resultant fragments transferred into a host cell or organism and homologously recombined to form shuffled Rubisco large subunit polynucleotides, in vivo. In one aspect, Rubisco large subunit polynucleotides, e.g. library members, may be cloned or amplified on episomally replicable vectors, a multiplicity of said vectors may be transferred into a cell and homologously recombined to form Rubisco large subunit polynucleotides, e.g. library members, in vivo.

In one aspect, Rubisco large subunit polynucleotides, e.g. library members, may be not fragmented, but may be cloned or amplified on an episomally replicable vector as a direct repeat or indirect (or inverted) repeat, which each repeat comprising a distinct species of selected Rubisco large subunit polynucleotide sequences, said vector may be transferred into a cell and homologously recombined by intra-vector or inter-vector recombination to form shuffled library members in vivo.

In one aspect, combinations of in vitro and in vivo shuffling are provided to enhance combinatorial diversity. The recombination cycles (in vitro or in vivo) can be performed in any order desired by the practitioner. In one aspect, the first plurality of selected library members may be fragmented and homologously recombined by PCR in vitro. Fragment generation may be by nuclease digestion, partial extension PCR amplification, PCR stuttering, or other suitable fragmenting means, such as described herein and in the documents incorporated herein by reference. Stuttering may be fragmentation by incomplete polymerase extension of templates.

In one aspect, Rubisco large subunit polynucleotides, e.g. library members, may be fragmented in vitro, the resultant fragments transferred into a host cell or organism and homologously recombined to form shuffled Rubisco large subunit polynucleotides, e.g. library members, in vivo. In an aspect, the host cell may be a unicellular photosynthetic eukaryotic organism or a plant cell. In one aspect, the plant cell has been engineered to contain enhanced recombination systems, such as an enhanced system for general homologous recombination (e.g., a plant expressing a recA protein or a plant recombinase from a transgene or plant virus) or a site-specific recombination system (e.g., a cre/LOX or frt/FLP system encoded on a transgene or plant virus).

In one aspect, Rubisco large subunit polynucleotides, e.g. library members, may be cloned or amplified on episomally replicable vectors, a multiplicity of said vectors may be transferred into a cell and homologously recombined to form shuffled library members in vivo in a plant cell, algae cell, or bacterial cell. Other cell types may be used, if desired.

In one aspect, Rubisco large subunit polynucleotides, e.g. library members, may not be fragmented, but may be cloned or amplified on an episomally replicable vector as a direct repeat or indirect (or inverted) repeat, with each repeat comprising a distinct species of Rubisco large subunit polynucleotide sequences, said vector may be transferred into a cell and homologously recombined by intra-vector or inter-vector recombination to form shuffled library members in vivo in a plant cell, algae cell, or microorganism.

In one aspect, the method employs at least one parental polynucleotide sequence that encodes a Rubisco subunit of a marine algae, such as, for example and not limitation, an rbcL (large Rubisco subunit) polynucleotide sequence, for example, gene or cDNA sequence from *Chlamydomonas reinhardtii, Cylindrotheca fusiformis, Olisthodiscus luteus, Cryptomonas*, and *Porphyridium*, among others having Rubisco enzymes with a high ratio of carboxylase to oxygenase activity (Read B A and Tabita F R (1994) Arch. Biochem. Biophys. 312:210) or a species from a C3 or C4 plant. The parental Rubisco polynucleotide may be subjected to mutagenesis and/or shuffling or combinations thereof to generate a population of mutagenized Rubisco large subunit polynucleotides which have substantial sequence identity to the parental Rubisco large subunit polynucleotide sequence. The population of mutagenized polynucleotides may be transferred into a population of host cells wherein the mutagenized polynucleotides are expressed and the resultant transformed host cell population (transformants) may be selected or screened for increased Rubisco activity or a phenotype thereof.

A variety of suitable host cells for shuffling or determining Rubisco large subunit sequences will be apparent to those skilled in the art. Any suitable host cell may be used so long as the host cell allows for the Rubisco large and small subunits to form a Rubisco enzyme so that Rubisco activity can occur. In one aspect, the host cell allows for proper folding and processing of the Form I large subunit of Rubisco. In another aspect, the host cell is deficient in the large subunit of Rubisco but expresses the Rubisco small subunit so that Rubisco activity can occur with an exogenous Rubisco large subunit. The Rubisco small subunit may be endogenous or exogenous to the host cell.

The method of the present invention may include replacing the endogenous rbcL gene of a host cell with a polynucleotide that encodes a Rubisco large subunit variant. The polynucleotide may be operably linked to a polynucleotide encoding a selectable marker gene, for example, in an expression cassette. Such selectable markers will be known by one skilled in the art and as described elsewhere herein. Transformants may be propagated on a selective medium to select for those transformants that contain a sequence encoding a Rubisco variant in expressible form.

In some instances, the present invention may include replacing the endogenous rbcL gene of a host cell with a selectable marker gene, for example, in an expression cassette and maintaining the cells with medium having sugar that allows the cells to compensate for the loss of the endogenous Rubisco large subunit and bypass the photosynthetic pathway. Transformants may be propagated on a selective medium to select for those transformants that contain the selectable marker. The cells may then be further transformed with a polynucleotide that encodes a Rubisco large subunit variant and cells containing the Rubisco variant identified, for example, by the ability of the cell to grow in the absence of supplemented sugar. See, for example, Example 11.

In one aspect, the host cell is a unicellular photosynthetic eukaryotic organism. In one aspect, the unicellular photosynthetic eukaryotic organism is algae. In one aspect, the algae is *Chlamydomonas* (Weeks, 1992, The Plant Cell), such as *Chlamydomonas reinhardtii*, *Synechococcus* ($S^+L^-$; for selecting L gene shufflants, $S^-L^+$; for selecting S gene shufflants). In another aspect, the host cell is *Chlamydomonas* rbcL deletion mutant, for example, the deltarbcL mutant named MX3312 (See Zhu G, Kurek I, True T, Zhang X, Majumdar M, Liu L and Lassner M (2005) Enhancing Photosynthesis by Improving Rubisco Carboxylase Activity and Specificity, and Rubisco Activase Thermostability through DNA Shuffling. In Photosynthesis: fundamental aspects to global perspectives. Proceedings of 13th International Congress on Photosynthesis, pp 841-843, Lawrence, Kans., USA). In another aspect, the host is a lower plant cell. In another aspect, the host cell is a higher plant cell, for example, a Rubisco-deficient tobacco mutant (e.g., H7 and Sp25; (Foyer et al. (1995) J. Exp. Botany 266:1445). In another aspect, the host cell is a maize, wheat, rice, sorghum, rye, millet, barley, soybean, sunflower, safflower, tobacco, alfalfa, potato, *Brassica* spp., cotton, tomato, or tobacco cell.

In one aspect, a method of identifying Rubisco large subunits that, when expressed with a Rubisco small subunit, have increased Rubisco activity in a higher plant cell includes transforming a host cell with a polynucleotide encoding the Rubisco large subunit variant to obtain a transformant. In one aspect, the Rubisco large subunit polynucleotide encodes a polypeptide containing 1, 2, 3, 4, 5, 6, 7, 8, 9, 10 or more amino acid substitutions compared to the polypeptide encoded by a parental or template Rubisco large subunit polynucleotide. In another aspect, the method includes transferring a library of Rubisco large subunit polynucleotides encoding polypeptides into a plurality of host cells, for example, unicellular photosynthetic eukaryotic organisms, thereby forming a library of transformants wherein the Rubisco large subunit polynucleotides encoding Rubisco large subunit variants are expressed. In one aspect, the unicellular photosynthetic eukaryotic organism is algae.

The host cells comprising polynucleotides encoding Rubisco large subunit variants may be screened to isolate or identify host cells and/or their progeny which express Rubisco large subunit(s) having the desired enhanced phenotype. For example, host cells, such as unicellular photosynthetic eukaryotic organisms, comprising the variant Rubisco large subunit encoding sequences may be identified as having Rubisco activity, that is, a functional Rubisco enzyme, using complementation assays. For example, photoautotrophic growth assays using a host cell such as MX3312 that requires a functional large Rubisco subunit to restore photoautotrophic growth may be employed. The medium conditions necessary for non-autotrophic or autotrophic growth of a host organism will be known to those skilled in the art.

Tables 1A and 1B set forth the positions and amino acid residue or nucleotide substitutions of at least 111 Rubisco large subunit variants of wild type *Chlamydomonas* Rubisco (SEQ ID NO:2 and SEQ ID NO:1) identified by the present inventors. These Rubisco large subunits have Rubisco activity, specifically they were found to generate a functional Rubisco when combined with a wild type *Chlamydomonas* Rubisco small subunit and many confer competitive growth advantages to host cells that contain them. (See Table 2 and Examples 2-3).

TABLE 2A

Sequence analysis of photosynthesis-competent variants. (PS: the substitutions found in the photosynthesis-competent variants. CG: the substitutions appeared with high frequency after competitive growth)

| | Position | | | | | | | | | |
|---|---|---|---|---|---|---|---|---|---|---|
| | 10 | 11 | 12 | 22 | 31 | 32 | 38 | 41 | 42 | 46 |
| WT | G | A | G | L | V | R | A | R | M | P |
| PS | S | V | A | V | I | G | G | G/C | V | S |
| CG | | | | | | | | | V | |

| | Position | | | | | | | | | |
|---|---|---|---|---|---|---|---|---|---|---|
| | 54 | 71 | 76 | 78 | 81 | 83 | 86 | 88 | 94 | 95 |
| WT | G | T | S | D | K | R | D | E | D | N |
| PS | S | S/A | C/G | G | R | C | G | G | E | D |
| CG | | | | | | | G | | | |

| | Position | | | | | | | | | |
|---|---|---|---|---|---|---|---|---|---|---|
| | 99 | 101 | 102 | 108 | 113 | 117 | 141 | 144 | 147 | 148 |
| WT | A | V | A | F | V | F | P | Y | T | F |
| PS | T | A | V | L | I | L | S | H | A | L |
| CG | T | | V | | | | | | | |

| | Position | | | | | | | | | |
|---|---|---|---|---|---|---|---|---|---|---|
| | 149 | 179 | 182 | 198 | 221 | 225 | 231 | 246 | 249 | 251 |
| WT | V | G | A | D | V | I | E | T | E | M |
| PS | A | S/V | G | V | A | T | Q | I | G | V |
| CG | | | | | | | | | | |

TABLE 2A-continued

Sequence analysis of photosynthesis-competent variants. (PS: the substitutions found in the photosynthesis-competent variants. CG: the substitutions appeared with high frequency after competitive growth)

| | Position | | | | | | | | |
|---|---|---|---|---|---|---|---|---|---|
| | 255 | 262 | 265 | 280 | 281 | 313 | 347 | 348 | 351 | 352 |
| WT | V | V | I | L | A | V | D | L | D | D |
| PS | I | V | V | S | S | I | E | S | H | G |
| CG |   | V | V |   | S |   |   |   |   | G |

| | Position | | | | | | | | |
|---|---|---|---|---|---|---|---|---|---|
| | 353 | 354 | 359 | 361 | 370 | 371 | 387 | 388 | 391 | 392 |
| WT | Y | V | S | G | S | M | M | P | V | E |
| PS | C/H/R | A | D/G | R | A | T | I | S | T | G |
| CG | H |   |   |   | A |   |   |   |   |   |

| | Position | | | | | | | | |
|---|---|---|---|---|---|---|---|---|---|
| | 398 | 422 | 435 | 444 | 448 | 456 | 458 | 462 | 465 | 466 | 472* |
| WT | A | V | R | V | A | A | A | W | I | K | I |
| PS | T | A | L | I/L | G | T | P | C | V | T | L |
| CG |   |   |   | I |   |   | P |   | V |   |   |

*Please note that this position 472 corresponds to position 473 in the alignment in FIG. 2.

TABLE 2B below shows nucleotide changes that cause amino acid substitutions as listed in the table 1A.

| | Position | | | | | | | | |
|---|---|---|---|---|---|---|---|---|---|
| | 28 | 32 | 35 | 64 | 91 | 94 | 113 | 121 | 124 | 136 |
| WT | g | c | g | t | g | a | c | c | a | c |
| Mutation | a | t | c | g | a | g | g | g/t | g | t |

| | Position | | | | | | | | |
|---|---|---|---|---|---|---|---|---|---|
| | 160 | 211 | 212 | 226 | 233 | 242 | 247 | 257 | 263 | 282 |
| WT | g | a | c | a | a | a | c | a | a | c |
| Mutation | a | g | g | t/g | g | g | t | g | g | a |

| | Position | | | | | | | |
|---|---|---|---|---|---|---|---|---|
| | 283 | 295 | 302 | 305 | 324 | 337 | 351 | 421 | 430 |
| WT | a | g | t | c | c | g | c | c | t |
| Mutation | g | a | c | t | a | a | a | t | c |

| | Position | | | | | | | | |
|---|---|---|---|---|---|---|---|---|---|
| | 439 | 444 | 446 | 535 | 536 | 545 | 593 | 662 | 674 | 691 |
| WT | a | c | t | g | g | c | a | t | t | g |
| Mutation | g | a | c | a | t | g | t | c | c | c |

| | Position | | | | | | | | |
|---|---|---|---|---|---|---|---|---|---|
| | 737 | 746 | 751 | 763 | 785 | 793 | 839 | 841 | 843 | 937 |
| WT | c | a | a | g | t | a | t | g | t | g |
| Mutation | t | g | g | a | c | g | c | t | a | a |

| | Position | | | | | | | | |
|---|---|---|---|---|---|---|---|---|---|
| | 1041 | 1043 | 1051 | 1055 | 1057 | 1058 | 1061 | 1075 | 1076 | 1081 |
| WT | c | t | g | a | t | a | t | a | g | g |
| Mutation | a | c | c | g | c | g | c | g | a | c |

TABLE 2B-continued below shows nucleotide changes that cause amino acid substitutions as listed in the table 1A.

| | Position | | | | | | | | | |
|---|---|---|---|---|---|---|---|---|---|---|
| | 1108 | 1112 | 1161 | 1162 | 1171 | 1172 | 1175 | 1192 | 1265 | 1304 |
| WT | t | t | g | c | g | t | a | g | t | g |
| Mutation | g | c | a | t | a | c | g | a | c | t |

| | Position | | | | | | | | |
|---|---|---|---|---|---|---|---|---|---|
| | 1330 | 1343 | 1366 | 1372 | 1386 | 1393 | 1394 | 1397 | 1414 |
| WT | g | c | g | g | g | a | t | a | a |
| Mutation | a/c | g | a | c | t | g | c | c | c |

Host cells comprising the Rubisco variants may also be identified as having Rubisco activity, for example, increased Rubisco activity, when compared to a control, such as the host cells possessing other Rubisco large subunit variants or wild type Rubisco enzyme. In another aspect, Rubisco large subunits of the present invention may be selected for increased Rubisco activity in vivo or in vitro as compared to the Rubisco activity of other Rubisco large subunits, including wild type Rubisco, such as that set forth in SEQ ID NOS: 2 and 6-18, including algae, rice, wheat, sugarcane, sorghum, corn, cotton, soybean, alfalfa, spinach, tobacco, tomato, potato, barley, and the like, known Rubisco variants or those identified or generated by site-directed mutagenesis, shuffling, and the like.

Improved host cell growth conferred by Rubisco large subunits of the present invention may be identified using competitive growth assays, including those described herein. Cells containing variants of Rubisco large subunits (transformants) that result in increased Rubisco activity will grow faster than cells with defective or wild type Rubisco large subunits and will become dominant populations which may be selected. In another aspect, the competitive growth assays may include the use of carbonic anhydrase inhibitor in the media to disrupt the $CO_2$ concentrating mechanism of the host cell. Thus, according to the invention, single cell clones from the competitive growth assays may be obtained and the Rubisco large subunit variants polypeptides and/or polynucleotides recovered from the isolated or segregated host cells using standard techniques. In another aspect, rbcL variants having one or more substitutions may be identified by sequence analysis. Rubisco activity of the Rubisco large subunit variants may be determined in vivo in a host cell or in vitro using standard assays as evidenced by photoautotrophic, competitive growth, and/or carboxylase activity assays or other methods known to one skilled in the art or described herein.

For illustration and not to limit the invention, examples of a desired Rubisco activity include but are not limited to increased carboxylase activity and specificity, for example, increased RuBP carboxylase rate, decreased RuBP oxygenase rate, increased Km for $O_2$, decreased Km for $CO_2$, decreased ratio of Km for $CO_2$ to Km for $O_2$, velocity for $O_2$ or $CO_2$ and the like as compared to a wild type Rubisco enzyme. As used herein, increased Rubisco activity includes but is not limited to increasing carboxylase activity and/or specificity, for example, increased RuBP carboxylase rate, decreased RuBP oxygenase rate, increased Km for $O_2$, decreased Km for $CO_2$, decreased ratio of Km for $CO_2$ to Km for $O_2$. The carboxylation rate and specificity properties of Rubisco large subunit as part of a Rubisco enzyme with a Rubisco small subunit may be assayed for using any standard techniques and/or assays, for example, carboxylase activity assay, or $CO_2/O_2$ specificity assays. Rubisco activity may be determined in vitro and/or in vivo, for example, in algae, such as Chlamydomonas or plants such as tobacco, maize, wheat, rice, sorghum, rye, millet, barley, soybean, sunflower, safflower, tobacco, alfalfa, potato, Brassica spp., cotton, tomato, and the like. Measurement of Rubisco carbamylation, $CO_2$ assimilation rates, molar activity, and content may be determined as described by Kobza and Seemann, for example, determining the enzyme content in the extract using $^{14}C$-labeled 2-carboxyarabinitol 1,5-bisphosphate binding and determining molar activity of Rubisco calculated by dividing the total activity (fully carbamylated activity) by the Rubisco content. (Kobza J, Seemann J R (1988) Mechanisms for the light regulation of ribulose-1,5-bisphosphate carboxylase activity and photosynthesis in intact leaves. Proc Natl Acad Sci USA 85:3815-3819). Likewise, calculations of evaporation, conductance to gas exchange, $CO_2$ assimilation rate, and $C_i$ may be determined according to Caemmerer and Farquhar (Caemmerer S von, Farquhar G D (1981) Some relationships between the biochemistry of photosynthesis and the gas exchange of leaves. Planta 153:376-387).

The Rubisco large subunit variants' effect on photosynthesis may be determined using standard assays, including but not limited to $O_2$ evolution assay using an $O_2$ electrode, or an open type leaf gas-exchange system using an infrared gas analyzer. Since about one-fourth of total N in a leaf may be contained in Rubisco, changes in Rubisco activity may have an effect on nitrogen use efficiency (NUE) (Ghannoum et al 2005 "Fast Rubisco is the key to superior nitrogen-use efficiency in NADP-malic enzyme relative to NAD-malic enzyme C4 grasses". Plant Physiol.). Rubisco large subunits of the present invention or identified by methods of the present invention may be assayed for their ability to increase NUE in plants using the above referenced assays.

In one aspect, the sequences of the isolated Rubisco large subunit polynucleotides and/or polypeptides may be obtained using standard techniques known in the art. The sequence may be compared to the sequence of the wild type Rubisco large subunit polynucleotide and/or polypeptide sequence or the parental/template Rubisco large subunit polynucleotide and/or polypeptide sequence to identify one or more amino acids (substitutions) that are different. The nature and position of these substitutions may be used to make corresponding amino acid substitutions in a Rubisco large subunit, for example, a Rubisco large subunit polynucleotide that encodes a Rubisco large subunit that is functional in a higher plant cell using routine molecular biology techniques. See Examples 9 and 10. In one aspect, the Rubisco large subunit subjected to the corresponding amino acid substitutions is endogenous to a higher plant cell, including but not limited to a tobacco, maize, wheat, rice, sorghum, rye, millet, barley, soybean, sunflower, safflower, tobacco, alfalfa, potato, *Brassica* spp., cotton, tomato cell, and the like.

The amino acid substituted Rubisco large subunit variant may be introduced into a higher plant cell using standard techniques known in the art. In one aspect, the method of identifying Rubisco large subunits that have increased Rubisco activity includes determining the Rubisco activity in the higher plant cell. See Examples 9 and 10. As described previously, Rubisco activity in a higher plant cell may be determined using any number of assays or techniques including those that measure, for example, Rubisco activity or a phenotype resulting from increased Rubisco activity, for example, increased plant productivity, for example, increased plant growth rate and/or size, seed weight, seed viability, biomass, plant yield, photosynthesis, enhanced plant development, such as earlier flowering, or nitrogen use efficiency or combinations thereof in an agricultural organism into which the polynucleotide has been transferred. The phenotypes are described in detail elsewhere in the specification and are known to those skilled in the art, see, for example, Application Nos. WO/2005/085454 and WO/2004/101751.

Compositions

Compositions include plants having altered levels of Rubisco large subunits and/or activities of a Rubisco enzyme when a Rubisco large subunit of the present invention is expressed with a small subunit of Rubisco to form a functional Rubisco enzyme.

In specific compositions, the plants have an altered level of a Rubisco large subunit polypeptide of the present invention or identified by the methods of the present invention or an active variant or fragment thereof. These, include, but are not limited to higher plant Rubisco large subunit polypeptide variants having one or more of the amino acid substitutions listed in Tables 1A and 2A. For example, the higher plant Rubisco large subunit polypeptide comprises an amino acid sequence that has been substituted with at least one amino acid substitution at a position that that corresponds to position 10, 11, 12, 22, 31, 32, 38, 41, 42, 46, 54, 71, 76, 78, 81, 83, 86, 88, 94, 95, 99, 101, 102, 108, 113, 117, 141, 144, 147, 148, 149, 179, 182, 198, 221, 225, 231, 246, 249, 251, 255, 262, 265, 280, 281, 313, 347, 348, 351, 352, 353, 354, 359, 361, 370, 371, 387, 388, 391, 392, 398, 422, 435, 444, 448, 456, 458, 462, 465, 466 or 472 of the amino acid sequence of the wild type *Chlamydomonas reinhardtii* Rubisco large subunit polypeptide (SEQ ID NO: 2) or a combination thereof. The variant has Rubisco activity.

In another aspect, the plants have an altered level of Rubisco activity when a Rubisco large subunit polypeptide of the present invention or identified by the methods of the present invention or an active variant or fragment thereof is expressed with a small subunit of Rubisco to form a functional Rubisco enzyme. These, include, but are not limited to polypeptides having one or more of the amino acid substitutions listed in Tables 1A and 2A. For example, the higher plant Rubisco large subunit polypeptide comprises an amino acid sequence that has been substituted with at least one amino acid substitution at a position that that corresponds to position 10, 11, 12, 22, 31, 32, 38, 41, 42, 46, 54, 71, 76, 78, 81, 83, 86, 88, 94, 95, 99, 101, 102, 108, 113, 117, 141, 144, 147, 148, 149, 179, 182, 198, 221, 225, 231, 246, 249, 251, 255, 262, 265, 280, 281, 313, 347, 348, 351, 352, 353, 354, 359, 361, 370, 371, 387, 388, 391, 392, 398, 422, 435, 444, 448, 456, 458, 462, 465, 466 or 472 of the amino acid sequence of the wild type *Chlamydomonas reinhardtii* Rubisco large subunit polypeptide (SEQ ID NO: 2) or a combination thereof. Exemplary higher plant Rubisco large subunit polypeptides will be known to one skilled in the art and include without limitation, *Oryza sativa* (SEQ ID NO: 7), *Triticum aestivum* (SEQ ID NO: 8), *Saccharum* hybrid (SEQ ID NO: 9), *Sorghum bicolor* (SEQ ID NO: 10), *Zea mays* (SEQ ID NO: 11), *Gossypium hirsutum* (SEQ ID NO: 12), *Glycine max* (SEQ ID NO: 13), *Medicago sativa* (SEQ ID NO: 14), *Spinacia oleracea* (SEQ ID NO: 15), *Nicotiana tabacum* (SEQ ID NO: 6), *Solanum lycopersium*(SEQ ID NO: 16), *Solanum tuberosum* (SEQ ID NO: 17), or *Hordeum vulgare*(SEQ ID NO: 18) and the like. The variants can be tested to determine Rubisco activity.

Further provided are plants having an altered level of Rubisco large subunit polypeptides or an active variant or fragment thereof and/or Rubisco activity. In one aspect, the plants comprise the higher plant Rubisco large subunit polypeptide encoded by a polynucleotide having any of the substitutions of Tables 1B and 2B or identified using any of the methods of the present invention. Exemplary substitutions include a Rubisco large subunit polynucleotide comprising at least one nucleotide substitution at a position that that corresponds to position 28, 32, 35, 64, 91, 94, 113, 121, 124, 136, 160, 211, 212, 226, 233, 242, 247, 257, 263, 282, 283, 295, 302, 305, 324, 337, 351, 421, 430, 439, 444, 446, 535, 536, 545, 593, 662, 674, 691, 737, 746, 751, 763, 785, 793, 839, 841, 843, 937, 1041, 1043, 1051, 1055, 1057, 1058, 1061, 1075, 1076, 1081, 1108, 1112, 1161, 1162, 1171, 1172, 1175, 1192, 1265, 1304, 1330, 1343, 1366, 1372, 1386, 1393, 1394, 1397, or 1414 of the wild type *Chlamydomonas reinhardtii* polynucleotide sequence encoding a Rubisco large subunit (SEQ ID NO: 2) or a combination thereof. The plants of the invention may exhibit modulation in plant productivity including but not limited to plant growth rate and/or size, such as increased plant leaf size, shoot growth, plant vigor, leaf senescence, shoot regeneration, root growth, seed weight, seed viability, enhanced plant development, such as earlier flowering, biomass, plant yield, photosynthesis, nitrogen use efficiency, Rubisco activity, for example, increased $CO_2$ fixation rate, Rubisco carboxylase activity and/or specificity, or increased photosynthetic rate as compared to plants with wild type Rubiscos or those plants not transgenic for Rubiscos of the present invention. The wild type *Chlamydomonas reinhardtii* Rubisco large subunit sequence is set forth in SEQ ID NO:2 and can be found in Genbank Accession No. NP_958405.

In specific embodiments, the plants of the invention have stably incorporated into their chloroplast genomes a Rubisco large subunit sequence of the present invention. In further embodiments, the Rubisco large subunit sequence is operably linked to a promoter functional in a chloroplast or plant cell in the plant.

Other embodiments provide plants such as maize, wheat, rice, sorghum, rye, millet, barley, soybean, sunflower, safflower, tobacco, alfalfa, potato, *Brassica* spp., cotton, tomato, or tobacco, which have been genetically modified at a native genomic locus encoding a Rubisco large subunit polypeptide. By "native genomic locus" is intended a naturally occurring genomic sequence. In some embodiments, the native genomic locus is set forth in SEQ ID NO:19 (FIG. 4). Genetic modification encompasses either introduction of a Rubisco large subunit sequence or modification of a native genomic locus encoding a Rubisco large subunit, or both, and may result in phenotypic change. By "phenotypic change" is intended a measurable change in one or more cell functions. For example, plants having genetic modification at a genomic locus encoding a Rubisco large subunit polypeptide may show reduced or eliminated expression or activity of the Rubisco large subunit polypeptide. Certain phenotypic changes may be observed at the organ, tissue or whole-plant level, for example, increased plant growth rate and/or size, such as increased plant leaf size, increased shoot growth, increased plant vigor, increased shoot regeneration, increased root growth, increased seed weight, increased seed viability, enhanced plant development, such as earlier flowering, increased biomass, increased plant yield, increased photosynthesis rate, increased nitrogen use efficiency, increased Rubisco activity, for example, increased $CO_2$ fixation rate, Rubisco carboxylase activity and/or specificity, as compared to plants with wild type or non-transgenic Rubisco large subunits of the present invention. Various methods of genetic modification are described in more detail elsewhere herein, as are examples of phenotypes that can result from modification affecting the level of Rubisco large subunit sequences and/or Rubisco activity of a Rubisco enzyme comprising a Rubisco large subunit of the invention and a Rubisco small subunit. The Rubisco small subunit may be endogenous or exogenous to the plant cell or chloroplast.

Modified plants are of interest, as are modified plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" means the mature seed produced by commercial growers for purposes other than advancing or reproducing the species, e.g. for such end uses as feed, food, or fiber. Progeny, variants, and mutants of the regenerated plants are also included within the scope of the invention, provided that such plants or plant parts comprise the genetic modification.

The Rubisco large subunit polypeptides employed in the invention share sequence identity with members of the Rubisco large subunit family of proteins. Changes in Rubisco activity may alter the rate of photosynthetic carbon fixation.

As described herein, the inventors have identified at least 111 novel *Chlamydomonas reinhardtii* Rubisco large subunit polypeptides and cDNAs and at least 78 substitutions that confer Rubisco activity or increased Rubisco activity. The amino acid and nucleotide substitutions and their positions in wild type *Chlamydomonas reinhardtii* Rubisco large subunit sequences can be found in Tables 1A-B and 2A-B. The full length novel *Chlamydomonas reinhardtii* Rubisco large subunit polypeptides share approximately 98-99% amino acid identity with respect to one another and 98-99% overall amino acid identity to the *Chlamydomonas* wild type Rubisco polypeptide (SEQ ID NO:2, also see GenBank Accession No. NP_958405). The *Chlamydomonas reinhardtii* Rubisco large subunit variants were evaluated for functionality in restoring photosynthesis of a *Chlamydomonas* rbcL deletion mutant (ΔrbcL named MX3312) and their ability to confer faster growth on the mutants than other Rubisco large subunit variants using functional complementation and competitive growth assays (See Examples described herein). At least 111 substitutions were identified in photosynthesis competent clones of the of the *Chlamydomonas* transformants with shuffled rbcL library variants.

Three of the Rubisco large subunits having the substitutions of M42V, I265V, S370A, I465V; A99T, A281S, D352G; or A102V, I265V, Y353H, S370A, with a Rubisco small subunit were assayed for Rubisco activity and their respective specificity values determined and compared to the values obtained for wild type Rubisco enzymes. Amino acid substitutions, S370A, I465V or A99T, A281S, D352G were introduced into a wild type tobacco Rubisco large subunit (SEQ ID NO:6, GenBank Accession No. NC_001879 of the *Nicotiana tabacum* plastid, complete genome). The rbcL coding sequence begins at 57595-59025 in the GenBank Accession No. NC_001879 sequence) and transformed into the chloroplast of tobacco rbcL deletion line T657-1-2 (Icon Genetics: unpublished data)). Both of these tobacco Rubisco large subunit variants together with a Rubisco small subunit form a Rubisco enzyme with increased Rubisco activity or specificity or reduced Km for $CO_2$ compared to wild type tobacco Rubisco enzyme as determined using spectrophotometric methods.

Using nine identified substitutions, oligonucleotides were spiked for constructing a tobacco rbcL library that has the potential of generating 225 variants, each with 1-4 substitutions per gene. Variants from this library were transformed into the tobacco rbcL deletion line of T657-1-2 and selected using a positive selection marker and generated into plants. Four Rubisco large subunit variants from these plants were isolated and sequenced and found to contain the substitutions of A281S, S370A, A458P; R86G, D352G, S370A, M387T; A281S, D352G, I465V; or A99T, F353H, S370A compared to wild type tobacco Rubisco large subunits.

Without wishing to be bound by this theory, the present inventors believe that Rubisco large subunit variants of the present invention will be useful for increasing plant productivity. As used herein, the term "increased plant productivity" includes but is not limited to increased plant growth rate and/or size, such as increased plant leaf size, increased shoot growth, increased plant vigor, increased leaf senescence, increased shoot regeneration, increased root growth, increased seed weight, increased seed viability, enhanced plant development, such as earlier flowering, increased biomass, increased plant yield, increased photosynthesis and/or photosynthetic rate, and/or nitrogen use efficiency as compared to plants with wild type Rubisco large subunits. Increased plant productivity may be achieved using Rubisco large subunits of the present invention. Thus, increased Rubisco activity using Rubisco large subunits of the present invention together with Rubisco small subunits in a plant cell provides a novel strategy for increasing plant productivity in plants.

Plant productivity is increased in plants having Rubisco large subunit variants of the present invention relative to the plant productivity of a control plant that is non-transgenic for a Rubisco large subunit of the present invention. For example, increased plant productivity may be assessed by comparing physical features and characteristics of plant productivity, such as, plant height and weight, leaf area, plant water relations, ability to flower, ability to generate seeds, yield, plant vigor, leaf senescence, shoot regeneration, root growth, seed weight, seed viability, biomass, photosynthetic rate, flowering time, nitrogen use efficiency and sugar content of transgenic plants and non-transgenic control plants. Preferably, the plant productivity in a transgenic plant (or transformed plant cell, plant component, plant tissue, or plant organ) of the invention is at least 5%, 10%, or 20% (and preferably 30% or 40%) greater than the plant productivity exhibited in a non-transgenic control plant (or control plant cell, plant component, plant tissue, or plant organ). In other preferred embodiments, the level of plant productivity is 50% greater, 60% greater, and more preferably even 75% or 90% greater than a control plant, with up to 100% above the level of plant productivity as compared to a control plant being most preferred. The level of plant productivity is measured by conventional methods used to determine plant productivity.

Fragments and variants of the Rubisco large subunit polynucleotides and proteins encoded thereby can be employed in the present invention. By "fragment" is intended a portion of the polynucleotide or a portion of the amino acid sequence and hence of the protein encoded thereby. Fragments of a polynucleotide may encode protein fragments that retain the biological activity of the native protein and hence retain Rubisco enzyme activity when it forms a complex with a Rubisco small subunit or fragment thereof.

Alternatively, fragments of a Rubisco large subunit polynucleotide that are useful as hybridization probes or PCR primers generally do not encode fragment proteins retaining Rubisco biological activity when part of the Rubisco enzyme complex. Thus, fragments of a nucleotide sequence may range from at least about 20 nucleotides, about 50 nucleotides, about 100 nucleotides, up to the full-length polynucleotide encoding the proteins employed in the invention.

A fragment of a Rubisco large subunit polynucleotide that encodes a biologically active portion of a Rubisco enzyme employed in the invention will encode at least 15, 25, 30, 50, 75, 100, 125, 150, 175, 200, 220, or 225 contiguous amino acids, or up to the total number of amino acids present in a full-length Rubisco large subunit protein of the invention.

A biologically active portion of a Rubisco large subunit protein can be prepared by isolating a portion of one of the Rubisco large subunit polynucleotides employed in the invention, expressing the encoded portion of the Rubisco large subunit protein (e.g., by recombinant expression in vitro) with a Rubisco small subunit protein or fragment thereof, and assessing the activity of the Rubisco enzyme. Polynucleotides that are fragments of a Rubisco large subunit nucleotide sequence comprise at least 16, 20, 50, 75, 100, 150, 200, 250, 300, 350, 500, 550, 500, 550, 600, 650, 700, 800, 900, 1,000, 1,100 nucleotides, or up to the number of nucleotides present in a full-length Rubisco large protein polynucleotide disclosed herein.

As used herein, the term "variants" with respect to polynucleotides includes polynucleotides having a deletion and/or addition and/or substitution of one or more nucleotides at one or more sites within the native, parental or template polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the Rubisco large subunit polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a Rubisco large subunit protein employed in the invention. Generally, variants of a particular polynucleotide of the invention will have at least about 50%, 55%, 50%, 55%, 60%, 65%, 70%, 75%, 80%, 85%, 90%, 91%, 92%, 93%, 95%, 95%, 96%, 97%, 98%, 99% or more sequence identity to that particular polynucleotide as determined by sequence alignment programs and parameters described elsewhere herein.

Variants of a particular polynucleotide employed in the invention (i.e., the reference polynucleotide) can also be evaluated by comparison of the sequence identity between the polypeptide encoded by a variant polynucleotide and the polypeptide encoded by the reference polynucleotide. Thus, for example, an isolated Rubisco large subunit polynucleotide that encodes a polypeptide with a given percent sequence identity to any one of the *Chlamydomonas reinhardtii* Rubisco large subunit polypeptide variants is encompassed, for example, those variants having one or more of the nucleotide or amino acid substitutions described in Tables 1A-B and 2A-B. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 50%, 55%, 50%, 55%, 60%, 65%, 70%, 75%, 80%, 85%, 90%, 91%, 92%, 93%, 95%, 95%, 96%, 97%, 98%, 99% or more sequence identity.

As used herein, the term, the term "Variant" with respect to polypeptides or proteins includes a protein or polypeptide derived from the native protein by substitution, deletion or addition of one or more amino acids at one or more sites in the native protein. Variant proteins encompassed by the present invention are biologically active, that is they continue to possess the desired biological activity of the native protein or have increased biological activity of the native protein, that is, Rubisco activity as described herein. Such variants may result from, for example, genetic polymorphism or from human manipulation (mutation). Biologically active variants of a native Rubisco large subunit protein of the invention will have at least about 50%, 55%, 60%, 65%, 70%, 75%, 80%, 85%, 90%, 91%, 92%, 93%, 95%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 5, 3, 2, or even 1 amino acid residue. Variants of the invention include but are not limited to Rubisco large subunits of unicellular photoautotrophic organisms, or lower and/or higher plants having one or more amino acid substitutions described in Tables 1A and 2A, for example, an amino acid sequence that has been substituted with at least one amino acid substitution at a position that that corresponds to position 10, 11, 12, 22, 31, 32, 38, 41, 42, 46, 54, 71, 76, 78, 81, 83, 86, 88, 94, 95, 99, 101, 102, 108, 113, 117, 141, 144, 147, 148, 149, 179, 182, 198, 221, 225, 231, 246, 249, 251, 255, 262, 265, 280, 281, 313, 347, 348, 351, 352, 353, 354, 359, 361, 370, 371, 387, 388, 391, 392, 398, 422, 435, 444, 448, 456, 458, 462, 465, 466 or 472 of the amino acid sequence of the wild type *Chlamydomonas reinhardtii* Rubisco large subunit polypeptide (SEQ ID NO: 2).

The proteins employed or identified in the methods of the invention may be altered in various ways including amino acid substitutions, deletions, truncations, and insertions. Methods for such manipulations are generally known in the art. For example, amino acid sequence variants and fragments of the Rubisco large subunit proteins can be prepared by mutations in the DNA. Methods for mutagenesis and polynucleotide alterations are well known in the art. See, for example, Kunkel (1985) *Proc. Natl. Acad. Sci. USA* 82:588-592; Kunkel et al. (1987) *Methods in Enzymol.* 155:367-382; U.S. Pat. No. 5,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Variants of Rubisco large subunit polypeptides can also include isolating natural variants from plants cells that exist in nature or creating recombinant Rubisco large subunits.

Thus, amino acid substitutions employed or identified in the invention include both the naturally-occurring sequences as well as mutant forms. Likewise, the polynucleotides and proteins comprising one or more polymorphisms or mutations identified or employed by methods of the invention encompass naturally occurring polynucleotides and/or proteins as well as natural variations and modified or mutated forms thereof. Such variants will continue to possess the desired Rubisco activity. Obviously, the mutations that will be made in the DNA encoding the variant must not place the sequence out of reading frame and optimally will not create complementary regions that could produce secondary mRNA structure.

The effect of substituting amino acids or nucleotides in polynucleotide or protein sequences identified by the methods described herein or encompassed by sequences described herein may be evaluated by routine screening assays.

In one aspect of the present invention, variants of the Rubisco large subunit may be evaluated for Rubisco activity in a cell, for example, in a unicellular photosynthetic eukaryotic organism, a lower plant cell, or a higher plant cell. In another aspect, Rubisco activity may be determined by the ability of the variant to confer photoautotrophic growth or a growth advantage to the host cell, for example, using a competitive growth assay. In yet another aspect, Rubisco activity and/or expression of the Rubisco large subunit can be evaluated by Northern, Western blot analysis, real time PCR, carboxylase activity assay and/or specificity assay $O_2$ or $CO_2$, or $^{14}C$-labeled 2-carboxyarabinitol 1,5-bisphosphate binding assays or combinations thereof Additional assays for detecting such activity or expression are known to one skilled in the art. Alternately, they are described in detail elsewhere herein. For example, an oligonucleotide of at least 15, 30, 50, 100, 200, 300, 400, 500, 600, 700, 800, 900 or 1000 nucleotides in length and sufficient to specifically hybridize under stringent conditions to Rubisco large subunit mRNA may be used in Northern blot analysis. Rubisco large subunit proteins may be detected using a labeled antibody capable of binding to Rubisco large subunit proteins of the present invention. Antibodies can be polyclonal, or more preferably, monoclonal. An isolated Rubisco large subunit protein, or fragment thereof, can be used as an immunogen to generate antibodies that bind specifically to Rubisco large subunits of the present invention using standard techniques for polyclonal and monoclonal antibody preparation. Techniques for detection of Rubisco large subunit protein include enzyme linked immunosorbent assays (ELISAs), Western blots, immunoprecipitations and immunofluorescence.

Variant Rubisco large subunit polynucleotides and proteins also encompass sequences and proteins derived from a mutagenic and/or recombinogenic procedure such as DNA shuffling. With such a procedure, one or more different Rubisco large subunit coding sequences can be manipulated to create a new Rubisco large subunit possessing the desired properties, for example, when expressed with a Rubisco small subunit to form a Rubisco enzyme. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain or polymorphism or mutation of interest may be shuffled between the Rubisco large subunit polynucleotides of the invention and other known Rubisco genes or cDNAs or fragment thereof to obtain a new gene or cDNA coding for a protein with an improved property of interest, such as an increased $K_m$ in the case of an enzyme. Strategies for such DNA shuffling are known in the art. See, for example, Stemmer (1995) *Proc. Natl. Acad. Sci. USA* 91:10757-10751; Stemmer (1995) *Nature* 370:389-391; Crameri et al. (1997) *Nature Biotech.* 15:536-538; Moore et al. (1997) *J. Mol. Biol.* 272:336-357; Zhang et al. (1997) *Proc. Natl. Acad. Sci. USA* 95:5505-5509; Crameri et al. (1998) *Nature* 391:288-291; and U.S. Pat. Nos. 5,605,793 and 5,837,558.

Improved Plants

Rubisco large subunit variants of the present invention may be transformed into other plant cells other than the host cells of a unicellular photosynthetic eukaryotic organism, for example, rice, wheat, sugarcane, sorghum, corn, cotton, alfalfa, spinach, tomato, potato, barley, tobacco, or soybean plant cells, etc. The plant cells may or may not naturally contain a functional Rubisco enzyme or a Rubisco large or small subunit. The present invention provides methods, compositions, and uses related to creating novel or improved plants, plant cells, algal cells, soil microbes, plant pathogens, commensal microbes, or other plant related organisms having art-recognized importance to the agricultural, horticultural, and argonomic areas (collectively, "agricultural organisms") with improved plant productivity. In particular, any plant, plant cell, algal cell, etc. can be transduced or transformed with a Rubisco large subunit polynucleotide of the present invention using routine transformation techniques. (Svab and Maliga. (1993). High frequency plastid transformation in tobacco by selection for a chimeric aadA gene. PNAS USA 90: 913-17). For example, agronomically and horticulturally important plant species can be transduced. Such species include, but are not restricted to, members of the families: Graminae (including corn, rye, triticale, barley, millet, rice, wheat, oats, etc.); Leguminosae (including pea, beans, lentil, peanut, yam bean, cowpeas, velvet beans, soybean, clover, alfalfa, lupine, vetch, lotus, sweet clover, wisteria, and sweetpea); Compositae (the largest family of vascular plants, including at least 1,000 genera, including important commercial crops such as sunflower) and Rosaciae (including raspberry, apricot, almond, peach, rose, etc.), as well as nut plants (including, walnut, pecan, hazelnut, etc.) Targets for modification the evolved vectors of the invention, as well as those specified above, include plants from the genera: *Agrostis, Allium, Antirrhinum, Apium, Arach* may be, *Asparagus, Atropa, Avena* (e.g., oats), *Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum* (e.g., barley), *Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza* (e.g., rice), *Panicum, Pelargonium, Pennisetum* (e.g., millet), *Petunia, Pisum, Phaseolus, Phleum, Poa, Prunus, Ranunculus, Raphanus, Ribes, Ricinus, Rubus, Saccharum, Salpiglossis, Secale* (e.g., rye), *Senecio, Setaria, Sinapis, Solanum, Sorghum, Stenotaphrum, Theobroma, Trifolium, Trigonella, Triticum* (e.g., wheat), *Vicia, Vigna, Vitis, Zea* (e.g., corn), the Olyreae, the Pharoideae and many others.

For example, common crop plants which are targets of the present invention include corn, rice, triticale, rye, cotton, sugarcane, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea and nut plants (e.g., walnut, pecan, etc). In certain variations, naturally occurring in vivo recombination mechanisms of plants, agricultural microorganisms, or vector-host cells for intermediate replication can be used in conjunction with a collection of shuffled Rubisco large subunit polynucleotide sequence variants having a desired phenotypic property to be optimized further; in this way, a natural recombination mechanism can be combined with intelligent selection of variants in an iterative manner to produce optimized variants by "forced evolution". One skilled in the art may further elect to supplement mutations by introducing intentionally mutated polynucleotide species or "spiked" oligonucleotides suitable for shuffling, or portions thereof, into the pool of initial Rubisco large subunit polynucleotide species and/or into the plurality of selected, shuffled polynucleotide species which are to be recombined. Mutational drift may also be supplemented by the use of mutagens (e.g., chemical mutagens or mutagenic irradiation), or by employing replication conditions which enhance the mutation rate.

In one aspect, the invention provides novel Rubisco large subunit polypeptides having increased carboxylase activity or specificity or combinations thereof as well as the means and method to generate additional Rubisco large subunit variants and/or suitable host cells and/or a library of Rubisco L-subunits, as well as providing methods for evaluating the Rubisco enzymes containing the Rubisco large subunit variants for Rubisco activity.

Transcriptional Regulatory Sequences

Suitable transcriptional regulatory sequences include: cauliflower mosaic virus 19S and 35S promoters, NOS promoter, OCS promoter, rbcS promoter, *Brassica* heat shock promoter, synthetic promoters, non-plant promoters modified, if necessary, for function in plant cells, substantially any promoter that naturally occurs in a plant genome, promoters of plant viruses or Ti plasmids, tissue-preferential promoters or cis-acting elements, light-responsive promoters or cis-acting elements (e.g., rbcS LRE), hormone-responsive cis-acting elements, developmental stage-specific promoters and cis-acting elements, viral promoters (e.g., from Tobacco Mosaic virus, Brome Mosaic Virus, Cauliflower Mosaic virus, and the like), and the like. In a variation, a transcriptional regulatory sequence from a first plant species may be optimized for functionality in a second plant species by application of recursive sequence shuffling. Transcriptional regulatory sequences for expression of shuffled rbcL sequences in chloroplasts may be known in the art (Daniell et al. (1998) op.cit; O'Neill et al. (1993) The Plant Journal 3: 729; Maliga P (1993) op.cit), as are homologous recombination vectors. Maliga P (1993) op.cit), as are homologous recombination vectors.

Transformation

The transformation of plants and protoplasts in accordance with the invention may be carried out in essentially any of the various ways known to those skilled in the art of plant molecular biology. See, in general, Methods in Enzymology Vol. 153 ("Recombinant DNA Part D") 1987, Wu and Grossman Eds., Academic Press, incorporated herein by reference. Additional useful general references for plant cell cloning, culture and regeneration include Jones (ed) (1995) Plant Gene Transfer and Expression Protocols—Methods in Molecular Biology. Volume 49 Humana Press Towata N.J.; Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture: Fundamental Methods Springer Lab Manual, Springer-Verlag (Berlin Heidelberg New York) (Gamborg). A variety of cell culture media are described in Atlas and Parks (eds) The Handbook of Microbiological Media (1993) CRC Press, Boca Raton, Fla. (Atlas). Additional information for plant cell culture may be found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology Bios Scientific Publishers, Oxford, U.K. General texts discussing cloning and other techniques relevant to the present invention, in a variety of contexts, include: Berger and Kimmel, Guide to Molecular Cloning Techniques. Methods in Enzymology volume 152 Academic Press, Inc., San Diego, Calif. (Berger); Sambrook et al., Molecular Cloning—A Laboratory Manual (2nd Ed.), Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")).

As used herein, the term "transformation" means alteration of the genotype of a host plant by the introduction of a polynucleotide sequence. The polynucleotide sequence need not necessarily originate from a different source, but it will, at some point, have been external to the cell into which it may be to be introduced.

In one aspect, the Rubisco large subunit variants polynucleotide may be mechanically transferred by microinjection directly into plant cells by use of micropipettes. Alternatively, the foreign polynucleotide may be transferred into the plant cell by using polyethylene glycol. This forms a precipitation complex with the genetic material that may be taken up by the cell (e.g., by incubation of protoplasts with "naked DNA" in the presence of polyethylenelycol)(Paszkowski et al., (1984) EMBO J. 3:2717-22; Baker et al. (1985) Plant Genetics, 201-211; Li et al. (1990) Plant Molecular Biology Report 8(4)276-291].

In another aspect of this invention, the introduced Rubisco large subunit polynucleotide may be introduced into the plant cells by electroporation (Fromm et al., (1985) "Expression of Genes Transferred into Monocot and Dicot Plant Cells by Electroporation," Proc. Natl. Acad. Sci. USA 82:5824, which may be incorporated herein by reference). In this technique, plant protoplasts are electroporated in the presence of plasmids or polynucleotides containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) may also be used as a vector for introducing the foreign polynucleotide into plant cells (Hohn et al., (1982) "Molecular Biology of Plant Tumors," Academic Press, New York, pp. 549-560; Howell, U.S. Pat. No. 4,407,956). CaMV viral DNA genome may be inserted into a parent bacterial plasmid creating a recombinant DNA molecule which can be propagated in bacteria. After cloning, the recombinant plasmid again may be cloned and further modified by introduction of the desired DNA sequence into the unique restriction site of the linker. The modified viral portion of the recombinant plasmid may be then excised from the parent bacterial plasmid, and used to inoculate the plant cells or plants.

Another method of introduction of Rubisco large subunit polynucleotide segments may be high velocity ballistic penetration by small particles with the polynucleotide either within the matrix of small beads or particles, or on the surface (Klein et al., (1987) Nature 327:70-73). Although typically only a single introduction of a new polynucleotide segment may be required, this method particularly provides for multiple introductions.

A method of introducing the Rubisco large subunit polynucleotide segments into plant cells may be to infect a plant cell, an explant, a meristem or a seed with *Agrobacterium tumefaciens* transformed with the segment. Under appropriate conditions known in the art, the transformed plant cells are grown to form shoots, roots, and develop further into plants. The polynucleotide segments can be introduced into appropriate plant cells, for example, by means of the Ti plasmid of *Agrobacterium tumefaciens*. The Ti plasmid may be transmitted to plant cells upon infection by *Agrobacterium tumefaciens*, and may be stably integrated into the plant genome (Horsch et al., (1984) "Inheritance of Functional Foreign Genes in Plants," Science, 233:496-498; Fraley et al., (1983) Proc. Natl. Acad. Sci. USA 80:4803).

Ti plasmids contain two regions essential for the production of transformed cells. One of these, named transfer DNA (T DNA), induces tumor formation. The other, termed virulent region, may be essential for the introduction of the T DNA into plants. The transfer DNA region, which transfers to the plant genome, can be increased in size by the insertion of the foreign polynucleotide sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector."

All plant cells which can be transformed by *Agrobacterium* and whole plants regenerated from the transformed cells can also be transformed according to the invention so as to produce transformed whole plants which contain the transferred foreign polynucleotide sequence. Three different ways to transform plant cells with *Agrobacterium* include: (1) co-cultivation of *Agrobacterium* with cultured isolated protoplasts; (2) transformation of cells or tissues with *Agrobacterium*, or (3) transformation of seeds, apices or meristems with *Agrobacterium*. Method (1) uses an established culture system that allows culturing protoplasts and plant regeneration from cultured protoplasts. Method (2) implies (a) that the plant cells or tissues can be transformed by *Agrobacterium* and (b) that the transformed cells or tissues can be induced to regenerate into whole plants. Method (3) uses micropropagation. In the binary system, to have infection, two plasmids are needed: a T-DNA containing plasmid and a vir plasmid. Any one of a number of T-DNA containing plasmids can be used, the main issue being that one be able to select independently for each of the two plasmids. After transformation of the plant cell or plant, those plant cells or plants transformed by the Ti plasmid so that the desired DNA segment may be integrated can be selected by an appropriate phenotypic marker. These phenotypic markers include, but are not limited to, antibiotic resistance, herbicide resistance or visual observation. Other phenotypic markers are known in the art and may be used in this invention.

Protoplast Transformation

Numerous protocols for establishment of transformable protoplasts from a variety of plant types and subsequent transformation of the cultured protoplasts are available in the art and are incorporated herein by general reference. For examples, see Hashimoto et al. (1990) Plant Physiol. 93: 857; Plant Protoplasts, Fowke L C and Constabel F, eds., CRC Press (1994); Saunders et al. (1993) Applications of Plant in vitro Technology Symposium, UPM, 16-18 Nov. 1993; and Lyznik et al. (1991) BioTechniques 10: 295, each of which may be incorporated herein by reference).

All plants from which protoplasts can be isolated and cultured to give whole regenerated plants can be transformed by the present invention so that whole plants are recovered which contain the transferred Rubisco large subunit polynucleotide. Some suitable plants include, for example, species from the *Fragaria, Lotus, Medicago, Onobrychis, Trifolium, Trigonella, Viana, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

It may be known that practically all plants can be regenerated from cultured cells or tissues, including but not limited to all major cereal crop species, sugarcane, sugar beet, cotton, fruit and other trees, legumes and vegetables. Species which are a natural plant host for *Agrobacterium* may be transformable in vitro. Although monocotyledonous plants, and in particular, cereals and grasses, are not natural hosts to *Agrobacterium*, work to transform them using *Agrobacterium* has also been successfully carried out by numerous investigators (Hooykas-Van Slogteren et al., (1984) Nature 311:763-764; Hemalsteens et al., (1984) EMBO J. 3:3039-41; Byteiber, et al. (1987) Proc. Natl. Acad. Sci. USA: 5345-5349; Graves and Goldman, (1986) Plant Mol. Biol 7:43-50; Grimsley et al. (1988) Biochemistry 6:185-189; WO86/03776; Shimamoto et al. Nature (1989) 338: 274-276). Monocots may also be transformed by techniques or with vectors other than *Agrobacterium*. For example, monocots have been transformed by electroporation (Fromm et al. [1986] Nature 319:791-793; Rhodes et al. Science [1988] 240: 204-207), direct gene transfer (Baker et al. [1985] Plant Genetics 201-211), by using pollen-mediated vectors (EP 0 270 356), and by injection of DNA into floral tillers (de la Pena et al. [1987], Nature 325: 274-276). Additional plant genera that may be transformed by *Agrobacterium* include *Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus* and *Pisum*.

Chloroplast Transformation.

Rubisco large subunit polynucleotides of the present invention may be transformed into higher plants, for example, tobacco, using techniques known to one skilled in the art. As the Rubisco large subunit gene of higher plants may be encoded on the chloroplast genome and expressed in chloroplasts, it may be generally useful to transform the Rubisco large subunit polynucleotides of the present invention into chloroplasts if the host cells are derived from higher plants. Numerous methods are available in the art to accomplish the chloroplast transformation and expression (Daniell et al. (1998) op.cit; O'Neill et al. (1993) The Plant Journal 3: 729; Maliga P (1993) op.cit). The Rubisco large subunit expression construct may comprise a transcriptional regulatory sequence functional in chloroplasts and/or in plants operably linked to a polynucleotide encoding an enhanced Rubisco protein subunit.

The Rubisco large subunit polynucleotides may be coupled to a chloroplast transit sequence or peptide or other signal sequence or peptide thereby providing polypeptide expression in different cellular compartments, organelles or secretion of one or more of the polypeptides. In one aspect, a polynucleotide encoding the Rubisco large subunit is expressed in the cytosol with a chloroplast transit peptide sequence and translocated into the chloroplast for function. A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide.

A "signal peptide" is an amino acid sequence which is translated in conjunction with a protein and directs the protein to the secretory system (Chrispeels (1991) *Ann. Rev. Plant Phys. Plant Mol. Biol.* 42: 21-53). If the protein is to be directed to a vacuole, a vacuolar targeting signal can further be added, or if to the endoplasmic reticulum, an endoplasmic reticulum retention signal may be added. If the protein is to be directed to the nucleus, any signal peptide present should be removed and instead a nuclear localization signal included (Raikhel. (1992) *Plant Phys.* 100: 1627-1632).

In some aspects, the Rubisco polypeptide can be part of a fusion protein comprising a functional addition such as, for example, a secretion signal, a chloroplast transit peptide, a purification tag, or any of the numerous other functional groups that will be apparent to the skilled artisan and which are described in more detail elsewhere in this specification.

Polynucleotides of the invention can also be fused, for example, in-frame to nucleic acids encoding a secretion/localization sequence, to target polypeptide expression to a desired cellular compartment, membrane, or organelle of a host cell, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, and chloroplast transit sequences), membrane localization/anchor sequences (e.g., stop transfer sequences, GPI anchor sequences), and the like.

Polynucleotide of the invention can be fused in frame with an N-terminal chloroplast transit sequence (or chloroplast transit peptide sequence) derived from a gene encoding a polypeptide that is normally targeted to the chloroplast. Such sequences are typically rich in serine and threonine; are deficient in aspartate, glutamate, and tyrosine; and generally have a central domain rich in positively charged amino acids.

In preparing expression vectors of the invention, sequences other than the promoter and the encoding polynucleotide can be used. If proper polypeptide expression is desired, a polyadenylation region can be derived from the natural gene, from a variety of other plant genes, or from T-DNA. Signal/localization peptides, which, e.g., facilitate translocation of the expressed polypeptide to internal organelles (e.g., chloroplasts) or extracellular secretion, can also be employed.

With respect to polynucleotide sequences encoding Form I Rubisco L subunit proteins, it may be generally desirable to express such encoding sequences in plastids, such as chloroplasts, for appropriate transcription, translation, and processing. With reference to expression cassettes which are designed to function in chloroplasts, such as an expression cassette encoding a large subunit of Rubisco (rbcL) in a higher plant, the expression cassette comprises the sequences necessary to ensure expression in chloroplasts—typically the Rubisco large subunit encoding sequence may be flanked by two regions of homology to the plastid genome so as to effect a homologous recombination with the chloroplastid genome; often a selectable marker gene may be also present within the flanking plastid DNA sequences to facilitate selection of genetically stable transformed chloroplasts in the resultant transplastonic plant cells (see Maliga P (1993) TIBTECH 11: 101; Daniell et al. (1998) Nature Biotechnology 16: 346, and references cited therein).

In one aspect of the invention, the polynucleotides encoding Rubisco large subunit polynucleotide of the present invention or identified by methods of the present invention may be operably linked to a polynucleotide encoding a selectable marker gene, for example, in an expression cassette. Transformants are propagated on a selective medium to ensure that transformants which are assayed for Rubisco activity contain a sequence-shuffled Rubisco encoding sequence in expressible form. In embodiments wherein a polynucleotide encoding an large (L) subunit are to be introduced into host cells which possess chloroplasts, the L subunit encoding sequence is generally operably linked to a transcriptional regulatory sequence functional in chloroplasts and the resultant expression cassette is transferred into the host cell chloroplasts, such as by biolistics, polyethylene glycol (PEG) treatment of protoplasts, or an other suitable method.

For transcription and translation of the DNA sequence encoding a polypeptide of interest, the entire promoter region from a gene capable of expression in the chloroplast general is used. The promoter region may include promoters obtainable from chloroplast genes, such as the psbA gene from spinach or pea, the rbcL and atpB promoter region from maize and rRNA promoters. Examples of promoters are described in Hanley-Bowdoin and Chua, TIBS (1987) 12:67 70; Mullet et al., Plant Molec Biol. (1985) 4:39 54; Hanley-Bowdoin (1986) PhD. Dissertation, the Rockefeller University; Krebbers et al., Nucleic Acids Res. (1982) 10:4985 5002; Zurawaki et al., Nucleic Acids Res. (1981) 9:3251 3270; and Zurawski et al., Proc. Nat'l Acad Sci. U.S.A. (1982) 79:7699 7703. Other promoters may be identified and the relative strength of promoters so identified evaluated, by placing a promoter of interest 5' to a promoterless marker gene and observing its effectiveness relative to transcription obtained from, for example, the promoter from the psbA gene, the strongest chloroplast promoter identified to date. The efficiency of foreign gene expression additionally may be enhanced by a variety of techniques. These include the use of multiple promoters inserted in tandem 5' to the DNA sequence of interest, for example a double psbA promoter, the addition of enhancer sequences and the like.

For the most part, promoters functional in the chloroplast are constitutive rather than inducible. However, where it is desired to provide for inducible expression of the polypeptide of interest, a regulatable promoter and/or a 5' untranslated region containing sequences which provide for regulation at the level of transcription and/or translation (at 3' end) may be provided. Transcription and RNA stability appear to be important determinants of chloroplast gene expression. For example, the 5' untranslated region may be used from a gene wherein expression is regulatable by light. Similarly, 3' inverted repeat regions could be used to stabilize RNA of foreign genes. Regulatable genes may be identified by enhanced expression in response to a particular stimulus of interest and low or absent expression in the absence of the stimulus. For example, a light regulatable gene may be identified where enhanced expression occurs during irradiation with light, while substantially reduced expression or no expression occurs in the negligible of light.

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. Convenient termination regions are available from. (See, for example, Chen and Orozco, Nucleic Acids Res. (1988) 16:8411).

The presence of the Rubisco large subunit polynucleotide in the plant chloroplast can be established in a variety of ways, depending upon the nature of the gene. Techniques such as the Northern blot can be employed for detecting messenger RNA which codes for the polypeptide of interest. In addition, the presence of expression can be detected in a variety of ways. Where the expression product provides a detectable phenotype, such as a novel phenotype or modification of an endogenous trait, the expression of the desired product may be determined by detecting the phenotype. Where a detectable phenotype is not available, antibodies specific for the mature product may be employed. The chloroplasts may be isolated in accordance with conventional ways, disrupted and the western or other technique employed to identify the presence of a desired product. The presence of a gene which produces an exogenous product may be detected by isolation and lysis of the chloroplast. The resulting cellular material may then be assayed for the exogenous product or the exogenous gene. The exogenous product may be detected by electrophoresis, chromatography, immunoassay or the like. The gene may be detected for example by hybridization using Southern blotting. The transient expression system should facilitate studies on Rubisco large subunit polynucleotide expression, regulation, or DNA replication in plastids in vivo.

Once the chloroplast has been shown to have been transformed, the cells of the plant may be used repeatedly for tissue culture, followed by a growth of callus tissue where desired or regeneration of a plant. Thus, the modified plant cell may be repetitively regenerated by use of cell and tissue culture. In some instances, proper propagation may be maintained from seed.

Biochemical assays that measure Rubisco enzyme activity may be performed to determine Km for $CO_2$, the Km for $O_2$ and $CO_2/O_2$ specificity for each Rubisco large subunit polynucleotide as part of a complex that includes a Rubisco small subunit. Sequence-shuffled polynucleotides encoding Rubisco large subunit are obtained from transformants exhibiting a decrease in said ratio as compared to the ratio in a Rubisco large subunit produced from the parental encoding polynucleotide(s) to provide selected sequence shuffled Rubisco large subunit polynucleotides which can be used as parental sequences for at least one additional round of sequence shuffling by any suitable method and selection for a decreased $K_m(CO_2)$, increased specific activity and/or specificity for any detectable changes which are indicative of improved Rubisco cayalytic property. The shuffling and selection process is performed iteratively until sequence shuffled polynucleotides encoding at least one Rubisco enzyme having a desired enzyme properties, such as decreased $K_m(CO_2)$, increased specific activity and/or specificity, are obtained, or until the optimization of the property has plateaued and no further improvement is seen in subsequent rounds of shuffling and selection. Multiple rounds of recombination can be performed prior to any selection step to increase the diversity of resulting populations of nucleic acids prior to selection. Indeed, this approach can be used for recombination and selection processes indicated throughout this disclosure.

Recovery of Selected Polynucleotide Sequences

A variety of selection and screening methods will be apparent to those skilled in the art, and will depend upon the particular phenotypic properties that are desired. The selected shuffled genetic Rubisco large subunit sequences can be recovered for further shuffling or for direct use by any applicable method, including but not limited to: recovery of DNA, RNA, or cDNA from cells (or PCR-amplified copies thereof) from cells or medium, recovery of sequences from host chromosomal DNA or PCR-amplified copies thereof, recovery of episome (e.g., expression vector) such as a plasmid, cosmid, viral vector, artificial chromosome, and the like, or other suitable recovery method known in the art. Any suitable art-known method, including RT-PCR or PCR, can be used to obtain the selected shufflant Rubisco large subunit sequence(s) for subsequent manipulation and shuffling.

Backcrossing

After a desired Rubisco phenotype is acquired to a satisfactory extent by a selected shuffled Rubisco large subunit gene or portion thereof, it may be often desirable to remove mutations which are not essential or substantially important to retention of the desired phenotype ("superfluous mutations"). This may be particularly desirable when the shuffled gene sequence may be to be reintroduced back into a higher plant, as it may be often preferred to harmonize the shufflant Rubisco large subunit sequence with the endogenous Rubisco large subunit sequence in the higher plant taxonomic species genome while retaining the desired Rubisco phenotype obtained from the iterative shuffling/selection process. Superfluous mutations can be removed by backcrossing, which may be shuffling the selected shuffled rbcL gene(s) with one or more parental rbcL gene and/or naturally-occurring rbcL gene(s) (or portions thereof) and selecting the resultant collection of shufflants for those species that retain the desired phenotype. The same process may be employed for the rbcS genes. By employing this method, typically in two or more recursive cycles of shuffling against parental or naturally-occurring viral genome(s) (or portions thereof) and selection for retention of the desired Rubisco activity or phenotype, it may be possible to generate and isolate selected shufflants which incorporate substantially only those mutations necessary to confer the desired phenotype, whilst having the remainder of the genome (or portion thereof) consist of sequence which may be substantially identical to the parental (or wild-type) sequence(s). After several cycles of such backcrossing, the backcrossing will yield gene(s) which contain the mutations necessary for the desired phenotype, and will otherwise have a genomic sequence substantially identical to the genome(s) of the host genome. Isolated components (e.g., genes, regulatory sequences, replication origins, and the like) can be optimized and then backcrossed with parental sequences so as to obtain optimized components which are substantially free of superfluous mutations.

Transgenic Hosts

Transgenes and expression vectors to express shufflant Rubisco large subunit sequences can be constructed by any suitable method known in the art; by either PCR or RTPCR amplification from a suitable cell type or by ligating or amplifying a set of overlapping synthetic oligonucleotides; publicly available sequence databases and the literature can be used to select the polynucleotide sequence(s) to encode the specific protein desired, including any mutations, consensus sequence, or mutation kernal desired by the practitioner. In one aspect, oligonucleotides containing nucleotides sequences that give rise to Rubisco large subunit variants that form a complex or complement a small Rubisco subunit to generate a functional Rubisco enzyme or confer a growth advantage to a host cell are "spiked". In one aspect, the oligonulceotides encode any of the amino acid variations of Tables 1A and 1B. The coding sequence(s) are operably linked to a transcriptional regulatory sequence and, if desired, an origin of replication. Antisense or sense-suppression transgenes and genetic sequences can be optimized or adapted for particular host cells and organisms by the described methods.

The transgene(s) and/or expression vectors are transferred into host cells, protoplasts, pluripotent embryonic plant cells, microbes, or fungi by a suitable method, such as for example lipofection, electroporation, microinjection, biolistics, *Agrobacterium tumefaciens* transduction of Ti plasmid, calcium phosphate precipitation, PEG-mediated DNA uptake, electroporation, electrofusion, or other method. Stable transfectant host cells can be prepared by art-known methods, as can transgenic cell lines.

The polynucleotides of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to any of the Rubisco large subunit sequences of the present invention, for example, polynucleotide sequences of unicellular photoautotrophic organisms, lower and/or higher plants, which encode Rubisco large subunits, having one or more amino acid substitutions described in Tables 1A and 2A, for example, amino acid sequences substituted with at least one amino acid substitution at a position that that corresponds to position 10, 11, 12, 22, 31, 32, 38, 41, 42, 46, 54, 71, 76, 78, 81, 83, 86, 88, 94, 95, 99, 101, 102, 108, 113, 117, 141, 144, 147, 148, 149, 179, 182, 198, 221, 225, 231, 246, 249, 251, 255, 262, 265, 280, 281, 313, 347, 348, 351, 352, 353, 354, 359, 361, 370, 371, 387, 388, 391, 392, 398, 422, 435, 444, 448, 456, 458, 462, 465, 466 or 472 of the amino acid sequence of the wild type *Chlamydomonas reinhardtii* Rubisco large subunit polypeptide set forth in SEQ ID NOS: SEQ ID NOS: 4, 21, 23, 25, 27, 29, 31, 33, 35, and 37 or to additional variants and fragments thereof are encompassed by the present invention. Additional sequences may be isolated based on their sequence identity to any polynucleotide, which encodes a Rubisco large subunit, and has any of the substitutions of Tables 1B and 2B, for example, a polynucleotide sequence substituted with at least one nucleotide substitution at a position that that corresponds to position 28, 32, 35, 64, 91, 94, 113, 121, 124, 136, 160, 211, 212, 226, 233, 242, 247, 257, 263, 282, 283, 295, 302, 305, 324, 337, 351, 421, 430, 439, 444, 446, 535, 536, 545, 593, 662, 674, 691, 737, 746, 751, 763, 785, 793, 839, 841, 843, 937, 1041, 1043, 1051, 1055, 1057, 1058, 1061, 1075, 1076, 1081, 1108, 1112, 1161, 1162, 1171, 1172, 1175, 1192, 1265, 1304, 1330, 1343, 1366, 1372, 1386, 1393, 1394, 1397, or 1414 of the wild type *Chlamydomonas reinhardtii* polynucleotide sequence of SEQ ID NO: 1 or a combination thereof. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 95%, 95%, 96%, 97%, 98%, 99%, or greater sequence identity. Functions of orthologs are often highly conserved among species. Thus, isolated polynucleotides that encode a Rubisco large subunit protein and which hybridize under stringent conditions to the any of the sequences encoding Rubisco large subunit variants of the present invention as described elsewhere herein, for example, as set forth in SEQ ID NOS: 3, 20, 22, 24, 26, 28, 30, 32, 34, and 36, or to complements, variants, or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or another detectable marker. Thus, for example, probes for hybridization can be made by labeling synthetic oligonucleotides based on the Rubisco polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, any of the entire Rubisco large subunit polynucleotides disclosed herein, or one or more portions thereof, may be used as a probe capable of specifically hybridizing to corresponding Rubisco large subunit polynucleotide and messenger RNAs. To achieve specific hybridization under a variety of conditions, such probes include sequences that are unique among Rubisco large subunit polynucleotide sequences and are optimally at least about 10 nucleotides in length, and most optimally at least about 20 nucleotides in length. Such probes may be used to amplify corresponding Rubisco large subunit polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 50 to 55% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 25 hours, usually about 5 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1985) *Anal. Biochem.* 138:267-285: $T_m$=81.5° C.+16.6 (log M)+0.51 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 5° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 15, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 55° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 50, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 5:11-17; the local alignment algorithm of Smith et al. (1981) *Adv. Appl. Math.* 2:582; the global alignment algorithm of Needleman and Wunsch (1970) *J. Mol. Biol.* 58:553-553; the search-for-local alignment method of Pearson and Lipman (1988) *Proc. Natl. Acad. Sci.* 85:2555-2558; the algorithm of Karlin and Altschul (1990) *Proc. Natl. Acad. Sci. USA* 872265, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA Accelrys GCG (Accelrys Inc., 9685 Scranton Road, San Diego, Calif., USA). Alignments using these programs can be performed using the default parameters. The CLUSTAL program is well described by Higgins et al. (1988) *Gene* 73:237-255 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1995) *Meth. Mol. Biol.* 25:307-331. The ALIGN program is based on the algorithm of Myers and Miller (1988) supra. A PAM120 weight residue table, a gap length penalty of 12, and a gap penalty of 5 can be used with the ALIGN program when comparing amino acid sequences. The BLAST programs of Altschul et al (1990) *J. Mol. Biol.* 215:503 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997)

supra. When utilizing BLAST, Gapped BLAST, PSI-BLAST, the default parameters of the respective programs (e.g., BLASTN for nucleotide sequences, BLASTX for proteins) can be used. The United States' National Center for Biotechnology Information and the European Bioinformatics Institute of the European Molecular Biology Laboratory provide such tools, as do various commercial entities known to those of skill in the art. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix.

GAP uses the algorithm of Needleman and Wunsch (1970) J. Mol. Biol. 58:553-553, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 5, 5, 6, 7, 8, 9, 10, 15, 20, 25, 30, 35, 50, 55, 50, 55, 60, 65 or greater.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 5 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Methods

I. Providing Sequences

The sequences of the present invention can be introduced/expressed in a host cell such as algae, or optimally plant cells, such as Tobacco. It is expected that those of skill in the art are knowledgeable in the numerous systems available for the introduction of a polypeptide or a nucleotide sequence of the present invention into a host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally-occurring molecules and synthetic analogues. The polynucleotides of the invention also encompass all forms of sequences including, but not limited to, single-stranded forms, double-stranded forms, hairpins, stem-and-loop structures, and the like.

A Rubisco large subunit polynucleotide of the invention or identified by methods of the present invention can be provided in expression cassettes for expression in the plant of interest. The cassette will include 5' and 3' regulatory sequences operably linked to a Rubisco large subunit polynucleotide. "Operably linked" is intended to mean a functional linkage between two or more elements. For example, an operable linkage between a polynucleotide of interest and a promoter is a functional link that allows for expression of the polynucleotide of interest. Operably linked elements may be contiguous or non-contiguous. When used to refer to the joining of two protein coding regions, operably linked means that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Rubisco large subunit polynucleotide to be under the transcriptional regulation of the regulatory regions. The expression cassette may additionally contain selectable marker genes.

The expression cassette will include, in the 5'-3' direction of transcription, a transcriptional and translational initiation region (i.e., a promoter), a Rubisco large subunit polynucleotide of the invention, and a transcriptional and translational termination region (i.e., termination region) functional in plants. The regulatory regions (including promoters, transcriptional regulatory regions, and translational termination regions) and/or the Rubisco large subunit polynucleotide of the invention may be native/analogous to the host cell and/or to each other. Alternatively, the regulatory regions and/or the Rubisco large subunit polynucleotide of the invention may be foreign/heterologous to the host cell and/or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a promoter that is heterologous to the coding sequence.

While it may be optimal to express the sequences using heterologous promoters, the native promoter sequences may be used. Such constructs can change the expression levels of the Rubisco large subunit in the plant or plant cell. Thus, the phenotype of the plant or plant cell can be altered.

The termination region may be native with the transcriptional initiation region, may be native with the operably linked Rubisco polynucleotide of interest, may be native with the plant host, or may be derived from another source (i.e., foreign or heterologous) to the promoter, the Rubisco large subunit polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:151-155; Proudfoot (1991) *Cell* 65:671-675; Sanfacon et al. (1991) *Genes Dev.* 5:151-159; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant by using plant-preferred codons. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,536,391, and Murray et al. (1989) *Nucleic Acids Res.* 17:577-598, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 155:9-20), and human immunoglobulin heavy-chain binding protein (BiP) (Macejak et al. (1991) *Nature* 353:90-95); untranslated leader from the coat protein mRNA of alfalfa mosaic virus (AMV RNA 5) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 85:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,5-dichlorophenoxyacetate (2,5-D). Additional selectable markers include phenotypic markers such as β-galactosidase and fluorescent proteins such as green fluorescent protein (GFP) (Su et al. (2005) *Biotechnol Bioeng* 85:610-9 and Fetter et al. (2005) *Plant Cell* 16:215-28), cyan fluorescent protein (CYP) (Bolte et al. (2005) *J. Cell Science* 117:953-55 and Kato et al. (2002) *Plant Physiol* 129:913-52), and yellow fluorescent protein (PhiYFP™ from Evrogen, see, Bolte et al. (2005) *J. Cell Science* 117:953-55). For additional selectable markers, see generally, Yarranton (1992) *Curr. Opin. Biotech.* 3:506-511; Christopherson et al. (1992) *Proc. Natl. Acad. Sci. USA* 89:6315-6318; Yao et al. (1992) *Cell* 71:63-72; Reznikoff (1992) *Mol. Microbiol.* 6:2519-2522; Barkley et al. (1980) in *The Operon*, pp. 177-220; Hu et al. (1987) *Cell* 58:555-566; Brown et al. (1987) *Cell* 59:603-612; Figge et al (1988) *Cell* 52:713-722; Deuschle et al. (1989) *Proc. Natl. Acad. Sci. USA* 86:5500-5505; Fuerst et al (1989) *Proc. Natl. Acad. Sci. USA* 86:2559-2553; Deuschle et al (1990) *Science* 258:580-583; Gossen (1993) Ph.D. Thesis, University of Heidelberg; Reines et al (1993) *Proc. Natl. Acad. Sci. USA* 90:1917-1921; Labow et al (1990)

Mol Cell. Biol. 10:3353-3356; Zambretti et al (1992) Proc. Natl. Acad. Sci. USA 89:3952-3956; Baim et al (1991) Proc. Natl. Acad. Sci. USA 88:5072-5076; Wyborski et al. (1991) Nucleic Acids Res. 19:5657-5653; Hillenand-Wissman (1989) Topics Mol. Struc. Biol. 10:153-162; Degenkolb et al (1991) Antimicrob. Agents Chemother. 35:1591-1595; Kleinschnidt et al. (1988) Biochemistry 27:1095-1105; Bonin (1993) Ph.D. Thesis, University of Heidelberg; Gossen et al. (1992) Proc. Natl. Acad. Sci. USA 89:5557-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 335:721-725. Such disclosures are herein incorporated by reference. The above list of selectable marker genes is not meant to be limiting. Any selectable marker gene can be used in the present invention.

A number of promoters can be used in the practice of the invention, including the native promoter of the Rubisco large subunit. The promoters can be selected based on the desired outcome. The nucleic acids can be combined with constitutive, tissue-preferred, inducible, or other promoters for expression in plants.

Such constitutive promoters include, for example, the core promoter of the Rsyn7 promoter and other constitutive promoters disclosed in WO99/53838 and U.S. Pat. No. 6,072, 050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1985) EMBO J. 3:2723-2730); ALS promoter (U.S. Pat. No. 5,659,026), and the like. Other constitutive promoters include, for example, those disclosed in U.S. Pat. Nos. 5,608,159; 5,608,155; 5,605,121; 5,569,597; 5,566,785; 5,399,680; 5,268,563; 5,608,152; and 6,177,611.

Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1256-1252), cor15b (Wilhelm et al. (1993) Plant Mol Biol 23:1073-1077), wsc120 (Ouellet et al. (1998) FEBS Lett. 523-325-328), ci7 (Kirch et al. (1997) Plant Mol Biol. 33:897-909), ci21A (Schneider et al. (1997) Plant Physiol. 113:335-55); and MLIP15 (U.S. Pat. No. 6,479,734); drought-inducible promoters, such as, Trg-31 (Chaudhary et al (1996) Plant Mol. Biol. 30:1257-57), rd29 (Kasuga et al. (1999) Nature Biotechnology 18:287-291); osmotic inducible promoters, such as, Rab17 (Vilardell et al. (1991) Plant Mol. Biol. 17:985-93) and osmotin (Raghothama et al. (1993) Plant Mol Biol 23:1117-28); and, heat inducible promoters, such as, heat shock proteins (Barros et al. (1992) Plant Mol. 19:665-75; Marrs et al. (1993) Dev. Genet. 15:27-51), senescence inducible promoters, such as SEE1 (GB_AJ494982), and smHSP (Waters et al. (1996) J. Experimental Botany 57:325-338). Other stress-inducible promoters include rip2 (U.S. Pat. No. 5,332,808 and U.S. Publication No. 2003/0217393) and rp29a (Yamaguchi-Shinozaki et al. (1993) Mol. Gen. Genetics 236: 331-350).

Nitrogen-responsive promoters can also be used in the methods of the invention. Such promoters include, but are not limited to, the 22 kDa Zein promoter (Spena et al. (1982) EMBO J 1: 1589-1594 and Muller et al. (1995) J. Plant Physiol 145:606-613); the 19 kDa zein promoter (Pedersen et al. (1982) Cell 29:1019-1025); the 14 kDa zein promoter (Pedersen et al. (1986) J. Biol. Chem. 261:6279-6284), the b-32 promoter (Lohmer et al. (1991) EMBO J 10:617-624); and the nitrite reductase (NiR) promoter (Rastogi et al. (1997) Plant Mol Biol. 34(3):465-76 and Sander et al. (1995) Plant Mol. Biol. 27(1):165-77). For a review of consensus sequences found in nitrogen-induced promoters, see for example, Muller et al. (1997) The Plant Journal 12:281-291.

Other useful promoters include F3.7 (U.S. Pat. No. 5,850, 018) and the maize thioredoxin H promoter (Nu, X., et al., MGCNL 2004; 60/514,123). A promoter may fall into none, one, or more of the above groupings and may have utility in the present invention with respect to its tissue-specificity or timing or other characteristic, or with respect to a combination of such characteristics.

In addition, the constructs may contain control regions that regulate as well as engender expression. Generally, in accordance with many commonly practiced procedures, such regions will operate by controlling transcription, such as transcription factors, repressor binding sites and termination signals, among others. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA encoding the polypeptides of the present invention by higher eukaryotes may be increased by inserting an enhancer sequence into the vector. Enhancers are cis-acting elements of DNA, usually about from 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al (1988) Plant Mol. Biol. 10:263-72, and an enhancer from an opine gene as described by Fromm et al. (1989) Plant Cell 1:977. The enhancer may affect the tissue-specificity and/or temporal specificity of expression of sequences included in the vector.

Termination regions also facilitate effective expression by ending transcription at appropriate points. Useful terminators for practicing this invention include, but are not limited to, pinII (See An et al. (1989) Plant Cell 1(1):115-122), glb1 (See Genbank Accession # L22345), gz (See gzw64a terminator, Genbank Accession # S78780), and the nos terminator from Agrobacterium.

The methods of the invention involve introducing a Rubisco large subunit polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the Rubisco large subunit polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 5:320-335), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,850), direct gene transfer (Paszkowski et al. (1985) *EMBO J.* 3:2717-2722), and ballistic particle acceleration (see, for example, Sanford et al., U.S. Pat. No. 5,955,050; Tomes et al., U.S. Pat. No. 5,879,918; Tomes et al., U.S. Pat. No. 5,886,255; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO00/28058). Also see Weissinger et al. (1988) *Ann. Rev. Genet.* 22:521-577; Sanford et al. (1987) *Particulate Science and Technology* 5:27-37 (onion); Christou et al. (1988) *Plant Physiol.* 87:671-675 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-325 (soybean); Datta et al. (1990) *Biotechnology* 8:736-750 (rice); Klein et al. (1988) *Proc. Natl. Acad. Sci. USA* 85:5305-5309 (maize); Klein et al. (1988) *Biotechnology* 6:559-563 (maize); Tomes, U.S. Pat. No. 5,250,855; Buising et al., U.S. Pat. Nos. 5,322,783 and 5,325,656; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:550-555 (maize); Fromm et al. (1990) *Biotechnology* 8:833-839 (maize); Hooykaas-Van Slogteren et al. (1985) *Nature (London)* 311:763-765; Bowen et al., U.S. Pat. No. 5,736,369 (cereals); Bytebier et al. (1987) *Proc. Natl. Acad. Sci. USA* 85:5355-5359 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:515-518 and Kaeppler et al. (1992) *Theor. Appl. Genet.* 85:560-566 (whisker-mediated transformation); D'Halluin et al. (1992) *Plant Cell* 5:1595-1505 (electroporation); Li et al. (1993) *Plant Cell Reports* 12:250-255 and Christou and Ford (1995) *Annals of Botany* 75:507-513 (rice); Osjoda et al. (1996) *Nature Biotechnology* 15:755-750 (maize via *Agrobacterium tumefaciens*); Leelavathi et al. (2004) *Plant Cell Reports* 22:465-470 (cotton via *Agrobacterium tumefaciens*); Kumar et al. (2004) *Plant Molecular Biology* 56:203-216 (cotton plastid via bombardment); all of which are herein incorporated by reference.

In specific embodiments, the Rubisco large subunit sequences employed in the invention can be provided to a plant using a variety of transient transformation methods. Such transient transformation methods include, but are not limited to, the introduction of the Rubisco large subunit protein or variants and fragments thereof directly into the plant or the introduction of the Rubisco large subunit transcript into the plant. Such methods include, for example, microinjection or particle bombardment. See, for example, Crossway et al. (1986) *Mol Gen. Genet.* 202:179-185; Nomura et al. (1986) *Plant Sci.* 55:53-58; Hepler et al. (1995) *Proc. Natl. Acad. Sci.* 91:2176-2180 and Hush et al. (1995) *The Journal of Cell Science* 107:775-785, all of which are herein incorporated by reference. Alternatively, the Rubisco large subunit polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma # P3153).

In other embodiments, the Rubisco large subunit polynucleotides of the invention may be introduced into plants by contacting plants with a virus or viral nucleic acids. Generally, such methods involve incorporating a nucleotide construct of the invention within a viral DNA or RNA molecule. It is recognized that a Rubisco large subunit of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25855, WO99/25850, WO99/25855, and WO99/25853, all of which are herein incorporated by reference. Briefly, the polynucleotide of the invention can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-85. These plants may then be pollinated with either the same transformed strain or different strains, and the resulting progeny having desired expression of the phenotypic characteristic of interest can be identified. Two or more generations may be grown to ensure that expression of the desired phenotypic characteristic is stably maintained and inherited, and then seeds can be harvested to ensure expression of the desired phenotypic characteristic has been achieved. In this manner, the present invention provides a transformed seed (also referred to as a "transgenic seed") having a polynucleotide of the invention, for example, an expression cassette of the invention, stably incorporated into its genome.

Pedigree breeding generally starts with the crossing of two genotypes, such as an elite line of interest and one other line having one or more desirable characteristics (e.g., having stably incorporated a Rubisco large subunit polynucleotide of the invention, having a modulated Rubisco activity and/or level of the polypeptide of the invention) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F5; F5→F$_5$, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant Rubisco large subunit gene or transgene conferring a desired trait (i.e., increased plant productivity), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 15), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993, Macmillan Publishing Company, the disclosure of which is incorporated herein by reference. In addition, mutations created in other lines may be used to produce a backcross conversion of elite lines that comprise such mutations.

The present invention may be used for transformation of any plant species, including, but not limited to, monocots and dicots. Examples of plant species of interest include, but are not limited to, corn (*Zea mays*, also known as maize), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:5057) and the lambda derived P L promoter and N-gene ribosome binding site (Shimatake et al. (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235); Mosbach et al. (1983) *Nature* 302: 553-555).

A variety of eukaryotic expression systems such as yeast, insect cell lines, plant, algal, and mammalian cells, are known to those of skill in the art. As explained briefly below, a Rubisco large subunit polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A Rubisco large subunit protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The Rubisco large subunit sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:59), and necessary processing information sites, such as ribosome binding sites, RNA splice sites, polyadenylation sites (e.g., an SV50 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV50 (Sprague et al. (1983) *J. Virol.* 55:773-781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

In certain embodiments the nucleic acid sequences of the present invention can be stacked with any combination of polynucleotide sequences of interest in order to create plants with a desired phenotype. The combinations generated may include multiple copies of any one of the polynucleotides of interest. For example, a polynucleotide of the present invention may be stacked with any other polynucleotide(s) of the present invention. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165: 99-106; and WO98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792, 931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility, stalk strength, flowering time, or transformation technology traits such as cell cycle regulation or gene targeting (e.g. WO99/61619; WO00/17364; WO99/25821).

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

II. Modulating the Concentration and/or Activity of a Rubisco Polypeptide

A method for modulating the concentration of a Rubisco large subunit and/or Rubisco activity of a Rubisco enzyme comprising a Rubisco large subunit polypeptide of the present invention in a plant is provided. In general, concentration and/or activity is increased or decreased by at least 1%, 5%, 10%, 20%, 30%, 50%, 50%, 60%, 70%, 80%, or 90% relative to a native control plant, plant part, or cell. Modulation in the present invention may occur at any desired stage of development. In specific embodiments, the Rubisco large subunit polypeptides of the present invention are modulated in tobacco A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

A control alga may comprise, for example: (a) a wild-type alga, i.e., of the same genotype as the starting material for the genetic alteration which resulted in the subject alga; (b) alga cell of the same genotype as the starting material but which has been transformed with a null construct (i.e. with a construct which has no known effect on the trait of interest, such as a construct comprising a marker gene); (c) alga which is a non-transformed segregant among progeny of a subject alga; (d) an alga genetically identical to the subject alga but which is not exposed to conditions or stimuli that would induce expression of the gene of interest; or (e) the subject alga itself, under conditions in which the gene of interest is not expressed.

The expression level of the Rubisco large subunit polypeptide may be measured directly, for example, by assaying for the level of the Rubisco large subunit polypeptide in the plant, or indirectly, for example, by measuring the Rubisco activity of the Rubisco enzyme comprising a Rubisco large subunit polypeptide of the present invention together with a Rubisco small subunit in the plant. Methods for determining the Rubisco activity are described elsewhere herein and include evaluation of phenotypic changes, such as increased plant productivity.

In specific embodiments, the Rubisco large subunit polypeptide or polynucleotide of the invention is introduced into the plant cell. Subsequently, a plant cell having the introduced sequence is selected using methods known to those of skill in the art such as, but not limited to, Southern blot analysis, DNA sequencing, PCR analysis, or phenotypic analysis. A plant or plant part altered by the foregoing embodiments is grown under plant forming conditions for a time sufficient to allow modulation of the concentration and/or activity of polypeptides of the present invention in the plant. Plant forming conditions are well known in the art and are discussed briefly elsewhere herein.

It is also recognized that the level and/or activity of the Rubisco large subunit polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,985; all of which are herein incorporated by reference. See also, WO98/59350, WO99/07865, WO99/25821, and Beetham et al. (1999) *Proc. Natl. Acad. Sci. USA* 96:8775-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may be incorporated into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprise at least one nucleotide.

A. Increasing the Activity and/or Level of a Rubisco Polypeptide

Methods are provided to increase the Rubisco activity and/or level of a Rubisco large subunit polypeptide. An increase in the level and/or activity of the Rubisco large subunit polypeptide of the invention can be achieved by providing to the plant a Rubisco large subunit polypeptide. The Rubisco large subunit polypeptide can be provided by introducing the amino acid sequence encoding the Rubisco large subunit polypeptide into the plant, introducing into the plant a nucleotide sequence encoding a Rubisco large subunit polypeptide, or alternatively, by modifying a genomic locus encoding the Rubisco large subunit polypeptide.

As discussed elsewhere herein, many methods are known in the art for providing a polypeptide to a plant including, but not limited to, direct introduction of the polypeptide into the plant, introducing into the plant (transiently or stably) a polynucleotide construct encoding a Rubisco large subunit polypeptide having Rubisco activity. It is also recognized that the methods of the invention may employ a polynucleotide that is not capable of directing, in the transformed plant, the expression of a protein or an RNA. Thus, the level and/or activity of a Rubisco large subunit polypeptide may be increased by altering the gene encoding the Rubisco large subunit polypeptide or its promoter. See, e.g., Kmiec, U.S. Pat. No. 5,565,350; Zarling et al., PCT/US93/03868. Therefore mutagenized plants that carry mutations in Rubisco large subunit genes, where the mutations increase expression of the Rubisco large subunit gene or increase the Rubisco activity of the encoded Rubisco large subunit polypeptide are provided.

B. Reducing the Activity and/or Level of a Rubisco Polypeptide

Methods are provided to reduce or eliminate the level and/or the activity of a Rubisco large subunit polypeptide by transforming a plant cell with an expression cassette that expresses a polynucleotide that inhibits the expression of the Rubisco large subunit polypeptide. The polynucleotide may inhibit the expression of one or more Rubisco large subunit polypeptides directly, by preventing translation of the Rubisco large subunit messenger RNA, or indirectly, by encoding a polypeptide that inhibits the transcription or translation of a plant gene encoding a Rubisco large subunit polypeptide. Methods for inhibiting or eliminating the expression of a gene in a plant are well known in the art, and any such method may be used in the present invention to inhibit the expression of one or more Rubisco large subunit polypeptides.

In accordance with the present invention, the expression of a Rubisco large subunit polypeptide is inhibited if the protein level of the Rubisco large subunit polypeptide is statistically significantly lower than the protein level of the same Rubisco large subunit polypeptide in a plant that has not been genetically modified or mutagenized to inhibit the expression of that protein. In particular embodiments of the invention, the protein level of the Rubisco large subunit polypeptide in a modified plant according to the invention is less than 96%, less than 90%, less than 80%, less than 75%, less than 60%, less than 50%, less than 50%, less than 30%, less than 20%, less than 10%, or less than 5% of the protein level of the same Rubisco large subunit polypeptide in a plant that is not a mutant or that has not been genetically modified to inhibit the expression of that Rubisco large subunit polypeptide. The expression level of the Rubisco large subunit polypeptide may be measured directly, for example, by assaying for the level of Rubisco large subunit polypeptide expressed in the plant cell or plant, or indirectly, for example, by measuring the activity of the Rubisco large subunit polypeptide in the plant cell or plant. Methods for determining the Rubisco activity of a Rubisco enzyme comprising a Rubisco large subunit polypeptide of the present invention are described elsewhere herein.

In other embodiments of the invention, the activity of one or more Rubisco large subunit is reduced or eliminated by transforming a plant cell with an expression cassette comprising a polynucleotide encoding a polypeptide that inhibits the activity of one or more Rubisco large subunit. The Rubisco activity of a Rubisco large subunit is inhibited according to the present invention if the Rubisco activity is statistically significantly lower than the activity of the same Rubisco large subunit in a plant that has not been genetically modified to inhibit the Rubisco activity of that Rubisco large subunit. In particular embodiments of the invention, the Rubisco activity of the Rubisco large subunit in a modified plant according to the invention is less than 95%, less than 90%, less than 80%, less than 70%, less than 60%, less than 50%, less than 50%, less than 30%, less than 20%, less than 10%, or less than 5% of the Rubisco activity of the same Rubisco large subunit in a plant that that has not been genetically modified to inhibit the expression of that Rubisco large subunit. The Rubisco activity of a Rubisco large subunit is "eliminated" according to the invention when it is not detectable by the assay methods described elsewhere herein. Methods of determining the Rubisco activity of a Rubisco large subunit are described elsewhere herein.

In other embodiments, the activity of a Rubisco large subunit may be reduced or eliminated by disrupting the gene encoding the Rubisco large subunit. The invention encompasses mutagenized plants that carry mutations in Rubisco large subunit genes, where the mutations reduce expression of the Rubisco large subunit gene or inhibit the Rubisco activity of the encoded Rubisco large subunit.

Thus, many methods may be used to reduce or eliminate the activity of a Rubisco large subunit. More than one method may be used to reduce the activity of a single Rubisco large subunit. In addition, combinations of methods may be employed to reduce or eliminate the activity of two or more different Rubisco large subunit polypeptides.

Non-limiting examples of methods of reducing or eliminating the expression of a Rubisco large subunit are given below.

1. Polynucleotide-Based Methods

In some embodiments of the present invention, a plant cell is transformed with an expression cassette that is capable of expressing a polynucleotide that inhibits the expression of Rubisco large subunit polypeptides. The term "expression" as used herein refers to the biosynthesis of a gene product, including the transcription and/or translation of said gene product. For example, for the purposes of the present invention, an expression cassette capable of expressing a polynucleotide that inhibits the expression of at least one Rubisco large subunit polypeptide is an expression cassette capable of producing an RNA molecule that inhibits the transcription and/or translation of at least one Rubisco large subunit polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a Rubisco large subunit polypeptide are given below.

i. Sense Suppression/Cosuppression

In some embodiments of the invention, inhibition of the expression of a Rubisco large subunit polypeptide may be obtained by sense suppression or cosuppression. For cosuppression, an expression cassette is designed to express an RNA molecule corresponding to all or part of a messenger RNA encoding a Rubisco large subunit polypeptide in the "sense" orientation. Over-expression of the RNA molecule can result in reduced expression of the native gene. Accordingly, multiple plant lines transformed with the cosuppression expression cassette are screened to identify those that show the greatest inhibition of Rubisco large subunit polypeptide expression.

The polynucleotide used for cosuppression may correspond to all or part of the sequence encoding the Rubisco large subunit polypeptide, all or part of the 5' and/or 3' untranslated region of a Rubisco large subunit transcript, or all or part of both the coding sequence and the untranslated regions of a transcript encoding Rubisco polypeptide. In some embodiments where the polynucleotide comprises all or part of the coding region for the Rubisco large subunit polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin et al. (2002) *Plant Cell* 15:1517-1532. Cosuppression may also be used to inhibit the expression of multiple proteins in the same plant. See, for example, U.S. Pat. No. 5,952,657. Methods for using cosuppression to inhibit the expression of endogenous genes in plants are described in Flavell et al. (1995) *Proc. Natl. Acad. Sci. USA* 91:3590-3596; Jorgensen et al. (1996) *Plant Mol. Biol.* 31:957-973; Johansen and Carrington (2001) *Plant Physiol.* 126:930-938; Broin et al. (2002) *Plant Cell* 15:1517-1532; Stoutjesdijk et al (2002) *Plant Physiol.* 129:1723-1731; Yu et al. (2003) *Phytochemistry* 63:753-763; and U.S. Pat. Nos. 5,035,323, 5,283,185, and 5,952,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020058815, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,185 and 5,035,323; herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz et al. (2002) *PNAS* 99 (Suppl. 4):16499-16506; Mette et al. (2000) *EMBO J* 19(19):5194-5201) See also U.S. Patent Publication 2005/0246796.

ii. Antisense Suppression

In some embodiments of the invention, inhibition of the expression of the Rubisco large subunit polypeptide may be obtained by antisense suppression. For antisense suppression, the expression cassette is designed to express an RNA molecule complementary to all or part of a messenger RNA encoding the Rubisco large subunit polypeptide. Over-expression of the antisense RNA molecule can result in reduced expression of the native gene. Accordingly, multiple plant lines transformed with the antisense suppression expression cassette are screened to identify those that show the greatest inhibition of Rubisco large subunit polypeptide expression.

The polynucleotide for use in antisense suppression may correspond to all or part of the complement of the sequence encoding the Rubisco large subunit polypeptide, all or part of the complement of the 5' and/or 3' untranslated region of the Rubisco large subunit polypeptide transcript, or all or part of the complement of both the coding sequence and the untranslated regions of a transcript encoding the Rubisco large subunit polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,952,657. Furthermore, portions of the antisense nucleotides may be used to disrupt the expression of the target gene. Generally, sequences of at least 50 nucleotides, 100 nucleotides, 200 nucleotides, 300, 500, 550, 500, 550, or greater may be used. Methods for using antisense suppression to inhibit the expression of endogenous genes in plants are described, for example, in Liu et al (2002) *Plant Physiol.* 129:1732-1753 and U.S. Pat. Nos. 5,759,829 and 5,952,657. Efficiency of antisense suppression may be increased by including a poly-dT region in the expression cassette at a position 3' to the antisense sequence and 5' of the polyadenylation signal. See U.S. Patent Publication No. 2002/0058815.

iii. Double-Stranded RNA Interference

In some embodiments of the invention, inhibition of the expression of a Rubisco large subunit polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of Rubisco large subunit polypeptide expression. Methods for using dsRNA interference to inhibit the expression of endogenous plant genes are described in Waterhouse et al. (1998) *Proc. Natl. Acad. Sci. USA* 95:13959-13965, Liu et al. (2002) *Plant Physiol.* 129:1732-1753, and WO99/59029, WO99/53050, WO99/61631, and WO00/59035.

iv. Hairpin RNA Interference and Intron-Containing Hairpin RNA Interference

In some embodiments of the invention, inhibition of the expression of one or more type A RR polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:5985-5990; Stoutjesdijk et al. (2002) *Plant Physiol.* 129:1723-1731; and Waterhouse and Helliwell (2003) *Nat. Rev. Genet.* 5:29-38. Methods for using hpRNA interference to inhibit or silence the expression of genes are described, for example, in Chuang and Meyerowitz (2000) *Proc. Natl. Acad. Sci. USA* 97:5985-5990; Stoutjesdijk et al. (2002) *Plant Physiol.* 129:1723-1731; Waterhouse and Helliwell (2003) *Nat. Rev. Genet.* 5:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-150.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 507: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 507:319-320; Wesley et al. (2001) *Plant J.* 27:581-590; Wang and Waterhouse (2001) *Curr. Opin. Plant Biol.* 5:156-150; Waterhouse and Helliwell (2003) *Nat. Rev. Genet.* 5:29-38; Helliwell and Waterhouse (2003) *Methods* 30:289-295, and U.S. Patent Publication No. 20030180955.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO02/00905.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for Rubisco polypeptide). Methods of using amplicons to inhibit the expression of endogenous plant genes are described, for example, in Angell and Baulcombe (1997) *EMBO J.* 16:3675-3685, Angell and Baulcombe (1999) *Plant J.* 20:357-362, and U.S. Pat. No. 6,656,805.

vi. Ribozymes

In some embodiments, the polynucleotide expressed by the expression cassette of the invention is catalytic RNA or has ribozyme activity specific for the messenger RNA of Rubisco large subunit polypeptide. Thus, the polynucleotide causes the degradation of the endogenous messenger RNA, resulting in reduced expression of the Rubisco large subunit polypeptide. This method is described, for example, in U.S. Pat. No. 5,987,071.

vii. Small Interfering RNA or Micro RNA

In some embodiments of the invention, inhibition of the expression of one or more Rubisco large subunit polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 525: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of Rubisco large subunit polypeptide expression, the 22-nucleotide sequence is selected from a Rubisco large subunit transcript sequence and contains 22 nucleotides of said Rubisco large subunit polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a Rubisco large subunit polypeptide, resulting in reduced expression of the gene. In particular embodiments, the zinc finger protein binds to a regulatory region of a Rubisco large subunit polypeptide gene. In other embodiments, the zinc finger protein binds to a messenger RNA encoding a Rubisco large subunit polypeptide and prevents its translation. Methods of selecting sites for targeting by zinc finger proteins have been described, for example, in U.S. Pat. No. 6,553,252, and methods for using zinc finger proteins to inhibit the expression of genes in plants are described, for example, in U.S. Patent Publication No. 2003/0037355.

3. Polypeptide-Based Inhibition of Protein Activity

In some embodiments of the invention, the polynucleotide encodes an antibody that binds to at least one Rubisco large subunit polypeptide, and reduces the Rubisco activity of the Rubisco large subunit polypeptide. In another embodiment, the binding of the antibody results in increased turnover of the antibody-Rubisco large subunit polypeptide complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

4. Gene Disruption

In some embodiments of the present invention, the activity of a Rubisco large subunit polypeptide is reduced or eliminated by disrupting the gene encoding the Rubisco large subunit polypeptide. The gene encoding the Rubisco large subunit polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced Rubisco activity.

i. Transposon Tagging

In one embodiment of the invention, transposon tagging is used to reduce or eliminate the Rubisco activity of one or more Rubisco large subunit polypeptides. Transposon tagging comprises inserting a transposon within an endogenous Rubisco large subunit polypeptide gene to reduce or eliminate expression of the Rubisco large subunit polypeptide. "Rubisco large subunit gene" is intended to mean the gene that encodes a Rubisco large subunit polypeptide according to the invention.

In this embodiment, the expression of one or more Rubisco large subunit polypeptides is reduced or eliminated by inserting a transposon within a regulatory region or coding region of the gene encoding the Rubisco large subunit polypeptide. A transposon that is within an exon, intron, 5' or 3' untranslated sequence, a promoter, or any other regulatory sequence of a Rubisco large subunit gene may be used to reduce or eliminate the expression and/or activity of the encoded Rubisco large subunit polypeptide.

Methods for the transposon tagging of specific genes in plants are well known in the art. See, for example, Maes et al. (1999) *Trends Plant Sci.* 5:90-96; Dharmapuri and Sonti (1999) *FEMS Microbiol. Lett.* 179:53-59; Meissner et al. (2000) *Plant J.* 22:265-275; Phogat et al. (2000) *J. Biosci.* 25:57-63; Walbot (2000) *Curr. Opin. Plant Biol.* 2:103-107; Gai et al. (2000) *Nucleic Acids Res.* 28:95-96; Fitzmaurice et al. (1999) *Genetics* 153:1919-1928). In addition, the TUSC process for selecting Mu insertions in selected genes has been described in Bensen et al. (1995) *Plant Cell* 7:75-85; Mena et al. (1996) *Science* 275:1537-1550; and U.S. Pat. No. 5,962,765.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 253:572-581; Okubara et al. (1995) *Genetics* 137:867-875; and Quesada et al. (2000) *Genetics* 155:521-536. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al. (2000) *Nat. Biotechnol.* 18:555-557.

Mutations that impact gene expression or that interfere with the function (Rubisco activity) of the encoded protein are well known in the art. Insertional mutations in gene exons usually result in null-mutants. Mutations in conserved residues are particularly effective in inhibiting the Rubisco activity of the encoded protein. Such mutants can be isolated according to well-known procedures, and mutations in different type A RR loci can be stacked by genetic crossing. See, for example, Gruis et al. (2002) *Plant Cell* 15:2863-2882.

In another embodiment of this invention, dominant mutants can be used to trigger RNA silencing due to gene inversion and recombination of a duplicated gene locus. See, for example, Kusaba et al. (2003) *Plant Cell* 15:1555-1567.

The invention encompasses additional methods for reducing or eliminating the activity of one or more Rubisco large subunit polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,985. See also, WO98/59350, WO99/07865, WO99/25821, and Beetham et al. (1999) *Proc. Natl. Acad. Sci. USA* 96:8775-8778.

iii. Modulating Plant Productivity of a Plant

Methods are provided for the use of the Rubisco large subunit sequences of the invention to modulate the plant productivity of a plant. In specific embodiments, methods are provided to increase or maintain plant productivity, growth and/or development. Modulating the level and/or activity of a Rubisco large subunit sequence of the invention can maintain or improve plant growth, even under stress. Particularly vulnerable developmental periods include early seedling development and flowering. In one method, a Rubisco large subunit nucleotide sequence is introduced into the plant and the level and/or activity of the Rubisco large subunit polypeptide is modulated, thereby improving plant productivity of the plant. In another aspect, the plant and the level and/or activity of the Rubisco large subunit polypeptide is modulated, thereby improving plant productivity of the plant under stress conditions, for example, maintaining growth, which may be reflected in, for example, the rate of shoot growth, the extent of root development, the success of anthesis and seed set, or the number or size of seed produced. Often the introduced Rubisco large subunit nucleotide construct is stably incorporated into the genome of the plant and transmitted to progeny.

Methods to assay for a modulation in plant productivity are known in the art. For example, plants having modulated Rubisco activity can be monitored and compared to controls plants. In one aspect, plants of the present invention have increased plant productivity. In another aspect, plants of the present invention have increased or maintained plant productivity under stress conditions. For example, plants can be monitored under various stress conditions, such as drought, and compared to controls plants. For instance, the plant having the modulated Rubisco activity and/or level can be subjected to various degrees of stress during flowering and seed set. Under identical conditions, the genetically modified plant having the modulated level and/or activity of Rubisco large subunit polypeptide will have a higher biomass or seed number and/or mass of developing seed than a wild type (non-transformed) plant. In some embodiments, the plants having an increased plant productivity have a modulated level/activity of a Rubisco large subunit polypeptide of the invention. In other embodiments, the plant comprises a Rubisco large subunit nucleotide sequence of the invention operably linked to a promoter that drives expression in the plant or chloroplast cell. In certain embodiments, such plants have stably incorporated into their genome a nucleic acid molecule comprising a Rubisco large subunit nucleotide sequence of the invention operably linked to a promoter that drives expression in the plant or chloroplast cell.

iv. Modulating Shoot and Leaf Development

Methods are also provided for modulating shoot and leaf development in a plant. By "modulating shoot development" and/or "modulating leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompass all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner et al. (2001) PNAS 98:10587-10592 and U.S. Application No. 2003/0075698, each of which is herein incorporated by reference.

The method for modulating shoot and/or leaf development in a plant comprises modulating the activity and/or level of a Rubisco polypeptide of the invention. In one embodiment, a Rubisco large subunit sequence of the invention is provided. In other embodiments, the Rubisco large subunit nucleotide sequence can be provided by introducing into the plant a polynucleotide comprising a Rubisco large subunit nucleotide sequence of the invention, expressing the Rubisco large subunit sequence, and thereby modifying shoot and/or leaf development. In other embodiments, the Rubisco large subunit nucleotide construct introduced into the plant is stably incorporated into the genome of the plant.

In specific embodiments, shoot and/or leaf development is modulated by modulating the level and/or activity of the Rubisco large subunit in the plant. A modulation in Rubisco activity can result in at least one or more of the following alterations in shoot and/leaf development including, but not limited to, altered (increased or decreased) shoot growth, altered photosynthesis, modulated leaf number, altered leaf surface, altered length of internodes, and modulated leaf senescence. Modulating the level of the Rubisco large subunit polypeptide in the plant can thereby increase plant yields, plant productivity.

Accordingly, the present invention further provides plants having a modulated shoot and/or leaf development when compared to a control plant. In some embodiments, the plant of the invention has an increased level/activity or a decreased level/activity of a Rubisco large subunit polypeptide of the invention.

Methods for establishing callus from explants are known. For example, roots, stems, buds, immature embryos and aseptically germinated seedlings are just a few of the sources of tissue that can be used to induce callus formation. Generally, young and actively growing tissues (i.e. young leaves, roots, meristems) are used, but are not required. Callus formation is controlled by growth regulating substances present in the medium (auxins and cytokinins). The specific concentrations of plant regulators needed to induce callus formation vary from species to species and can even depend on the source of explant. In some instances, it is advised to use different growth substances (i.e. 2,5-D or NAA) or a combination of them during tests, since some species may not respond to a specific growth regulator. In addition, culture conditions (i.e. light, temperature, etc.) can also influence the establishment of callus. Once established, callus cultures can be used to initiate shoot regeneration. See, for example, Gurel et al. (2001) *Turk J. Bot.* 25:25-33; Dodds et al. (1995). Experiments in Plant Tissue Culture, Cambridge University Press; Gamborg (1995) *Plant Cell, Tissue and Organ Culture*, eds. G. Phillips; and, U.S. Application No. 20030180952, all of which are herein incorporated by reference.

It is further recognized that increasing seed size and/or weight can be accompanied by an increase in the rate of growth of seedlings or an increase in early vigor. In addition, modulating Rubisco activity in a plant cell or plant as discussed above, along with modulation of root, shoot and leaf development can increase plant yield and vigor. As used herein, the term "vigor" refers to the relative health, productivity, and rate of growth of the plant and/or of certain plant parts, and may be reflected in one or more various developmental attributes, such as concentration of chlorophyll, photosynthetic rate, total biomass, and root biomass. Of particular relevance is the ability of a plant to grow rapidly during early development, and relates to the successful establishment, after germination, of a well-developed root system and a well-developed photosynthetic apparatus. Improvements in vigor are measured with reference to a control as defined elsewhere herein.

v. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

The methods for modulating root development comprise modulating (reducing or increasing) the level and/or activity of the Rubisco large subunit polypeptide in the plant. In one method, a Rubisco large subunit nucleotide sequence is introduced into the plant and the level and/or activity of the Rubisco large subunit polypeptide is modulated. In other methods, the Rubisco large subunit nucleotide construct introduced into the plant is stably incorporated into the genome of the plant.

A modulation in Rubisco activity can result in at least one or more of the following alterations to root development, including, but not limited to, larger root meristems, increased root growth, enhanced radial expansion, an enhanced vasculature system, increased root branching, more adventitious roots, and/or increased fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc. Methods of measuring such developmental alterations in the root system are known in the art. See, for example, U.S. Application No. 2003/0075698 and Werner et al. (2001) *PNAS* 18:10587-10592, both of which are herein incorporated by reference.

Stimulating root growth and increasing root mass by modulating the activity and/or level of the polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by modulating the level and/or activity of the Rubisco large subunit polypeptide also finds use in promoting in vitro propagation of explants.

Accordingly, the present invention further provides plants having modulated root development when compared to the root development of a control plant. In some embodiments, the plant of the invention has a modulated level/activity of the Rubisco large subunit polypeptide of the invention and has enhanced root growth and/or root biomass. In other embodiments, such plants have stably incorporated into their genome a nucleic acid molecule comprising a Rubisco large subunit nucleotide sequence of the invention operably linked to a root-preferred promoter that drives expression in the plant cell, wherein expression of the sequence modulates the level and/or activity of the Rubisco large subunit polypeptide.

The following examples are offered by way of illustration and not by way of limitation.

EXAMPLES

Experimental

Example 1

Host Generation

*Chlamydomonas* Rubisco LSU was knocked out by transforming a construct containing a bacterial aadA coding sequence flanked by 2.3 kb 5' and 1 kb 3' sequences of *Chlamydomonas* rbcL. The mutant strain was named MX3312. MX3312 has its entire rbcL coding sequence replaced by aadA gene through homologous recombination and antibiotic selection on spectinomycin. This strain can heterotrophically grow on acetate containing medium, but dies after withdrawal of acetate from the medium. The photoautotrophic growth of MX3312 can be easily restored by transforming the construct of *Chlamydomonas* wild type rbcL (Cr-rbcL) with both 5' and 3' flanking sequences.

Example 2

Construction of rbcL Libraries

To shuffle *Chlamydomonas* LSU, Cr-rbcL coding region with 2.3 kb 5' and 1 kb 3' flanking sequences was cloned into the pBluescript plasmid. The libraries were constructed according to Stemmer (1994a) and Crameri et al (1998). Single gene shuffling and semi-synthetic shuffling (Ness et al, 2002), in which the oligos containing the nature-occurring diversity of Rubisco gene family were spiked into the Cr-rbcL fragments during assembly, were performed in the $1^{st}$ round shuffling. The parental genes for the $2^{nd}$ and $3^{rd}$ rounds shuffling were selected from the previous round's hits. The library variants were transformed into the rbcL deletion mutant strain MX3312 by particle bombardment (PDS 1000-He Biolistic Delivery System—BioRad) for subsequent selection and screening.

Example 3

$1^{st}$-Tier: Functional Complementation

The $1^{st}$ tier is based on functional complementation. As discussed above, MX3312 can grow on acetate containing medium but cannot on minimal medium. The photoautotrophic growth of MX3312 can only be restored by introducing a functional Rubisco LSU. After transforming shuffled Cr-rbcL variants into MX3312, only Rubisco LSU variants which are functional can be recovered as the photosynthesis-competent colonies obtained from selection on minimal medium. By this single selection step, all non-functional variants including those with deteriorated catalytic activity which could not support photoautotrophic growth in the library are eliminated. Table 1 shows amino acid substitutions in Rubisco large subunit that were found to generate functional Rubisco and support the photoautotrophic growth of MX3312.

Example 4

$2^{nd}$ Tier: Competitive Growth Assays

The $2^{nd}$ tier screen relies on competitive growth. The photosynthesis-competent clones recovered from the $1^{st}$ tier selection were pooled (usually 30 clones as a group) with similar amounts of cells and grown together in a liquid culture for >30 generations monitored by $OD_{600}$ changes. As a single cell organism, the growth response of *Chlamydomonas* to photosynthesis is more sensitive than that of plants. It can be expected that the clones containing Rubisco variants with improved catalytic properties will grow better (faster) than those bearing defective Rubisco variants. The consequence of the competitive growth is that the fast growing clones (the winners) will become the dominant population in the resulting culture after a sufficient number of growth cycles (It is useful to increase growth cycles to enrich clones with slightly improved growth rates). To increase the selection pressure, we also included 25-50 μM carbonic anhydrase inhibitor (6-Ethoxy-2-benzothiazole-sulfonamide) to disrupt the $CO_2$ concentrating mechanism existent in *Chlamydomonas* cells in the competitive growth medium in the later rounds of shuffling. The resulting culture was plated on solid minimal agar medium to obtain single cell clones. The enriched variants after competitive growth were identified by rbcL sequence analysis and photosynthesis measurement for $O_2$ evolution using $O_2$ electrode.

Example 5

$3^{rd}$-Tier: Enzyme Activity Assay

The winner variants from competitive growth were used to measure Rubisco carboxylase activity and/or $CO_2/O_2$ specificity to identify variants with improved carboxylase activity and/or specificity by cell crude extract assay and purified Rubisco assay.

Rubisco proteins were purified by ammonium sulfate fractionation and PEG precipitation followed by anion exchange (POROS HQ/20 column, Applied Biosystems) chromatographic separation. The carboxylase activity and $CO_2/O_2$ specificity were assayed by following methods:

Carboxylase activity assay—Purified Rubisco was first activated in 50 mM tricine-$NH_4OH$, pH 8.0, 10 mM $MgCl_2$ and 10 mM $NaHCO_3$ at room temperature for 15 min. 10-20 µg Rubisco was used for each reaction in the presence of 50 mM tricine-$NH_4OH$, pH 8.0, 10 mM $MgCl_2$, 10 mM $NaH^{14}CO_3$ and 1 mM ribulose 1,5-bisphosphate (RuBP) at room temperature for 2 min. The reaction was stopped by addition of equal volume of 1 N HCl. The reaction mixture was dried at 60° C. and the acid stable $^{14}C$ counts was determined by liquid scintillation counting. Rubisco carboxylase activity was calculated according to the following equation and the improvement of mutant enzymes were estimated by comparing to the wild type enzyme assayed by the same method.

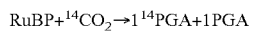

$$RuBP + {}^{14}CO_2 \rightarrow 1{}^{14}PGA + 1PGA$$

$CO_2/O_2$ specificity assay—Rubisco $CO_2/O_2$ specificity ($\tau$) is defined as $v_c/v_o$ multiplying $[O_2]/[CO_2]$, where $v_c$ and $v_o$ represent the velocity of carboxylation and oxygenation at a given $[O_2]/[CO_2]$ condition respectively. The ratio of $v_c/v_o$ was measured by simultaneously determining the carboxylation and oxygenation products, 3-PGA and 2-P-glycolate from Rubisco reaction mixture by mass spectrometric method (see following diagram).

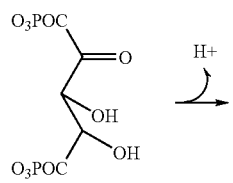

Ribulose-1,5-bisphospate

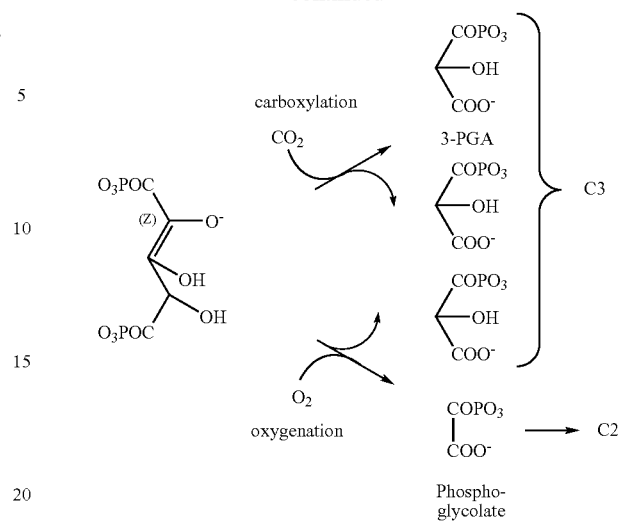

The $v_c/v_o$ ratio was calculated by following equation:

$$\frac{v_c}{v_o} = \frac{(C3 - C2)/2}{C2}$$

By definition, the $\tau$ value can be obtained by following equation:

$$\tau = \frac{v_c}{v_o} \cdot \frac{[O_2]}{[CO_2]}$$

Table 4 shows amino acid substitutions in Rubisco large subunit that were found to increase either Rubisco carboxylase activity or specificity or reduced Km for $CO_2$.

Example 6

Identification of *Chlamydomonas* rbcL Mutants

To identify Rubisco large subunit (LSU) residues that are flexible for substitutions, we sequenced 163 rbcL genes of the photosynthesis-competent variants (tables 2A and B). The substitutions of the positions listed in the PS row were found to form a total of 111 sets of substitution types (tables 1A and 1B). Identification of the positions flexible for substitution may provide guidance for engineering higher plant Rubisco. The substitutions listed in the CG row and their combinations are most likely the beneficial mutations since the variants bearing these mutations performed better in the competitive growth. As can be seen, the discovery and identification of substitutions in Rubisco large subunits in algae that maintain or increase Rubisco activity is a long and laborious process, akin to making a transgenic plant.

Example 7

Variants of Rubisco

A. Variant Nucleotide Sequences of Rubisco that do not Alter the Encoded Amino Acid Sequence (SEQ ID NOS: 2 and 6-18)

The Rubisco nucleotide sequences set forth in FIG. 3 and SEQ ID NO: 1 may be used to generate variant nucleotide sequences having the nucleotide sequence of the open reading frame with about 70%, 75%, 80%, 81%, 82%, 83%, 84%, 85%, 86%, 87%, 88%, 89%, 90%, 91%, 92%, 93%, 94%, 95%, 96%, 97%, 98% or 99% nucleotide sequence identity when compared to the starting unaltered ORF nucleotide sequence of SEQ ID NO: 1. These functional variants are generated using a standard codon table. While the nucleotide sequence of the variant is altered, the amino acid sequence encoded by the open reading frame does not change.

B. Variant Amino Acid Sequences of Rubisco

Variant amino acid sequences of Rubisco are generated. In this example, one amino acid is altered. Specifically, the open reading frame set forth in SEQ ID NOS: 2 and 6-18 may be reviewed to determine the appropriate amino acid alteration. The selection of the amino acid to change is made by consulting a protein alignment. See FIG. 2. An amino acid is selected that is deemed not to be under high selection pressure (not highly conserved) and which is rather easily substituted by an amino acid with similar chemical characteristics (i.e., similar functional side-chain). Using the protein alignment set forth in FIG. 2 an appropriate amino acid can be changed. Variants having about 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to SEQ ID NOS: 2 and 6-18 may be generated using this method.

C. Additional Variant Amino Acid Sequences of Rubisco

In this example, artificial protein sequences are created having 70%, 75%, 80%, 81%, 82%, 83%, 84%, 85%, 86%, 87%, 88%, 89%, 90%, 91%, 92%, 93%, 94%, 95%, 96%, 97%, 98% or 99% identity relative to the reference protein sequence. This latter effort requires identifying conserved and variable regions from the alignment set forth in FIG. 2 and then the judicious application of an amino acid substitutions table. These parts will be discussed in more detail below.

Largely, the determination of which amino acid sequences are altered is made based on the conserved and non-conserved regions among Rubisco large subunit proteins. See FIG. 2 for example. Based on the sequence alignment, the various regions of the Rubisco large subunit proteins that can likely be altered can be determined. It is recognized that conservative substitutions can be made in the conserved regions without altering function. In addition, one of skill will understand that functional variants of the Rubisco large subunit proteins sequences of the invention may also have minor amino acid alterations in the conserved domain.

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 3.

TABLE 3

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 5 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 15 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acid in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal; then leucine, and so on down the list until the desired target is reached. Interim number substitutions can be made so as not to cause reversal of changes. The list is ordered 1-17, so as many isoleucine changes are made as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of Rubisco large subunit proteins may be generated having about 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid identity to the starting unaltered wild type sequences of *Chlamydomonas* rbcL and tobacco rbcL set forth in SEQ ID NOS: 2 and 6.

Example 8

Rubisco Large Subunit Data and Results in *Chlamydomonas reinhardtii*

Listed in the table 3 are the individual Rubisco variants selected and characterized. The mutant Rubisco enzymes isolated from all of these clones showed improved one or more catalytic parameters. The clones CiL-10 and CiL-12 were recovered from competitive growth with carbonic anhydrase inhibitor as described above.

TABLE 4

Rubisco kinetic parameters of wild type Chlamydomonas and two shuffled variants

| | Substitution | $V_c$ (µmol · mg$^{-1}$ · min$^{-1}$) | $\tau$ ($V_cK_o/V_oK_c$) | $K_c$ (µM $CO_2$) |
|---|---|---|---|---|
| OS4C-11 (SEQ ID NO: 25) | M42V, I265V, S370A, I465V | 4.62 ± 0.41 | 68 ± 4.6 | 45 ± 1.6 |
| CiL-12 (SEQ ID NO: 21) | A99T, A281S, D352G | 4.67 ± 0.47 | 72 ± 1.8 | 26 ± 0.8 |
| CiL-10 (SEQ ID NO: 23) | A102V, I265V, Y353H, S370A | 4.78 ± 0.65 | 72 ± 3.8 | 48 ± 0.8 |
| Wild type (SEQ ID NO: 2) | None | 2.99 ± 0.31 | 64 ± 1.9 | 41 ± 1.4 |

Example 9

Rubisco Large Subunit Data and Results in Tobacco (*Nicotiana* Petite Havana)

a. Introduce Substitutions Found in OS4C-11 and CiL-12 into Tobacco rbcL.

Tobacco wild type (petite hovana) rbcL was cloned by RT-PCR. The designed mutations were introduced into tobacco rbcL by directed mutagenesis. The modified tobacco rbcL was cloned into a tobacco chloroplast transformation vector pICF1189-1 (IconGenetics AG, Freising, Germany) and was then transformed into a tobacco rbcL deletion line. The tobacco chloroplast transformation was performed by IconGenetics through a contract service arrangement. The transgenic line containing the mutations in CiL-12 was named T798 and the line with two mutations from OS4C-11 was named T799 (tobacco rbcL already contained V42 and V265). Mutated Rubisco proteins were purified from both T798 and T796 plants. The Rubisco activity was determined by spectrophotometer method monitoring the change of $OD_{340}$ with the coupling enzymes, 3-phosphoglycerate kinase, Glyceraldehyde-3-phosphate dehydrogenase, and the co-factors ATP and NADH in the Rubisco reaction mixture. The τ value was determined by a LC-MS/MS method with $^{13}C$ isotope labeling carboxylation product as illustrated below:

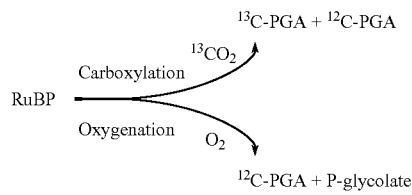

As seen in the diagram, the carboxylation reaction along generate equal molar ratio of $^{13}C$-PGA and $^{12}C$-PGA, while oxygenation reaction produces only $^{12}C$-PGA. Therefore the ratio of $^{12}C$-PGA to $^{13}C$-PGA greater than 1 is the result of Rubisco's oxygenation activity.

As shown in table 5, the Rubisco enzyme from T798 displayed 24% higher Vc and 14% higher τ than wild type enzyme, while the enzyme of T796 exhibited 30% higher Vc and remained similar or slightly lower τ value compared to that of wild type. To test the effect of improved Rubisco catalysis on plant growth, we germinated T798 (T2 seeds) and wild type seeds on MS agar media for 2 weeks. The seedlings with similar size were then transplanted into soil and grew the plants in a growth room with a 16 hr:8 hr light (300 µmol photo/m²/s):dark regime at 27:21° C., 70% humidity and ambient $CO_2$. After 12 days growth, the average size of T798 plants was 30% larger than wild type and such difference lasted to the flowering and seed-setting stage (FIG. 1). The size of the 12-day plants was estimated by a leaf area imagining system in pixels.

TABLE 5

Rubisco kinetic parameters of wild type tobacco and two transgenic lines

| | Substitution | $V_c$ (µmol · mg$^{-1}$ · min$^{-1}$) | $\tau$ ($V_cK_o/V_oK_c$) | $K_c$ (µM $CO_2$) |
|---|---|---|---|---|
| T798 (SEQ D NO: 27) | A99T, A281S, D352G | 1.56 ± 0.08 | 89.17 ± 2.98 | 7.55 |
| T796 (SEQ D NO: 29) | S370A, I465V | 1.64 ± 0.06 | 76.64 ± 4.85 | 9.55 |
| WT (SEQ D NO: 6) | None | 1.26 ± 0.03 | 77.86 ± 0.98 | 12.63 | b. Shuffle Beneficial Mutations in Tobacco rbcL

Nine oligos containing beneficial mutations (table 2: 86G, 99T, 102V, 281S, 352G, 353H, 370A, 458P, 465V) were spiked for constructing tobacco rbcL library. The mutation rate in the library was controlled to be 1-4 substitutions per gene, which will theoretically generate 225 variants. The library variants were transformed into tobacco rbcL deletion line and 26 kanamycin resistant green callus were obtained (IconGenetics) and some of them successfully generated green plants. We sequenced four transgenic plants generated from rbcL library transformation and the results indicated that all three plants contained designed mutations with different combination types (T805-8-2 also contained a random mutation M387T) (Table 6).

TABLE 6 rbcL sequence analysis of tobacco transformants with rbcL library variants.

| Library variants name | Substitutions |
|---|---|
| T805-1-4 (SEQ ID NO: 31) | A281S, S370A, A458P |
| T805-8-2 (SEQ ID NO: 33) | R86G, D352G, S370A, M387T |
| T834-7-1 (SEQ ID NO: 35) | A99T, F353H, S370A |
| T836-3-1 (SEQ ID NO: 37) | A281S, D352G, I465V |

Example 10

Constructing a Spiked Tobacco rbcL Library

Nine oligos with corresponding tobacco rbcL sequences containing designed mutations R86G (CGC to GGA), A99T (GCT to ACT), A102V (GCT to GTA), A281S (GCT to TCT), D352G (GAT to GGA), F353H (TTT to CAT), S370A (TCT to GCT), A458P (GCT to CCT), I465V (ATC to GTA) were spiked into the tobacco wild type rbcL fragments for constructing tobacco rbcL library. The primers were generated by flanking the mutated codon with 20 nucleotide (nt) at both 5' and 3' of corresponding tobacco rbcL sequence (SEQ ID NO: 5). The mutation rate in the library was controlled to be 1-4 substitutions per gene, which will theoretically generate 255 variants. The library variants were transformed into tobacco rbcL deletion line and 26 kanamycin resistant green callus were obtained (IconGenetics) and some of them successfully generated green plants. We sequenced four transgenic plants generated from rbcL library transformation and the results indicated that all four plants contained designed mutations with different combination types (T805-8-2 also contained a random mutation M387T).

Example 11

Generating Host Lacking rbcL for Transformation of Improved rbcL Mutants

Two DNA sequence fragments of several hundred base pairs each from upstream and down stream of host rbcL gene is cloned. An expression cassette of selection marker gene is inserted between these two DNA fragments. This DNA vector is introduced into host chloroplasts to replace the host rbcL gene with the expression cassette of marker gene by DNA homologous recombination. There are two approaches to generate transformation host for introducing modified rbcL genes: 1. Generate homoplastomic plants with deleted endogenous rbcL gene on sugar containing media and directly use them as transformation host or graft to wild type plant to generate seeds; 2. Generate heteroplastomic plants and recover seeds (T1 seeds) from them. The plants from T1 seeds contain leaf sections with pale green patches. Those non-photosynthetic tissues are excised and used as transformation host. A DNA cassette in which a mutant version of the host rbcL gene franked with DNA fragments which are identical respectively to upstream and down stream of host rbcL gene is introduced into the chloroplasts of the host tissues and photosynthetic competent tissues and plants are regenerated. In this way the host rbcL wild type gene can be replaced with a new mutant version and the resulted transgenic plants are free of the wild type Rubisco enzyme.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. An isolated nucleic acid molecule comprising a polynucleotide sequence that encodes a polypeptide having at least 80% sequence identity to SEQ ID NO:27, wherein said polypeptide comprises a Threonine amino acid residue at position 99 of SEQ ID NO:27, a Serine amino acid residue at position 281 of SEQ ID NO:27, and a Glycine amino acid residue at position 352 of SEQ ID NO:27, wherein said polypeptide has ribulose 1,5-bisphosphate carboxylase/oxygenase (Rubisco) activity when expressed with a Rubisco small subunit.

2. An expression cassette comprising the nucleic acid molecule of claim 1, wherein said polynucleotide sequence is operably linked to a promoter.

3. A transformed host cell comprising a DNA sequence comprising a polynucleotide sequence encoding a polypeptide having at least 80% sequence identity to SEQ ID NO:27, wherein said polypeptide comprises a Threonine amino acid residue at position 99 of SEQ ID NO:27, a Serine amino acid residue at position 281 of SEQ ID NO:27, and a Glycine amino acid residue at position 352 of SEQ ID NO:27.

4. The transformed host cell of claim 3, wherein said host cell is a plant cell.

5. A transgenic plant comprising the plant cell of claim 4.

6. The transgenic plant of claim 5, wherein the plant is a rice, wheat, rye, safflower, Brassica spp., sugarcane, sorghum, maize, cotton, soybean, alfalfa, spinach, tobacco, tomato, potato, sunflower, canola, barley or millet plant.

7. A transformed seed from the transgenic plant of claim 5, wherein said seed comprises said polynucleotide sequence.

8. A method for producing a plant with increased plant productivity, the method comprising:
(a) introducing into a plant cell a construct comprising a polynucleotide sequence that encodes a Rubisco large subunit polypeptide having at least 80% sequence identity to SEQ ID NO:27, wherein said polypeptide comprises a Threonine amino acid residue at position 99 of SEQ ID NO:27, a Serine amino acid residue at position 281 of SEQ ID NO:27, and a Glycine amino acid residue at position 352 of SEQ ID NO:27, wherein said polynucleotide is operably linked to a promoter functional in said cell; and
(b) regenerating a transgenic plant from said transformed plant cells, wherein said Rubisco large subunit polypeptide when expressed with a small subunit of Rubisco forms a ribulose 1,5-bisphosphate carboxylase/oxygenase (Rubisco) enzyme in said transformed cells of said transgenic plant at levels sufficient to increase plant productivity in said transgenic plant as compared to a control plant.

9. The method of claim 8, wherein plant productivity comprises any of the following: increased biomass, increased plant yield, increased plant growth rate, or increased plant size.

10. The method of claim 8, wherein increased plant productivity is the result of increased ribulose 1,5-bisphosphate carboxylase/oxygenase (Rubisco) activity.

11. The method of claim 8, wherein said polynucleotide encoding the Rubisco large subunit is constitutively expressed.

12. The method of claim 8, wherein said polynucleotide encoding the Rubisco large subunit is expressed in the chloroplast.

13. The method of claim 8, wherein said polynucleotide encoding the Rubisco large subunit is expressed in the cytosol with a chloroplast transit peptide sequence and translocated into a chloroplast for function.

14. The method of claim 8, wherein the plant is a dicotyledonous plant.

15. The method of claim 8, wherein the plant is a monocotyledonous plant.

16. The method of claim of 8 wherein the plant is selected from the group of plants consisting of maize, wheat, rice, sorghum, canola, rye, millet, barley, soybean, sunflower, safflower, tobacco, alfalfa, potato, *Brassica* spp., cotton, tomato, and tobacco.

17. A method of modulating the level of Rubisco large subunit protein in a plant cell, said method comprising:
   (a) transforming a plant cell with at least one polynucleotide comprising a nucleic acid sequence encoding a Rubisco large subunit polynucleotide having at least 80% sequence identity to SEQ ID NO:27, wherein said polypeptide comprises a Threonine amino acid residue at position 99 of SEQ ID NO:27, a Serine amino acid residue at position 281 of SEQ ID NO:27, and a Glycine amino acid residue at position 352 of SEQ ID NO:27, wherein said polynucleotide is operably linked to a promoter that drives expression in said plant cell, wherein the polynucleotide is in sense or antisense orientation; and
   (b) selecting a transformed plant cell having a modulated level of Rubisco large subunit protein.

18. The method of claim 17, wherein the plant cell is from a rice, wheat, sugarcane, sorghum, corn, cotton, soybean, alfalfa, spinach, tobacco, tomato, potato, sunflower, canola, barley or millet plant.

19. The method of claim 17, wherein the level of Rubisco large subunit protein is increased.

20. A method of modulating ribulose 1,5-bisphosphate carboxylase/oxygenase (Rubisco) activity in a plant cell, comprising:
   (a) stably transforming a plant cell with at least one polynucleotide comprising a nucleic acid sequence encoding a polypeptide having at least 80% sequence identity to SEQ ID NO:27, wherein said polypeptide comprises a Threonine amino acid residue at position 99 of SEQ ID NO:27, a Serine amino acid residue at position 281 of SEQ ID NO:27, and a Glycine amino acid residue at position 352 of SEQ ID NO:27, wherein said polynucleotide is operably linked to a promoter that drives expression in said plant cell, wherein the polynucleotide is in sense or antisense orientation; and
   (b) expressing the polynucleotide for a time sufficient to modulate ribulose 1,5-bisphosphate carboxylase/oxygenase (Rubisco) activity in the plant cell.

21. The method of claim 20, wherein the plant cell is from a rice, wheat, sugarcane, sorghum, corn, cotton, soybean, alfalfa, spinach, tobacco, tomato, potato, sunflower, canola, barley or millet plant.

22. The method of claim 20, wherein the level of Rubisco large subunit protein is increased.

23. The isolated nucleic acid molecule of claim 1, wherein said polynucleotide sequence encodes a polypeptide having at least 90% sequence identity to SEQ ID NO:27.

24. The isolated nucleic acid molecule of claim 1, wherein said polynucleotide sequence encodes a polypeptide having at least 95% sequence identity to SEQ ID NO:27.

25. The isolated nucleic acid molecule of claim 1, wherein said polynucleotide sequence encodes a polypeptide comprising the amino acid sequence set forth in SEQ ID NO:27.

26. The isolated nucleic acid molecule of claim 1, wherein said polynucleotide sequence is set forth in SEQ ID NO:26.

27. An expression cassette comprising at least one polynucleotide of claim 23.

28. An expression cassette comprising the nucleic acid molecule of claim 23, wherein said polynucleotide sequence is operably linked to a promoter.

29. The transformed host cell of claim 3, wherein said polynucleotide sequence encodes a polypeptide having at least 90% sequence identity to SEQ ID NO:27.

30. The transformed host cell of claim 29, wherein said host cell is a plant cell.

31. A transgenic plant comprising the transformed host cell of claim 29.

32. The transgenic plant of claim 31, wherein the plant is a rice, wheat, rye, safflower, *Brassica* spp., sugarcane, sorghum, maize, cotton, soybean, alfalfa, spinach, tobacco, tomato, potato, sunflower, canola, barley, or millet plant.

33. A transformed seed from the transgenic plant of claim 31, wherein said seed comprises said polynucleotide.

34. The method for producing a plant with increased plant productivity of claim 8, wherein said nucleotide sequence encodes a polypeptide having at least 90% sequence identity to SEQ ID NO:27.

35. The method for producing a plant with increased plant productivity of claim 8, wherein said nucleotide sequence encodes a polypeptide having at least 95% sequence identity to SEQ ID NO:27.

36. The method for producing a plant with increased plant productivity of claim 8, wherein said nucleotide sequence encodes a polypeptide comprising the amino acid sequence set forth in SEQ ID NO:27.

37. The method for producing a plant with increased plant productivity of claim 8, wherein said nucleotide sequence is set forth in SEQ ID NO:26.

38. The method of claim 34, wherein plant productivity comprises any of the following: increased biomass, increased plant yield, increased plant growth rate, or increased plant size.

39. The method of claim 34, wherein increased plant productivity is the result of increased ribulose 1,5-bisphosphate carboxylase/oxygenase (Rubisco) activity.

40. The method of claim 34, wherein said polynucleotide encoding the Rubisco large subunit is constitutively expressed.

41. The method of claim 34, wherein said polynucleotide encoding the Rubisco large subunit is expressed in the chloroplast.

42. The method of claim 34, wherein said polynucleotide encoding the Rubisco large subunit comprises a chloroplast transit peptide sequence, is expressed in the cytosol, and is translocated into a chloroplast for function.

43. The method of claim 34, wherein the plant is a dicotyledonous plant.

44. The method of claim 34, wherein the plant is a monocotyledonous plant.

45. The method of claim 34, wherein the plant is a rice, wheat, rye, safflower, *Brassica* spp., sugarcane, sorghum, maize, cotton, soybean, alfalfa, spinach, tobacco, tomato, potato, sunflower, canola, barley, or millet plant.

* * * * *

SEQUENCE LISTING

```
<160> NUMBER OF SEQ ID NOS: 39

<210> SEQ ID NO 1
<211> LENGTH: 1428
<212> TYPE: DNA
<213> ORGANISM: Chlamydomonas reinhardtii
<220> FEATURE:
<221> NAME/KEY: CDS
<222> LOCATION: (1)..(1425)

<400> SEQUENCE: 1 atg gtt cca caa aca gaa act aaa gca ggt gct gga ttc aaa gcc ggt      48
Met Val Pro Gln Thr Glu Thr Lys Ala Gly Ala Gly Phe Lys Ala Gly
1               5                   10                  15 gta aaa gac tac cgt tta aca tac tac aca cct gat tac gta gta aga      96
Val Lys Asp Tyr Arg Leu Thr Tyr Tyr Thr Pro Asp Tyr Val Val Arg
                20                  25                  30 gat act gat att tta gct gca ttc cgt atg act cca caa cca ggt gtt     144
Asp Thr Asp Ile Leu Ala Ala Phe Arg Met Thr Pro Gln Pro Gly Val
            35                  40                  45 cca cct gaa gaa tgt ggt gct gct gta gct gct gaa tct tca aca ggt     192
Pro Pro Glu Glu Cys Gly Ala Ala Val Ala Ala Glu Ser Ser Thr Gly
        50                  55                  60 aca tgg act aca gta tgg act gac ggt tta aca agt ctt gac cgt tac     240
```

-continued

```
Thr Trp Thr Thr Val Trp Thr Asp Gly Leu Thr Ser Leu Asp Arg Tyr
 65              70                  75                  80 aaa ggt cgt tgt tac gat atc gaa cca gtt ccg ggt gaa gac aac caa    288
Lys Gly Arg Cys Tyr Asp Ile Glu Pro Val Pro Gly Glu Asp Asn Gln
                 85                  90                  95 tac att gct tac gta gct tac cca atc gac tta ttc gaa gaa ggt tca    336
Tyr Ile Ala Tyr Val Ala Tyr Pro Ile Asp Leu Phe Glu Glu Gly Ser
                100                 105                 110 gta act aac atg ttc act tct att gta ggt aac gta ttc ggt ttc aaa    384
Val Thr Asn Met Phe Thr Ser Ile Val Gly Asn Val Phe Gly Phe Lys
            115                 120                 125 gct tta cgt gct cta cgt ctt gaa gac ctt cgt att cca cct gct tac    432
Ala Leu Arg Ala Leu Arg Leu Glu Asp Leu Arg Ile Pro Pro Ala Tyr
        130                 135                 140 gtt aaa aca ttc gta ggt cct cca cac ggt att cag gta gaa cgt gac    480
Val Lys Thr Phe Val Gly Pro Pro His Gly Ile Gln Val Glu Arg Asp
145                 150                 155                 160 aaa tta aac aaa tat ggt cgt ggt ctt tta ggt tgt aca atc aaa cct    528
Lys Leu Asn Lys Tyr Gly Arg Gly Leu Leu Gly Cys Thr Ile Lys Pro
                165                 170                 175 aaa tta ggt ctt tca gct aaa aac tac ggt cgt gca gtt tat gaa tgt    576
Lys Leu Gly Leu Ser Ala Lys Asn Tyr Gly Arg Ala Val Tyr Glu Cys
                180                 185                 190 tta cgt ggt ggt ctt gac ttt act aaa gac gac gaa aac gta aac tca    624
Leu Arg Gly Gly Leu Asp Phe Thr Lys Asp Asp Glu Asn Val Asn Ser
            195                 200                 205 caa cca ttc atg cgt tgg cgt gac cgt ttc ctt ttc gtt gct gaa gct    672
Gln Pro Phe Met Arg Trp Arg Asp Arg Phe Leu Phe Val Ala Glu Ala
        210                 215                 220 att tac aaa gct caa gca gaa aca ggt gaa gtt aaa ggt cac tac tta    720
Ile Tyr Lys Ala Gln Ala Glu Thr Gly Glu Val Lys Gly His Tyr Leu
225                 230                 235                 240 aac gct act gct ggt act tgt gaa gaa atg atg aaa cgt gca gta tgt    768
Asn Ala Thr Ala Gly Thr Cys Glu Glu Met Met Lys Arg Ala Val Cys
                245                 250                 255 gct aaa gaa tta ggt gta cct att att atg cac gac tac tta aca ggt    816
Ala Lys Glu Leu Gly Val Pro Ile Ile Met His Asp Tyr Leu Thr Gly
                260                 265                 270 ggt ttc aca gct aac act tca tta gct atc tac tgt cgt gac aac ggt    864
Gly Phe Thr Ala Asn Thr Ser Leu Ala Ile Tyr Cys Arg Asp Asn Gly
            275                 280                 285 ctt ctt cta cac atc cac cgt gct atg cac gcg gtt att gac cgt caa    912
Leu Leu Leu His Ile His Arg Ala Met His Ala Val Ile Asp Arg Gln
        290                 295                 300 cgt aac cac ggt att cac ttc cgt gtt ctt gct aaa gct ctt cgt atg    960
Arg Asn His Gly Ile His Phe Arg Val Leu Ala Lys Ala Leu Arg Met
305                 310                 315                 320 tct ggt ggt gac cac ctt cac tct ggt act gtt gta ggt aaa cta gaa   1008
Ser Gly Gly Asp His Leu His Ser Gly Thr Val Val Gly Lys Leu Glu
                325                 330                 335 ggt gaa cgt gaa gtt act cta ggt ttc gta gac tta atg cgt gat gac   1056
Gly Glu Arg Glu Val Thr Leu Gly Phe Val Asp Leu Met Arg Asp Asp
                340                 345                 350 tac gtt gaa aaa gac cgt agc cgt ggt att tac ttc act caa gac tgg   1104
Tyr Val Glu Lys Asp Arg Ser Arg Gly Ile Tyr Phe Thr Gln Asp Trp
            355                 360                 365 tgt tca atg cca ggt gtt atg cca gtt gct tca ggt ggt att cac gta   1152
Cys Ser Met Pro Gly Val Met Pro Val Ala Ser Gly Gly Ile His Val
        370                 375                 380 tgg cac atg cca gct tta gtt gaa atc ttc ggt gat gac gca tgt ctt   1200
```

```
Trp His Met Pro Ala Leu Val Glu Ile Phe Gly Asp Asp Ala Cys Leu
385                 390                 395                 400 cag ttc ggt ggt ggt act cta ggt cac cct tgg ggt aac gct cca ggt    1248
Gln Phe Gly Gly Gly Thr Leu Gly His Pro Trp Gly Asn Ala Pro Gly
            405                 410                 415 gct gca gct aac cgt gta gct ctt gaa gct tgt act caa gct cgt aac    1296
Ala Ala Ala Asn Arg Val Ala Leu Glu Ala Cys Thr Gln Ala Arg Asn
                420                 425                 430 gaa ggt cgt gac ctt gct cgt gaa ggt ggc gac gta att cgt tca gct    1344
Glu Gly Arg Asp Leu Ala Arg Glu Gly Gly Asp Val Ile Arg Ser Ala
            435                 440                 445 tgt aaa tgg tct cca gaa ctt gct gct gca tgt gaa gtt tgg aaa gaa    1392
Cys Lys Trp Ser Pro Glu Leu Ala Ala Ala Cys Glu Val Trp Lys Glu
        450                 455                 460 att aaa ttc gaa ttt gat act att gac aaa ctt taa                    1428
Ile Lys Phe Glu Phe Asp Thr Ile Asp Lys Leu
465                 470                 475
```

<210> SEQ ID NO 2
<211> LENGTH: 475
<212> TYPE: PRT
<213> ORGANISM: Chlamydomonas reinhardtii

<400> SEQUENCE: 2

```
Met Val Pro Gln Thr Glu Thr Lys Ala Gly Ala Gly Phe Lys Ala Gly
1               5                   10                  15

Val Lys Asp Tyr Arg Leu Thr Tyr Tyr Thr Pro Asp Tyr Val Val Arg
                20                  25                  30

Asp Thr Asp Ile Leu Ala Ala Phe Arg Met Thr Pro Gln Pro Gly Val
            35                  40                  45

Pro Pro Glu Glu Cys Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Asp Asn Gln
                85                  90                  95

Tyr Ile Ala Tyr Val Ala Tyr Pro Ile Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
130                 135                 140

Val Lys Thr Phe Val Gly Pro Pro His Gly Ile Gln Val Glu Arg Asp
145                 150                 155                 160

Lys Leu Asn Lys Tyr Gly Arg Gly Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
210                 215                 220

Ile Tyr Lys Ala Gln Ala Glu Thr Gly Glu Val Lys Gly His Tyr Leu
225                 230                 235                 240

Asn Ala Thr Ala Gly Thr Cys Glu Glu Met Met Lys Arg Ala Val Cys
                245                 250                 255

Ala Lys Glu Leu Gly Val Pro Ile Ile Met His Asp Tyr Leu Thr Gly
```

```
                 260                 265                 270
Gly Phe Thr Ala Asn Thr Ser Leu Ala Ile Tyr Cys Arg Asp Asn Gly
            275                 280                 285

Leu Leu Leu His Ile His Arg Ala Met His Ala Val Ile Asp Arg Gln
            290                 295                 300

Arg Asn His Gly Ile His Phe Arg Val Leu Ala Lys Ala Leu Arg Met
305                 310                 315                 320

Ser Gly Gly Asp His Leu His Ser Gly Thr Val Val Gly Lys Leu Glu
                325                 330                 335

Gly Glu Arg Glu Val Thr Leu Gly Phe Val Asp Leu Met Arg Asp Asp
            340                 345                 350

Tyr Val Glu Lys Asp Arg Ser Arg Gly Ile Tyr Phe Thr Gln Asp Trp
            355                 360                 365

Cys Ser Met Pro Gly Val Met Pro Val Ala Ser Gly Gly Ile His Val
            370                 375                 380

Trp His Met Pro Ala Leu Val Glu Ile Phe Gly Asp Asp Ala Cys Leu
385                 390                 395                 400

Gln Phe Gly Gly Gly Thr Leu Gly His Pro Trp Gly Asn Ala Pro Gly
            405                 410                 415

Ala Ala Ala Asn Arg Val Ala Leu Glu Ala Cys Thr Gln Ala Arg Asn
            420                 425                 430

Glu Gly Arg Asp Leu Ala Arg Glu Gly Gly Asp Val Ile Arg Ser Ala
            435                 440                 445

Cys Lys Trp Ser Pro Glu Leu Ala Ala Ala Cys Glu Val Trp Lys Glu
            450                 455                 460

Ile Lys Phe Glu Phe Asp Thr Ile Asp Lys Leu
465                 470                 475

<210> SEQ ID NO 3
<211> LENGTH: 1428
<212> TYPE: DNA
<213> ORGANISM: Artificial Sequence
<220> FEATURE:
<223> OTHER INFORMATION: Description for artificial sequence: shuffled
      Chlamydomonas Rubisco large subunit variants.
<220> FEATURE:
<221> NAME/KEY: CDS
<222> LOCATION: (1)..(1425)
<220> FEATURE:
<221> NAME/KEY: misc_feature
<222> LOCATION: (28)..(28)
<223> OTHER INFORMATION: R = A or G
<220> FEATURE:
<221> NAME/KEY: misc_feature
<222> LOCATION: (32)..(32)
<223> OTHER INFORMATION: Y= C or T
<220> FEATURE:
<221> NAME/KEY: misc_feature
<222> LOCATION: (35)..(35)
<223> OTHER INFORMATION: S = G or C
<220> FEATURE:
<221> NAME/KEY: misc_feature
<222> LOCATION: (64)..(64)
<223> OTHER INFORMATION: K = G or T
<220> FEATURE:
<221> NAME/KEY: misc_feature
<222> LOCATION: (91)..(91)
<223> OTHER INFORMATION: R = A or G
<220> FEATURE:
<221> NAME/KEY: misc_feature
<222> LOCATION: (94)..(94)
<223> OTHER INFORMATION: R = A or G
<220> FEATURE:
<221> NAME/KEY: misc_feature
<222> LOCATION: (113)..(113)
<223> OTHER INFORMATION: S = G or C
```

```
<220> FEATURE:
<221> NAME/KEY: misc_feature
<222> LOCATION: (121)..(121)
<223> OTHER INFORMATION: B = C, G or T
<220> FEATURE:
<221> NAME/KEY: misc_feature
<222> LOCATION: (124)..(124)
<223> OTHER INFORMATION: R = A or G
<220> FEATURE:
<221> NAME/KEY: misc_feature
<222> LOCATION: (136)..(136)
<223> OTHER INFORMATION: Y = C or T
<220> FEATURE:
<221> NAME/KEY: misc_feature
<222> LOCATION: (160)..(160)
<223> OTHER INFORMATION: R = A or G
<220> FEATURE:
<221> NAME/KEY: misc_feature
<222> LOCATION: (211)..(211)
<223> OTHER INFORMATION: R = A or G
<220> FEATURE:
<221> NAME/KEY: misc_feature
<222> LOCATION: (212)..(212)
<223> OTHER INFORMATION: S = G or C
<220> FEATURE:
<221> NAME/KEY: misc_feature
<222> LOCATION: (226)..(226)
<223> OTHER INFORMATION: D = G, T or A
<220> FEATURE:
<221> NAME/KEY: misc_feature
<222> LOCATION: (233)..(233)
<223> OTHER INFORMATION: R = A or G
<220> FEATURE:
<221> NAME/KEY: misc_feature
<222> LOCATION: (242)..(242)
<223> OTHER INFORMATION: R = A or G
<220> FEATURE:
<221> NAME/KEY: misc_feature
<222> LOCATION: (247)..(247)
<223> OTHER INFORMATION: Y = C or T
<220> FEATURE:
<221> NAME/KEY: misc_feature
<222> LOCATION: (257)..(257)
<223> OTHER INFORMATION: R = A or G
<220> FEATURE:
<221> NAME/KEY: misc_feature
<222> LOCATION: (263)..(263)
<223> OTHER INFORMATION: R = A or G
<220> FEATURE:
<221> NAME/KEY: misc_feature
<222> LOCATION: (282)..(282)
<223> OTHER INFORMATION: M = A or C
<220> FEATURE:
<221> NAME/KEY: misc_feature
<222> LOCATION: (283)..(283)
<223> OTHER INFORMATION: R = A or G
<220> FEATURE:
<221> NAME/KEY: misc_feature
<222> LOCATION: (295)..(295)
<223> OTHER INFORMATION: R = A or G
<220> FEATURE:
<221> NAME/KEY: misc_feature
<222> LOCATION: (302)..(302)
<223> OTHER INFORMATION: Y = C or T
<220> FEATURE:
<221> NAME/KEY: misc_feature
<222> LOCATION: (305)..(305)
<223> OTHER INFORMATION: Y = C or T
<220> FEATURE:
<221> NAME/KEY: misc_feature
<222> LOCATION: (324)..(324)
<223> OTHER INFORMATION: M = A or C
<220> FEATURE:
<221> NAME/KEY: misc_feature
<222> LOCATION: (337)..(337)
<223> OTHER INFORMATION: R = A or G
<220> FEATURE:
<221> NAME/KEY: misc_feature
<222> LOCATION: (351)..(351)
<223> OTHER INFORMATION: M = A or C
```

```
<220> FEATURE:
<221> NAME/KEY: misc_feature
<222> LOCATION: (421)..(421)
<223> OTHER INFORMATION: Y = C or T
<220> FEATURE:
<221> NAME/KEY: misc_feature
<222> LOCATION: (430)..(430)
<223> OTHER INFORMATION: Y = C or T
<220> FEATURE:
<221> NAME/KEY: misc_feature
<222> LOCATION: (439)..(439)
<223> OTHER INFORMATION: R = A or G
<220> FEATURE:
<221> NAME/KEY: misc_feature
<222> LOCATION: (444)..(444)
<223> OTHER INFORMATION: M = A or C
<220> FEATURE:
<221> NAME/KEY: misc_feature
<222> LOCATION: (446)..(446)
<223> OTHER INFORMATION: Y = C or T
<220> FEATURE:
<221> NAME/KEY: misc_feature
<222> LOCATION: (535)..(535)
<223> OTHER INFORMATION: R = A or G
<220> FEATURE:
<221> NAME/KEY: misc_feature
<222> LOCATION: (536)..(536)
<223> OTHER INFORMATION: K = G or T
<220> FEATURE:
<221> NAME/KEY: misc_feature
<222> LOCATION: (545)..(545)
<223> OTHER INFORMATION: S = C or G
<220> FEATURE:
<221> NAME/KEY: misc_feature
<222> LOCATION: (593)..(593)
<223> OTHER INFORMATION: W = A or T
<220> FEATURE:
<221> NAME/KEY: misc_feature
<222> LOCATION: (662)..(662)
<223> OTHER INFORMATION: Y = C or T
<220> FEATURE:
<221> NAME/KEY: misc_feature
<222> LOCATION: (674)..(674)
<223> OTHER INFORMATION: Y = C or T
<220> FEATURE:
<221> NAME/KEY: misc_feature
<222> LOCATION: (691)..(691)
<223> OTHER INFORMATION: S = C or G
<220> FEATURE:
<221> NAME/KEY: misc_feature
<222> LOCATION: (737)..(737)
<223> OTHER INFORMATION: Y = C or T
<220> FEATURE:
<221> NAME/KEY: misc_feature
<222> LOCATION: (746)..(746)
<223> OTHER INFORMATION: R = A or G
<220> FEATURE:
<221> NAME/KEY: misc_feature
<222> LOCATION: (751)..(751)
<223> OTHER INFORMATION: R = A or G
<220> FEATURE:
<221> NAME/KEY: misc_feature
<222> LOCATION: (763)..(763)
<223> OTHER INFORMATION: R = A or G
<220> FEATURE:
<221> NAME/KEY: misc_feature
<222> LOCATION: (785)..(785)
<223> OTHER INFORMATION: Y = C or T
<220> FEATURE:
<221> NAME/KEY: misc_feature
<222> LOCATION: (793)..(793)
<223> OTHER INFORMATION: R = A or G
<220> FEATURE:
<221> NAME/KEY: misc_feature
<222> LOCATION: (839)..(839)
<223> OTHER INFORMATION: Y = C or T
<220> FEATURE:
<221> NAME/KEY: misc_feature
<222> LOCATION: (841)..(841)
<223> OTHER INFORMATION: R = G or T
```

```
<220> FEATURE:
<221> NAME/KEY: misc_feature
<222> LOCATION: (843)..(843)
<223> OTHER INFORMATION: W = A or T
<220> FEATURE:
<221> NAME/KEY: misc_feature
<222> LOCATION: (937)..(937)
<223> OTHER INFORMATION: R = A or G
<220> FEATURE:
<221> NAME/KEY: misc_feature
<222> LOCATION: (1041)..(1041)
<223> OTHER INFORMATION: M = A or C
<220> FEATURE:
<221> NAME/KEY: misc_feature
<222> LOCATION: (1043)..(1043)
<223> OTHER INFORMATION: Y = C or T
<220> FEATURE:
<221> NAME/KEY: misc_feature
<222> LOCATION: (1051)..(1051)
<223> OTHER INFORMATION: S = C or G
<220> FEATURE:
<221> NAME/KEY: misc_feature
<222> LOCATION: (1055)..(1055)
<223> OTHER INFORMATION: R = A or G
<220> FEATURE:
<221> NAME/KEY: misc_feature
<222> LOCATION: (1057)..(1057)
<223> OTHER INFORMATION: Y = C or T
<220> FEATURE:
<221> NAME/KEY: misc_feature
<222> LOCATION: (1058)..(1058)
<223> OTHER INFORMATION: R = A or G
<220> FEATURE:
<221> NAME/KEY: misc_feature
<222> LOCATION: (1061)..(1061)
<223> OTHER INFORMATION: Y = C or T
<220> FEATURE:
<221> NAME/KEY: misc_feature
<222> LOCATION: (1075)..(1075)
<223> OTHER INFORMATION: R = A or G
<220> FEATURE:
<221> NAME/KEY: misc_feature
<222> LOCATION: (1076)..(1076)
<223> OTHER INFORMATION: R = A or G
<220> FEATURE:
<221> NAME/KEY: misc_feature
<222> LOCATION: (1081)..(1081)
<223> OTHER INFORMATION: S = G or C
<220> FEATURE:
<221> NAME/KEY: misc_feature
<222> LOCATION: (1108)..(1108)
<223> OTHER INFORMATION: K = G or T
<220> FEATURE:
<221> NAME/KEY: misc_feature
<222> LOCATION: (1112)..(1112)
<223> OTHER INFORMATION: Y = C or T
<220> FEATURE:
<221> NAME/KEY: misc_feature
<222> LOCATION: (1161)..(1161)
<223> OTHER INFORMATION: R = A or G
<220> FEATURE:
<221> NAME/KEY: misc_feature
<222> LOCATION: (1162)..(1162)
<223> OTHER INFORMATION: Y = C or T
<220> FEATURE:
<221> NAME/KEY: misc_feature
<222> LOCATION: (1171)..(1171)
<223> OTHER INFORMATION: R = A or G
<220> FEATURE:
<221> NAME/KEY: misc_feature
<222> LOCATION: (1172)..(1172)
<223> OTHER INFORMATION: Y = C or T
<220> FEATURE:
<221> NAME/KEY: misc_feature
<222> LOCATION: (1175)..(1175)
<223> OTHER INFORMATION: R = A or G
<220> FEATURE:
<221> NAME/KEY: misc_feature
<222> LOCATION: (1192)..(1192)
<223> OTHER INFORMATION: R = A or G
```

```
<220> FEATURE:
<221> NAME/KEY: misc_feature
<222> LOCATION: (1265)..(1265)
<223> OTHER INFORMATION: Y = T or C
<220> FEATURE:
<221> NAME/KEY: misc_feature
<222> LOCATION: (1304)..(1304)
<223> OTHER INFORMATION: K = G or T
<220> FEATURE:
<221> NAME/KEY: misc_feature
<222> LOCATION: (1330)..(1330)
<223> OTHER INFORMATION: V = A, C or G
<220> FEATURE:
<221> NAME/KEY: misc_feature
<222> LOCATION: (1343)..(1343)
<223> OTHER INFORMATION: S = C or G
<220> FEATURE:
<221> NAME/KEY: misc_feature
<222> LOCATION: (1366)..(1366)
<223> OTHER INFORMATION: R = A or G
<220> FEATURE:
<221> NAME/KEY: misc_feature
<222> LOCATION: (1372)..(1372)
<223> OTHER INFORMATION: S = C or G
<220> FEATURE:
<221> NAME/KEY: misc_feature
<222> LOCATION: (1386)..(1386)
<223> OTHER INFORMATION: K = G or T
<220> FEATURE:
<221> NAME/KEY: misc_feature
<222> LOCATION: (1393)..(1393)
<223> OTHER INFORMATION: R = A or G
<220> FEATURE:
<221> NAME/KEY: misc_feature
<222> LOCATION: (1394)..(1394)
<223> OTHER INFORMATION: Y = C or T
<220> FEATURE:
<221> NAME/KEY: misc_feature
<222> LOCATION: (1397)..(1397)
<223> OTHER INFORMATION: M = A or C
<220> FEATURE:
<221> NAME/KEY: misc_feature
<222> LOCATION: (1414)..(1414)
<223> OTHER INFORMATION: M = A or C

<400> SEQUENCE: 3 atg gtt cca caa aca gaa act aaa gca rgt gyt gsa ttc aaa gcc ggt     48
Met Val Pro Gln Thr Glu Thr Lys Ala Xaa Xaa Xaa Phe Lys Ala Gly
1               5                   10                  15 gta aaa gac tac cgt kta aca tac tac aca cct gat tac gta rta rga     96
Val Lys Asp Tyr Arg Xaa Thr Tyr Tyr Thr Pro Asp Tyr Val Xaa Xaa
            20                  25                  30 gat act gat att tta gst gca ttc bgt rtg act cca caa yca ggt gtt    144
Asp Thr Asp Ile Leu Xaa Ala Phe Xaa Xaa Thr Pro Gln Xaa Gly Val
        35                  40                  45 cca cct gaa gaa tgt rgt gct gct gta gct gct gaa tct tca aca ggt    192
Pro Pro Glu Glu Cys Xaa Ala Ala Val Ala Ala Glu Ser Ser Thr Gly
50                  55                  60 aca tgg act aca gta tgg rst gac ggt tta aca dgt ctt grc cgt tac    240
Thr Trp Thr Thr Val Trp Xaa Asp Gly Leu Thr Xaa Leu Xaa Arg Tyr
65                  70                  75                  80 ara ggt ygt tgt tac grt atc gra cca gtt ccg ggt gaa gam rac caa    288
Xaa Gly Xaa Cys Tyr Xaa Ile Xaa Pro Val Pro Gly Glu Xaa Xaa Gln
                85                  90                  95 tac att rct tac gya gyt tac cca atc gac tta ttm gaa gaa ggt tca    336
Tyr Ile Xaa Tyr Xaa Xaa Tyr Pro Ile Asp Leu Xaa Glu Glu Gly Ser
            100                 105                 110 rta act aac atg ttm act tct att gta ggt aac gta ttc ggt ttc aaa    384
Xaa Thr Asn Met Xaa Thr Ser Ile Val Gly Asn Val Phe Gly Phe Lys
        115                 120                 125 gct tta cgt gct cta cgt ctt gaa gac ctt cgt att yca cct gct yac    432
Ala Leu Arg Ala Leu Arg Leu Glu Asp Leu Arg Ile Xaa Pro Ala Xaa
```

```
                Ala Leu Arg Ala Leu Arg Leu Glu Asp Leu Arg Ile Xaa Pro Ala Xaa
                            130                 135                 140 gtt aaa rca ttm gya ggt cct cca cac ggt att cag gta gaa cgt gac        480
Val Lys Xaa Xaa Xaa Gly Pro Pro His Gly Ile Gln Val Glu Arg Asp
145                 150                 155                 160 aaa tta aac aaa tat ggt cgt ggt ctt tta ggt tgt aca atc aaa cct        528
Lys Leu Asn Lys Tyr Gly Arg Gly Leu Leu Gly Cys Thr Ile Lys Pro
                165                 170                 175 aaa tta rkt ctt tca gst aaa aac tac ggt cgt gca gtt tat gaa tgt        576
Lys Leu Xaa Leu Ser Xaa Lys Asn Tyr Gly Arg Ala Val Tyr Glu Cys
            180                 185                 190 tta cgt ggt ggt ctt gwc ttt act aaa gac gac gaa aac gta aac tca        624
Leu Arg Gly Gly Leu Xaa Phe Thr Lys Asp Asp Glu Asn Val Asn Ser
        195                 200                 205 caa cca ttc atg cgt tgg cgt gac cgt ttc ctt ttc gyt gct gaa gct        672
Gln Pro Phe Met Arg Trp Arg Asp Arg Phe Leu Phe Xaa Ala Glu Ala
    210                 215                 220 ayt tac aaa gct caa gca saa aca ggt gaa gtt aaa ggt cac tac tta        720
Xaa Tyr Lys Ala Gln Ala Xaa Thr Gly Glu Val Lys Gly His Tyr Leu
225                 230                 235                 240 aac gct act gct ggt ayt tgt gaa gra atg rtg aaa cgt gca rta tgt        768
Asn Ala Thr Ala Gly Xaa Cys Glu Xaa Met Xaa Lys Arg Ala Xaa Cys
                245                 250                 255 gct aaa gaa tta ggt gya cct att rtt atg cac gac tac tta aca ggt        816
Ala Lys Glu Leu Gly Xaa Pro Ile Xaa Met His Asp Tyr Leu Thr Gly
                260                 265                 270 ggt ttc aca gct aac act tca tya kcw atc tac tgt cgt gac aac ggt        864
Gly Phe Thr Ala Asn Thr Ser Xaa Xaa Ile Tyr Cys Arg Asp Asn Gly
            275                 280                 285 ctt ctt cta cac atc cac cgt gct atg cac gcg gtt att gac cgt caa        912
Leu Leu Leu His Ile His Arg Ala Met His Ala Val Ile Asp Arg Gln
        290                 295                 300 cgt aac cac ggt att cac ttc cgt rtt ctt gct aaa gct ctt cgt atg        960
Arg Asn His Gly Ile His Phe Arg Xaa Leu Ala Lys Ala Leu Arg Met
305                 310                 315                 320 tct ggt ggt gac cac ctt cac tct ggt act gtt gta ggt aaa cta gaa       1008
Ser Gly Gly Asp His Leu His Ser Gly Thr Val Val Gly Lys Leu Glu
                325                 330                 335 ggt gaa cgt gaa gtt act cta ggt ttc gta gam tya atg cgt sat grc       1056
Gly Glu Arg Glu Val Thr Leu Gly Phe Val Xaa Xaa Met Arg Xaa Xaa
                340                 345                 350 yrc gyt gaa aaa gac cgt rrc cgt sgt att tac ttc act caa gac tgg       1104
Xaa Xaa Glu Lys Asp Arg Xaa Arg Xaa Ile Tyr Phe Thr Gln Asp Trp
            355                 360                 365 tgt kca ayg cca ggt gtt atg cca gtt gct tca ggt ggt att cac gta       1152
Cys Xaa Xaa Pro Gly Val Met Pro Val Ala Ser Gly Gly Ile His Val
        370                 375                 380 tgg cac atr yca gct tta ryt gra atc ttc ggt gat gac rca tgt ctt       1200
Trp His Xaa Xaa Ala Leu Xaa Xaa Ile Phe Gly Asp Asp Xaa Cys Leu
385                 390                 395                 400 cag ttc ggt ggt ggt act cta ggt cac cct tgg ggt aac gct cca ggt       1248
Gln Phe Gly Gly Gly Thr Leu Gly His Pro Trp Gly Asn Ala Pro Gly
                405                 410                 415 gct gca gct aac cgt gya gct ctt gaa gct tgt act caa gct cgt aac       1296
Ala Ala Ala Asn Arg Xaa Ala Leu Glu Ala Cys Thr Gln Ala Arg Asn
                420                 425                 430 gaa ggt ckt gac ctt gct cgt gaa ggt ggc gac vta att cgt tca gst       1344
Glu Gly Xaa Asp Leu Ala Arg Glu Gly Gly Asp Xaa Ile Arg Ser Xaa
            435                 440                 445 tgt aaa tgg tct cca gaa ctt rct gct sca tgt gaa gtt tgk aaa gaa       1392
```

```
Cys Lys Trp Ser Pro Glu Leu Xaa Ala Xaa Cys Glu Val Xaa Lys Glu
450                 455                 460 ryt ama ttc gaa ttt gat act mtt gac aaa ctt taa                        1428
Xaa Xaa Phe Glu Phe Asp Thr Xaa Asp Lys Leu
465                 470                 475
```

<210> SEQ ID NO 4
<211> LENGTH: 475
<212> TYPE: PRT
<213> ORGANISM: Artificial Sequence
<220> FEATURE:
<221> NAME/KEY: misc_feature
<222> LOCATION: (10)..(10)
<223> OTHER INFORMATION: The 'Xaa' at location 10 stands for Gly, or Ser.
<220> FEATURE:
<221> NAME/KEY: misc_feature
<222> LOCATION: (11)..(11)
<223> OTHER INFORMATION: The 'Xaa' at location 11 stands for Ala, or Val.
<220> FEATURE:
<221> NAME/KEY: misc_feature
<222> LOCATION: (12)..(12)
<223> OTHER INFORMATION: The 'Xaa' at location 12 stands for Gly, or Ala.
<220> FEATURE:
<221> NAME/KEY: misc_feature
<222> LOCATION: (22)..(22)
<223> OTHER INFORMATION: The 'Xaa' at location 22 stands for Val, or Leu.
<220> FEATURE:
<221> NAME/KEY: misc_feature
<222> LOCATION: (31)..(31)
<223> OTHER INFORMATION: The 'Xaa' at location 31 stands for Val, or Ile.
<220> FEATURE:
<221> NAME/KEY: misc_feature
<222> LOCATION: (32)..(32)
<223> OTHER INFORMATION: The 'Xaa' at location 32 stands for Gly, or Arg.
<220> FEATURE:
<221> NAME/KEY: misc_feature
<222> LOCATION: (38)..(38)
<223> OTHER INFORMATION: The 'Xaa' at location 38 stands for Gly, or Ala.
<220> FEATURE:
<221> NAME/KEY: misc_feature
<222> LOCATION: (41)..(41)
<223> OTHER INFORMATION: The 'Xaa' at location 41 stands for Gly, Arg, or Cys.
<220> FEATURE:
<221> NAME/KEY: misc_feature
<222> LOCATION: (42)..(42)
<223> OTHER INFORMATION: The 'Xaa' at location 42 stands for Val, or Met.
<220> FEATURE:
<221> NAME/KEY: misc_feature
<222> LOCATION: (46)..(46)
<223> OTHER INFORMATION: The 'Xaa' at location 46 stands for Pro, or Ser.
<220> FEATURE:
<221> NAME/KEY: misc_feature
<222> LOCATION: (54)..(54)
<223> OTHER INFORMATION: The 'Xaa' at location 54 stands for Gly, or Ser.
<220> FEATURE:
<221> NAME/KEY: misc_feature
<222> LOCATION: (71)..(71)
<223> OTHER INFORMATION: The 'Xaa' at location 71 stands for Gly, Ala, Ser, or Thr.
<220> FEATURE:
<221> NAME/KEY: misc_feature
<222> LOCATION: (76)..(76)
<223> OTHER INFORMATION: The 'Xaa' at location 76 stands for Ser, Gly, or Cys.
<220> FEATURE:
<221> NAME/KEY: misc_feature
<222> LOCATION: (78)..(78)

-continued

```
<223> OTHER INFORMATION: The 'Xaa' at location 78 stands for Gly, or
      Asp.
<220> FEATURE:
<221> NAME/KEY: misc_feature
<222> LOCATION: (81)..(81)
<223> OTHER INFORMATION: The 'Xaa' at location 81 stands for Arg, or
      Lys.
<220> FEATURE:
<221> NAME/KEY: misc_feature
<222> LOCATION: (83)..(83)
<223> OTHER INFORMATION: The 'Xaa' at location 83 stands for Arg, or
      Cys.
<220> FEATURE:
<221> NAME/KEY: misc_feature
<222> LOCATION: (86)..(86)
<223> OTHER INFORMATION: The 'Xaa' at location 86 stands for Gly, or
      Asp.
<220> FEATURE:
<221> NAME/KEY: misc_feature
<222> LOCATION: (88)..(88)
<223> OTHER INFORMATION: The 'Xaa' at location 88 stands for Gly, or
      Glu.
<220> FEATURE:
<221> NAME/KEY: misc_feature
<222> LOCATION: (94)..(94)
<223> OTHER INFORMATION: The 'Xaa' at location 94 stands for Glu, or
      Asp.
<220> FEATURE:
<221> NAME/KEY: misc_feature
<222> LOCATION: (95)..(95)
<223> OTHER INFORMATION: The 'Xaa' at location 95 stands for Asp, or
      Asn.
<220> FEATURE:
<221> NAME/KEY: misc_feature
<222> LOCATION: (99)..(99)
<223> OTHER INFORMATION: The 'Xaa' at location 99 stands for Ala, or
      Thr.
<220> FEATURE:
<221> NAME/KEY: misc_feature
<222> LOCATION: (101)..(101)
<223> OTHER INFORMATION: The 'Xaa' at location 101 stands for Ala, or
      Val.
<220> FEATURE:
<221> NAME/KEY: misc_feature
<222> LOCATION: (102)..(102)
<223> OTHER INFORMATION: The 'Xaa' at location 102 stands for Ala, or
      Val.
<220> FEATURE:
<221> NAME/KEY: misc_feature
<222> LOCATION: (108)..(108)
<223> OTHER INFORMATION: The 'Xaa' at location 108 stands for Leu, or
      Phe.
<220> FEATURE:
<221> NAME/KEY: misc_feature
<222> LOCATION: (113)..(113)
<223> OTHER INFORMATION: The 'Xaa' at location 113 stands for Val, or
      Ile.
<220> FEATURE:
<221> NAME/KEY: misc_feature
<222> LOCATION: (117)..(117)
<223> OTHER INFORMATION: The 'Xaa' at location 117 stands for Leu, or
      Phe.
<220> FEATURE:
<221> NAME/KEY: misc_feature
<222> LOCATION: (141)..(141)
<223> OTHER INFORMATION: The 'Xaa' at location 141 stands for Pro, or
      Ser.
<220> FEATURE:
<221> NAME/KEY: misc_feature
<222> LOCATION: (144)..(144)
<223> OTHER INFORMATION: The 'Xaa' at location 144 stands for His, or
      Tyr.
<220> FEATURE:
<221> NAME/KEY: misc_feature
<222> LOCATION: (147)..(147)
<223> OTHER INFORMATION: The 'Xaa' at location 147 stands for Ala, or
      Thr.
<220> FEATURE:
<221> NAME/KEY: misc_feature
<222> LOCATION: (148)..(148)
```

```
<223> OTHER INFORMATION: The 'Xaa' at location 148 stands for Leu, or
      Phe.
<220> FEATURE:
<221> NAME/KEY: misc_feature
<222> LOCATION: (149)..(149)
<223> OTHER INFORMATION: The 'Xaa' at location 149 stands for Ala, or
      Val.
<220> FEATURE:
<221> NAME/KEY: misc_feature
<222> LOCATION: (179)..(179)
<223> OTHER INFORMATION: The 'Xaa' at location 179 stands for Gly, Val,
      Ser, or Ile.
<220> FEATURE:
<221> NAME/KEY: misc_feature
<222> LOCATION: (182)..(182)
<223> OTHER INFORMATION: The 'Xaa' at location 182 stands for Gly, or
      Ala.
<220> FEATURE:
<221> NAME/KEY: misc_feature
<222> LOCATION: (198)..(198)
<223> OTHER INFORMATION: The 'Xaa' at location 198 stands for Asp, or
      Val.
<220> FEATURE:
<221> NAME/KEY: misc_feature
<222> LOCATION: (221)..(221)
<223> OTHER INFORMATION: The 'Xaa' at location 221 stands for Ala, or
      Val.
<220> FEATURE:
<221> NAME/KEY: misc_feature
<222> LOCATION: (225)..(225)
<223> OTHER INFORMATION: The 'Xaa' at location 225 stands for Thr, or
      Ile.
<220> FEATURE:
<221> NAME/KEY: misc_feature
<222> LOCATION: (231)..(231)
<223> OTHER INFORMATION: The 'Xaa' at location 231 stands for Glu, or
      Gln.
<220> FEATURE:
<221> NAME/KEY: misc_feature
<222> LOCATION: (246)..(246)
<223> OTHER INFORMATION: The 'Xaa' at location 246 stands for Thr, or
      Ile.
<220> FEATURE:
<221> NAME/KEY: misc_feature
<222> LOCATION: (249)..(249)
<223> OTHER INFORMATION: The 'Xaa' at location 249 stands for Gly, or
      Glu.
<220> FEATURE:
<221> NAME/KEY: misc_feature
<222> LOCATION: (251)..(251)
<223> OTHER INFORMATION: The 'Xaa' at location 251 stands for Val, or
      Met.
<220> FEATURE:
<221> NAME/KEY: misc_feature
<222> LOCATION: (255)..(255)
<223> OTHER INFORMATION: The 'Xaa' at location 255 stands for Val, or
      Ile.
<220> FEATURE:
<221> NAME/KEY: misc_feature
<222> LOCATION: (262)..(262)
<223> OTHER INFORMATION: The 'Xaa' at location 262 stands for Ala, or
      Val.
<220> FEATURE:
<221> NAME/KEY: misc_feature
<222> LOCATION: (265)..(265)
<223> OTHER INFORMATION: The 'Xaa' at location 265 stands for Val, or
      Ile.
<220> FEATURE:
<221> NAME/KEY: misc_feature
<222> LOCATION: (280)..(280)
<223> OTHER INFORMATION: The 'Xaa' at location 280 stands for Ser, or
      Leu.
<220> FEATURE:
<221> NAME/KEY: misc_feature
<222> LOCATION: (281)..(281)
<223> OTHER INFORMATION: The 'Xaa' at location 281 stands for Ala, or
      Ser.
<220> FEATURE:
<221> NAME/KEY: misc_feature
<222> LOCATION: (313)..(313)
```

-continued

```
<223> OTHER INFORMATION: The 'Xaa' at location 313 stands for Val, or
      Ile.
<220> FEATURE:
<221> NAME/KEY: misc_feature
<222> LOCATION: (347)..(347)
<223> OTHER INFORMATION: The 'Xaa' at location 347 stands for Glu, or
      Asp.
<220> FEATURE:
<221> NAME/KEY: misc_feature
<222> LOCATION: (348)..(348)
<223> OTHER INFORMATION: The 'Xaa' at location 348 stands for Ser, or
      Leu.
<220> FEATURE:
<221> NAME/KEY: misc_feature
<222> LOCATION: (351)..(351)
<223> OTHER INFORMATION: The 'Xaa' at location 351 stands for Asp, or
      His.
<220> FEATURE:
<221> NAME/KEY: misc_feature
<222> LOCATION: (352)..(352)
<223> OTHER INFORMATION: The 'Xaa' at location 352 stands for Gly, or
      Asp.
<220> FEATURE:
<221> NAME/KEY: misc_feature
<222> LOCATION: (353)..(353)
<223> OTHER INFORMATION: The 'Xaa' at location 353 stands for Arg, His,
      Cys, or Tyr.
<220> FEATURE:
<221> NAME/KEY: misc_feature
<222> LOCATION: (354)..(354)
<223> OTHER INFORMATION: The 'Xaa' at location 354 stands for Ala, or
      Val.
<220> FEATURE:
<221> NAME/KEY: misc_feature
<222> LOCATION: (359)..(359)
<223> OTHER INFORMATION: The 'Xaa' at location 359 stands for Gly, Asp,
      Ser, or Asn.
<220> FEATURE:
<221> NAME/KEY: misc_feature
<222> LOCATION: (361)..(361)
<223> OTHER INFORMATION: The 'Xaa' at location 361 stands for Gly, or
      Arg.
<220> FEATURE:
<221> NAME/KEY: misc_feature
<222> LOCATION: (370)..(370)
<223> OTHER INFORMATION: The 'Xaa' at location 370 stands for Ala, or
      Ser.
<220> FEATURE:
<221> NAME/KEY: misc_feature
<222> LOCATION: (371)..(371)
<223> OTHER INFORMATION: The 'Xaa' at location 371 stands for Thr, or
      Met.
<220> FEATURE:
<221> NAME/KEY: misc_feature
<222> LOCATION: (387)..(387)
<223> OTHER INFORMATION: The 'Xaa' at location 387 stands for Met, or
      Ile.
<220> FEATURE:
<221> NAME/KEY: misc_feature
<222> LOCATION: (388)..(388)
<223> OTHER INFORMATION: The 'Xaa' at location 388 stands for Pro, or
      Ser.
<220> FEATURE:
<221> NAME/KEY: misc_feature
<222> LOCATION: (391)..(391)
<223> OTHER INFORMATION: The 'Xaa' at location 391 stands for Ala, Val,
      Thr, or Ile.
<220> FEATURE:
<221> NAME/KEY: misc_feature
<222> LOCATION: (392)..(392)
<223> OTHER INFORMATION: The 'Xaa' at location 392 stands for Gly, or
      Glu.
<220> FEATURE:
<221> NAME/KEY: misc_feature
<222> LOCATION: (398)..(398)
<223> OTHER INFORMATION: The 'Xaa' at location 398 stands for Ala, or
      Thr.
<220> FEATURE:
<221> NAME/KEY: misc_feature
<222> LOCATION: (422)..(422)
```

```
<223> OTHER INFORMATION: The 'Xaa' at location 422 stands for Ala, or
      Val.
<220

```
              145                 150                 155                 160
Lys Leu Asn Lys Tyr Gly Arg Gly Leu Leu Gly Cys Thr Ile Lys Pro
            165                 170                 175

Lys Leu Xaa Leu Ser Xaa Lys Asn Tyr Gly Arg Ala Val Tyr Glu Cys
        180                 185                 190

Leu Arg Gly Gly Leu Xaa Phe Thr Lys Asp Asp Glu Asn Val Asn Ser
    195                 200                 205

Gln Pro Phe Met Arg Trp Arg Asp Arg Phe Leu Phe Xaa Ala Glu Ala
210                 215                 220

Xaa Tyr Lys Ala Gln Ala Xaa Thr Gly Glu Val Lys Gly His Tyr Leu
225                 230                 235                 240

Asn Ala Thr Ala Gly Xaa Cys Glu Xaa Met Xaa Lys Arg Ala Xaa Cys
                245                 250                 255

Ala Lys Glu Leu Gly Xaa Pro Ile Xaa Met His Asp Tyr Leu Thr Gly
            260                 265                 270

Gly Phe Thr Ala Asn Thr Ser Xaa Xaa Ile Tyr Cys Arg Asp Asn Gly
        275                 280                 285

Leu Leu Leu His Ile His Arg Ala Met His Ala Val Ile Asp Arg Gln
    290                 295                 300

Arg Asn His Gly Ile His Phe Arg Xaa Leu Ala Lys Ala Leu Arg Met
305                 310                 315                 320

Ser Gly Gly Asp His Leu His Ser Gly Thr Val Val Gly Lys Leu Glu
                325                 330                 335

Gly Glu Arg Glu Val Thr Leu Gly Phe Val Xaa Xaa Met Arg Xaa Xaa
            340                 345                 350

Xaa Xaa Glu Lys Asp Arg Xaa Arg Xaa Ile Tyr Phe Thr Gln Asp Trp
        355                 360                 365

Cys Xaa Xaa Pro Gly Val Met Pro Val Ala Ser Gly Gly Ile His Val
    370                 375                 380

Trp His Xaa Xaa Ala Leu Xaa Xaa Ile Phe Gly Asp Asp Xaa Cys Leu
385                 390                 395                 400

Gln Phe Gly Gly Gly Thr Leu Gly His Pro Trp Gly Asn Ala Pro Gly
                405                 410                 415

Ala Ala Ala Asn Arg Xaa Ala Leu Glu Ala Cys Thr Gln Ala Arg Asn
            420                 425                 430

Glu Gly Xaa Asp Leu Ala Arg Glu Gly Gly Asp Xaa Ile Arg Ser Xaa
        435                 440                 445

Cys Lys Trp Ser Pro Glu Leu Xaa Ala Xaa Cys Glu Val Xaa Lys Glu
    450                 455                 460

Xaa Xaa Phe Glu Phe Asp Thr Xaa Asp Lys Leu
465                 470                 475

<210> SEQ ID NO 5
<211> LENGTH: 1434
<212> TYPE: DNA
<213> ORGANISM: Nicotiana tabacum
<220> FEATURE:
<221> NAME/KEY: CDS
<222> LOCATION: (1)..(1431)

<400> SEQUENCE: 5 atg tca cca caa aca gag act aaa gca agt gtt gga ttc aaa gct ggt    48
Met Ser Pro Gln Thr Glu Thr Lys Ala Ser Val Gly Phe Lys Ala Gly
1               5                   10                  15 gtt aaa gag tac aaa ttg act tat tat act cct gag tac caa acc aag    96
Val Lys Glu Tyr Lys Leu Thr Tyr Tyr Thr Pro Glu Tyr Gln Thr Lys
            20                  25                  30
```

```
gat act gat ata ttg gca gca ttc cga gta act cct caa cct gga gtt      144
Asp Thr Asp Ile Leu Ala Ala Phe Arg Val Thr Pro Gln Pro Gly Val
         35                  40                  45 cca cct gaa gaa gca ggg gcc gcg gta gct gcc gaa tct tct act ggt      192
Pro Pro Glu Glu Ala Gly Ala Ala Val Ala Ala Glu Ser Ser Thr Gly
 50                  55                  60 aca tgg aca act gta tgg acc gat gga ctt acc agc ctt gat cgt tac      240
Thr Trp Thr Thr Val Trp Thr Asp Gly Leu Thr Ser Leu Asp Arg Tyr
 65                  70                  75                  80 aaa ggg cga tgc tac cgc atc gag cgt gtt gtt gga gaa aaa gat caa      288
Lys Gly Arg Cys Tyr Arg Ile Glu Arg Val Val Gly Glu Lys Asp Gln
                 85                  90                  95 tat att gct tat gta gct tac cct tta gac ctt ttt gaa gaa ggt tct      336
Tyr Ile Ala Tyr Val Ala Tyr Pro Leu Asp Leu Phe Glu Glu Gly Ser
            100                 105                 110 gtt acc aac atg ttt act tcc att gta ggt aac gta ttt ggg ttc aaa      384
Val Thr Asn Met Phe Thr Ser Ile Val Gly Asn Val Phe Gly Phe Lys
        115                 120                 125 gcc ctg cgc gct cta cgt ctg gaa gat ctg cga atc cct cct gct tat      432
Ala Leu Arg Ala Leu Arg Leu Glu Asp Leu Arg Ile Pro Pro Ala Tyr
130                 135                 140 gtt aaa act ttc caa ggt ccg cct cat ggg atc caa gtt gaa aga gat      480
Val Lys Thr Phe Gln Gly Pro Pro His Gly Ile Gln Val Glu Arg Asp
145                 150                 155                 160 aaa ttg aac aag tat ggt cgt ccc ctg ttg gga tgt act att aaa cct      528
Lys Leu Asn Lys Tyr Gly Arg Pro Leu Leu Gly Cys Thr Ile Lys Pro
                165                 170                 175 aaa ttg ggg tta tct gct aaa aac tac ggt aga gct gtt tat gaa tgt      576
Lys Leu Gly Leu Ser Ala Lys Asn Tyr Gly Arg Ala Val Tyr Glu Cys
            180                 185                 190 ctt cgc ggt gga ctt gat ttt acc aaa gat gat gag aac gtg aac tca      624
Leu Arg Gly Gly Leu Asp Phe Thr Lys Asp Asp Glu Asn Val Asn Ser
        195                 200                 205 caa cca ttt atg cgt tgg aga gat cgt ttc tta ttt tgt gcc gaa gca      672
Gln Pro Phe Met Arg Trp Arg Asp Arg Phe Leu Phe Cys Ala Glu Ala
    210                 215                 220 ctt tat aaa gca cag gct gaa aca ggt gaa atc aaa ggg cat tac ttg      720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt      768
Asn Ala Thr Ala Gly Thr Cys Glu Glu Met Ile Lys Arg Ala Val Phe
                245                 250                 255 gct aga gaa ttg ggc gtt ccg atc gta atg cat gac tac tta acg ggg      816
Ala Arg Glu Leu Gly Val Pro Ile Val Met His Asp Tyr Leu Thr Gly
            260                 265                 270 gga ttc acc gca aat act agc ttg gct cat tat tgc cga gat aat ggt      864
Gly Phe Thr Ala Asn Thr Ser Leu Ala His Tyr Cys Arg Asp Asn Gly
        275                 280                 285 cta ctt ctt cac atc cac cgt gca atg cat gcg gtt att gat aga cag      912
Leu Leu Leu His Ile His Arg Ala Met His Ala Val Ile Asp Arg Gln
    290                 295                 300 aag aat cat ggt atc cac ttc cgg gta tta gca aaa gcg tta cgt atg      960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa     1008
Ser Gly Gly Asp His Ile His Ser Gly Thr Val Val Gly Lys Leu Glu
                325                 330                 335 ggt gaa aga gac ata act ttg ggc ttt gtt gat tta ctg cgt gat gat     1056
Gly Glu Arg Asp Ile Thr Leu Gly Phe Val Asp Leu Leu Arg Asp Asp
            340                 345                 350
```

| | | | | | | | | | | | | | | |
|---|---|---|---|---|---|---|---|---|---|---|---|---|---|---|
| ttt | gtt | gaa | caa | gat | cga | agt | cgc | ggt | att | tat | ttc | act | caa | gat | tgg | 1104 |
| Phe | Val | Glu | Gln | Asp | Arg | Ser | Arg | Gly | Ile | Tyr | Phe | Thr | Gln | Asp | Trp | |
| | | 355 | | | | 360 | | | | | 365 | | | | | |
| gtc | tct | tta | cca | ggt | gtt | cta | ccc | gtg | gct | tca | gga | ggt | att | cac | gtt | 1152 |
| Val | Ser | Leu | Pro | Gly | Val | Leu | Pro | Val | Ala | Ser | Gly | Gly | Ile | His | Val | |
| 370 | | | | | 375 | | | | | 380 | | | | | | |
| tgg | cat | atg | cct | gct | ctg | acc | gag | atc | ttt | ggg | gat | gat | tcc | gta | cta | 1200 |
| Trp | His | Met | Pro | Ala | Leu | Thr | Glu | Ile | Phe | Gly | Asp | Asp | Ser | Val | Leu | |
| 385 | | | | 390 | | | | | 395 | | | | | 400 | | |
| cag | ttc | ggt | gga | gga | act | tta | gga | cat | cct | tgg | ggt | aat | gcg | cca | ggt | 1248 |
| Gln | Phe | Gly | Gly | Gly | Thr | Leu | Gly | His | Pro | Trp | Gly | Asn | Ala | Pro | Gly | |
| | | | 405 | | | | | 410 | | | | | 415 | | | |
| gcc | gta | gct | aat | cga | gta | gct | cta | gaa | gca | tgt | gta | aaa | gct | cgt | aat | 1296 |
| Ala | Val | Ala | Asn | Arg | Val | Ala | Leu | Glu | Ala | Cys | Val | Lys | Ala | Arg | Asn | |
| | | 420 | | | | 425 | | | | | 430 | | | | | |
| gaa | gga | cgt | gat | ctt | gct | cag | gaa | ggt | aat | gaa | att | att | cgc | gag | gct | 1344 |
| Glu | Gly | Arg | Asp | Leu | Ala | Gln | Glu | Gly | Asn | Glu | Ile | Ile | Arg | Glu | Ala | |
| | | 435 | | | | | 440 | | | | | 445 | | | | |
| tgc | aaa | tgg | agc | ccg | gaa | cta | gct | gct | gct | tgt | gaa | gta | tgg | aaa | gag | 1392 |
| Cys | Lys | Trp | Ser | Pro | Glu | Leu | Ala | Ala | Ala | Cys | Glu | Val | Trp | Lys | Glu | |
| 450 | | | | | 455 | | | | | 460 | | | | | | |
| atc | gta | ttt | aat | ttt | gca | gca | gtg | gac | gtt | ttg | gat | aag | taa | | | 1434 |
| Ile | Val | Phe | Asn | Phe | Ala | Ala | Val | Asp | Val | Leu | Asp | Lys | | | | |
| 465 | | | | 470 | | | | | 475 | | | | | | | |

<210> SEQ ID NO 6
<211> LENGTH: 477
<212> TYPE: PRT
<213> ORGANISM: Nicotiana tabacum

<400> SEQUENCE: 6

Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

```
Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
        355                 360                 365

Val Ser Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
    450                 455                 460

Ile Val Phe Asn Phe Ala Ala Val Asp Val Leu Asp Lys
465                 470                 475

<210> SEQ ID NO 7
<211> LENGTH: 484
<212> TYPE: PRT
<213> ORGANISM: Oryza sativa

<400> SEQUENCE: 7

Met Ser Cys Arg Glu Gly Arg Met Ser Pro Gln Thr Glu Thr Lys Ala
1               5                   10                  15

Ser Val Gly Phe Lys Ala Gly Val Lys Asp Tyr Lys Leu Thr Tyr Tyr
            20                  25                  30

Thr Pro Glu Tyr Glu Thr Lys Asp Thr Asp Ile Leu Ala Ala Phe Arg
        35                  40                  45

Val Thr Pro Gln Pro Gly Val Pro Pro Glu Glu Ala Gly Ala Ala Val
    50                  55                  60

Ala Ala Glu Ser Ser Thr Gly Thr Trp Thr Thr Val Trp Thr Asp Gly
65                  70                  75                  80

Leu Thr Ser Leu Asp Arg Tyr Lys Gly Arg Cys Tyr His Ile Glu Pro
                85                  90                  95

Val Val Gly Glu Asp Asn Gln Tyr Ile Ala Tyr Val Ala Tyr Pro Leu
            100                 105                 110
```

```
Asp Leu Phe Glu Glu Gly Ser Val Thr Asn Met Phe Thr Ser Ile Val
        115                 120                 125

Gly Asn Val Phe Gly Phe Lys Ala Leu Arg Ala Leu Arg Leu Glu Asp
    130                 135                 140

Leu Arg Ile Pro Pro Thr Tyr Ser Lys Thr Phe Gln Gly Pro Pro His
145                 150                 155                 160

Gly Ile Gln Val Glu Arg Asp Lys Leu Asn Lys Tyr Gly Arg Pro Leu
                165                 170                 175

Leu Gly Cys Thr Ile Lys Pro Lys Leu Gly Leu Ser Ala Lys Asn Tyr
            180                 185                 190

Gly Arg Ala Cys Tyr Glu Cys Leu Arg Gly Gly Leu Asp Phe Thr Lys
        195                 200                 205

Asp Asp Glu Asn Val Asn Ser Gln Pro Phe Met Arg Trp Arg Asp Arg
210                 215                 220

Phe Val Phe Cys Ala Glu Ala Ile Tyr Lys Ser Gln Ala Glu Thr Gly
225                 230                 235                 240

Glu Ile Lys Gly His Tyr Leu Asn Ala Thr Ala Gly Thr Cys Glu Glu
                245                 250                 255

Met Ile Lys Arg Ala Val Phe Ala Arg Glu Leu Gly Val Pro Ile Val
            260                 265                 270

Met His Asp Tyr Leu Thr Gly Gly Phe Thr Ala Asn Thr Ser Leu Ala
        275                 280                 285

His Tyr Cys Arg Asp Asn Gly Leu Leu Leu His Ile His Arg Ala Met
        290                 295                 300

His Ala Val Ile Asp Arg Gln Lys Asn His Gly Met His Phe Arg Val
305                 310                 315                 320

Leu Ala Lys Ala Leu Arg Met Ser Gly Gly Asp His Ile His Ala Gly
                325                 330                 335

Thr Val Val Gly Lys Leu Glu Gly Glu Arg Glu Met Thr Leu Gly Phe
            340                 345                 350

Val Asp Leu Leu Arg Asp Asp Phe Ile Glu Lys Asp Arg Ala Arg Gly
        355                 360                 365

Ile Phe Phe Thr Gln Asp Trp Val Ser Met Pro Gly Val Ile Pro Val
        370                 375                 380

Ala Ser Gly Gly Ile His Val Trp His Met Pro Ala Leu Thr Glu Ile
385                 390                 395                 400

Phe Gly Asp Asp Ser Val Leu Gln Phe Gly Gly Thr Leu Gly His
                405                 410                 415

Pro Trp Gly Asn Ala Pro Gly Ala Ala Ala Asn Arg Val Ala Leu Glu
            420                 425                 430

Ala Cys Val Gln Ala Arg Asn Glu Gly Arg Asp Leu Ala Arg Glu Gly
        435                 440                 445

Asn Glu Ile Ile Arg Ser Ala Cys Lys Trp Ser Pro Glu Leu Ala Ala
    450                 455                 460

Ala Cys Glu Ile Trp Lys Ala Ile Lys Phe Glu Phe Glu Pro Val Asp
465                 470                 475                 480

Lys Leu Asp Ser

<210> SEQ ID NO 8
<211> LENGTH: 477
<212> TYPE: PRT
<213> ORGANISM: Triticum aestivum

<400> SEQUENCE: 8

Met Ser Pro Gln Thr Glu Thr Lys Ala Gly Val Gly Phe Lys Ala Gly
```

```
             1               5                  10                 15
Val Lys Asp Tyr Lys Leu Thr Tyr Tyr Thr Pro Glu Tyr Glu Thr Lys
                    20                 25                 30

Asp Thr Asp Ile Leu Ala Ala Phe Arg Val Ser Pro Gln Pro Gly Val
            35                 40                 45

Pro Pro Glu Glu Ala Gly Ala Ala Val Ala Ala Glu Ser Ser Thr Gly
        50                 55                 60

Thr Trp Thr Thr Val Trp Thr Asp Gly Leu Thr Ser Leu Asp Arg Tyr
65                      70                 75                 80

Lys Gly Arg Cys Tyr His Ile Glu Pro Val Ala Gly Glu Asp Ser Gln
                    85                 90                 95

Trp Ile Cys Tyr Val Ala Tyr Pro Leu Asp Leu Phe Glu Glu Gly Ser
            100                105                110

Val Thr Asn Met Phe Thr Ser Ile Val Gly Asn Val Phe Gly Phe Lys
        115                120                125

Ala Leu Arg Ala Leu Arg Leu Glu Asp Leu Arg Ile Pro Pro Thr Tyr
        130                135                140

Ser Lys Thr Phe Gln Gly Pro Pro His Gly Ile Gln Val Glu Arg Asp
145                150                155                160

Lys Leu Asn Lys Tyr Gly Arg Pro Leu Leu Gly Cys Thr Ile Lys Pro
                165                170                175

Lys Leu Gly Leu Ser Ala Lys Asn Tyr Gly Arg Ala Cys Tyr Glu Cys
            180                185                190

Leu Arg Gly Gly Leu Asp Phe Thr Lys Asp Asp Glu Asn Val Asn Ser
        195                200                205

Gln Pro Phe Met Arg Trp Arg Asp Arg Phe Val Phe Cys Ala Glu Ala
        210                215                220

Ile Tyr Lys Ser Gln Ala Glu Thr Gly Glu Ile Lys Gly His Tyr Leu
225                230                235                240

Asn Ala Thr Ala Gly Thr Cys Glu Glu Met Ile Lys Arg Ala Val Phe
                245                250                255

Ala Arg Glu Leu Gly Val Pro Ile Val Met His Asp Tyr Leu Thr Gly
            260                265                270

Gly Phe Thr Ala Asn Thr Thr Leu Ala His Tyr Cys Arg Asp Asn Gly
        275                280                285

Leu Leu Leu His Ile His Arg Ala Met His Ala Val Ile Asp Arg Gln
        290                295                300

Lys Asn His Gly Met His Phe Arg Val Leu Ala Lys Ala Leu Arg Met
305                310                315                320

Ser Gly Gly Asp His Ile His Ser Gly Thr Val Val Gly Lys Leu Glu
                325                330                335

Gly Glu Arg Glu Met Thr Leu Gly Phe Val Asp Leu Leu Arg Asp Asp
            340                345                350

Phe Ile Glu Lys Asp Arg Ala Arg Gly Ile Phe Phe Thr Gln Asp Trp
        355                360                365

Val Ser Met Pro Gly Val Ile Pro Val Ala Ser Gly Gly Ile His Val
        370                375                380

Trp His Met Pro Ala Leu Thr Glu Ile Phe Gly Asp Asp Ser Val Leu
385                390                395                400

Gln Phe Gly Gly Gly Thr Leu Gly His Pro Trp Gly Asn Ala Pro Gly
                405                410                415

Ala Ala Ala Asn Arg Val Ala Leu Glu Ala Cys Val Gln Ala Arg Asn
            420                425                430
```

```
Glu Gly Arg Asp Leu Ala Arg Glu Gly Asn Glu Ile Ile Arg Ala Ala
            435                 440                 445

Cys Lys Trp Ser Pro Glu Leu Ala Ala Ala Cys Glu Val Trp Lys Ala
    450                 455                 460

Ile Lys Phe Glu Phe Glu Pro Val Asp Thr Ile Asp Lys
465                 470                 475

<210> SEQ ID NO 9
<211> LENGTH: 476
<212> TYPE: PRT
<213> ORGANISM: Saccharum hybrid

<400> SEQUENCE: 9

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Lys
                20                  25                  30

Asp Thr Asp Ile Leu Ala Ala Phe Arg Val Thr Pro Gln Leu Gly Val
            35                  40                  45

Pro Pro Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr His Ile Glu Pro Val Pro Gly Asp Pro Asp Gln
                85                  90                  95

Tyr Ile Cys Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Cys Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Lys Glu Leu Gly Val Pro Ile Val Met His Asp Tyr Leu Thr Gly
            260                 265                 270

Gly Phe Thr Ala Asn Thr Thr Leu Ser His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335
```

```
Gly Glu Arg Glu Ile Thr Leu Gly Phe Val Asp Leu Leu Arg Asp Asp
                340                 345                 350

Phe Ile Glu Lys Asp Arg Ser Arg Gly Ile Phe Phe Thr Gln Asp Trp
                355                 360                 365

Val Ser Met Pro Gly Val Ile Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Ala Ala Asn Arg Val Ala Leu Glu Ala Cys Val Gln Ala Arg Asn
                420                 425                 430

Glu Gly Arg Asp Leu Ala Arg Glu Gly Asn Glu Ile Ile Lys Ala Ala
                435                 440                 445

Cys Lys Trp Ser Ala Glu Leu Ala Ala Ala Cys Glu Ile Trp Lys Glu
        450                 455                 460

Ile Lys Phe Asp Thr Phe Lys Ala Met Asp Thr Leu
465                 470                 475

<210> SEQ ID NO 10
<211> LENGTH: 476
<212> TYPE: PRT
<213> ORGANISM: Sorghum bicolor

<400> SEQUENCE: 10

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Lys
                20                  25                  30

Asp Thr Asp Ile Leu Ala Ala Phe Arg Val Thr Pro Gln Leu Gly Val
            35                  40                  45

Pro Pro Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr His Ile Glu Pro Val Pro Gly Asp Pro Asp Gln
                85                  90                  95

Tyr Ile Cys Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Cys Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Ile Tyr Lys Ala Gln Ala Glu Thr Gly Glu Ile Lys Gly His Tyr Leu
225                 230                 235                 240
```

Asn Ala Thr Ala Gly Thr Cys Glu Glu Met Ile Lys Arg Ala Val Phe
            245                 250                 255

Ala Lys Glu Leu Gly Val Pro Ile Val Met His Asp Tyr Leu Thr Gly
        260                 265                 270

Gly Phe Thr Ala Asn Thr Thr Leu Ser His Tyr Cys Arg Asp Asn Gly
            275                 280                 285

Leu Leu Leu His Ile His Arg Ala Met His Ala Val Ile Asp Arg Gln
        290                 295                 300

Lys Asn His Gly Met His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Glu Ile Thr Leu Gly Phe Val Asp Leu Leu Arg Asp Asp
            340                 345                 350

Phe Ile Glu Lys Asp Arg Ser Arg Gly Ile Phe Phe Thr Gln Asp Trp
        355                 360                 365

Val Ser Met Pro Gly Val Ile Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Ala Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Lys Ala Ala
        435                 440                 445

Cys Lys Trp Ser Ala Glu Leu Ala Ala Ala Cys Glu Ile Trp Lys Glu
450                 455                 460

Ile Lys Phe Asp Thr Phe Lys Ala Met Asp Thr Leu
465                 470                 475

<210> SEQ ID NO 11
<211> LENGTH: 496
<212> TYPE: PRT
<213> ORGANISM: Zea mays

<400> SEQUENCE: 11

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Lys
            20                  25                  30

Asp Thr Asp Ile Leu Ala Ala Phe Arg Val Thr Pro Gln Leu Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Pro Ala Tyr Val Lys Thr Phe Gln Gly
65                  70                  75                  80

Pro Pro His Gly Ile Gln Val Glu Arg Asp Thr Asp Gly Leu Thr Ser
                85                  90                  95

Leu Asp Arg Tyr Lys Gly Arg Cys Tyr His Ile Glu Pro Val Pro Gly
            100                 105                 110

Asp Pro Asp Gln Tyr Ile Cys Tyr Val Ala Tyr Pro Leu Asp Leu Phe
        115                 120                 125

Glu Glu Gly Ser Val Thr Asn Met Phe Thr Ser Ile Val Gly Asn Val
    130                 135                 140

```
Phe Gly Phe Lys Ala Leu Arg Ala Leu Arg Leu Glu Asp Leu Arg Ile
145                 150                 155                 160

Pro Pro Ala Tyr Ser Lys Thr Phe Gln Gly Pro Pro His Gly Ile Gln
                165                 170                 175

Val Glu Arg Asp Lys Leu Asn Lys Tyr Gly Arg Pro Leu Leu Gly Cys
            180                 185                 190

Thr Ile Lys Pro Lys Leu Gly Leu Ser Ala Lys Asn Tyr Gly Arg Ala
        195                 200                 205

Cys Tyr Glu Cys Leu Arg Gly Leu Asp Phe Thr Lys Asp Asp Glu
210                 215                 220

Asn Val Asn Ser Gln Pro Phe Met Arg Trp Arg Asp Arg Phe Val Phe
225                 230                 235                 240

Cys Ala Glu Ala Ile Tyr Lys Ala Gln Ala Glu Thr Gly Glu Ile Lys
                245                 250                 255

Gly His Tyr Leu Asn Ala Thr Ala Gly Thr Cys Glu Glu Met Ile Lys
                260                 265                 270

Arg Ala Val Phe Ala Arg Glu Leu Gly Val Pro Ile Val Met His Asp
            275                 280                 285

Tyr Leu Thr Gly Gly Phe Thr Ala Asn Thr Thr Leu Ser His Tyr Cys
        290                 295                 300

Arg Asp Asn Gly Leu Leu Leu His Ile His Arg Ala Met His Ala Val
305                 310                 315                 320

Ile Asp Arg Gln Lys Asn His Gly Met His Phe Arg Val Leu Ala Lys
                325                 330                 335

Ala Leu Arg Met Ser Gly Gly Asp His Ile His Ser Gly Thr Val Val
                340                 345                 350

Gly Lys Leu Glu Gly Glu Arg Glu Ile Thr Leu Gly Phe Val Asp Leu
            355                 360                 365

Leu Arg Asp Asp Phe Ile Glu Lys Asp Arg Ser Arg Gly Ile Phe Phe
        370                 375                 380

Thr Gln Asp Trp Val Ser Met Pro Gly Val Ile Pro Val Ala Ser Gly
385                 390                 395                 400

Gly Ile His Val Trp His Met Pro Ala Leu Thr Glu Ile Phe Gly Asp
                405                 410                 415

Asp Ser Val Leu Gln Phe Gly Gly Thr Leu Gly His Pro Trp Gly
                420                 425                 430

Asn Ala Pro Gly Ala Ala Ala Asn Arg Val Ala Leu Glu Ala Cys Val
            435                 440                 445

Gln Ala Arg Asn Glu Gly Arg Asp Leu Ala Arg Glu Gly Asn Glu Ile
        450                 455                 460

Ile Lys Ala Ala Cys Lys Trp Ser Ala Glu Leu Ala Ala Ala Cys Glu
465                 470                 475                 480

Ile Trp Lys Glu Ile Lys Phe Asp Gly Phe Lys Ala Met Asp Thr Ile
                485                 490                 495

<210> SEQ ID NO 12
<211> LENGTH: 480
<212> TYPE: PRT
<213> ORGANISM: Gossypium hirsutum

<400> SEQUENCE: 12

Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Glu Val Lys
            20                  25                  30
```

-continued

```
Asp Thr Asp Ile Leu Ala Ala Phe Arg Val Thr Pro Gln Pro Gly Val
         35                  40                  45
Pro Pro Glu Glu Ala Gly Ala Ala Val Ala Ala Glu Ser Ser Thr Gly
 50                  55                  60
Thr Trp Thr Thr Val Trp Thr Asp Gly Leu Thr Ser Leu Asp Arg Tyr
 65                  70                  75                  80
Lys Gly Arg Cys Tyr Asp Ile Glu Pro Val Pro Gly Glu Glu Asp Gln
                 85                  90                  95
Tyr Ile Cys Tyr Val Ala Tyr Pro Leu Asp Leu Phe Glu Glu Gly Ser
             100                 105                 110
Val Thr Asn Met Phe Thr Ser Ile Val Gly Asn Val Phe Gly Phe Lys
         115                 120                 125
Ala Leu Arg Ala Leu Arg Leu Glu Asp Leu Arg Val Pro Thr Ala Tyr
 130                 135                 140
Ile Lys Thr Phe Gln Gly Pro Pro His Gly Ile Gln Val Glu Arg Asp
145                 150                 155                 160
Lys Leu Asn Lys Tyr Gly Arg Pro Leu Leu Gly Cys Thr Ile Lys Pro
                 165                 170                 175
Lys Leu Gly Leu Ser Ala Lys Asn Tyr Gly Arg Ala Val Tyr Glu Cys
             180                 185                 190
Leu Arg Gly Gly Leu Asp Phe Thr Lys Asp Asp Glu Asn Val Asn Ser
         195                 200                 205
Gln Pro Phe Met Arg Trp Arg Asp Arg Phe Leu Phe Cys Ala Glu Ala
 210                 215                 220
Ile Phe Lys Ser Gln Ala Glu Thr Gly Glu Ile Lys Gly His Tyr Leu
225                 230                 235                 240
Asn Ala Thr Ala Gly Thr Cys Glu Glu Met Ile Lys Arg Ala Met Cys
                 245                 250                 255
Ala Arg Glu Leu Gly Val Pro Ile Val Met His Asp Tyr Leu Thr Gly
             260                 265                 270
Gly Phe Thr Ala Asn Thr Ser Leu Ala His Tyr Cys Arg Asp Asn Gly
         275                 280                 285
Leu Leu Leu His Ile His Arg Ala Met His Ala Val Ile Asp Arg Gln
 290                 295                 300
Lys Asn His Gly Met His Phe Arg Val Leu Ala Lys Ala Leu Arg Met
305                 310                 315                 320
Ser Gly Gly Asp His Ile His Ala Gly Thr Val Val Gly Lys Leu Glu
                 325                 330                 335
Gly Glu Arg Asp Ile Thr Leu Gly Phe Val Asp Leu Leu Arg Asp Asp
             340                 345                 350
Phe Ile Glu Lys Asp Arg Ser Arg Gly Ile Tyr Phe Thr Gln Asp Trp
         355                 360                 365
Val Ser Met Pro Gly Val Leu Pro Val Ala Ser Gly Gly Ile His Val
 370                 375                 380
Trp His Met Pro Ala Leu Thr Glu Ile Phe Gly Asp Asp Ser Val Leu
385                 390                 395                 400
Gln Phe Gly Gly Gly Thr Leu Gly His Pro Trp Gly Asn Ala Pro Gly
                 405                 410                 415
Ala Val Ala Asn Arg Val Ala Leu Glu Ala Cys Val Gln Ala Arg Asn
             420                 425                 430
Glu Gly Arg Asp Leu Ala Arg Glu Gly Asn Glu Ile Ile Arg Glu Ala
         435                 440                 445
Ser Lys Trp Ser Pro Glu Leu Ala Ala Ala Cys Glu Val Trp Lys Ala
 450                 455                 460
```

```
Ile Lys Phe Glu Phe Asp Ala Val Asp Lys Leu Asp Lys Val Glu Lys
465                 470                 475                 480

<210> SEQ ID NO 13
<211> LENGTH: 475
<212> TYPE: PRT
<213> ORGANISM: Glycine max

<400> SEQUENCE: 13

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Asp Tyr Glu Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Gly Leu Glu Pro Val Ala Gly Glu Glu Asn Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Thr Ala Tyr
130                 135                 140

Ile Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Ile Phe Lys Ser Gln Ala Glu Thr Gly Glu Ile Lys Gly His Tyr Leu
225                 230                 235                 240

Asn Ala Thr Ala Gly Thr Cys Glu Glu Met Met Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Leu
305                 310                 315                 320

Ser Gly Gly Asp His Val His Ala Gly Thr Val Val Gly Lys Leu Glu
                325                 330                 335

Gly Glu Arg Glu Ile Thr Leu Gly Phe Val Asp Leu Leu Arg Asp Asp
            340                 345                 350

Phe Val Glu Lys Asp Arg Ser Arg Gly Ile Tyr Phe Thr Gln Asp Trp
        355                 360                 365
```

```
Val Ser Leu Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Arg Glu Ala
        435                 440                 445

Ser Lys Trp Ser Pro Glu Leu Ala Ala Ala Cys Glu Val Trp Lys Glu
    450                 455                 460

Ile Lys Phe Glu Phe Glu Ala Met Asp Thr Leu
465                 470                 475

<210> SEQ ID NO 14
<211> LENGTH: 474
<212> TYPE: PRT
<213> ORGANISM: Medicago sativa

<400> SEQUENCE: 14

Met Ser Pro Gln Thr Glu Thr Lys Ala Thr Val Gly Phe Lys Ala Gly
1               5                   10                  15

Val Lys Asp Tyr Arg Leu Thr Tyr Tyr Thr Pro Asp Tyr Glu Thr Lys
            20                  25                  30

Asp Thr Asp Ile Leu Ala Ala Phe Arg Val Ser Pro Gln Pro Gly Val
        35                  40                  45

Pro Ala Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr His Ile Glu Pro Val Ala Gly Glu Glu Thr Gln
                85                  90                  95

Phe Ile Ala Tyr Val Ala Tyr Pro Leu Asp Leu Phe Glu Glu Gly Ser
            100                 105                 110

Val Asn Tyr Met Phe Thr Ser Ile Val Gly Asn Val Phe Gly Phe Lys
        115                 120                 125

Ala Leu Arg Ala Leu Arg Leu Glu Asp Leu Arg Ile Pro Ala Ala Tyr
    130                 135                 140

Val Lys Thr Phe Gln Gly Pro Pro Gln Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Met Lys Arg Ala Val Phe
                245                 250                 255

Ala Arg Glu Leu Gly Val Pro Ile Val Met His Asp Tyr Leu Thr Val
            260                 265                 270
```

```
Gly Phe Thr Ala Asn Thr Thr Leu Ala His Tyr Cys Arg Asp Asn Gly
            275                 280                 285

Leu Leu Leu His Ile His Arg Ala Met His Ala Val Ile Asp Arg Gln
        290                 295                 300

Lys Asn His Gly Met His Phe Arg Val Leu Lys Ala Leu Arg Met
305                 310                 315                 320

Ser Gly Gly Asp His Ile His Ala Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Ile Glu Lys Asp Arg Ser Arg Gly Ile Phe Phe Thr Gln Asp Trp
        355                 360                 365

Val Ser Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Arg Glu Ala
        435                 440                 445

Thr Lys Trp Ser Pro Glu Leu Ala Ala Ala Cys Glu Val Trp Lys Glu
    450                 455                 460

Ile Lys Phe Glu Phe Pro Ala Met Asp Asn
465                 470

<210> SEQ ID NO 15
<211> LENGTH: 475
<212> TYPE: PRT
<213> ORGANISM: Spinacia oleracea

<400> SEQUENCE: 15

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Leu
            20                  25                  30

Asp Thr Asp Ile Leu Ala Ala Phe Arg Val Ser Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Asn Leu Asp Arg Tyr
65                  70                  75                  80

Lys Gly Arg Cys Tyr His Ile Glu Pro Val Ala Gly Glu Glu Asn Gln
                85                  90                  95

Tyr Ile Cys Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Val Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175
```

```
Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
            210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Asp Met Met Lys Arg Ala Val Phe
            245                 250                 255

Ala Arg Glu Leu Gly Val Pro Ile Val Met His Asp Tyr Leu Thr Gly
            260                 265                 270

Gly Phe Thr Ala Asn Thr Thr Leu Ser His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Met His Phe Arg Val Leu Ala Lys Ala Leu Arg Leu
305                 310                 315                 320

Ser Gly Gly Asp His Ile His Ser Gly Thr Val Val Gly Lys Leu Glu
            325                 330                 335

Gly Glu Arg Asp Ile Thr Leu Gly Phe Val Asp Leu Leu Arg Asp Asp
            340                 345                 350

Tyr Thr Glu Lys Asp Arg Ser Arg Gly Ile Tyr Phe Thr Gln Ser Trp
            355                 360                 365

Val Ser Thr Pro Gly Val Leu Pro Val Ala Ser Gly Gly Ile His Val
            370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
            405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Thr Ile Ile Arg Glu Ala
            435                 440                 445

Thr Lys Trp Ser Pro Glu Leu Ala Ala Ala Cys Glu Val Trp Lys Glu
            450                 455                 460

Ile Lys Phe Glu Phe Pro Ala Met Asp Thr Val
465                 470                 475

<210> SEQ ID NO 16
<211> LENGTH: 477
<212> TYPE: PRT
<213> ORGANISM: Solanum lycopersium

<400> SEQUENCE: 16

Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
            35                  40                  45

Pro Pro Glu Glu Ala Gly Ala Ala Val Ala Ala Glu Ser Ser Thr Gly
            50                  55                  60

Thr Trp Thr Thr Val Trp Thr Asp Gly Leu Thr Ser Leu Asp Arg Tyr
65                  70                  75                  80
```

Lys Gly Arg Cys Tyr Arg Ile Glu Arg Val Val Gly Glu Lys Asp Gln
             85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
210                 215                 220

Leu Phe Lys Ala Gln Thr Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Thr Leu Ala His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Arg Glu Gly Asn Glu Ile Ile Arg Glu Ala
            435                 440                 445

Cys Lys Trp Ser Pro Glu Leu Ala Ala Ala Cys Glu Val Trp Lys Glu
450                 455                 460

Ile Val Phe Asn Phe Ala Ala Val Asp Val Leu Asp Lys
465                 470                 475

<210> SEQ ID NO 17
<211> LENGTH: 477
<212> TYPE: PRT

-continued

<213> ORGANISM: Solanum tuberosum

<400> SEQUENCE: 17

```
Met Ser Pro Gln Thr Glu Thr Lys Ala Ser Val Gly Phe Lys Ala Gly
1               5                   10                  15
Val Lys Glu Tyr Lys Leu Thr Tyr Tyr Thr Pro Glu Tyr Gln Thr Lys
            20                  25                  30
Asp Thr Asp Ile Leu Ala Ala Phe Arg Val Thr Pro Gln Pro Gly Val
        35                  40                  45
Pro Pro Glu Glu Ala Gly Ala Ala Val Ala Ala Glu Ser Ser Thr Gly
    50                  55                  60
Thr Trp Thr Thr Val Trp Thr Asp Gly Leu Thr Ser Leu Asp Arg Tyr
65                  70                  75                  80
Lys Gly Arg Cys Tyr Arg Ile Glu Arg Val Val Gly Glu Lys Asp Gln
                85                  90                  95
Tyr Ile Ala Tyr Val Ala Tyr Pro Leu Asp Leu Phe Glu Glu Gly Ser
            100                 105                 110
Val Thr Asn Met Leu Thr Ser Ile Val Gly Asn Val Phe Gly Phe Lys
        115                 120                 125
Ala Leu Arg Ala Leu Arg Leu Glu Asp Leu Arg Ile Pro Val Ala Tyr
    130                 135                 140
Val Lys Thr Phe Gln Gly Pro Pro His Gly Ile Gln Val Glu Arg Asp
145                 150                 155                 160
Lys Leu Asn Lys Tyr Gly Arg Pro Leu Leu Gly Cys Thr Ile Lys Pro
                165                 170                 175
Lys Leu Gly Leu Ser Ala Lys Asn Tyr Gly Arg Ala Val Tyr Glu Cys
            180                 185                 190
Leu Arg Gly Gly Leu Asp Phe Thr Lys Asp Asp Glu Asn Val Asn Ser
    195                 200                 205
Gln Pro Phe Met Arg Trp Arg Asp Arg Phe Leu Phe Cys Ala Glu Ala
    210                 215                 220
Leu Phe Lys Ala Gln Ala Glu Thr Gly Glu Ile Lys Gly His Tyr Leu
225                 230                 235                 240
Asn Ala Thr Ala Gly Thr Cys Glu Glu Met Met Lys Arg Ala Val Phe
                245                 250                 255
Ala Arg Glu Leu Gly Thr Pro Ile Val Met His Asp Tyr Leu Thr Gly
            260                 265                 270
Gly Phe Thr Ala Asn Thr Thr Leu Ala His Tyr Cys Arg Asp Asn Gly
        275                 280                 285
Leu Leu Leu His Ile His Arg Ala Met His Ala Val Ile Asp Arg Gln
    290                 295                 300
Lys Asn His Gly Met His Phe Arg Val Leu Ala Lys Ala Leu Arg Met
305                 310                 315                 320
Ser Gly Gly Asp His Ile His Ser Gly Thr Val Val Gly Lys Leu Glu
                325                 330                 335
Gly Glu Arg Asp Ile Thr Leu Gly Phe Val Asp Leu Leu Arg Asp Asp
            340                 345                 350
Phe Ile Glu Gln Asp Arg Ser Arg Gly Ile Tyr Phe Thr Gln Asp Trp
        355                 360                 365
Val Ser Leu Pro Gly Val Leu Pro Val Ala Ser Gly Gly Ile His Val
    370                 375                 380
Trp His Met Pro Ala Leu Thr Glu Ile Phe Gly Asp Asp Ser Val Leu
385                 390                 395                 400
Gln Phe Gly Gly Gly Thr Leu Gly His Pro Trp Gly Asn Ala Pro Gly
```

-continued

```
                405                 410                 415
Ala Val Ala Asn Arg Val Ala Leu Glu Ala Cys Val Lys Ala Arg Asn
                420                 425                 430

Glu Gly Arg Asp Leu Ala Arg Glu Gly Asn Glu Ile Ile Arg Glu Ala
                435                 440                 445

Ala Lys Trp Ser Pro Glu Leu Ala Ala Cys Glu Val Trp Lys Glu
    450                 455                 460

Ile Val Phe Asn Phe Ala Ala Met Asp Val Leu Asp Lys
465                 470                 475

<210> SEQ ID NO 18
<211> LENGTH: 479
<212> TYPE: PRT
<213> ORGANISM: Hordeum vulgare

<400> SEQUENCE: 18

Met Ser Pro Gln Thr Glu Thr Lys Ala Gly Val Gly Phe Gln Ala Gly
1               5                   10                  15

Val Lys Asp Tyr Lys Leu Thr Tyr Tyr Thr Pro Glu Tyr Glu Thr Lys
                20                  25                  30

Asp Thr Asp Ile Leu Ala Ala Phe Arg Val Ser Pro Gln Pro Gly Val
            35                  40                  45

Pro Pro Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr His Ile Glu Pro Val Ala Gly Glu Asp Ser Gln
                85                  90                  95

Trp Ile Cys Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Thr Tyr
    130                 135                 140

Ser Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Cys Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Ile Tyr Lys Ser Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Thr Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
```

```
            305                 310                 315                 320
Ser Gly Gly Asp His Ile His Ser Gly Thr Val Val Gly Lys Leu Glu
                325                 330                 335

Gly Glu Arg Glu Met Thr Leu Gly Phe Val Asp Leu Leu Arg Asp Asp
                340                 345                 350

Phe Ile Glu Lys Asp Arg Ala Arg Gly Ile Phe Phe Thr Gln Asp Trp
                355                 360                 365

Val Ser Met Pro Gly Val Ile Pro Val Ala Ser Gly Gly Ile His Val
            370                 375                 380

Trp His Met Pro Ala Leu Thr Glu Ile Phe Gly Asp Asp Ser Val Leu
385                 390                 395                 400

Gln Phe Gly Gly Thr Leu Gly His Pro Trp Gly Asn Ala Pro Gly
                405                 410                 415

Ala Ala Ala Asn Arg Val Ala Leu Glu Ala Cys Val Gln Ala Arg Asn
                420                 425                 430

Glu Gly Arg Asp Leu Ala Arg Glu Gly Asn Glu Ile Ile Arg Ala Ala
                435                 440                 445

Cys Lys Trp Ser Pro Glu Leu Ala Ala Ala Cys Glu Val Trp Lys Ala
        450                 455                 460

Ile Lys Phe Glu Phe Glu Pro Val Asp Thr Ile Asp Lys Lys Val
465                 470                 475

<210> SEQ ID NO 19
<211> LENGTH: 3120
<212> TYPE: DNA
<213> ORGANISM: Nicotiana tabacum

<400> SEQUENCE: 19
tgaatcagaa tcttgagaaa gtctttcatt tgtctatcat tatagacaat cccatccata      60
ttatctattc tatggaattc gaacctgaac tttattttct atttctatta cgattcatta     120
tttgtatcta attggctcct cttcttattt attttttgatt tcaatttcag catatcgatt    180
tatgcctagc ctattctttt ctttgtgttt ttctttcttt tttataccct tcatagattc     240
atagaggaat tccgtatatt ttcacatcta ggatttacat atacaacata taccactgtc     300 aaggggggaag ttcttattat ttaggttagt caggtatttc catttcaaaa aaaaaaaag    360 taaaaagaa aaattgggtt gcgctatata tatgaaagag tatacaataa tgatgtattt     420
ggcaaatcaa ataccatggt ctaataatca acattctga ttagttgata atattagtat     480
tagttggaaa ttttgtgaaa gattcctatg aaaagtttca ttaacacgga attcgtgtcg     540
agtagacctt gttgttgtga gaattcttaa ttcatgagtt gtagggaggg atttatgtca     600
ccacaaacag agactaaagc aagtgttgga ttcaaagctg gtgttaaaga gtacaaattg     660
acttattata ctcctgagta ccaaaccaag gatactgata tattggcagc attccgagta     720
actcctcaac ctggagttcc acctgaagaa gcaggggccg cggtagctgc cgaatcttct     780
actggtacat ggacaactgt atggaccgat ggacttacca gccttgatcg ttacaaaggg     840
cgatgctacc gcatcgagcg tgttgttgga gaaaaagatc aatatattgc ttatgtagct     900 tacccttag accttttga agaaggttct gttaccaaca tgtttacttc cattgtaggt     960
aacgtatttg ggttcaaagc cctgcgcgct ctacgtctgg aagatctgcg aatccctcct    1020
gcttatgtta aaacttttcca aggtccgcct catgggatcc aagttgaaag agataaattg    1080
aacaagtatg gtcgtcccct gttgggatgt actattaaac ctaaattggg gttatctgct    1140
aaaaactacg gtagagccgt ttatgaatgt cttcgcggtg gacttgattt tactaaagat    1200
```

```
gatgagaacg tgaactcaca accatttatg cgttggagag atcgtttctt attttgtgcc    1260
gaagcacttt ataaagcaca ggctgaaaca ggtgaaatca aagggcatta cttgaatgct    1320
actgcaggta catgcgaaga aatgatcaaa agagctgtat ttgctagaga attgggcgtt    1380
ccgatcgtaa tgcatgacta cttaacgggg ggattcaccg caaatactag cttggctcat    1440
tattgccgag ataatggtct acttcttcac atccaccgtg caatgcatgc ggttattgat    1500
agacagaaga atcatggtat ccacttccgg gtattagcaa aagcgttacg tatgtctggt    1560
ggagatcata ttcactctgg taccgtagta ggtaaacttg aaggtgaaag agacataact    1620
ttgggctttg ttgatttact gcgtgatgat tttgttgaac aagatcgaag tcgcggtatt    1680
tatttcactc aagattgggt ctctttacca ggtgttctac ccgtggcttc aggaggtatt    1740
cacgtttggc atatgcctgc tctgaccgag atctttgggg atgattccgt actacagttc    1800
ggtggaggaa ctttaggaca tccttggggt aatgcgccag gtgccgtagc taatcgagta    1860
gctctagaag catgtgtaaa agctcgtaat gaaggacgtg atcttgctca ggaaggtaat    1920
gaaattattc gcgaggcttg caaatggagc ccggaactag ctgctgcttg tgaagtatgg    1980
aaagagatcg tatttaattt tgcagcagtg gacgttttgg ataagtaaaa acagtagaca    2040
ttagcagata aattagcagg aaataaagaa ggataaggag aaagaactca agtaattatc    2100
cttcgttctc ttaattgaat tgcaattaaa ctcggcccaa tcttttacta aaaggattga    2160
gccgaataca acaaagattc tattgcatat attttgacta agtatatact tacctagata    2220
tacaagattt gaaatacaaa atctagaaaa ctaaatcaaa atctaagact caaatctttc    2280
tattgttgtc ttggatccac aattaatcct acggatcctt aggattggta tattcttttc    2340
tatcctgtag tttgtagttt ccctgaatca agccaagtat cacacctctt tctacccatc    2400
ctgtatattg tcccctttgt tccgtgttga aatagaacct taatttatta cttattttt    2460 tattaaattt tagatttgtt agtgattaga tattagtatt agacgagatt ttacgaaaca    2520 attattttt tatttcttta taggagagga caaatctctt ttttcgatgc gaatttgaca    2580
cgacatagga gaagccgccc tttattaaaa attatattat tttaaataat ataaggggg    2640 ttccaacata ttaatatata gtgaagtgtt cccccagatt cagaactttt tttcaatact    2700
cacaatcctt attagttaat aatcctagtg attggatttc tatgcttagt ctgataggaa    2760
ataagatatt caaataaata atttatagc gaatgactat tcatctattg tattttcatg    2820 caaataggg gcaagaaaac tctatggaaa gatggtggtt taattcgatg ttgtttaaga    2880
aggagttcga acgcaggtgt gggctaaata aatcaatggg cagtcttggt cctattgaaa    2940
ataccaatga agatccaaat cgaaaagtga aaaacattca tagttggagg aatcgtgaca    3000
attctagttg cagtaatgtt gattatttat tcggcgttaa agacattcgg aatttcatct    3060
ctgatgacac tttttagtt agtgatagga atggagacag ttattccatc tatttgata     3120
```

<210> SEQ ID NO 20
<211> LENGTH: 1428
<212> TYPE: DNA
<213> ORGANISM: Artificial Sequence
<220> FEATURE:
<223> OTHER INFORMATION: Description for artificial sequence: shuffled
      Chlamydomonas Rubisco large subunit variant Cil-12.
<220> FEATURE:
<221> NAME/KEY: CDS
<222> LOCATION: (1)..(1425)

<400> SEQUENCE: 20

```
atg gtt cca caa aca gaa act aaa gca ggt gct gga ttc aaa gcc ggt    48
Met Val Pro Gln Thr Glu Thr Lys Ala Gly Ala Gly Phe Lys Ala Gly
```

```
              1               5              10              15
gta aaa gac tac cgt tta aca tac tac aca cct gat tac gta gta aga    96
Val Lys Asp Tyr Arg Leu Thr Tyr Tyr Thr Pro Asp Tyr Val Val Arg
             20                  25                  30 gat act gat att tta gct gca ttc cgt atg act cca caa cca ggt gtt   144
Asp Thr Asp Ile Leu Ala Ala Phe Arg Met Thr Pro Gln Pro Gly Val
         35                  40                  45 cca cct gaa gaa tgt ggt gct gct gta gct gct gaa tct tca aca ggt   192
Pro Pro Glu Glu Cys Gly Ala Ala Val Ala Ala Glu Ser Ser Thr Gly
     50                  55                  60 aca tgg act aca gta tgg act gac ggt tta aca agt ctt gac cgt tac   240
Thr Trp Thr Thr Val Trp Thr Asp Gly Leu Thr Ser Leu Asp Arg Tyr
 65                  70                  75                  80 aaa ggt cgt tgt tac gat atc gaa cca gtt ccg ggt gaa gac aac caa   288
Lys Gly Arg Cys Tyr Asp Ile Glu Pro Val Pro Gly Glu Asp Asn Gln
                 85                  90                  95 tac att act tac gta gct tac cca atc gac tta ttc gaa gaa ggt tca   336
Tyr Ile Thr Tyr Val Ala Tyr Pro Ile Asp Leu Phe Glu Glu Gly Ser
            100                 105                 110 gta act aac atg ttc act tct att gta ggt aac gta ttc ggt ttc aaa   384
Val Thr Asn Met Phe Thr Ser Ile Val Gly Asn Val Phe Gly Phe Lys
        115                 120                 125 gct tta cgt gct cta cgt ctt gaa gac ctt cgt att cca cct gct tac   432
Ala Leu Arg Ala Leu Arg Leu Glu Asp Leu Arg Ile Pro Pro Ala Tyr
    130                 135                 140 gtt aaa aca ttc gta ggt cct cca cac ggt att cag gta gaa cgt gac   480
Val Lys Thr Phe Val Gly Pro Pro His Gly Ile Gln Val Glu Arg Asp
145                 150                 155                 160 aaa tta aac aaa tat ggt cgt ggt ctt tta ggt tgt aca atc aaa cct   528
Lys Leu Asn Lys Tyr Gly Arg Gly Leu Leu Gly Cys Thr Ile Lys Pro
                165                 170                 175 aaa tta ggt ctt tca gct aaa aac tac ggt cgt gca gtt tat gaa tgt   576
Lys Leu Gly Leu Ser Ala Lys Asn Tyr Gly Arg Ala Val Tyr Glu Cys
            180                 185                 190 tta cgt ggt ggt ctt gac ttt act aaa gac gac gaa aac gta aac tca   624
Leu Arg Gly Gly Leu Asp Phe Thr Lys Asp Asp Glu Asn Val Asn Ser
        195                 200                 205 caa cca ttc atg cgt tgg cgt gac cgt ttc ctt ttc gtt gct gaa gct   672
Gln Pro Phe Met Arg Trp Arg Asp Arg Phe Leu Phe Val Ala Glu Ala
    210                 215                 220 att tac aaa gct caa gca gaa aca ggt gaa gtt aaa ggt cac tac tta   720
Ile Tyr Lys Ala Gln Ala Glu Thr Gly Glu Val Lys Gly His Tyr Leu
225                 230                 235                 240 aac gct act gct ggt act tgt gaa gaa atg atg aaa cgt gca gta tgt   768
Asn Ala Thr Ala Gly Thr Cys Glu Glu Met Met Lys Arg Ala Val Cys
                245                 250                 255 gct aaa gaa tta ggt gta cct att att atg cac gac tac tta aca ggt   816
Ala Lys Glu Leu Gly Val Pro Ile Ile Met His Asp Tyr Leu Thr Gly
            260                 265                 270 ggt ttc aca gct aac act tca tta tca atc tac tgt cgt gac aac ggt   864
Gly Phe Thr Ala Asn Thr Ser Leu Ser Ile Tyr Cys Arg Asp Asn Gly
        275                 280                 285 ctt ctt cta cac atc cac cgt gct atg cac gcg gtt att gac cgt caa   912
Leu Leu Leu His Ile His Arg Ala Met His Ala Val Ile Asp Arg Gln
    290                 295                 300 cgt aac cac ggt att cac ttc cgt gtt ctt gct aaa gct ctt cgt atg   960
Arg Asn His Gly Ile His Phe Arg Val Leu Ala Lys Ala Leu Arg Met
305                 310                 315                 320 tct ggt ggt gac cac ctt cac tct ggt act gtt gta ggt aaa cta gaa  1008
Ser Gly Gly Asp His Leu His Ser Gly Thr Val Val Gly Lys Leu Glu
```

```
                        325                 330                 335
ggt gaa cgt gaa gtt act cta ggt ttc gta gac tta atg cgt gat ggc      1056
Gly Glu Arg Glu Val Thr Leu Gly Phe Val Asp Leu Met Arg Asp Gly
            340                 345                 350 tac gtt gaa aaa gac cgt agc cgt ggt att tac ttc act caa gac tgg      1104
Tyr Val Glu Lys Asp Arg Ser Arg Gly Ile Tyr Phe Thr Gln Asp Trp
        355                 360                 365 tgt tca atg cca ggt gtt atg cca gtt gct tca ggt ggt att cac gta      1152
Cys Ser Met Pro Gly Val Met Pro Val Ala Ser Gly Gly Ile His Val
    370                 375                 380 tgg cac atg cca gct tta gtt gaa atc ttc ggt gat gac gca tgt ctt      1200
Trp His Met Pro Ala Leu Val Glu Ile Phe Gly Asp Asp Ala Cys Leu
385                 390                 395                 400 cag ttc ggt ggt ggt act cta ggt cac cct tgg ggt aac gct cca ggt      1248
Gln Phe Gly Gly Gly Thr Leu Gly His Pro Trp Gly Asn Ala Pro Gly
                405                 410                 415 gct gca gct aac cgt gta gct ctt gaa gct tgt act caa gct cgt aac      1296
Ala Ala Ala Asn Arg Val Ala Leu Glu Ala Cys Thr Gln Ala Arg Asn
            420                 425                 430 gaa ggt cgt gac ctt gct cgt gaa ggt ggc gac gta att cgt tca gct      1344
Glu Gly Arg Asp Leu Ala Arg Glu Gly Gly Asp Val Ile Arg Ser Ala
        435                 440                 445 tgt aaa tgg tct cca gaa ctt gct gct gca tgt gaa gtt tgg aaa gaa      1392
Cys Lys Trp Ser Pro Glu Leu Ala Ala Ala Cys Glu Val Trp Lys Glu
    450                 455                 460 att aaa ttc gaa ttt gat act att gac aaa ctt taa                       1428
Ile Lys Phe Glu Phe Asp Thr Ile Asp Lys Leu
465                 470                 475

<210> SEQ ID NO 21
<211> LENGTH: 475
<212> TYPE: PRT
<213> ORGANISM: Artificial Sequence
<220> FEATURE:
<223> OTHER INFORMATION: Synthetic Construct

<400> SEQUENCE: 21

Met Val Pro Gln Thr Glu Thr Lys Ala Gly Ala Gly Phe Lys Ala Gly
1               5                   10                  15

Val Lys Asp Tyr Arg Leu Thr Tyr Tyr Thr Pro Asp Tyr Val Val Arg
            20                  25                  30

Asp Thr Asp Ile Leu Ala Ala Phe Arg Met Thr Pro Gln Pro Gly Val
        35                  40                  45

Pro Pro Glu Glu Cys Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Asp Asn Gln
                85                  90                  95

Tyr Ile Thr Tyr Val Ala Tyr Pro Ile Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Val Gly Pro Pro His Gly Ile Gln Val Glu Arg Asp
145                 150                 155                 160

Lys Leu Asn Lys Tyr Gly Arg Gly Leu Leu Gly Cys Thr Ile Lys Pro
                165                 170                 175
```

```
Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Val Ala Glu Ala
            210                 215                 220

Ile Tyr Lys Ala Gln Ala Glu Thr Gly Glu Val Lys Gly His Tyr Leu
225                 230                 235                 240

Asn Ala Thr Ala Gly Thr Cys Glu Glu Met Met Lys Arg Ala Val Cys
            245                 250                 255

Ala Lys Glu Leu Gly Val Pro Ile Ile Met His Asp Tyr Leu Thr Gly
            260                 265                 270

Gly Phe Thr Ala Asn Thr Ser Leu Ser Ile Tyr Cys Arg Asp Asn Gly
            275                 280                 285

Leu Leu Leu His Ile His Arg Ala Met His Ala Val Ile Asp Arg Gln
            290                 295                 300

Arg Asn His Gly Ile His Phe Arg Val Leu Ala Lys Ala Leu Arg Met
305                 310                 315                 320

Ser Gly Gly Asp His Leu His Ser Gly Thr Val Val Gly Lys Leu Glu
            325                 330                 335

Gly Glu Arg Glu Val Thr Leu Gly Phe Val Asp Leu Met Arg Asp Gly
            340                 345                 350

Tyr Val Glu Lys Asp Arg Ser Arg Gly Ile Tyr Phe Thr Gln Asp Trp
            355                 360                 365

Cys Ser Met Pro Gly Val Met Pro Val Ala Ser Gly Gly Ile His Val
370                 375                 380

Trp His Met Pro Ala Leu Val Glu Ile Phe Gly Asp Asp Ala Cys Leu
385                 390                 395                 400

Gln Phe Gly Gly Gly Thr Leu Gly His Pro Trp Gly Asn Ala Pro Gly
            405                 410                 415

Ala Ala Ala Asn Arg Val Ala Leu Glu Ala Cys Thr Gln Ala Arg Asn
            420                 425                 430

Glu Gly Arg Asp Leu Ala Arg Glu Gly Gly Asp Val Ile Arg Ser Ala
            435                 440                 445

Cys Lys Trp Ser Pro Glu Leu Ala Ala Ala Cys Glu Val Trp Lys Glu
450                 455                 460

Ile Lys Phe Glu Phe Asp Thr Ile Asp Lys Leu
465                 470                 475

<210> SEQ ID NO 22
<211> LENGTH: 1428
<212> TYPE: DNA
<213> ORGANISM: Artificial Sequence
<220> FEATURE:
<223> OTHER INFORMATION: Description for artificial sequence: shuffled
      Chlamydomonas Rubisco large subunit variant Cil-10.
<220> FEATURE:
<221> NAME/KEY: CDS
<222> LOCATION: (1)..(1425)

<400> SEQUENCE: 22 atg gtt cca caa aca gaa act aaa gca ggt gct gga ttc aaa gcc ggt       48
Met Val Pro Gln Thr Glu Thr Lys Ala Gly Ala Gly Phe Lys Ala Gly
1               5                   10                  15 gta aaa gac tac cgt tta aca tac tac aca cct gat tac gta gta aga       96
Val Lys Asp Tyr Arg Leu Thr Tyr Tyr Thr Pro Asp Tyr Val Val Arg
            20                  25                  30
```

-continued

```
gat act gat att tta gct gca ttc cgt atg act cca caa cca ggt gtt      144
Asp Thr Asp Ile Leu Ala Ala Phe Arg Met Thr Pro Gln Pro Gly Val
        35                  40                  45 cca cct gaa gaa tgt ggt gct gct gta gct gct gaa tct tca aca ggt      192
Pro Pro Glu Glu Cys Gly Ala Ala Val Ala Ala Glu Ser Ser Thr Gly
    50                  55                  60 aca tgg act aca gta tgg act gac ggt tta aca agt ctt gac cgt tac      240
Thr Trp Thr Thr Val Trp Thr Asp Gly Leu Thr Ser Leu Asp Arg Tyr
65                  70                  75                  80 aaa ggt cgt tgt tac gat atc gaa cca gtt ccg ggt gaa gac aac caa      288
Lys Gly Arg Cys Tyr Asp Ile Glu Pro Val Pro Gly Glu Asp Asn Gln
                85                  90                  95 tac att gct tac gta gtt tac cca atc gac tta ttc gaa gaa ggt tca      336
Tyr Ile Ala Tyr Val Val Tyr Pro Ile Asp Leu Phe Glu Glu Gly Ser
            100                 105                 110 gta act aac atg ttc act tct att gta ggt aac gta ttc ggt ttc aaa      384
Val Thr Asn Met Phe Thr Ser Ile Val Gly Asn Val Phe Gly Phe Lys
        115                 120                 125 gct tta cgt gct cta cgt ctt gaa gac ctt cgt att cca cct gct tac      432
Ala Leu Arg Ala Leu Arg Leu Glu Asp Leu Arg Ile Pro Pro Ala Tyr
    130                 135                 140 gtt aaa aca ttc gta ggt cct cca cac ggt att cag gta gaa cgt gac      480
Val Lys Thr Phe Val Gly Pro Pro His Gly Ile Gln Val Glu Arg Asp
145                 150                 155                 160 aaa tta aac aaa tat ggt cgt ggt ctt tta ggt tgt aca atc aaa cct      528
Lys Leu Asn Lys Tyr Gly Arg Gly Leu Leu Gly Cys Thr Ile Lys Pro
                165                 170                 175 aaa tta ggt ctt tca gct aaa aac tac ggt cgt gca gtt tat gaa tgt      576
Lys Leu Gly Leu Ser Ala Lys Asn Tyr Gly Arg Ala Val Tyr Glu Cys
            180                 185                 190 tta cgt ggt ggt ctt gac ttt act aaa gac gac gaa aac gta aac tca      624
Leu Arg Gly Gly Leu Asp Phe Thr Lys Asp Asp Glu Asn Val Asn Ser
        195                 200                 205 caa cca ttc atg cgt tgg cgt gac cgt ttc ctt ttc gtt gct gaa gct      672
Gln Pro Phe Met Arg Trp Arg Asp Arg Phe Leu Phe Val Ala Glu Ala
    210                 215                 220 att tac aaa gct caa gca gaa aca ggt gaa gtt aaa ggt cac tac tta      720
Ile Tyr Lys Ala Gln Ala Glu Thr Gly Glu Val Lys Gly His Tyr Leu
225                 230                 235                 240 aac gct act gct ggt act tgt gaa gaa atg atg aaa cgt gca gta tgt      768
Asn Ala Thr Ala Gly Thr Cys Glu Glu Met Met Lys Arg Ala Val Cys
                245                 250                 255 gct aaa gaa tta ggt gta cct att gta atg cac gac tac tta aca ggt      816
Ala Lys Glu Leu Gly Val Pro Ile Val Met His Asp Tyr Leu Thr Gly
            260                 265                 270 ggt ttc aca gct aac act tca tta gct atc tac tgt cgt gac aac ggt      864
Gly Phe Thr Ala Asn Thr Ser Leu Ala Ile Tyr Cys Arg Asp Asn Gly
        275                 280                 285 ctt ctt cta cac atc cac cgt gct atg cac gcg gtt att gac cgt caa      912
Leu Leu Leu His Ile His Arg Ala Met His Ala Val Ile Asp Arg Gln
    290                 295                 300 cgt aac cac ggt att cac ttc cgt gtt ctt gct aaa gct ctt cgt atg      960
Arg Asn His Gly Ile His Phe Arg Val Leu Ala Lys Ala Leu Arg Met
305                 310                 315                 320 tct ggt ggt gac cac ctt cac tct ggt act gtt gta ggt aaa cta gaa     1008
Ser Gly Gly Asp His Leu His Ser Gly Thr Val Val Gly Lys Leu Glu
                325                 330                 335 ggt gaa cgt gaa gtt act cta ggt ttc gta gac tta atg cgt gat gac     1056
Gly Glu Arg Glu Val Thr Leu Gly Phe Val Asp Leu Met Arg Asp Asp
            340                 345                 350
```

```
cac gtt gaa aaa gac cgt agc cgt ggt att tac ttc act caa gac tgg    1104
His Val Glu Lys Asp Arg Ser Arg Gly Ile Tyr Phe Thr Gln Asp Trp
        355                 360                 365 tgt gca atg cca ggt gtt atg cca gtt gct tca ggt ggt att cac gta    1152
Cys Ala Met Pro Gly Val Met Pro Val Ala Ser Gly Gly Ile His Val
    370                 375                 380 tgg cac atg cca gct tta gtt gaa atc ttc ggt gat gac gca tgt ctt    1200
Trp His Met Pro Ala Leu Val Glu Ile Phe Gly Asp Asp Ala Cys Leu
385                 390                 395                 400 cag ttc ggt ggt ggt act cta ggt cac cct tgg ggt aac gct cca ggt    1248
Gln Phe Gly Gly Gly Thr Leu Gly His Pro Trp Gly Asn Ala Pro Gly
                405                 410                 415 gct gca gct aac cgt gta gct ctt gaa gct tgt act caa gct cgt aac    1296
Ala Ala Ala Asn Arg Val Ala Leu Glu Ala Cys Thr Gln Ala Arg Asn
            420                 425                 430 gaa ggt cgt gac ctt gct cgt gaa ggt ggc gac gta att cgt tca gct    1344
Glu Gly Arg Asp Leu Ala Arg Glu Gly Gly Asp Val Ile Arg Ser Ala
        435                 440                 445 tgt aaa tgg tct cca gaa ctt gct gct gca tgt gaa gtt tgg aaa gaa    1392
Cys Lys Trp Ser Pro Glu Leu Ala Ala Ala Cys Glu Val Trp Lys Glu
    450                 455                 460 att aaa ttc gaa ttt gat act att gac aaa ctt taa                    1428
Ile Lys Phe Glu Phe Asp Thr Ile Asp Lys Leu
465                 470                 475

<210> SEQ ID NO 23
<211> LENGTH: 475
<212> TYPE: PRT
<213> ORGANISM: Artificial Sequence
<220> FEATURE:
<223> OTHER INFORMATION: Synthetic Construct

<400> SEQUENCE: 23

Met Val Pro Gln Thr Glu Thr Lys Ala Gly Ala Gly Phe Lys Ala Gly
1               5                   10                  15

Val Lys Asp Tyr Arg Leu Thr Tyr Tyr Thr Pro Asp Tyr Val Val Arg
            20                  25                  30

Asp Thr Asp Ile Leu Ala Ala Phe Arg Met Thr Pro Gln Pro Gly Val
        35                  40                  45

Pro Pro Glu Glu Cys Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Asp Asn Gln
                85                  90                  95

Tyr Ile Ala Tyr Val Val Tyr Pro Ile Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Val Gly Pro Pro His Gly Ile Gln Val Glu Arg Asp
145                 150                 155                 160

Lys Leu Asn Lys Tyr Gly Arg Gly Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205
```

```
Gln Pro Phe Met Arg Trp Arg Asp Arg Phe Leu Phe Val Ala Glu Ala
    210                 215                 220

Ile Tyr Lys Ala Gln Ala Glu Thr Gly Glu Val Lys Gly His Tyr Leu
225                 230                 235                 240

Asn Ala Thr Ala Gly Thr Cys Glu Glu Met Met Lys Arg Ala Val Cys
                245                 250                 255

Ala Lys Glu Leu Gly Val Pro Ile Val Met His Asp Tyr Leu Thr Gly
            260                 265                 270

Gly Phe Thr Ala Asn Thr Ser Leu Ala Ile Tyr Cys Arg Asp Asn Gly
        275                 280                 285

Leu Leu Leu His Ile His Arg Ala Met His Ala Val Ile Asp Arg Gln
    290                 295                 300

Arg Asn His Gly Ile His Phe Arg Val Leu Ala Lys Ala Leu Arg Met
305                 310                 315                 320

Ser Gly Gly Asp His Leu His Ser Gly Thr Val Val Gly Lys Leu Glu
                325                 330                 335

Gly Glu Arg Glu Val Thr Leu Gly Phe Val Asp Leu Met Arg Asp Asp
            340                 345                 350

His Val Glu Lys Asp Arg Ser Arg Gly Ile Tyr Phe Thr Gln Asp Trp
        355                 360                 365

Cys Ala Met Pro Gly Val Met Pro Val Ala Ser Gly Gly Ile His Val
    370                 375                 380

Trp His Met Pro Ala Leu Val Glu Ile Phe Gly Asp Asp Ala Cys Leu
385                 390                 395                 400

Gln Phe Gly Gly Gly Thr Leu Gly His Pro Trp Gly Asn Ala Pro Gly
                405                 410                 415

Ala Ala Ala Asn Arg Val Ala Leu Glu Ala Cys Thr Gln Ala Arg Asn
            420                 425                 430

Glu Gly Arg Asp Leu Ala Arg Glu Gly Gly Asp Val Ile Arg Ser Ala
        435                 440                 445

Cys Lys Trp Ser Pro Glu Leu Ala Ala Ala Cys Glu Val Trp Lys Glu
    450                 455                 460

Ile Lys Phe Glu Phe Asp Thr Ile Asp Lys Leu
465                 470                 475

<210> SEQ ID NO 24
<211> LENGTH: 1428
<212> TYPE: DNA
<213> ORGANISM: Artificial Sequence
<220> FEATURE:
<223> OTHER INFORMATION: Description for artificial sequence: shuffled
      Chlamydomonas Rubisco large subunit variant Osc4-11.
<220> FEATURE:
<221> NAME/KEY: CDS
<222> LOCATION: (1)..(1425)

<400> SEQUENCE: 24 atg gtt cca caa aca gaa act aaa gca ggt gct gga ttc aaa gcc ggt      48
Met Val Pro Gln Thr Glu Thr Lys Ala Gly Ala Gly Phe Lys Ala Gly
1               5                   10                  15 gta aaa gac tac cgt tta aca tac tac aca cct gat tac gta gta aga      96
Val Lys Asp Tyr Arg Leu Thr Tyr Tyr Thr Pro Asp Tyr Val Val Arg
                20                  25                  30 gat act gat att tta gct gca ttc cgt gtg act cca caa cca ggt gtt     144
Asp Thr Asp Ile Leu Ala Ala Phe Arg Val Thr Pro Gln Pro Gly Val
            35                  40                  45 cca cct gaa gaa tgt ggt gct gct gta gct gct gaa tct tca aca ggt     192
Pro Pro Glu Glu Cys Gly Ala Ala Val Ala Ala Glu Ser Ser Thr Gly
```

```
                50                  55                  60
aca tgg act aca gta tgg act gac ggt tta aca agt ctt gac cgt tac    240
Thr Trp Thr Thr Val Trp Thr Asp Gly Leu Thr Ser Leu Asp Arg Tyr
 65                  70                  75                  80 aaa ggt cgt tgt tac gat atc gaa cca gtt ccg ggt gaa gac aac caa    288
Lys Gly Arg Cys Tyr Asp Ile Glu Pro Val Pro Gly Glu Asp Asn Gln
                 85                  90                  95 tac att gct tac gta gct tac cca atc gac tta ttc gaa gaa ggt tca    336
Tyr Ile Ala Tyr Val Ala Tyr Pro Ile Asp Leu Phe Glu Glu Gly Ser
            100                 105                 110 gta act aac atg ttc act tct att gta ggt aac gta ttc ggt ttc aaa    384
Val Thr Asn Met Phe Thr Ser Ile Val Gly Asn Val Phe Gly Phe Lys
        115                 120                 125 gct tta cgt gct cta cgt ctt gaa gac ctt cgt att cca cct gct tac    432
Ala Leu Arg Ala Leu Arg Leu Glu Asp Leu Arg Ile Pro Pro Ala Tyr
    130                 135                 140 gtt aaa aca ttc gta ggt cct cca cac ggt att cag gta gaa cgt gac    480
Val Lys Thr Phe Val Gly Pro Pro His Gly Ile Gln Val Glu Arg Asp
145                 150                 155                 160 aaa tta aac aaa tat ggt cgt ggt ctt tta ggt tgt aca atc aaa cct    528
Lys Leu Asn Lys Tyr Gly Arg Gly Leu Leu Gly Cys Thr Ile Lys Pro
                165                 170                 175 aaa tta ggt ctt tca gct aaa aac tac ggt cgt gca gtt tat gaa tgt    576
Lys Leu Gly Leu Ser Ala Lys Asn Tyr Gly Arg Ala Val Tyr Glu Cys
            180                 185                 190 tta cgt ggt ggt ctt gac ttt act aaa gac gac gaa aac gta aac tca    624
Leu Arg Gly Gly Leu Asp Phe Thr Lys Asp Asp Glu Asn Val Asn Ser
        195                 200                 205 caa cca ttc atg cgt tgg cgt gac cgt ttc ctt ttc gtt gct gaa gct    672
Gln Pro Phe Met Arg Trp Arg Asp Arg Phe Leu Phe Val Ala Glu Ala
    210                 215                 220 att tac aaa gct caa gca gaa aca ggt gaa gtt aaa ggt cac tac tta    720
Ile Tyr Lys Ala Gln Ala Glu Thr Gly Glu Val Lys Gly His Tyr Leu
225                 230                 235                 240 aac gct act gct ggt act tgt gaa gaa atg atg aaa cgt gca gta tgt    768
Asn Ala Thr Ala Gly Thr Cys Glu Glu Met Met Lys Arg Ala Val Cys
                245                 250                 255 gct aaa gaa tta ggt gta cct att gta atg cac gac tac tta aca ggt    816
Ala Lys Glu Leu Gly Val Pro Ile Val Met His Asp Tyr Leu Thr Gly
            260                 265                 270 ggt ttc aca gct aac act tca tta gct atc tac tgt cgt gac aac ggt    864
Gly Phe Thr Ala Asn Thr Ser Leu Ala Ile Tyr Cys Arg Asp Asn Gly
        275                 280                 285 ctt ctt cta cac atc cac cgt gct atg cac gcg gtt att gac cgt caa    912
Leu Leu Leu His Ile His Arg Ala Met His Ala Val Ile Asp Arg Gln
    290                 295                 300 cgt aac cac ggt att cac ttc cgt gtt ctt gct aaa gct ctt cgt atg    960
Arg Asn His Gly Ile His Phe Arg Val Leu Ala Lys Ala Leu Arg Met
305                 310                 315                 320 tct ggt ggt gac cac ctt cac tct ggt act gtt gta ggt aaa cta gaa    1008
Ser Gly Gly Asp His Leu His Ser Gly Thr Val Val Gly Lys Leu Glu
                325                 330                 335 ggt gaa cgt gaa gtt act cta ggt ttc gta gac tta atg cgt gat gac    1056
Gly Glu Arg Glu Val Thr Leu Gly Phe Val Asp Leu Met Arg Asp Asp
            340                 345                 350 tac gtt gaa aaa gac cgt agc cgt ggt att tac ttc act caa gac tgg    1104
Tyr Val Glu Lys Asp Arg Ser Arg Gly Ile Tyr Phe Thr Gln Asp Trp
        355                 360                 365 tgt gca atg cca ggt gtt atg cca gtt gct tca ggt ggt att cac gta    1152
Cys Ala Met Pro Gly Val Met Pro Val Ala Ser Gly Gly Ile His Val
```

-continued

```
         370                 375                 380
tgg cac atg cca gct tta gtt gaa atc ttc ggt gat gac gca tgt ctt    1200
Trp His Met Pro Ala Leu Val Glu Ile Phe Gly Asp Asp Ala Cys Leu
385                 390                 395                 400 cag ttc ggt ggt ggt act cta ggt cac cct tgg ggt aac gct cca ggt    1248
Gln Phe Gly Gly Gly Thr Leu Gly His Pro Trp Gly Asn Ala Pro Gly
            405                 410                 415 gct gca gct aac cgt gta gct ctt gaa gct tgt act caa gct cgt aac    1296
Ala Ala Ala Asn Arg Val Ala Leu Glu Ala Cys Thr Gln Ala Arg Asn
        420                 425                 430 gaa ggt cgt gac ctt gct cgt gaa ggc ggc gac gta att cgt tca gct    1344
Glu Gly Arg Asp Leu Ala Arg Glu Gly Gly Asp Val Ile Arg Ser Ala
    435                 440                 445 tgt aaa tgg tct cca gaa ctt gct gct gca tgt gaa gtt tgg aaa gaa    1392
Cys Lys Trp Ser Pro Glu Leu Ala Ala Ala Cys Glu Val Trp Lys Glu
450                 455                 460 gtt aaa ttc gaa ttt gat act att gac aaa ctt taa                    1428
Val Lys Phe Glu Phe Asp Thr Ile Asp Lys Leu
465                 470                 475
```

<210> SEQ ID NO 25
<211> LENGTH: 475
<212> TYPE: PRT
<213> ORGANISM: Artificial Sequence
<220> FEATURE:
<223> OTHER INFORMATION: Synthetic Construct

<400> SEQUENCE: 25

```
Met Val Pro Gln Thr Glu Thr Lys Ala Gly Ala Gly Phe Lys Ala Gly
1               5                   10                  15

Val Lys Asp Tyr Arg Leu Thr Tyr Tyr Thr Pro Asp Tyr Val Val Arg
            20                  25                  30

Asp Thr Asp Ile Leu Ala Ala Phe Arg Val Thr Pro Gln Pro Gly Val
        35                  40                  45

Pro Pro Glu Glu Cys Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Asp Asn Gln
                85                  90                  95

Tyr Ile Ala Tyr Val Ala Tyr Pro Ile Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Val Gly Pro Pro His Gly Ile Gln Val Glu Arg Asp
145                 150                 155                 160

Lys Leu Asn Lys Tyr Gly Arg Gly Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
    210                 215                 220

Ile Tyr Lys Ala Gln Ala Glu Thr Gly Glu Val Lys Gly His Tyr Leu
225                 230                 235                 240
```

```
Asn Ala Thr Ala Gly Thr Cys Glu Glu Met Met Lys Arg Ala Val Cys
            245                 250                 255

Ala Lys Glu Leu Gly Val Pro Ile Val Met His Asp Tyr Leu Thr Gly
        260                 265                 270

Gly Phe Thr Ala Asn Thr Ser Leu Ala Ile Tyr Cys Arg Asp Asn Gly
            275                 280                 285

Leu Leu Leu His Ile His Arg Ala Met His Ala Val Ile Asp Arg Gln
        290                 295                 300

Arg Asn His Gly Ile His Phe Arg Val Leu Ala Lys Ala Leu Arg Met
305                 310                 315                 320

Ser Gly Gly Asp His Leu His Ser Gly Thr Val Val Gly Lys Leu Glu
            325                 330                 335

Gly Glu Arg Glu Val Thr Leu Gly Phe Val Asp Leu Met Arg Asp Asp
        340                 345                 350

Tyr Val Glu Lys Asp Arg Ser Arg Gly Ile Tyr Phe Thr Gln Asp Trp
            355                 360                 365

Cys Ala Met Pro Gly Val Met Pro Val Ala Ser Gly Gly Ile His Val
        370                 375                 380

Trp His Met Pro Ala Leu Val Glu Ile Phe Gly Asp Asp Ala Cys Leu
385                 390                 395                 400

Gln Phe Gly Gly Gly Thr Leu Gly His Pro Trp Gly Asn Ala Pro Gly
            405                 410                 415

Ala Ala Ala Asn Arg Val Ala Leu Glu Ala Cys Thr Gln Ala Arg Asn
        420                 425                 430

Glu Gly Arg Asp Leu Ala Arg Glu Gly Gly Asp Val Ile Arg Ser Ala
            435                 440                 445

Cys Lys Trp Ser Pro Glu Leu Ala Ala Ala Cys Glu Val Trp Lys Glu
        450                 455                 460

Val Lys Phe Glu Phe Asp Thr Ile Asp Lys Leu
465                 470                 475

<210> SEQ ID NO 26
<211> LENGTH: 1434
<212> TYPE: DNA
<213> ORGANISM: Artificial Sequence
<220> FEATURE:
<223> OTHER INFORMATION: Description for artificial sequence: shuffled
      Tobacco Rubisco large subunit variant T798.
<220> FEATURE:
<221> NAME/KEY: CDS
<222> LOCATION: (1)..(1431)

<400> SEQUENCE: 26 atg tca cca caa aca gag act aaa gca agt gtt gga ttc aaa gct ggt      48
Met Ser Pro Gln Thr Glu Thr Lys Ala Ser Val Gly Phe Lys Ala Gly
1               5                   10                  15 gtt aaa gag tac aaa ttg act tat tat act cct gag tac caa acc aag      96
Val Lys Glu Tyr Lys Leu Thr Tyr Tyr Thr Pro Glu Tyr Gln Thr Lys
            20                  25                  30 gat act gat ata ttg gca gca ttc cga gta act cct caa cct gga gtt     144
Asp Thr Asp Ile Leu Ala Ala Phe Arg Val Thr Pro Gln Pro Gly Val
        35                  40                  45 cca cct gaa gaa gca ggg gcc gcg gta gct gcc gaa tct tct act ggt     192
Pro Pro Glu Glu Ala Gly Ala Ala Val Ala Ala Glu Ser Ser Thr Gly
    50                  55                  60 aca tgg aca act gta tgg acc gat gga ctt acc agc ctt gat cgt tac     240
Thr Trp Thr Thr Val Trp Thr Asp Gly Leu Thr Ser Leu Asp Arg Tyr
65                  70                  75                  80
```

```
aaa ggg cga tgc tac cgc atc gag cgt gtt gtt gga gaa aaa gat caa      288
Lys Gly Arg Cys Tyr Arg Ile Glu Arg Val Val Gly Glu Lys Asp Gln
             85                  90                  95 tat att act tat gta gct tac cct tta gac ctt ttt gaa gaa ggt tct      336
Tyr Ile Thr Tyr Val Ala Tyr Pro Leu Asp Leu Phe Glu Glu Gly Ser
        100                 105                 110 gtt acc aac atg ttt act tcc att gta ggt aac gta ttt ggg ttc aaa      384
Val Thr Asn Met Phe Thr Ser Ile Val Gly Asn Val Phe Gly Phe Lys
            115                 120                 125 gcc ctg cgc gct cta cgt ctg gaa gat ctg cga atc cct cct gct tat      432
Ala Leu Arg Ala Leu Arg Leu Glu Asp Leu Arg Ile Pro Pro Ala Tyr
        130                 135                 140 gtt aaa act ttc caa ggt ccg cct cat ggg atc caa gtt gaa aga gat      480
Val Lys Thr Phe Gln Gly Pro Pro His Gly Ile Gln Val Glu Arg Asp
145                 150                 155                 160 aaa ttg aac aag tat ggt cgt ccc ctg ttg gga tgt act att aaa cct      528
Lys Leu Asn Lys Tyr Gly Arg Pro Leu Leu Gly Cys Thr Ile Lys Pro
            165                 170                 175 aaa ttg ggg tta tct gct aaa aac tac ggt aga gct gtt tat gaa tgt      576
Lys Leu Gly Leu Ser Ala Lys Asn Tyr Gly Arg Ala Val Tyr Glu Cys
        180                 185                 190 ctt cgc ggt gga ctt gat ttt acc aaa gat gat gag aac gtg aac tca      624
Leu Arg Gly Gly Leu Asp Phe Thr Lys Asp Asp Glu Asn Val Asn Ser
        195                 200                 205 caa cca ttt atg cgt tgg aga gat cgt ttc tta ttt tgt gcc gaa gca      672
Gln Pro Phe Met Arg Trp Arg Asp Arg Phe Leu Phe Cys Ala Glu Ala
210                 215                 220 ctt tat aaa gca cag gct gaa aca ggt gaa atc aaa ggg cat tac ttg      720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt      768
Asn Ala Thr Ala Gly Thr Cys Glu Glu Met Ile Lys Arg Ala Val Phe
            245                 250                 255 gct aga gaa ttg ggc gtt ccg atc gta atg cat gac tac tta acg ggg      816
Ala Arg Glu Leu Gly Val Pro Ile Val Met His Asp Tyr Leu Thr Gly
        260                 265                 270 gga ttc acc gca aat act agc ttg tct cat tat tgc cga gat aat ggt      864
Gly Phe Thr Ala Asn Thr Ser Leu Ser His Tyr Cys Arg Asp Asn Gly
        275                 280                 285 cta ctt ctt cac atc cac cgt gca atg cat gcg gtt att gat aga cag      912
Leu Leu Leu His Ile His Arg Ala Met His Ala Val Ile Asp Arg Gln
        290                 295                 300 aag aat cat ggt atc cac ttc cgg gta tta gca aaa gcg tta cgt atg      960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa     1008
Ser Gly Gly Asp His Ile His Ser Gly Thr Val Val Gly Lys Leu Glu
            325                 330                 335 ggt gaa aga gac ata act ttg ggc ttt gtt gat tta ctg cgt gat ggt     1056
Gly Glu Arg Asp Ile Thr Leu Gly Phe Val Asp Leu Leu Arg Asp Gly
        340                 345                 350 ttt gtt gaa caa gat cga agt cgc ggt att tat ttc act caa gat tgg     1104
Phe Val Glu Gln Asp Arg Ser Arg Gly Ile Tyr Phe Thr Gln Asp Trp
        355                 360                 365 gtc tct tta cca ggt gtt cta ccc gtg gct tca gga ggt att cac gtt     1152
Val Ser Leu Pro Gly Val Leu Pro Val Ala Ser Gly Gly Ile His Val
        370                 375                 380 tgg cat atg cct gct ctg acc gag atc ttt ggg gat gat tcc gta cta     1200
Trp His Met Pro Ala Leu Thr Glu Ile Phe Gly Asp Asp Ser Val Leu
385                 390                 395                 400
```

```
cag ttc ggt gga gga act tta gga cat cct tgg ggt aat gcg cca ggt    1248
Gln Phe Gly Gly Gly Thr Leu Gly His Pro Trp Gly Asn Ala Pro Gly
            405                 410                 415 gcc gta gct aat cga gta gct cta gaa gca tgt gta aaa gct cgt aat    1296
Ala Val Ala Asn Arg Val Ala Leu Glu Ala Cys Val Lys Ala Arg Asn
        420                 425                 430 gaa gga cgt gat ctt gct cag gaa ggt aat gaa att att cgc gag gct    1344
Glu Gly Arg Asp Leu Ala Gln Glu Gly Asn Glu Ile Ile Arg Glu Ala
    435                 440                 445 tgc aaa tgg agc ccg gaa cta gct gct gct tgt gaa gta tgg aaa gag    1392
Cys Lys Trp Ser Pro Glu Leu Ala Ala Ala Cys Glu Val Trp Lys Glu
450                 455                 460 atc gta ttt aat ttt gca gca gtg gac gtt ttg gat aag taa            1434
Ile Val Phe Asn Phe Ala Ala Val Asp Val Leu Asp Lys
465                 470                 475
```

<210> SEQ ID NO 27
<211> LENGTH: 477
<212> TYPE: PRT
<213> ORGANISM: Artificial Sequence
<220> FEATURE:
<223> OTHER INFORMATION: Synthetic Construct

<400> SEQUENCE: 27

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Thr Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270
```

```
Gly Phe Thr Ala Asn Thr Ser Leu Ser His Tyr Cys Arg Asp Asn Gly
            275                 280                 285

Leu Leu Leu His Ile His Arg Ala Met His Ala Val Ile Asp Arg Gln
        290                 295                 300

Lys Asn His Gly Ile His Phe Arg Val Leu Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Gly
            340                 345                 350

Phe Val Glu Gln Asp Arg Ser Arg Gly Ile Tyr Phe Thr Gln Asp Trp
        355                 360                 365

Val Ser Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
    450                 455                 460

Ile Val Phe Asn Phe Ala Ala Val Asp Val Leu Asp Lys
465                 470                 475
```

```
<210> SEQ ID NO 28
<211> LENGTH: 1434
<212> TYPE: DNA
<213> ORGANISM: Artificial Sequence
<220> FEATURE:
<223> OTHER INFORMATION: Description for artificial sequence: shuffled
      Tobacco Rubisco large subunit variant T796.
<220> FEATURE:
<221> NAME/KEY: CDS
<222> LOCATION: (1)..(1431)

<400> SEQUENCE: 28
```

```
atg tca cca caa aca gag act aaa gca agt gtt gga ttc aaa gct ggt    48
Met Ser Pro Gln Thr Glu Thr Lys Ala Ser Val Gly Phe Lys Ala Gly
1               5                  10                  15 gtt aaa gag tac aaa ttg act tat tat act cct gag tac caa acc aag    96
Val Lys Glu Tyr Lys Leu Thr Tyr Tyr Thr Pro Glu Tyr Gln Thr Lys
                20                  25                  30 gat act gat ata ttg gca gca ttc cga gta act cct caa cct gga gtt   144
Asp Thr Asp Ile Leu Ala Ala Phe Arg Val Thr Pro Gln Pro Gly Val
            35                  40                  45 cca cct gaa gaa gca ggg gcc gcg gta gct gcc gaa tct tct act ggt   192
Pro Pro Glu Glu Ala Gly Ala Ala Val Ala Ala Glu Ser Ser Thr Gly
        50                  55                  60 aca tgg aca act gta tgg acc gat gga ctt acc agc ctt gat cgt tac   240
Thr Trp Thr Thr Val Trp Thr Asp Gly Leu Thr Ser Leu Asp Arg Tyr
65                  70                  75                  80 aaa ggg cga tgc tac cgc atc gag cgt gtt gtt gga gaa aaa gat caa   288
Lys Gly Arg Cys Tyr Arg Ile Glu Arg Val Val Gly Glu Lys Asp Gln
                85                  90                  95 tat att gct tat gta gct tac cct tta gac ctt ttt gaa gaa ggt tct   336
Tyr Ile Ala Tyr Val Ala Tyr Pro Leu Asp Leu Phe Glu Glu Gly Ser
```

```
                        100                 105                 110
gtt acc aac atg ttt act tcc att gta ggt aac gta ttt ggg ttc aaa          384
Val Thr Asn Met Phe Thr Ser Ile Val Gly Asn Val Phe Gly Phe Lys
        115                 120                 125 gcc ctg cgc gct cta cgt ctg gaa gat ctg cga atc cct cct gct tat          432
Ala Leu Arg Ala Leu Arg Leu Glu Asp Leu Arg Ile Pro Pro Ala Tyr
130                 135                 140 gtt aaa act ttc caa ggt ccg cct cat ggg atc caa gtt gaa aga gat          480
Val Lys Thr Phe Gln Gly Pro Pro His Gly Ile Gln Val Glu Arg Asp
145                 150                 155                 160 aaa ttg aac aag tat ggt cgt ccc ctg ttg gga tgt act att aaa cct          528
Lys Leu Asn Lys Tyr Gly Arg Pro Leu Leu Gly Cys Thr Ile Lys Pro
                165                 170                 175 aaa ttg ggg tta tct gct aaa aac tac ggt aga gct gtt tat gaa tgt          576
Lys Leu Gly Leu Ser Ala Lys Asn Tyr Gly Arg Ala Val Tyr Glu Cys
                180                 185                 190 ctt cgc ggt gga ctt gat ttt acc aaa gat gat gag aac gtg aac tca          624
Leu Arg Gly Gly Leu Asp Phe Thr Lys Asp Asp Glu Asn Val Asn Ser
                195                 200                 205 caa cca ttt atg cgt tgg aga gat cgt ttc tta ttt tgt gcc gaa gca          672
Gln Pro Phe Met Arg Trp Arg Asp Arg Phe Leu Phe Cys Ala Glu Ala
210                 215                 220 ctt tat aaa gca cag gct gaa aca ggt gaa atc aaa ggg cat tac ttg          720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt          768
Asn Ala Thr Ala Gly Thr Cys Glu Glu Met Ile Lys Arg Ala Val Phe
                245                 250                 255 gct aga gaa ttg ggc gtt ccg atc gta atg cat gac tac tta acg ggg          816
Ala Arg Glu Leu Gly Val Pro Ile Val Met His Asp Tyr Leu Thr Gly
                260                 265                 270 gga ttc acc gca aat act agc ttg gct cat tat tgc cga gat aat ggt          864
Gly Phe Thr Ala Asn Thr Ser Leu Ala His Tyr Cys Arg Asp Asn Gly
                275                 280                 285 cta ctt ctt cac atc cac cgt gca atg cat gcg gtt att gat aga cag          912
Leu Leu Leu His Ile His Arg Ala Met His Ala Val Ile Asp Arg Gln
                290                 295                 300 aag aat cat ggt atc cac ttc cgg gta tta gca aaa gcg tta cgt atg          960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa         1008
Ser Gly Gly Asp His Ile His Ser Gly Thr Val Val Gly Lys Leu Glu
                325                 330                 335 ggt gaa aga gac ata act ttg ggc ttt gtt gat tta ctg cgt gat gat         1056
Gly Glu Arg Asp Ile Thr Leu Gly Phe Val Asp Leu Leu Arg Asp Asp
                340                 345                 350 ttt gtt gaa caa gat cga agt cgc ggt att tat ttc act caa gat tgg         1104
Phe Val Glu Gln Asp Arg Ser Arg Gly Ile Tyr Phe Thr Gln Asp Trp
                355                 360                 365 gtc gct tta cca ggt gtt cta ccc gtg gct tca gga ggt att cac gtt         1152
Val Ala Leu Pro Gly Val Leu Pro Val Ala Ser Gly Gly Ile His Val
                370                 375                 380 tgg cat atg cct gct ctg acc gag atc ttt ggg gat gat tcc gta cta         1200
Trp His Met Pro Ala Leu Thr Glu Ile Phe Gly Asp Asp Ser Val Leu
385                 390                 395                 400 cag ttc ggt gga gga act tta gga cat cct tgg ggt aat gcg cca ggt         1248
Gln Phe Gly Gly Gly Thr Leu Gly His Pro Trp Gly Asn Ala Pro Gly
                405                 410                 415 gcc gta gct aat cga gta gct cta gaa gca tgt gta aaa gct cgt aat         1296
Ala Val Ala Asn Arg Val Ala Leu Glu Ala Cys Val Lys Ala Arg Asn
```

|   |   |   |   |   |   |   |   |   |   |   |   | 420 |   |   |   |   | 425 |   |   |   |   | 430 |   |   |   |   |
|---|---|---|---|---|---|---|---|---|---|---|---|---|---|---|---|---|---|---|---|---|---|---|---|---|---|---|

```
gaa gga cgt gat ctt gct cag gaa ggt aat gaa att att cgc gag gct   1344
Glu Gly Arg Asp Leu Ala Gln Glu Gly Asn Glu Ile Ile Arg Glu Ala
        435                 440                 445 tgc aaa tgg agc ccg gaa cta gct gct gct tgt gaa gta tgg aaa gag   1392
Cys Lys Trp Ser Pro Glu Leu Ala Ala Ala Cys Glu Val Trp Lys Glu
    450                 455                 460 gta gta ttt aat ttt gca gca gtg gac gtt ttg gat aag taa           1434
Val Val Phe Asn Phe Ala Ala Val Asp Val Leu Asp Lys
465                 470                 475
```

<210> SEQ ID NO 29
<211> LENGTH: 477
<212> TYPE: PRT
<213> ORGANISM: Artificial Sequence
<220> FEATURE:
<223> OTHER INFORMATION: Synthetic Construct

<400> SEQUENCE: 29

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300
```

```
Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
            325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
        355                 360                 365

Val Ala Leu Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
        450                 455                 460

Val Val Phe Asn Phe Ala Ala Val Asp Val Leu Asp Lys
465                 470                 475
```

<210> SEQ ID NO 30
<211> LENGTH: 1434
<212> TYPE: DNA
<213> ORGANISM: Artificial Sequence
<220> FEATURE:
<223> OTHER INFORMATION: Description for artificial sequence: shuffled Tobacco Rubisco large subunit variant T805-1-4.
<220> FEATURE:
<221> NAME/KEY: CDS
<222> LOCATION: (1)..(1431)

<400> SEQUENCE: 30

```
atg tca cca caa aca gag act aaa gca agt gtt gga ttc aaa gct ggt     48
Met Ser Pro Gln Thr Glu Thr Lys Ala Ser Val Gly Phe Lys Ala Gly
1               5                   10                  15 gtt aaa gag tac aaa ttg act tat tat act cct gag tac caa acc aag     96
Val Lys Glu Tyr Lys Leu Thr Tyr Tyr Thr Pro Glu Tyr Gln Thr Lys
                20                  25                  30 gat act gat ata ttg gca gca ttc cga gta act cct caa cct gga gtt    144
Asp Thr Asp Ile Leu Ala Ala Phe Arg Val Thr Pro Gln Pro Gly Val
            35                  40                  45 cca cct gaa gaa gca ggg gcc gcg gta gct gcc gaa tct tct act ggt    192
Pro Pro Glu Glu Ala Gly Ala Ala Val Ala Ala Glu Ser Ser Thr Gly
        50                  55                  60 aca tgg aca act gta tgg acc gat gga ctt acc agc ctt gat cgt tac    240
Thr Trp Thr Thr Val Trp Thr Asp Gly Leu Thr Ser Leu Asp Arg Tyr
65                  70                  75                  80 aaa ggg cga tgc tac cgc atc gag cgt gtt gtt gga gaa aaa gat caa    288
Lys Gly Arg Cys Tyr Arg Ile Glu Arg Val Val Gly Glu Lys Asp Gln
                85                  90                  95 tat att gct tat gta gct tac cct tta gac ctt ttt gaa gaa ggt tct    336
Tyr Ile Ala Tyr Val Ala Tyr Pro Leu Asp Leu Phe Glu Glu Gly Ser
            100                 105                 110 gtt acc aac atg ttt act tcc att gta ggt aac gta ttt ggg ttc aaa    384
Val Thr Asn Met Phe Thr Ser Ile Val Gly Asn Val Phe Gly Phe Lys
        115                 120                 125
```

```
gcc ctg cgc gct cta cgt ctg gaa gat ctg cga atc cct cct gct tat       432
Ala Leu Arg Ala Leu Arg Leu Glu Asp Leu Arg Ile Pro Pro Ala Tyr
    130             135                 140 gtt aaa act ttc caa ggt ccg cct cat ggg atc caa gtt gaa aga gat       480
Val Lys Thr Phe Gln Gly Pro Pro His Gly Ile Gln Val Glu Arg Asp
145             150                 155                 160 aaa ttg aac aag tat ggt cgt ccc ctg ttg gga tgt act att aaa cct       528
Lys Leu Asn Lys Tyr Gly Arg Pro Leu Leu Gly Cys Thr Ile Lys Pro
                165                 170                 175 aaa ttg ggg tta tct gct aaa aac tac ggt aga gct gtt tat gaa tgt       576
Lys Leu Gly Leu Ser Ala Lys Asn Tyr Gly Arg Ala Val Tyr Glu Cys
            180                 185                 190 ctt cgc ggt gga ctt gat ttt acc aaa gat gat gag aac gtg aac tca       624
Leu Arg Gly Gly Leu Asp Phe Thr Lys Asp Asp Glu Asn Val Asn Ser
    195                 200                 205 caa cca ttt atg cgt tgg aga gat cgt ttc tta ttt tgt gcc gaa gca       672
Gln Pro Phe Met Arg Trp Arg Asp Arg Phe Leu Phe Cys Ala Glu Ala
210                 215                 220 ctt tat aaa gca cag gct gaa aca ggt gaa atc aaa ggg cat tac ttg       720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt       768
Asn Ala Thr Ala Gly Thr Cys Glu Glu Met Ile Lys Arg Ala Val Phe
                245                 250                 255 gct aga gaa ttg ggc gtt ccg atc gta atg cat gac tac tta acg ggg       816
Ala Arg Glu Leu Gly Val Pro Ile Val Met His Asp Tyr Leu Thr Gly
            260                 265                 270 gga ttc acc gca aat act agc ttg tct cat tat tgc cga gat aat ggt       864
Gly Phe Thr Ala Asn Thr Ser Leu Ser His Tyr Cys Arg Asp Asn Gly
    275                 280                 285 cta ctt ctt cac atc cac cgt gca atg cat gcg gtt att gat aga cag       912
Leu Leu Leu His Ile His Arg Ala Met His Ala Val Ile Asp Arg Gln
290                 295                 300 aag aat cat ggt atc cac ttc cgg gta tta gca aaa gcg tta cgt atg       960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa      1008
Ser Gly Gly Asp His Ile His Ser Gly Thr Val Val Gly Lys Leu Glu
                325                 330                 335 ggt gaa aga gac ata act ttg ggc ttt gtt gat tta ctg cgt gat gat      1056
Gly Glu Arg Asp Ile Thr Leu Gly Phe Val Asp Leu Leu Arg Asp Asp
            340                 345                 350 ttt gtt gaa caa gat cga agt cgc ggt att tat ttc act caa gat tgg      1104
Phe Val Glu Gln Asp Arg Ser Arg Gly Ile Tyr Phe Thr Gln Asp Trp
    355                 360                 365 gtc gct tta cca ggt gtt cta ccc gtg gct tca gga ggt att cac gtt      1152
Val Ala Leu Pro Gly Val Leu Pro Val Ala Ser Gly Gly Ile His Val
370                 375                 380 tgg cat atg cct gct ctg acc gag atc ttt ggg gat gat tcc gta cta      1200
Trp His Met Pro Ala Leu Thr Glu Ile Phe Gly Asp Asp Ser Val Leu
385                 390                 395                 400 cag ttc ggt gga gga act tta gga cat cct tgg ggt aat gcg cca ggt      1248
Gln Phe Gly Gly Gly Thr Leu Gly His Pro Trp Gly Asn Ala Pro Gly
                405                 410                 415 gcc gta gct aat cga gta gct cta gaa gca tgt gta aaa gct cgt aat      1296
Ala Val Ala Asn Arg Val Ala Leu Glu Ala Cys Val Lys Ala Arg Asn
            420                 425                 430 gaa gga cgt gat ctt gct cag gaa ggt aat gaa att att cgc gag gct      1344
Glu Gly Arg Asp Leu Ala Gln Glu Gly Asn Glu Ile Ile Arg Glu Ala
    435                 440                 445
```

```
tgc aaa tgg agc ccg gaa cta gct gct cct tgt gaa gta tgg aaa gag    1392
Cys Lys Trp Ser Pro Glu Leu Ala Ala Pro Cys Glu Val Trp Lys Glu
    450                 455                 460 atc gta ttt aat ttt gca gca gtg gac gtt ttg gat aag taa            1434
Ile Val Phe Asn Phe Ala Ala Val Asp Val Leu Asp Lys
465                 470                 475
```

<210> SEQ ID NO 31
<211> LENGTH: 477
<212> TYPE: PRT
<213> ORGANISM: Artificial Sequence
<220> FEATURE:
<223> OTHER INFORMATION: Synthetic Construct

<400> SEQUENCE: 31

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ser His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335
```

```
Gly Glu Arg Asp Ile Thr Leu Gly Phe Val Asp Leu Leu Arg Asp Asp
                340                 345                 350

Phe Val Glu Gln Asp Arg Ser Arg Gly Ile Tyr Phe Thr Gln Asp Trp
            355                 360                 365

Val Ala Leu Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Pro Cys Glu Val Trp Lys Glu
    450                 455                 460

Ile Val Phe Asn Phe Ala Ala Val Asp Val Leu Asp Lys
465                 470                 475
```

<210> SEQ ID NO 32
<211> LENGTH: 1434
<212> TYPE: DNA
<213> ORGANISM: Artificial Sequence
<220> FEATURE:
<223> OTHER INFORMATION: Description for artificial sequence: shuffled
      Tobacco Rubisco large subunit variant T805-8-2.
<220> FEATURE:
<221> NAME/KEY: CDS
<222> LOCATION: (1)..(1431)

<400> SEQUENCE: 32

```
atg tca cca caa aca gag act aaa gca agt gtt gga ttc aaa gct ggt     48
Met Ser Pro Gln Thr Glu Thr Lys Ala Ser Val Gly Phe Lys Ala Gly
1               5                   10                  15 gtt aaa gag tac aaa ttg act tat tat act cct gag tac caa acc aag    96
Val Lys Glu Tyr Lys Leu Thr Tyr Tyr Thr Pro Glu Tyr Gln Thr Lys
                20                  25                  30 gat act gat ata ttg gca gca ttc cga gta act cct caa cct gga gtt   144
Asp Thr Asp Ile Leu Ala Ala Phe Arg Val Thr Pro Gln Pro Gly Val
            35                  40                  45 cca cct gaa gaa gca ggg gcc gcg gta gct gcc gaa tct tct act ggt   192
Pro Pro Glu Glu Ala Gly Ala Ala Val Ala Ala Glu Ser Ser Thr Gly
        50                  55                  60 aca tgg aca act gta tgg acc gat gga ctt acc agc ctt gat cgt tac   240
Thr Trp Thr Thr Val Trp Thr Asp Gly Leu Thr Ser Leu Asp Arg Tyr
65                  70                  75                  80 aaa ggg cga tgc tac gga atc gag cgt gtt gtt gga gaa aaa gat caa   288
Lys Gly Arg Cys Tyr Gly Ile Glu Arg Val Val Gly Glu Lys Asp Gln
                85                  90                  95 tat att gct tat gta gct tac cct tta gac ctt ttt gaa gaa ggt tct   336
Tyr Ile Ala Tyr Val Ala Tyr Pro Leu Asp Leu Phe Glu Glu Gly Ser
                100                 105                 110 gtt acc aac atg ttt act tcc att gta ggt aac gta ttt ggg ttc aaa   384
Val Thr Asn Met Phe Thr Ser Ile Val Gly Asn Val Phe Gly Phe Lys
            115                 120                 125 gcc ctg cgc gct cta cgt ctg gaa gat ctg cga atc cct cct gct tat   432
Ala Leu Arg Ala Leu Arg Leu Glu Asp Leu Arg Ile Pro Pro Ala Tyr
        130                 135                 140 gtt aaa act ttc caa ggt ccg cct cat ggg atc caa gtt gaa aga gat   480
Val Lys Thr Phe Gln Gly Pro Pro His Gly Ile Gln Val Glu Arg Asp
145                 150                 155                 160
```

```
                                                  -continued
       145               150               155               160
aaa ttg aac aag tat ggt cgt ccc ctg ttg gga tgt act att aaa cct      528
Lys Leu Asn Lys Tyr Gly Arg Pro Leu Leu Gly Cys Thr Ile Lys Pro
                165               170               175 aaa ttg ggg tta tct gct aaa aac tac ggt aga gct gtt tat gaa tgt      576
Lys Leu Gly Leu Ser Ala Lys Asn Tyr Gly Arg Ala Val Tyr Glu Cys
            180               185               190 ctt cgc ggt gga ctt gat ttt acc aaa gat gat gag aac gtg aac tca      624
Leu Arg Gly Gly Leu Asp Phe Thr Lys Asp Asp Glu Asn Val Asn Ser
        195               200               205 caa cca ttt atg cgt tgg aga gat cgt ttc tta ttt tgt gcc gaa gca      672
Gln Pro Phe Met Arg Trp Arg Asp Arg Phe Leu Phe Cys Ala Glu Ala
    210               215               220 ctt tat aaa gca cag gct gaa aca ggt gaa atc aaa ggg cat tac ttg      720
Leu Tyr Lys Ala Gln Ala Glu Thr Gly Glu Ile Lys Gly His Tyr Leu
225               230               235               240 aat gct act gca ggt aca tgc gaa gaa atg atc aaa aga gct gta ttt      768
Asn Ala Thr Ala Gly Thr Cys Glu Glu Met Ile Lys Arg Ala Val Phe
                245               250               255 gct aga gaa ttg ggc gtt ccg atc gta atg cat gac tac tta acg ggg      816
Ala Arg Glu Leu Gly Val Pro Ile Val Met His Asp Tyr Leu Thr Gly
            260               265               270 gga ttc acc gca aat act agc ttg gct cat tat tgc cga gat aat ggt      864
Gly Phe Thr Ala Asn Thr Ser Leu Ala His Tyr Cys Arg Asp Asn Gly
        275               280               285 cta ctt ctt cac atc cac cgt gca atg cat gcg gtt att gat aga cag      912
Leu Leu Leu His Ile His Arg Ala Met His Ala Val Ile Asp Arg Gln
    290               295               300 aag aat cat ggt atc cac ttc cgg gta tta gca aaa gcg tta cgt atg      960
Lys Asn His Gly Ile His Phe Arg Val Leu Ala Lys Ala Leu Arg Met
305               310               315               320 tct ggt gga gat cat att cac tct ggt acc gta gta ggt aaa ctt gaa     1008
Ser Gly Gly Asp His Ile His Ser Gly Thr Val Val Gly Lys Leu Glu
                325               330               335 ggt gaa aga gac ata act ttg ggc ttt gtt gat tta ctg cgt gat ggt     1056
Gly Glu Arg Asp Ile Thr Leu Gly Phe Val Asp Leu Leu Arg Asp Gly
            340               345               350 ttt gtt gaa caa gat cga agt cgc ggt att tat ttc act caa gat tgg     1104
Phe Val Glu Gln Asp Arg Ser Arg Gly Ile Tyr Phe Thr Gln Asp Trp
        355               360               365 gtc gct tta cca ggt gtt cta ccc gtg gct tca gga ggt att cac gtt     1152
Val Ala Leu Pro Gly Val Leu Pro Val Ala Ser Gly Gly Ile His Val
    370               375               380 tgg cat act cct gct ctg acc gag atc ttt ggg gat gat tcc gta cta     1200
Trp His Thr Pro Ala Leu Thr Glu Ile Phe Gly Asp Asp Ser Val Leu
385               390               395               400 cag ttc ggt gga gga act tta gga cat cct tgg ggt aat gcg cca ggt     1248
Gln Phe Gly Gly Gly Thr Leu Gly His Pro Trp Gly Asn Ala Pro Gly
                405               410               415 gcc gta gct aat cga gta gct cta gaa gca tgt gta aaa gct cgt aat     1296
Ala Val Ala Asn Arg Val Ala Leu Glu Ala Cys Val Lys Ala Arg Asn
            420               425               430 gaa gga cgt gat ctt gct cag gaa ggt aat gaa att att cgc gag gct     1344
Glu Gly Arg Asp Leu Ala Gln Glu Gly Asn Glu Ile Ile Arg Glu Ala
        435               440               445 tgc aaa tgg agc ccg gaa cta gct gct gct tgt gaa gta tgg aaa gag     1392
Cys Lys Trp Ser Pro Glu Leu Ala Ala Ala Cys Glu Val Trp Lys Glu
    450               455               460 atc gta ttt aat ttt gca gca gtg gac gtt ttg gat aag taa              1434
Ile Val Phe Asn Phe Ala Ala Val Asp Val Leu Asp Lys
```

```
                465                 470                475

<210> SEQ ID NO 33
<211> LENGTH: 477
<212> TYPE: PRT
<213> ORGANISM: Artificial Sequence
<220> FEATURE:
<223> OTHER INFORMATION: Synthetic Construct

<400> SEQUENCE: 33

Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Gly Ile Glu Arg Val Val Gly Glu Lys Asp Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Gly
            340                 345                 350

Phe Val Glu Gln Asp Arg Ser Arg Gly Ile Tyr Phe Thr Gln Asp Trp
        355                 360                 365
```

```
Val Ala Leu Pro Gly Val Leu Pro Val Ser Gly Gly Ile His Val
    370             375             380

Trp His Thr Pro Ala Leu Thr Glu Ile Phe Gly Asp Asp Ser Val Leu
385             390             395             400

Gln Phe Gly Gly Gly Thr Leu Gly His Pro Trp Gly Asn Ala Pro Gly
                405             410             415

Ala Val Ala Asn Arg Val Ala Leu Glu Ala Cys Val Lys Ala Arg Asn
            420             425             430

Glu Gly Arg Asp Leu Ala Gln Glu Gly Asn Glu Ile Ile Arg Glu Ala
            435             440             445

Cys Lys Trp Ser Pro Glu Leu Ala Ala Ala Cys Glu Val Trp Lys Glu
            450             455             460

Ile Val Phe Asn Phe Ala Ala Val Asp Val Leu Asp Lys
465             470             475

<210> SEQ ID NO 34
<211> LENGTH: 1434
<212> TYPE: DNA
<213> ORGANISM: Artificial Sequence
<220> FEATURE:
<223> OTHER INFORMATION: Description for artificial sequence: shuffled
      Tobacco Rubisco large subunit variant T834-7-1.
<220> FEATURE:
<221> NAME/KEY: CDS
<222> LOCATION: (1)..(1431)

<400> SEQUENCE: 34 atg tca cca caa aca gag act aaa gca agt gtt gga ttc aaa gct ggt      48
Met Ser Pro Gln Thr Glu Thr Lys Ala Ser Val Gly Phe Lys Ala Gly
1               5                   10                  15 gtt aaa gag tac aaa ttg act tat tat act cct gag tac caa acc aag      96
Val Lys Glu Tyr Lys Leu Thr Tyr Tyr Thr Pro Glu Tyr Gln Thr Lys
                20                  25                  30 gat act gat ata ttg gca gca ttc cga gta act cct caa cct gga gtt     144
Asp Thr Asp Ile Leu Ala Ala Phe Arg Val Thr Pro Gln Pro Gly Val
            35                  40                  45 cca cct gaa gaa gca ggg gcc gcg gta gct gcc gaa tct tct act ggt     192
Pro Pro Glu Glu Ala Gly Ala Ala Val Ala Ala Glu Ser Ser Thr Gly
        50                  55                  60 aca tgg aca act gta tgg acc gat gga ctt acc agc ctt gat cgt tac     240
Thr Trp Thr Thr Val Trp Thr Asp Gly Leu Thr Ser Leu Asp Arg Tyr
65                  70                  75                  80 aaa ggg cga tgc tac cgc atc gag cgt gtt gtt gga gaa aaa gat caa     288
Lys Gly Arg Cys Tyr Arg Ile Glu Arg Val Val Gly Glu Lys Asp Gln
                85                  90                  95 tat att act tat gta gct tac cct tta gac ctt ttt gaa gaa ggt tct     336
Tyr Ile Thr Tyr Val Ala Tyr Pro Leu Asp Leu Phe Glu Glu Gly Ser
            100                 105                 110 gtt acc aac atg ttt act tcc att gta ggt aac gta ttt ggg ttc aaa     384
Val Thr Asn Met Phe Thr Ser Ile Val Gly Asn Val Phe Gly Phe Lys
        115                 120                 125 gcc ctg cgc gct cta cgt ctg gaa gat ctg cga atc cct cct gct tat     432
Ala Leu Arg Ala Leu Arg Leu Glu Asp Leu Arg Ile Pro Pro Ala Tyr
    130                 135                 140 gtt aaa act ttc caa ggt ccg cct cat ggg atc caa gtt gaa aga gat     480
Val Lys Thr Phe Gln Gly Pro Pro His Gly Ile Gln Val Glu Arg Asp
145                 150                 155                 160 aaa ttg aac aag tat ggt cgt ccc ctg ttg gga tgt act att aaa cct     528
Lys Leu Asn Lys Tyr Gly Arg Pro Leu Leu Gly Cys Thr Ile Lys Pro
                165                 170                 175
```

```
aaa ttg ggg tta tct gct aaa aac tac ggt aga gct gtt tat gaa tgt    576
Lys Leu Gly Leu Ser Ala Lys Asn Tyr Gly Arg Ala Val Tyr Glu Cys
            180                 185                 190 ctt cgc ggt gga ctt gat ttt acc aaa gat gat gag aac gtg aac tca    624
Leu Arg Gly Gly Leu Asp Phe Thr Lys Asp Asp Glu Asn Val Asn Ser
        195                 200                 205 caa cca ttt atg cgt tgg aga gat cgt ttc tta ttt tgt gcc gaa gca    672
Gln Pro Phe Met Arg Trp Arg Asp Arg Phe Leu Phe Cys Ala Glu Ala
    210                 215                 220 ctt tat aaa gca cag gct gaa aca ggt gaa atc aaa ggg cat tac ttg    720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt    768
Asn Ala Thr Ala Gly Thr Cys Glu Glu Met Ile Lys Arg Ala Val Phe
            245                 250                 255 gct aga gaa ttg ggc gtt ccg atc gta atg cat gac tac tta acg ggg    816
Ala Arg Glu Leu Gly Val Pro Ile Val Met His Asp Tyr Leu Thr Gly
        260                 265                 270 gga ttc acc gca aat act agc ttg gct cat tat tgc cga gat aat ggt    864
Gly Phe Thr Ala Asn Thr Ser Leu Ala His Tyr Cys Arg Asp Asn Gly
    275                 280                 285 cta ctt ctt cac atc cac cgt gca atg cat gcg gtt att gat aga cag    912
Leu Leu Leu His Ile His Arg Ala Met His Ala Val Ile Asp Arg Gln
290                 295                 300 aag aat cat ggt atc cac ttc cgg gta tta gca aaa gcg tta cgt atg    960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa   1008
Ser Gly Gly Asp His Ile His Ser Gly Thr Val Val Gly Lys Leu Glu
            325                 330                 335 ggt gaa aga gac ata act ttg ggc ttt gtt gat tta ctg cgt gat gat   1056
Gly Glu Arg Asp Ile Thr Leu Gly Phe Val Asp Leu Leu Arg Asp Asp
        340                 345                 350 cat gtt gaa caa gat cga agt cgc ggt att tat ttc act caa gat tgg   1104
His Val Glu Gln Asp Arg Ser Arg Gly Ile Tyr Phe Thr Gln Asp Trp
    355                 360                 365 gtc gct tta cca ggt gtt cta ccc gtg gct tca gga ggt att cac gtt   1152
Val Ala Leu Pro Gly Val Leu Pro Val Ala Ser Gly Gly Ile His Val
370                 375                 380 tgg cat atg cct gct ctg acc gag atc ttt ggg gat gat tcc gta cta   1200
Trp His Met Pro Ala Leu Thr Glu Ile Phe Gly Asp Asp Ser Val Leu
385                 390                 395                 400 cag ttc ggt gga gga act tta gga cat cct tgg ggt aat gcg cca ggt   1248
Gln Phe Gly Gly Gly Thr Leu Gly His Pro Trp Gly Asn Ala Pro Gly
            405                 410                 415 gcc gta gct aat cga gta gct cta gaa gca tgt gta aaa gct cgt aat   1296
Ala Val Ala Asn Arg Val Ala Leu Glu Ala Cys Val Lys Ala Arg Asn
        420                 425                 430 gaa gga cgt gat ctt gct cag gaa ggt aat gaa att att cgc gag gct   1344
Glu Gly Arg Asp Leu Ala Gln Glu Gly Asn Glu Ile Ile Arg Glu Ala
    435                 440                 445 tgc aaa tgg agc ccg gaa cta gct gct gct tgt gaa gta tgg aaa gag   1392
Cys Lys Trp Ser Pro Glu Leu Ala Ala Ala Cys Glu Val Trp Lys Glu
450                 455                 460 atc gta ttt aat ttt gca gca gtg gac gtt ttg gat aag taa            1434
Ile Val Phe Asn Phe Ala Ala Val Asp Val Leu Asp Lys
465                 470                 475

<210> SEQ ID NO 35
<211> LENGTH: 477
<212> TYPE: PRT
```

<213> ORGANISM: Artificial Sequence
<220> FEATURE:
<223> OTHER INFORMATION: Synthetic Construct

<400> SEQUENCE: 35

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Thr Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

His Val Glu Gln Asp Arg Ser Arg Gly Ile Tyr Phe Thr Gln Asp Trp
        355                 360                 365

Val Ala Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400
```

```
Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
    450                 455                 460

Ile Val Phe Asn Phe Ala Ala Val Asp Val Leu Asp Lys
465                 470                 475

<210> SEQ ID NO 36
<211> LENGTH: 1434
<212> TYPE: DNA
<213> ORGANISM: Artificial Sequence
<220> FEATURE:
<223> OTHER INFORMATION: Description for artificial sequence: shuffled
      Tobacco Rubisco large subunit variant T836-3-1.
<220> FEATURE:
<221> NAME/KEY: CDS
<222> LOCATION: (1)..(1431)

<400> SEQUENCE: 36
```

| | | | | | | | | | | | | | | | | |
|---|---|---|---|---|---|---|---|---|---|---|---|---|---|---|---|---|
| atg | tca | cca | caa | aca | gag | act | aaa | gca | agt | gtt | gga | ttc | aaa | gct | ggt | 48 |
| Met | Ser | Pro | Gln | Thr | Glu | Thr | Lys | Ala | Ser | Val | Gly | Phe | Lys | Ala | Gly | |
| 1 | | | | 5 | | | | | 10 | | | | | 15 | | |
| gtt | aaa | gag | tac | aaa | ttg | act | tat | tat | act | cct | gag | tac | caa | acc | aag | 96 |
| Val | Lys | Glu | Tyr | Lys | Leu | Thr | Tyr | Tyr | Thr | Pro | Glu | Tyr | Gln | Thr | Lys | |
| | | | 20 | | | | | 25 | | | | | 30 | | | |
| gat | act | gat | ata | ttg | gca | gca | ttc | cga | gta | act | cct | caa | cct | gga | gtt | 144 |
| Asp | Thr | Asp | Ile | Leu | Ala | Ala | Phe | Arg | Val | Thr | Pro | Gln | Pro | Gly | Val | |
| | | 35 | | | | | 40 | | | | | 45 | | | | |
| cca | cct | gaa | gaa | gca | ggg | gcc | gcg | gta | gct | gcc | gaa | tct | tct | act | ggt | 192 |
| Pro | Pro | Glu | Glu | Ala | Gly | Ala | Ala | Val | Ala | Ala | Glu | Ser | Ser | Thr | Gly | |
| 50 | | | | | 55 | | | | | 60 | | | | | | |
| aca | tgg | aca | act | gta | tgg | acc | gat | gga | ctt | acc | agc | ctt | gat | cgt | tac | 240 |
| Thr | Trp | Thr | Thr | Val | Trp | Thr | Asp | Gly | Leu | Thr | Ser | Leu | Asp | Arg | Tyr | |
| 65 | | | | | 70 | | | | | 75 | | | | | 80 | |
| aaa | ggg | cga | tgc | tac | cgc | atc | gag | cgt | gtt | gtt | gga | gaa | aaa | gat | caa | 288 |
| Lys | Gly | Arg | Cys | Tyr | Arg | Ile | Glu | Arg | Val | Val | Gly | Glu | Lys | Asp | Gln | |
| | | | | 85 | | | | | 90 | | | | | 95 | | |
| tat | att | gct | tat | gta | gct | tac | cct | tta | gac | ctt | ttt | gaa | gaa | ggt | tct | 336 |
| Tyr | Ile | Ala | Tyr | Val | Ala | Tyr | Pro | Leu | Asp | Leu | Phe | Glu | Glu | Gly | Ser | |
| | | | 100 | | | | | 105 | | | | | 110 | | | |
| gtt | acc | aac | atg | ttt | act | tcc | att | gta | ggt | aac | gta | ttt | ggg | ttc | aaa | 384 |
| Val | Thr | Asn | Met | Phe | Thr | Ser | Ile | Val | Gly | Asn | Val | Phe | Gly | Phe | Lys | |
| | | 115 | | | | | 120 | | | | | 125 | | | | |
| gcc | ctg | cgc | gct | cta | cgt | ctg | gaa | gat | ctg | cga | atc | cct | cct | gct | tat | 432 |
| Ala | Leu | Arg | Ala | Leu | Arg | Leu | Glu | Asp | Leu | Arg | Ile | Pro | Pro | Ala | Tyr | |
| 130 | | | | | 135 | | | | | 140 | | | | | | |
| gtt | aaa | act | ttc | caa | ggt | ccg | cct | cat | ggg | atc | caa | gtt | gaa | aga | gat | 480 |
| Val | Lys | Thr | Phe | Gln | Gly | Pro | Pro | His | Gly | Ile | Gln | Val | Glu | Arg | Asp | |
| 145 | | | | | 150 | | | | | 155 | | | | | 160 | |
| aaa | ttg | aac | aag | tat | ggt | cgt | ccc | ctg | ttg | gga | tgt | act | att | aaa | cct | 528 |
| Lys | Leu | Asn | Lys | Tyr | Gly | Arg | Pro | Leu | Leu | Gly | Cys | Thr | Ile | Lys | Pro | |
| | | | 165 | | | | | 170 | | | | | 175 | | | |
| aaa | ttg | ggg | tta | tct | gct | aaa | aac | tac | ggt | aga | gct | gtt | tat | gaa | tgt | 576 |
| Lys | Leu | Gly | Leu | Ser | Ala | Lys | Asn | Tyr | Gly | Arg | Ala | Val | Tyr | Glu | Cys | |
| | | | 180 | | | | | 185 | | | | | 190 | | | |
| ctt | cgc | ggt | gga | ctt | gat | ttt | acc | aaa | gat | gat | gag | aac | gtg | aac | tca | 624 |
| Leu | Arg | Gly | Gly | Leu | Asp | Phe | Thr | Lys | Asp | Asp | Glu | Asn | Val | Asn | Ser | |

```
                195                 200                 205
caa cca ttt atg cgt tgg aga gat cgt ttc tta ttt tgt gcc gaa gca      672
Gln Pro Phe Met Arg Trp Arg Asp Arg Phe Leu Phe Cys Ala Glu Ala
210                 215                 220 ctt tat aaa gca cag gct gaa aca ggt gaa atc aaa ggg cat tac ttg      720
Leu Tyr Lys Ala Gln Ala Glu Thr Gly Glu Ile Lys Gly His Tyr Leu
225                 230                 235                 240 aat gct act gca ggt aca tgc gaa gaa atg atc aaa aga gct gta ttt      768
Asn Ala Thr Ala Gly Thr Cys Glu Glu Met Ile Lys Arg Ala Val Phe
                245                 250                 255 gct aga gaa ttg ggc gtt ccg atc gta atg cat gac tac tta acg ggg      816
Ala Arg Glu Leu Gly Val Pro Ile Val Met His Asp Tyr Leu Thr Gly
            260                 265                 270 gga ttc acc gca aat act agc ttg tct cat tat tgc cga gat aat ggt      864
Gly Phe Thr Ala Asn Thr Ser Leu Ser His Tyr Cys Arg Asp Asn Gly
        275                 280                 285 cta ctt ctt cac atc cac cgt gca atg cat gcg gtt att gat aga cag      912
Leu Leu Leu His Ile His Arg Ala Met His Ala Val Ile Asp Arg Gln
    290                 295                 300 aag aat cat ggt atc cac ttc cgg gta tta gca aaa gcg tta cgt atg      960
Lys Asn His Gly Ile His Phe Arg Val Leu Ala Lys Ala Leu Arg Met
305                 310                 315                 320 tct ggt gga gat cat att cac tct ggt acc gta gta ggt aaa ctt gaa     1008
Ser Gly Gly Asp His Ile His Ser Gly Thr Val Val Gly Lys Leu Glu
                325                 330                 335 ggt gaa aga gac ata act ttg ggc ttt gtt gat tta ctg cgt gat ggt     1056
Gly Glu Arg Asp Ile Thr Leu Gly Phe Val Asp Leu Leu Arg Asp Gly
            340                 345                 350 ttt gtt gaa caa gat cga agt cgc ggt att tat ttc act caa gat tgg     1104
Phe Val Glu Gln Asp Arg Ser Arg Gly Ile Tyr Phe Thr Gln Asp Trp
        355                 360                 365 gtc tct tta cca ggt gtt cta ccc gtg gct tca gga ggt att cac gtt     1152
Val Ser Leu Pro Gly Val Leu Pro Val Ala Ser Gly Gly Ile His Val
    370                 375                 380 tgg cat atg cct gct ctg acc gag atc ttt ggg gat gat tcc gta cta     1200
Trp His Met Pro Ala Leu Thr Glu Ile Phe Gly Asp Asp Ser Val Leu
385                 390                 395                 400 cag ttc ggt gga gga act tta gga cat cct tgg ggt aat gcg cca ggt     1248
Gln Phe Gly Gly Gly Thr Leu Gly His Pro Trp Gly Asn Ala Pro Gly
                405                 410                 415 gcc gta gct aat cga gta gct cta gaa gca tgt gta aaa gct cgt aat     1296
Ala Val Ala Asn Arg Val Ala Leu Glu Ala Cys Val Lys Ala Arg Asn
            420                 425                 430 gaa gga cgt gat ctt gct cag gaa ggt aat gaa att att cgc gag gct     1344
Glu Gly Arg Asp Leu Ala Gln Glu Gly Asn Glu Ile Ile Arg Glu Ala
        435                 440                 445 tgc aaa tgg agc ccg gaa cta gct gct gct tgt gaa gta tgg aaa gag     1392
Cys Lys Trp Ser Pro Glu Leu Ala Ala Ala Cys Glu Val Trp Lys Glu
    450                 455                 460 gta gta ttt aat ttt gca gca gtg gac gtt ttg gat aag taa             1434
Val Val Phe Asn Phe Ala Ala Val Asp Val Leu Asp Lys
465                 470                 475

<210> SEQ ID NO 37
<211> LENGTH: 477
<212> TYPE: PRT
<213> ORGANISM: Artificial Sequence
<220> FEATURE:
<223> OTHER INFORMATION: Synthetic Construct

<400> SEQUENCE: 37
```

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
            35                  40                  45

Pro Pro Glu Glu Ala Gly Ala Ala Val Ala Ala Glu Ser Ser Thr Gly
50                  55                  60

Thr Trp Thr Thr Val Trp Thr Asp Gly Leu Thr Ser Leu Asp Arg Tyr
65                  70                  75                  80

Lys Gly Arg Cys Tyr Arg Ile Glu Arg Val Val Gly Glu Lys Asp Gln
                85                  90                  95

Tyr Ile Ala Tyr Val Ala Tyr Pro Leu Asp Leu Phe Glu Glu Gly Ser
                100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
            130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
            210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ser His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Gly
            340                 345                 350

Phe Val Glu Gln Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430
```

```
Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
    450                 455                 460

Val Val Phe Asn Phe Ala Ala Val Asp Val Leu Asp Lys
465                 470                 475

<210> SEQ ID NO 38
<211> LENGTH: 23
<212> TYPE: DNA
<213> ORGANISM: Artificial Sequence
<220> FEATURE:
<223> OTHER INFORMATION: Artificial sequence - chemically synthesized
      primer for amplifying Rubisco large subunit.

<400> SEQUENCE: 38
cctaaaggcc ctttctatgc tcg                                          23

<210> SEQ ID NO 39
<211> LENGTH: 26
<212> TYPE: DNA
<213> ORGANISM: artificial sequence
<220> FEATURE:
<223> OTHER INFORMATION: Artificial sequence - chemically synthesized
      primer for amplifying Rubisco large subunit.

<400> SEQUENCE: 39
atgtttaggt atttaaccta aacacc                                       26
```